US007157049B2

(12) United States Patent
Valencia et al.

(10) Patent No.: US 7,157,049 B2
(45) Date of Patent: Jan. 2, 2007

(54) OPTICAL BIO-DISCS AND FLUIDIC CIRCUITS FOR ANALYSIS OF CELLS AND METHODS RELATING THERETO

(75) Inventors: Ramoncito Magpantay Valencia, Aliso Viejo, CA (US); YihFar Chen, Aliso Viejo, CA (US); Susan Newcomb Hurt, Lake Forest, CA (US); Joseph Roby Iringan Urcia, Westminster, CA (US); Gowri Pyapali Selvan, Irvine, CA (US)

(73) Assignee: Nagaoka & Co., Ltd. (JP)

( * ) Notice: Subject to any disclaimer, the term of this patent is extended or adjusted under 35 U.S.C. 154(b) by 0 days.

(21) Appl. No.: 10/293,214

(22) Filed: Nov. 13, 2002

(65) Prior Publication Data

US 2003/0219713 A1 Nov. 27, 2003

Related U.S. Application Data

(63) Continuation-in-part of application No. 09/988,728, filed on Nov. 16, 2001.

(60) Provisional application No. 60/382,327, filed on May 22, 2002, provisional application No. 60/358,479, filed on Feb. 19, 2002, provisional application No. 60/355,644, filed on Feb. 5, 2002, provisional application No. 60/349,449, filed on Jan. 18, 2002, provisional application No. 60/349,392, filed on Jan. 17, 2002.

(51) Int. Cl.
*G01N 15/06* (2006.01)
*G01N 33/00* (2006.01)
*G01N 33/48* (2006.01)

(52) U.S. Cl. .................. 422/68.1; 422/50; 422/55; 422/57; 422/58; 422/64; 422/82.05; 422/82.09; 422/101; 435/4; 435/7.24; 435/725; 435/7.92; 435/287.1; 435/287.9; 435/288.7; 436/63; 436/164

(58) Field of Classification Search ................ 422/50, 422/55, 57–58, 64, 68.1, 82.05, 82.09, 72; 435/4–6, 7.2, 7.24, 7.25–7.92, 287.1, 287.9, 435/288.7; 436/63, 164, 45, 172
See application file for complete search history.

(56) References Cited

U.S. PATENT DOCUMENTS 3,437,266 A 4/1969 Patterson (Continued)

FOREIGN PATENT DOCUMENTS

CN 1208464 2/1999

(Continued)

OTHER PUBLICATIONS

AskOxford.com (website) <http://www.askoxford.com/results/?view=dict&field-12668446=associate&branch=13842570&text-searchtype=exact&sortorder=score%2Cname> Oxford University Press, 2004.*

(Continued)

*Primary Examiner*—Long V. Le
*Assistant Examiner*—Leon Y. Lum
(74) *Attorney, Agent, or Firm*—Knobbe, Martens, Olson & Bear, LLP

(57) ABSTRACT

The present invention is directed to optical bio-discs, methods, and optical disc drives for clinical diagnostics. The present invention is further directed to methods for determining the quantity of a specific type of blood cell in a biological sample including on-disc sample preparation and processing, providing a pre-processed sample onto a capture zone, removing portions of the sample that are not bound in the capture zone, and counting bound cells. Also disclosed are fluidic circuits for processing blood samples for use in a cluster designation marker assay in the optical bio-disc.

21 Claims, 71 Drawing Sheets

U.S. PATENT DOCUMENTS

| | | |
|---|---|---|
| 3,679,367 A | 7/1972 | Negersmith et al. |
| 3,736,432 A | 5/1973 | Sweet |
| 3,798,459 A | 3/1974 | Anderson et al. |
| 3,901,658 A | 8/1975 | Burtis et al. |
| 3,939,350 A | 2/1976 | Kronick et al. |
| 3,966,322 A | 6/1976 | Greaves et al. |
| 3,973,913 A | 8/1976 | Louderback |
| 4,233,402 A | 11/1980 | Maggio et al. |
| 4,284,602 A | 8/1981 | Kelton et al. |
| 4,307,376 A | 12/1981 | Miller et al. |
| 4,456,581 A | 6/1984 | Edelmann et al. |
| 4,469,793 A | 9/1984 | Guigan |
| 4,478,946 A | 10/1984 | Van der Merwe et al. |
| 4,495,151 A | 1/1985 | Ohyama et al. |
| 4,673,657 A | 6/1987 | Christian |
| 4,687,638 A | 8/1987 | Benajam |
| 4,743,558 A | 5/1988 | Guigan |
| 4,790,026 A | 12/1988 | Gennery et al. |
| 4,816,168 A | 3/1989 | Carrol et al. |
| 4,940,527 A | 7/1990 | Kazlauskas et al. |
| 5,061,381 A | 10/1991 | Burd |
| 5,087,556 A | 2/1992 | Ertinghausen |
| 5,112,134 A | 5/1992 | Chow et al. |
| 5,122,284 A * | 6/1992 | Braynin et al. .............. 210/782 |
| 5,160,702 A | 11/1992 | Kopf-Sill et al. |
| 5,168,066 A | 12/1992 | Zahniser et al. |
| 5,173,193 A | 12/1992 | Schembri |
| 5,173,262 A | 12/1992 | Burtis et al. |
| H1183 H | 5/1993 | Zitko et al. |
| 5,212,063 A | 5/1993 | Ofenloch-Hahnle et al. |
| 5,213,964 A * | 5/1993 | Jones .......................... 435/11 |
| 5,225,350 A | 7/1993 | Watanabe et al. |
| 5,225,543 A | 7/1993 | Eppler et al. |
| 5,242,606 A | 9/1993 | Braynin et al. |
| 5,256,376 A | 10/1993 | Callan et al. |
| 5,262,302 A | 11/1993 | Russell |
| 5,265,169 A | 11/1993 | Ohta et al. |
| 5,287,272 A | 2/1994 | Rutenberg et al. |
| 5,310,523 A | 5/1994 | Smethers et al. |
| 5,329,461 A | 7/1994 | Allen et al. |
| 5,348,859 A * | 9/1994 | Brunhouse et al. ......... 435/7.24 |
| 5,374,531 A | 12/1994 | Jensen |
| 5,385,822 A | 1/1995 | Melnicoff et al. |
| 5,436,134 A | 7/1995 | Haugland et al. |
| 5,445,940 A | 8/1995 | Brenner et al. |
| 5,464,752 A | 11/1995 | Kortright et al. |
| 5,472,603 A | 12/1995 | Schembri |
| 5,478,527 A | 12/1995 | Gustafson et al. |
| 5,478,750 A | 12/1995 | Bernstein et al. |
| 5,486,335 A | 1/1996 | Wilding et al. |
| 5,510,270 A | 4/1996 | Fodor et al. |
| 5,518,930 A | 5/1996 | Burd |
| 5,534,416 A | 7/1996 | Millard et al. |
| 5,545,531 A | 8/1996 | Roth et al. |
| 5,585,069 A | 12/1996 | Zanzucchi et al. |
| 5,591,643 A | 1/1997 | Schembri |
| 5,593,838 A | 1/1997 | Zanzucchi et al. |
| 5,618,926 A | 4/1997 | Salamone et al. |
| 5,627,643 A | 5/1997 | Birnbaum et al. |
| 5,658,735 A | 8/1997 | Lee |
| 5,681,708 A * | 10/1997 | Kassis ....................... 435/7.24 |
| 5,736,410 A | 4/1998 | Zarling et al. |
| 5,744,366 A * | 4/1998 | Kricka et al. ................. 436/63 |
| 5,755,942 A | 5/1998 | Zanzucchi et al. |
| 5,795,755 A | 8/1998 | Lemelson |
| 5,807,522 A | 9/1998 | Brown et al. |
| 5,812,419 A | 9/1998 | Chupp et al. |
| 5,843,767 A | 12/1998 | Beattie |
| 5,852,191 A | 12/1998 | Karandikar et al. |
| 5,858,804 A | 1/1999 | Zanzucchi et al. |
| 5,863,708 A | 1/1999 | Zanzucchi et al. |
| 5,866,345 A | 2/1999 | Wilding et al. |
| 5,872,723 A | 2/1999 | DeCusatis et al. |
| 5,892,577 A * | 4/1999 | Gordon ........................ 356/73 |
| 5,932,428 A | 8/1999 | Dubrow et al. |
| 5,932,799 A | 8/1999 | Moles |
| 5,962,238 A | 10/1999 | Sizto et al. |
| 5,982,535 A | 11/1999 | Inoue et al. |
| 5,982,577 A | 11/1999 | Brown et al. |
| 5,993,665 A | 11/1999 | Terstappen et al. |
| 6,004,536 A | 12/1999 | Leung et al. |
| 6,007,690 A * | 12/1999 | Nelson et al. .............. 204/601 |
| 6,013,513 A | 1/2000 | Reber et al. |
| 6,030,581 A * | 2/2000 | Virtanen .................... 422/68.1 |
| 6,063,589 A | 5/2000 | Kellogg et al. |
| 6,117,630 A | 9/2000 | Reber et al. |
| 6,137,897 A | 10/2000 | Emi et al. |
| 6,143,247 A * | 11/2000 | Sheppard et al. .............. 422/63 |
| 6,143,248 A * | 11/2000 | Kellogg et al. ................ 422/72 |
| 6,231,812 B1 | 5/2001 | Rothberg et al. |
| 6,254,834 B1 | 7/2001 | Anderson et al. |
| 6,287,517 B1 | 9/2001 | Ackley et al. |
| 6,302,134 B1 | 10/2001 | Kellogg et al. |
| 6,319,469 B1 * | 11/2001 | Mian et al. ................... 422/64 |
| 6,327,031 B1 | 12/2001 | Gordon |
| 6,342,395 B1 | 1/2002 | Hammock et al. |
| 6,387,331 B1 | 5/2002 | Hunter |
| 6,399,361 B1 | 6/2002 | Brotherston et al. |
| 6,476,907 B1 | 11/2002 | Gordon |
| 6,514,461 B1 | 2/2003 | Lappe et al. |
| 6,632,399 B1 * | 10/2003 | Kellogg et al. ................ 422/72 |
| 2001/0055812 A1 | 12/2001 | Mian et al. ................... 436/45 |
| 2002/0047003 A1 | 4/2002 | Bedingham et al. ........ 219/388 |
| 2002/0076354 A1 | 6/2002 | Cohen ......................... 422/72 |
| 2002/0098528 A1 | 7/2002 | Gordon et al. ............. 435/7.21 |
| 2002/0106786 A1 | 8/2002 | Carvalho et al. |
| 2002/0137059 A1 | 9/2002 | Wu et al. ........................ 435/6 |
| 2002/0137218 A1 | 9/2002 | Mian et al. ................... 436/45 |
| 2002/0145960 A1 | 10/2002 | Worthington et al. .... 369/47.48 |
| 2002/0163642 A1 | 11/2002 | Zoval et al. |
| 2002/0168663 A1 | 11/2002 | Phan et al. .................... 435/6 |
| 2002/0171838 A1 | 11/2002 | Pal et al. |
| 2002/0172980 A1 | 11/2002 | Phan et al. .................. 435/7.1 |
| 2002/0187501 A1 | 12/2002 | Huang et al. ................... 435/6 |
| 2002/0196435 A1 | 12/2002 | Cohen et al. |
| 2003/0003464 A1 | 1/2003 | Phan et al. ..................... 435/6 |
| 2003/0054376 A1 | 3/2003 | Mullis et al. .................. 435/6 |
| 2003/0064507 A1 | 4/2003 | Gallagher et al. ........ 435/287.2 |

FOREIGN PATENT DOCUMENTS

| | | |
|---|---|---|
| CN | 1285916 A | 2/2001 |
| DE | 4410224 A | 9/1995 |
| EP | 0305210 | 3/1989 |
| EP | 0322657 A | 7/1989 |
| EP | 0 392 475 A2 | 10/1990 |
| EP | 0 417 305 A1 | 3/1991 |
| EP | 0 504 432 A1 | 9/1992 |
| EP | 0 521 421 A2 | 1/1993 |
| EP | 0616218 | 9/1994 |
| EP | 0 693 560 A2 | 1/1996 |
| EP | 0 866 449 A2 | 9/1998 |
| WO | WO 93/22053 * | 11/1993 |
| WO | WO 93/22058 A | 11/1993 |
| WO | WO 95/25815 | 9/1995 |
| WO | WO 95/33986 | 12/1995 |
| WO | WO 97/21090 | 6/1997 |
| WO | WO 98/01533 A | 1/1998 |
| WO | WO 98/07019 * | 2/1998 |
| WO | WO 98/12559 | 3/1998 |
| WO | WO 98/28623 | 7/1998 |
| WO | WO 98/38510 * | 9/1998 |
| WO | WO 98/53311 | 11/1998 |
| WO | WO 99/35499 | 7/1999 |

| WO | WO 99/58245 | 11/1999 |
| WO | WO 00/26677 | 5/2000 |
| WO | WO 00/78455 A1 | 12/2000 |
| WO | WO 01/02737 A1 | 1/2001 |
| WO | WO 01/47638 A2 | 7/2001 |
| WO | WO 01/87485 A2 | 11/2001 |
| WO | WO 01/87486 A2 | 11/2001 |
| WO | WO 01/87487 A2 | 11/2001 |

OTHER PUBLICATIONS

Tibbe et al., "Optical Tracking and Detection of Immunomagnetically Selected and Aligned Cells", Nature Biotecnology, vol. 17, Dec. 1999, pp. 1210-1213.

Schembri et al., "Centrifugation and Capillarity integrated into a Multiple Analyte Whole Blood Analyser", Journal of Automatic Chemistry, vol. 17, No. 3 (May-Jun. 1995), pp. 99-104.

Arquint P et al., "Micromachined Analyzers on a Silicon Chip." *Clinical Chemistry*, vol. 40 No. 9 p. 1805-1809, 1994.

Delaey et al. "A comparative study of the photosensitizing characteristics of some cyanine dyes." *Journal of Photochemistry and Photobiology*, B: Biology, vol. 55, pp. 27-36, 2000.

Hema Technologies, <website> http://www.hematek.com/vet4.html, updated Nov. 6, 2000, accessed Jun. 8, 2004.

Kido H et al., "Disc-Based Immunoassay Microarrays." Analytica Chimica Acta. vol. 411, No. 1/2, p. 1-11, 2000.

Merriam-Webster, Inc. (1990) Webster's Ninth New Collegiat Dictionary, pp. 1245.

Schembri C T et al., "Portable Simultaneous Multiple Analyte Whole-Blood Analyzer for Point-of Care Testing." vol. 38, No. 9 p. 1665-1670, XP000319980. (1992).

* cited by examiner

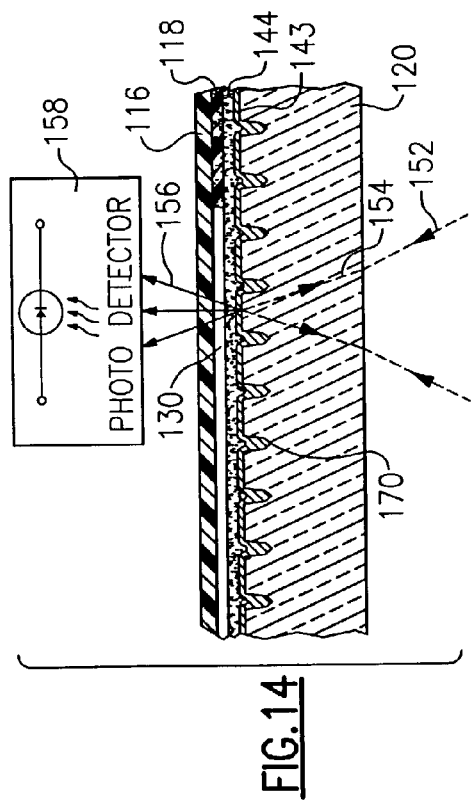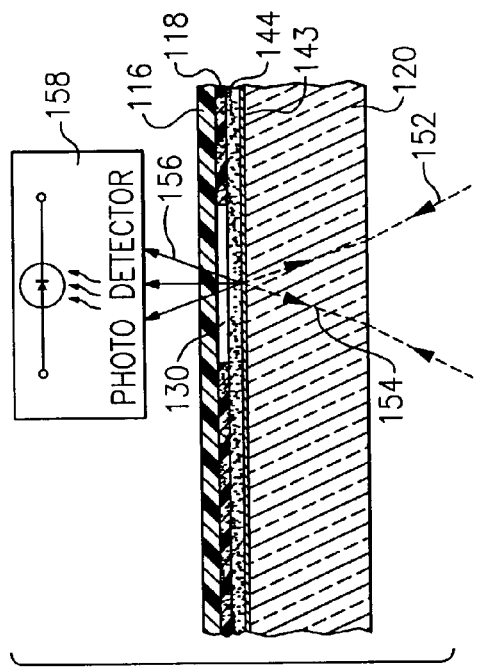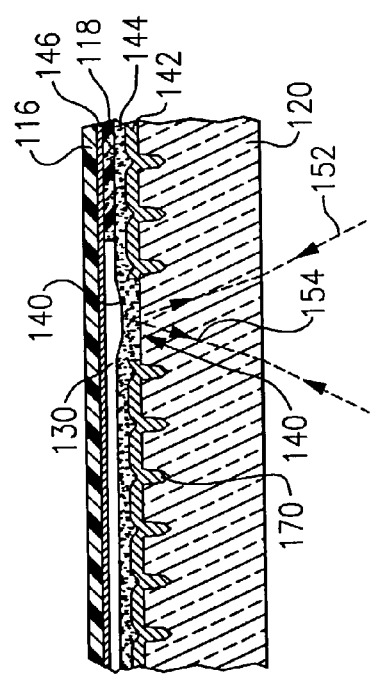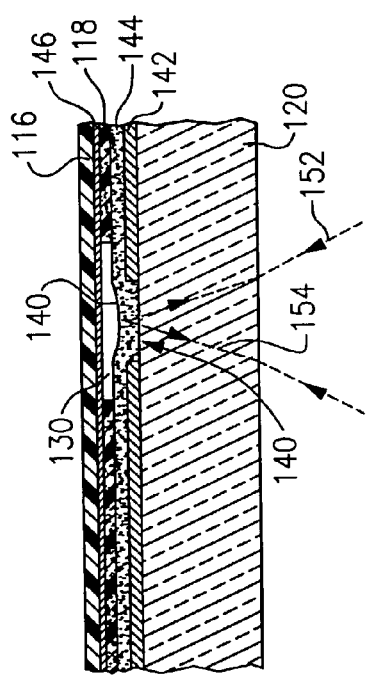

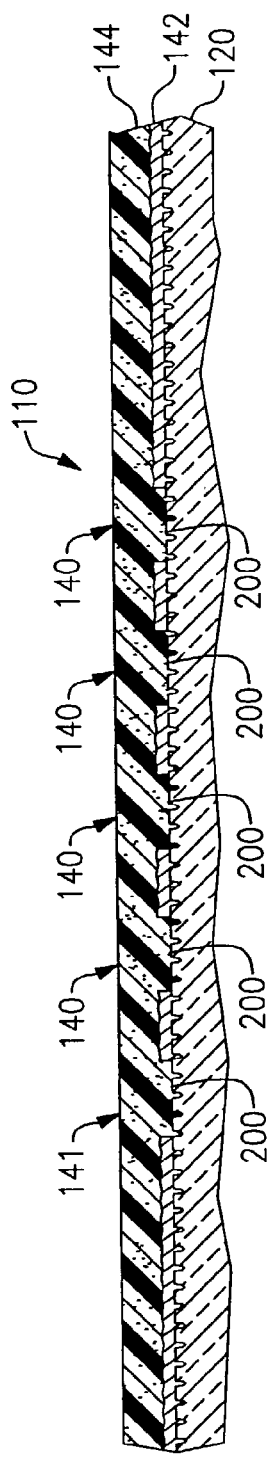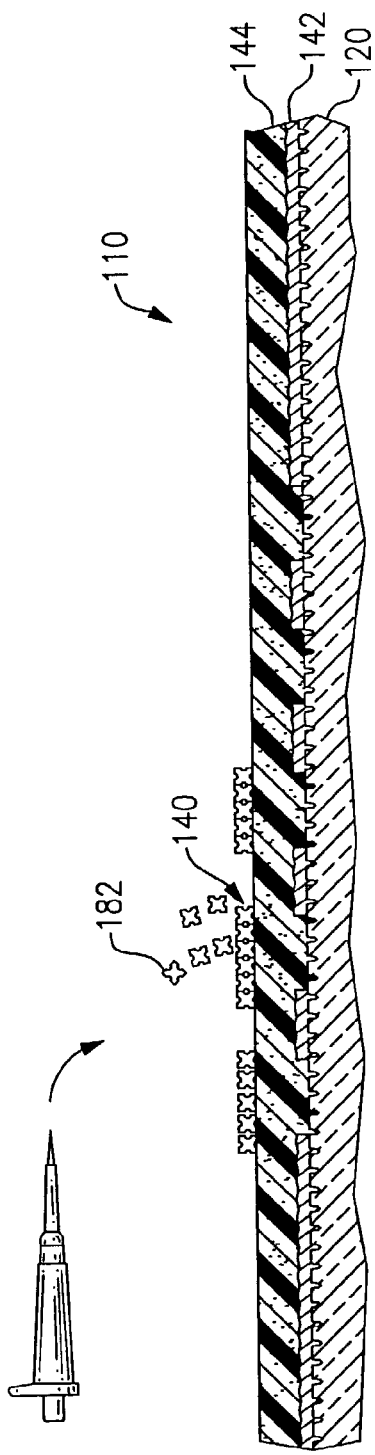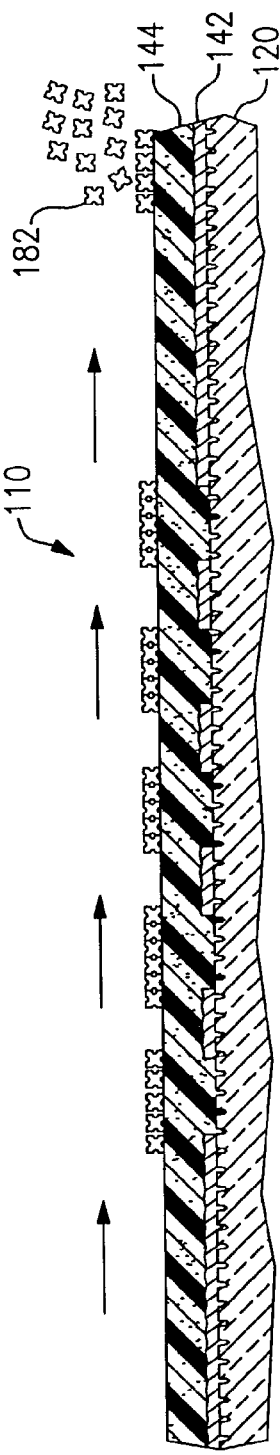

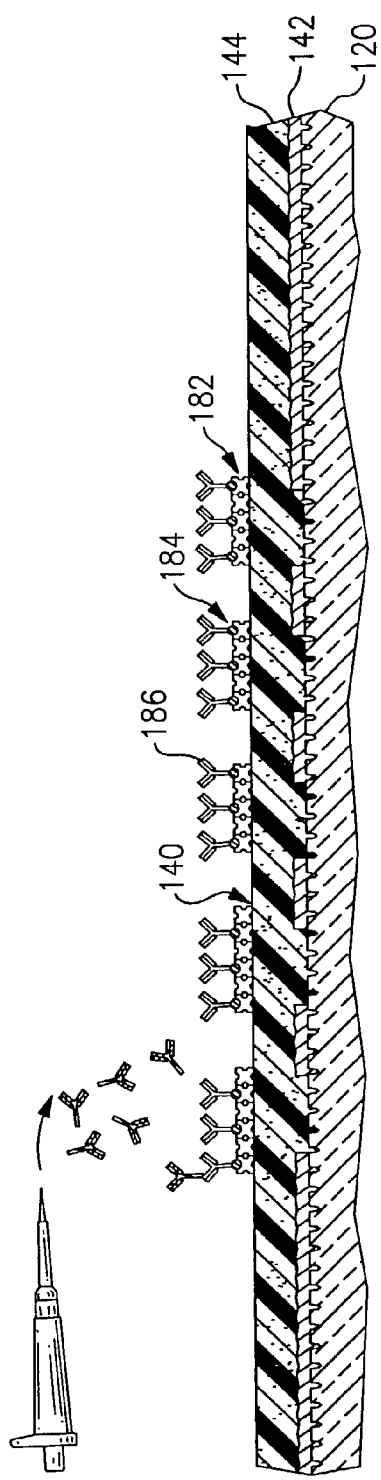
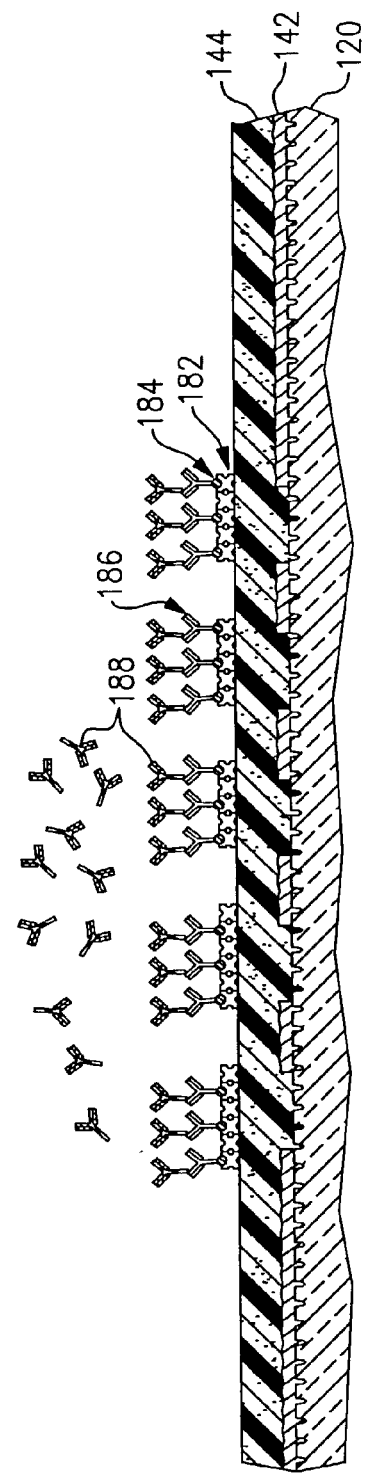
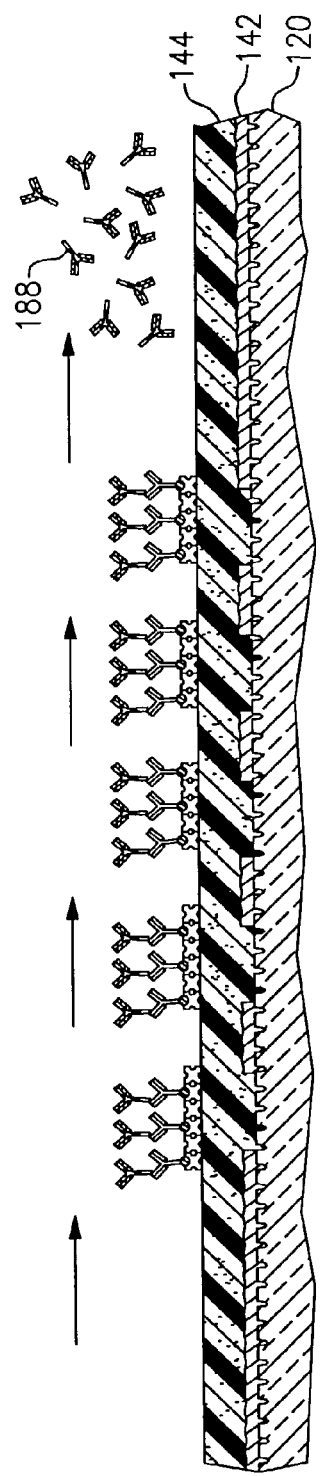
FIG.24G
FIG.24H
FIG.24I

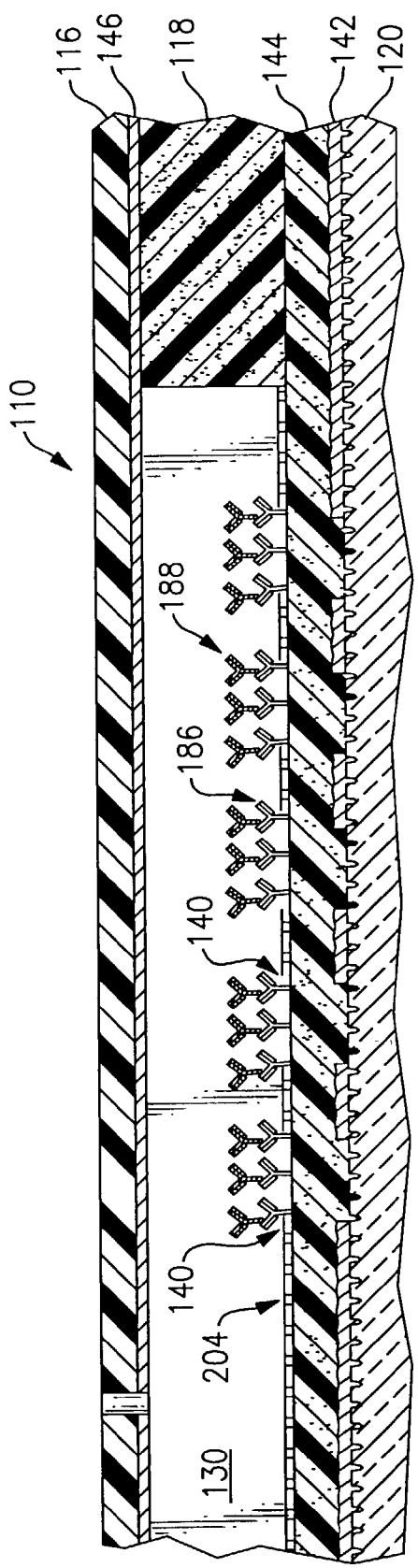
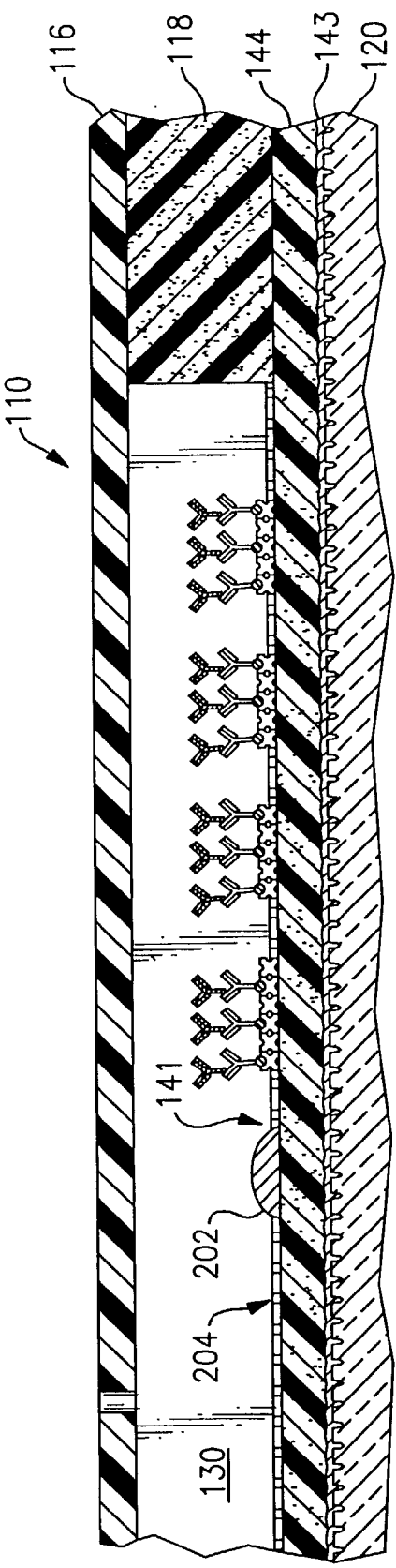

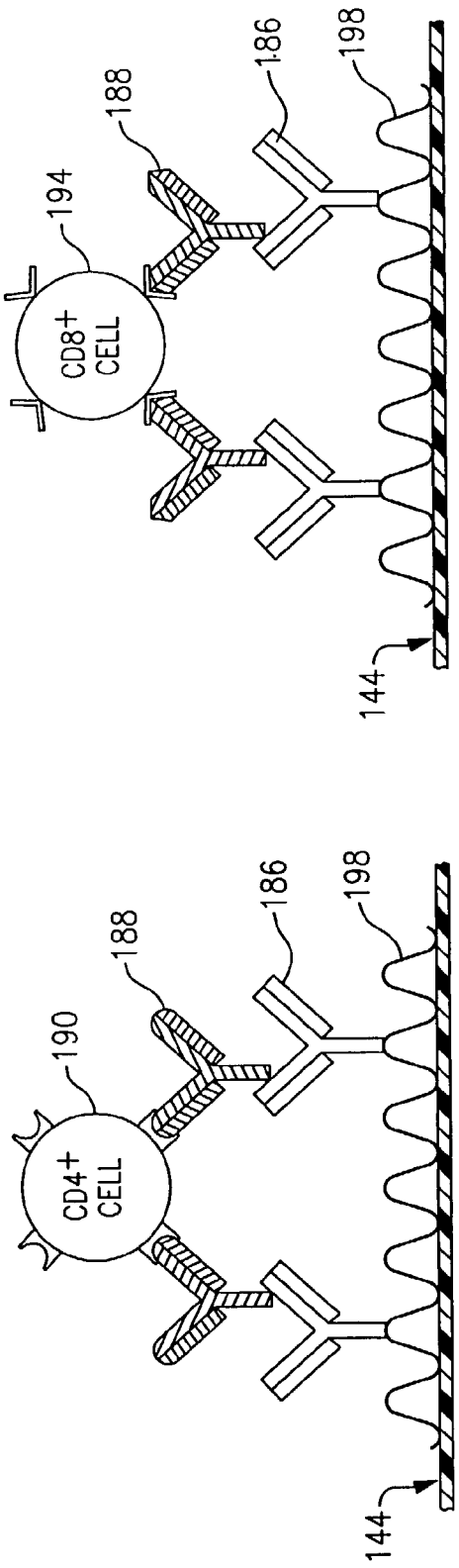
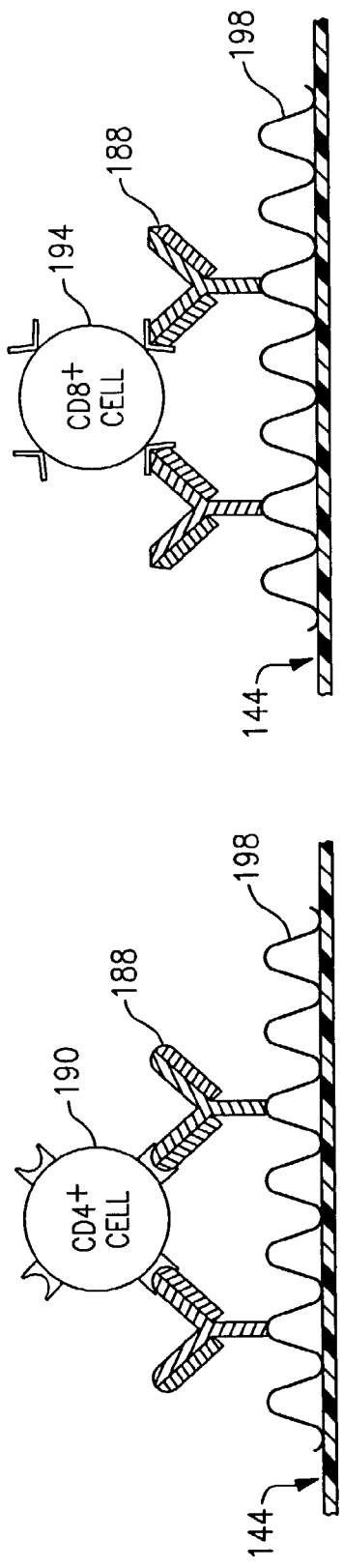
FIG.27A FIG.27B FIG.27C FIG.27D

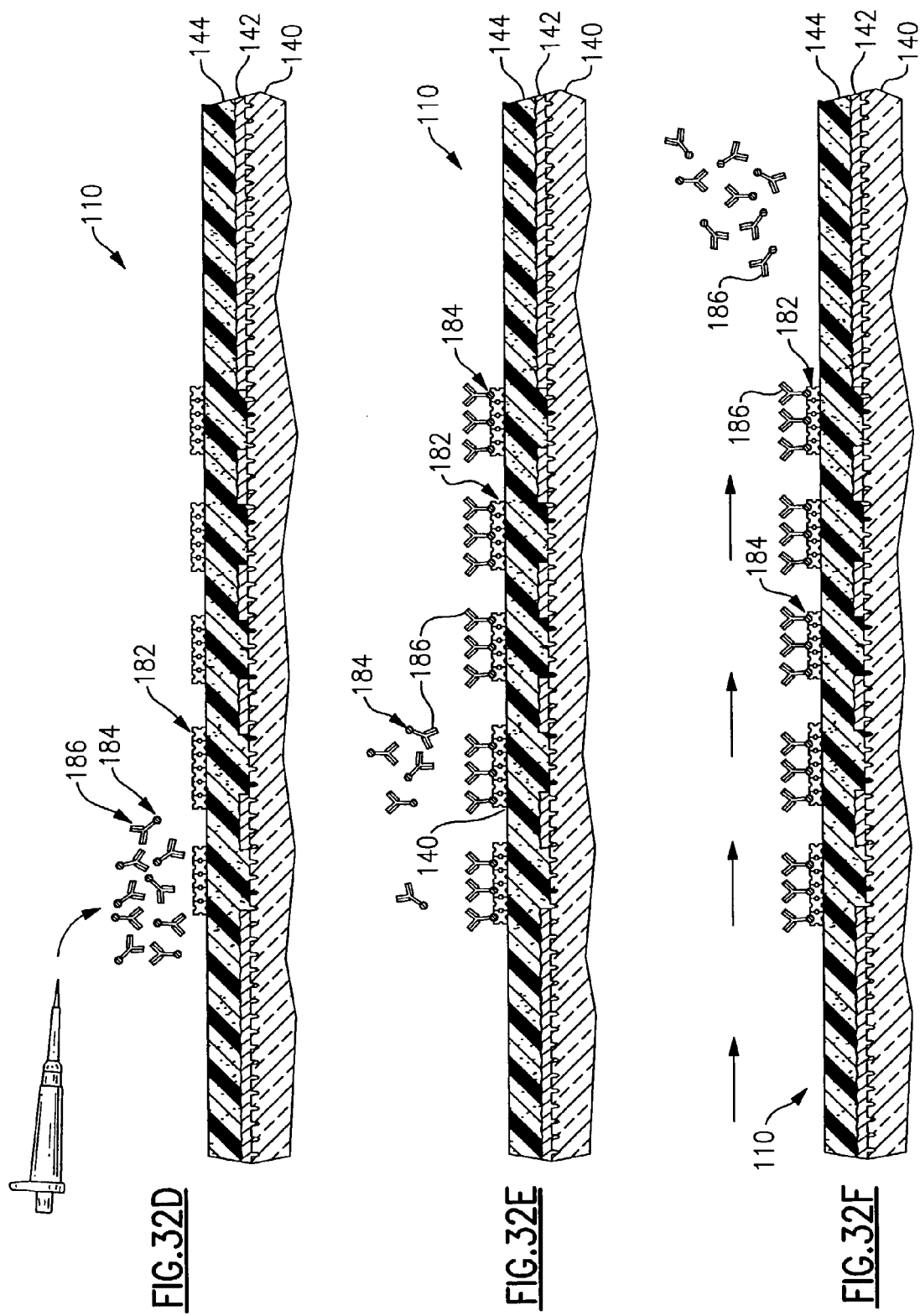

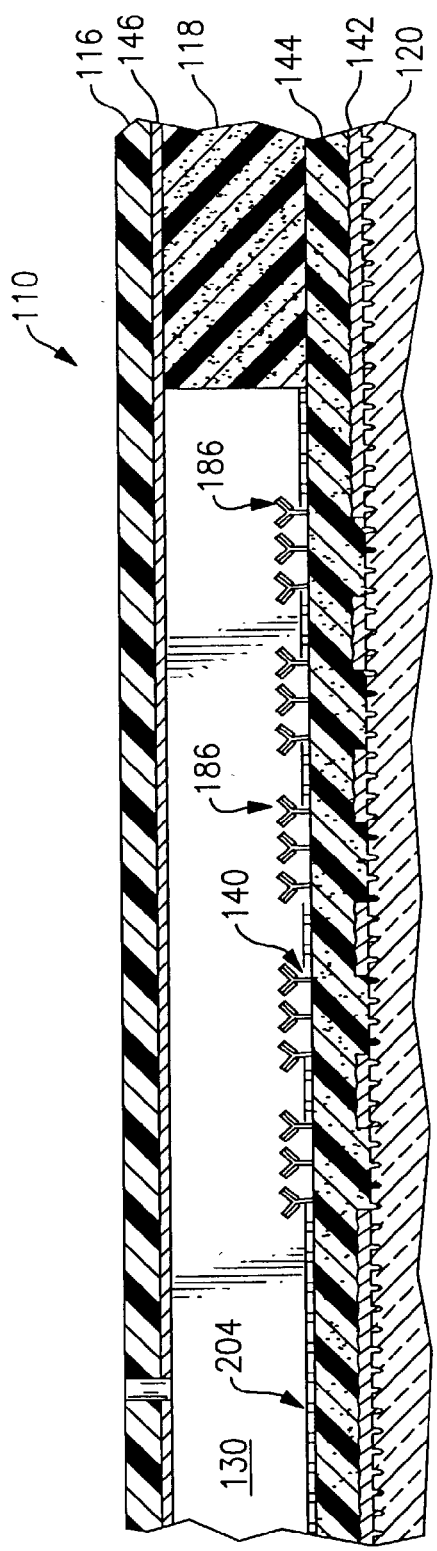
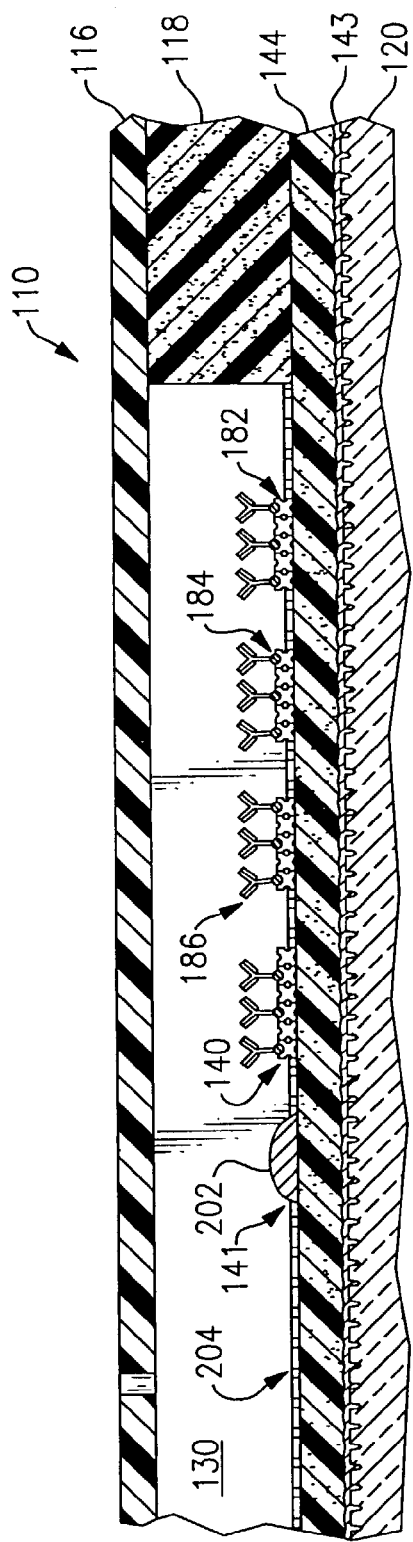
FIG.33
FIG.34

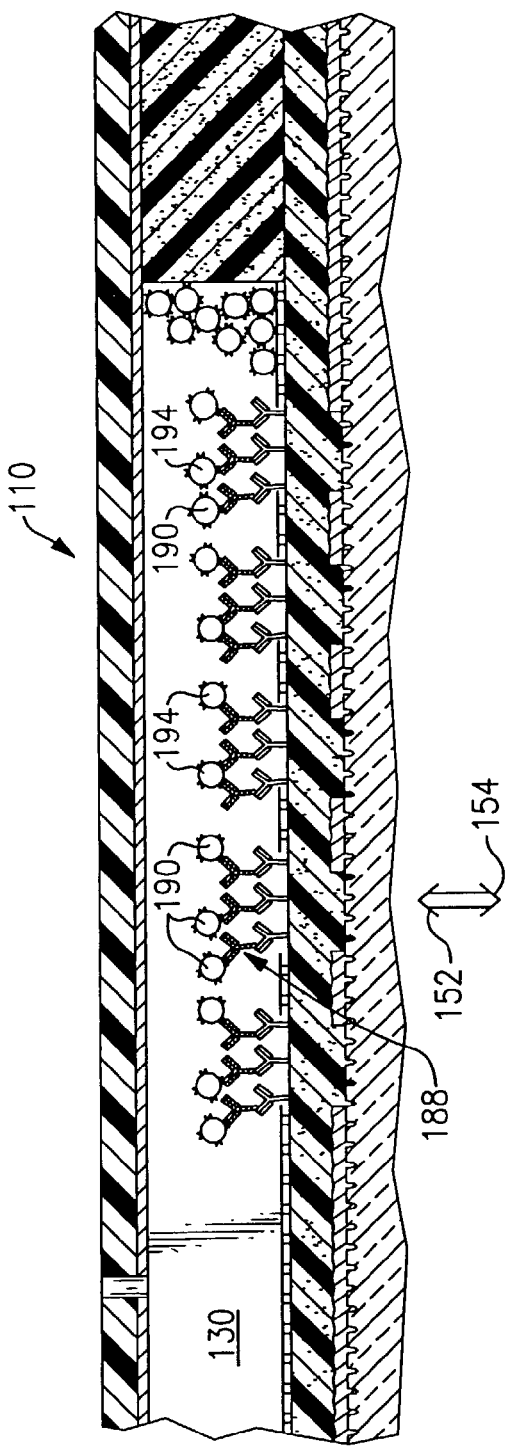
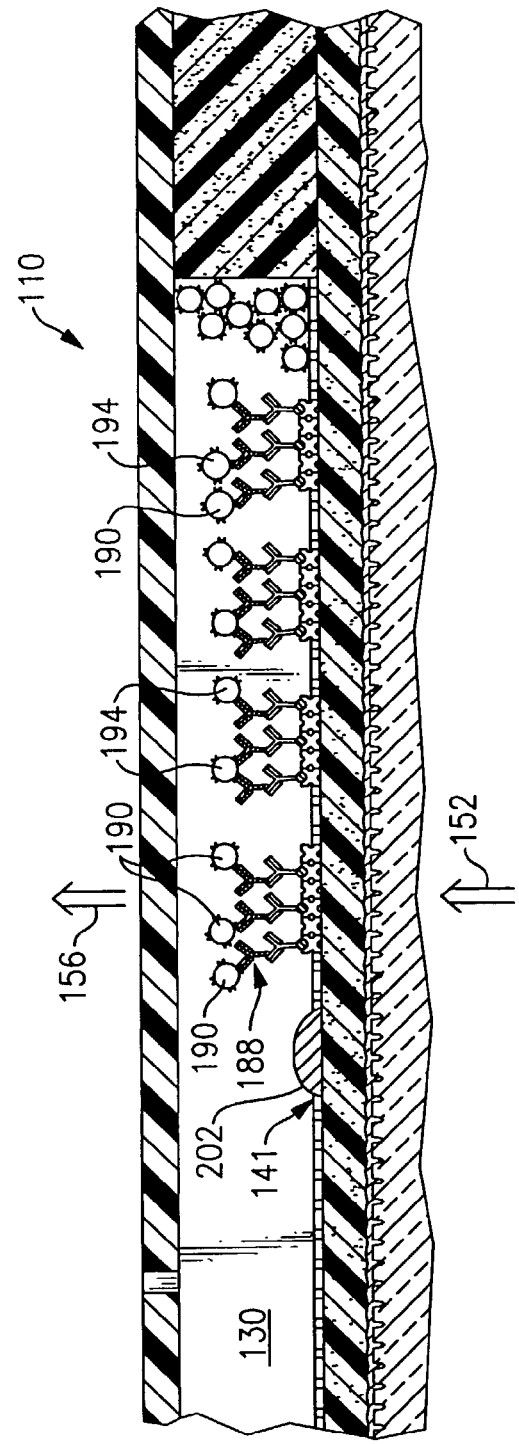
FIG. 39
FIG. 40

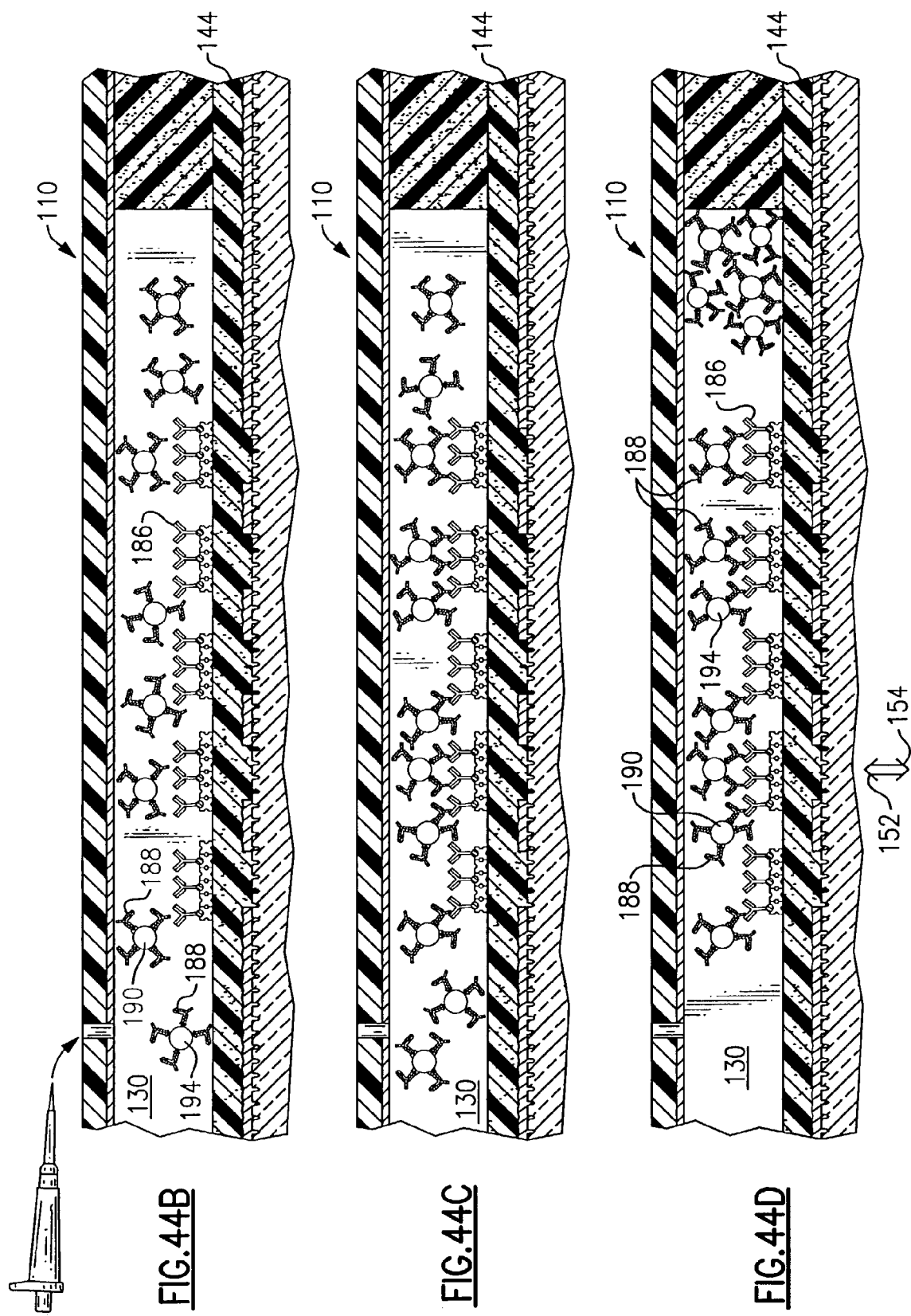

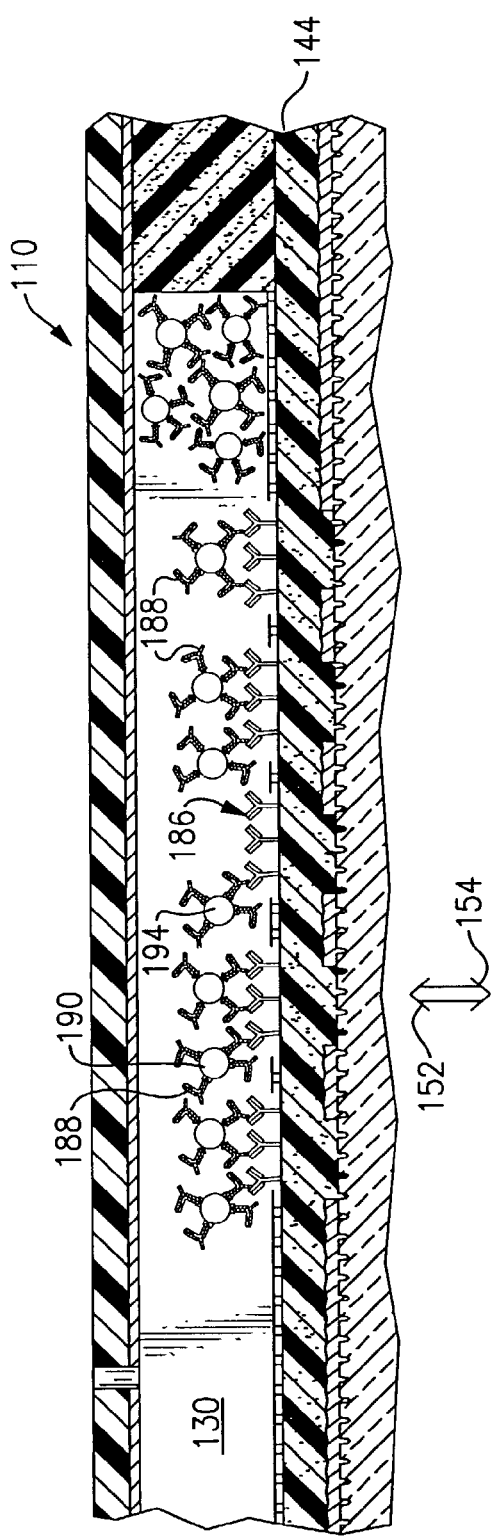
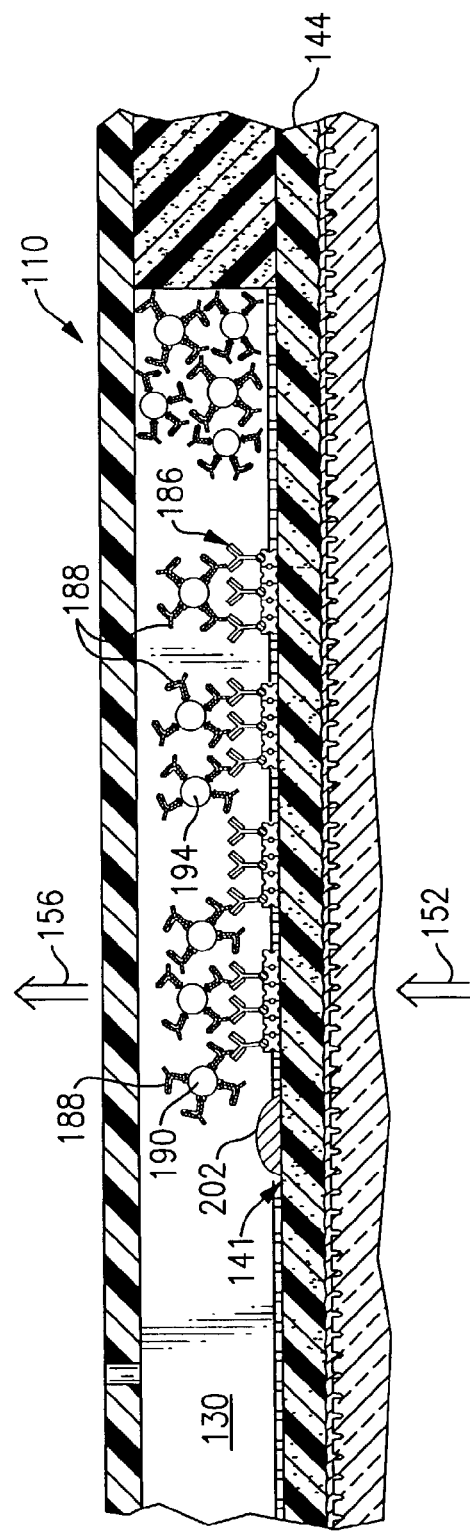
FIG.45
FIG.46

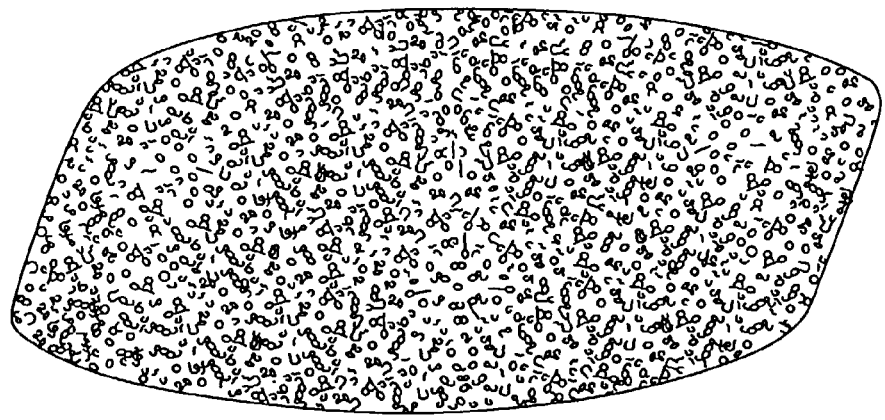
CD DERIVED IMAGE
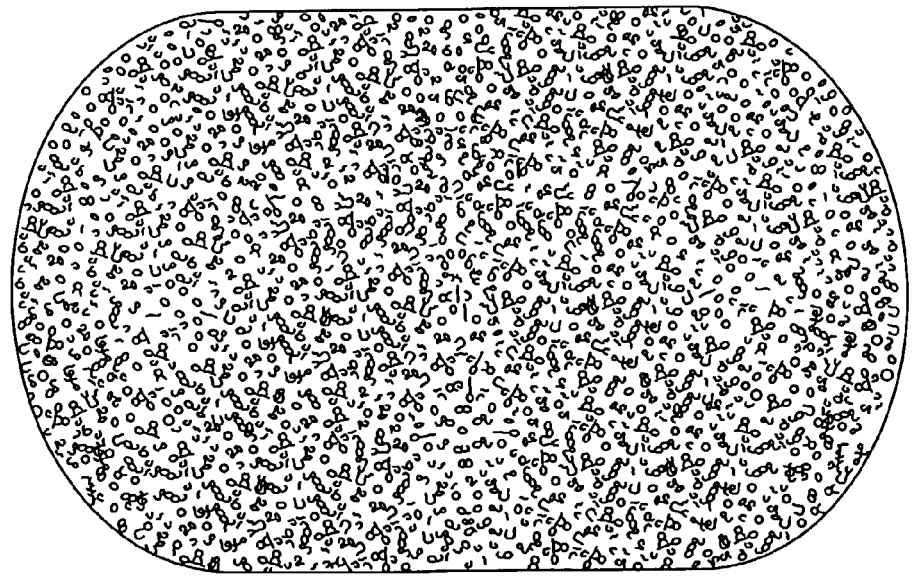
MICROSCOPE IMAGE
FIG. 49

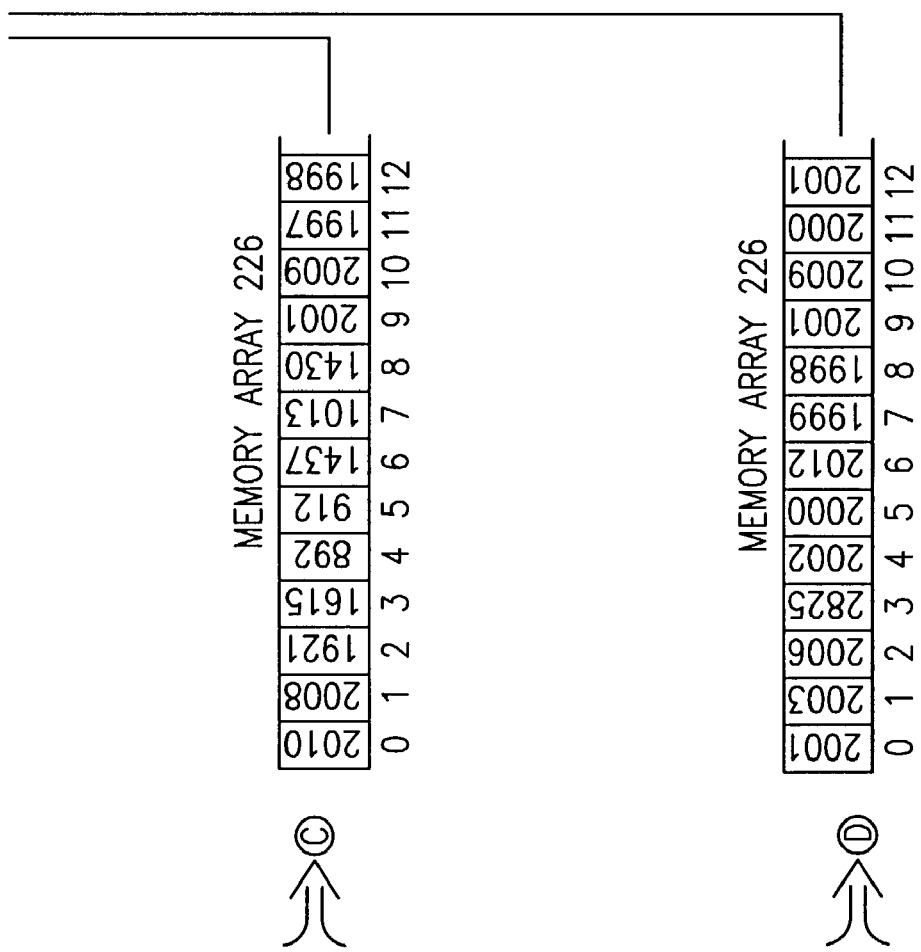

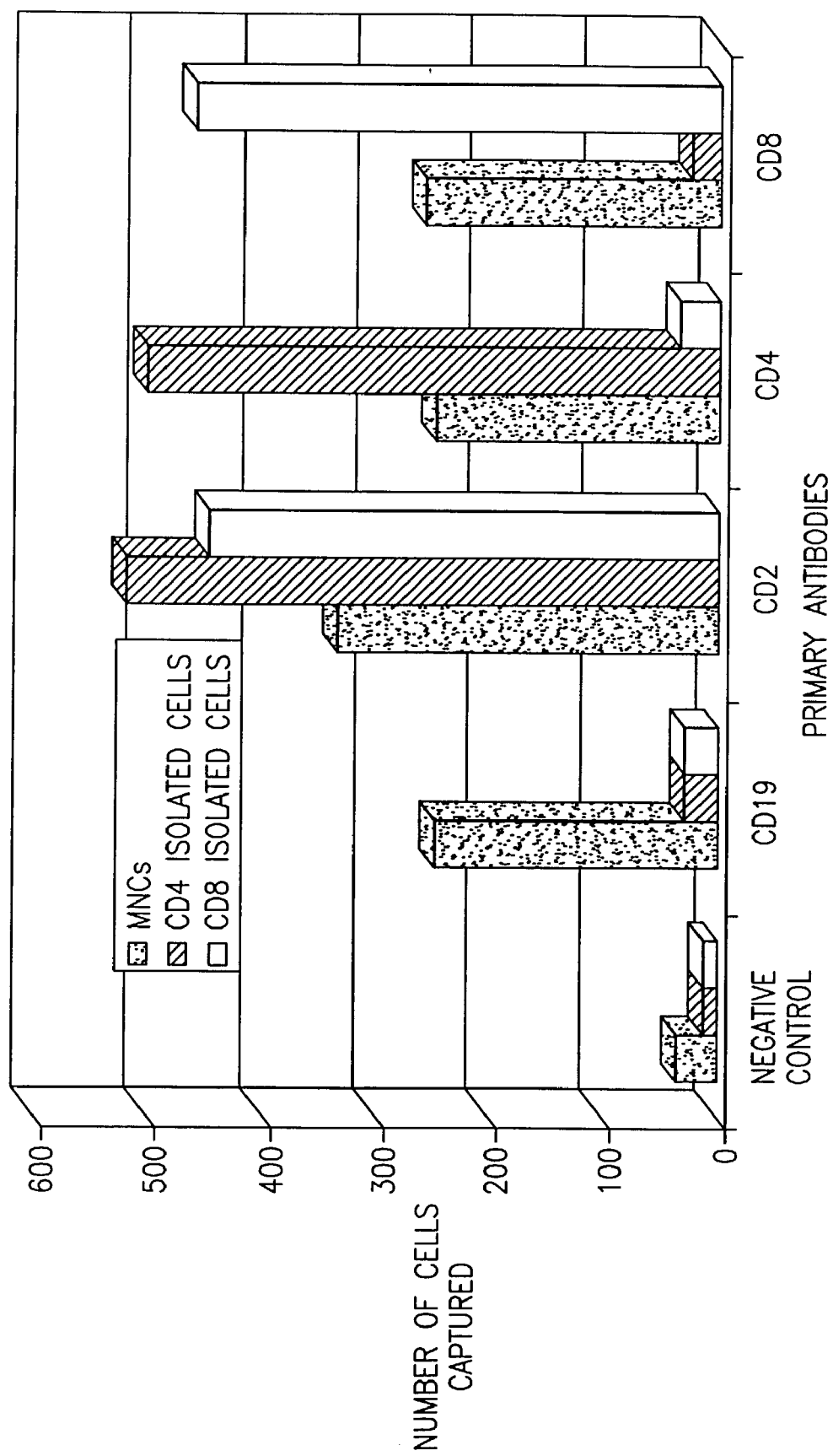

OPTICAL BIO-DISCS AND FLUIDIC CIRCUITS FOR ANALYSIS OF CELLS AND METHODS RELATING THERETO

CROSS-REFERENCE TO RELATED APPLICATIONS

This application is a continuation-in-part of U.S. application Ser. No. 09/988,728 filed Nov. 16, 2001.

This application also claims the benefit of priority from U.S. Provisional Application Ser. Nos. 60/349,392 filed Jan. 17, 2002; 60/349,449 filed Jan. 18, 2002; 60/355,644 filed Feb. 5, 2002; 60/358,479 filed Feb. 19, 2002; and 60/382,327 filed May 22, 2002. These applications are herein incorporated by reference in their entireties.

BACKGROUND OF THE INVENTION

1. Field of the Invention

This invention relates in general to biological assays and diagnostic assays and, in particular, to such assays conducted on optical bio-discs. More specifically, but without restriction to the particular embodiments hereinafter described in accordance with the best mode of practice, this invention is further directed at sample preparation methods for use in cellular assays and related optical bio-disc systems.

The present invention may be advantageously employed in combination with any of the discs, assays, and systems disclosed in the following commonly assigned and co-pending patent applications: U.S. Provisional Application Ser. No. 60/302,757 entitled "Clinical Diagnostic Optical Bio-Disc And Related Methods For Selection And Detection Of Lymphocytes Including Helper-Inducer/Suppressor-Cytotoxic Cells" filed Jul. 3, 2001; U.S. Provisional Application Ser. No. 60/306,035 entitled "Quantitative and Qualitative Methods for Cell Isolation and Typing Including Immunophenotyping" filed Jul. 17, 2001; U.S. Provisional Application Ser. No. 60/305,993 entitled "Capture Layer Assemblies and Optical Bio-Discs for Immunophenotyping" filed Jul. 17, 2001; U.S. Provisional Application Ser. No. 60/306,592 entitled "Methods for Imaging Blood Cells, Blood-Borne Parasites and Pathogens, and Other Biological Matter Including Related Optical Bio-Discs and Drive Assemblies" filed Jul. 19, 2001; U.S. Provisional Application Ser. No. 60/307,263 entitled "Quantitative and Qualitative Methods for Cell Isolation and Typing Including Immunophenotyping" filed Jul. 23, 2001; U.S. patent application Ser. No. 10/233,322 entitled "Capture Layer Assemblies for Cellular Assays Including Related Optical Analysis Discs and Methods" filed Aug. 30, 2002; and U.S. patent application Ser. No. 10/236,857 entitled "Nuclear Morphology Based Identification and Quantification of White Blood Cell Types Using Optical Bio-Disc Systems" filed Sep. 6, 2002. All of these applications are herein in incorporated by reference.

2. Discussion of the Related Art

Blood cell counts are used during diagnosis, treatment, and follow-up to determine the health of the patient. Complete blood count (CBC) is a collection of tests including hemoglobin, hematocrit, mean corpuscular hemoglobin, mean corpuscular hemoglobin concentration, mean corpuscular volume, platelet count, and white blood cell count. Blood count is the enumeration of the red corpuscles and the leukocytes per cubic mm of whole blood.

White Blood Cell Count (WBC, leukocytes) is the total number of white blood cells in a standard sample of blood. In a normal healthy person, typically the WBC counts are 4000 to 10800 cells per microliter (µl). Factors such as exercise, stress, and disease can affect these values. A high WBC may indicate infection, leukemia, or tissue damage. There is an increased risk of infection when the WBC count falls below 1000 cells per microliter.

Leukocyte differential testing is essential to gather information beyond that obtainable from the leukocyte count itself. Leukocyte differential count is used to evaluate newly suspected infection or fever (even if the CBC is normal), suspicion of a disorder associated with abnormalities, an abnormal leukocyte count, suspected leukemia, and other abnormalities such as eosinophilia, monocytosis, or basophilia. Repeated testing for leukocyte or leukocyte differential may be performed in the presence of severe leukopenia (e.g., secondary to drug therapy). During treatment, for example during chemotherapy or radiation therapy, blood counts are very important to determine whether the treatment is depleting healthy blood cells in addition to cancerous cells. Since chemotherapy affects the production of blood cells, it is important to check the amount of various kinds of cells in the blood.

Differential leukocyte counts are determined by computerized cell counting equipment. Such apparatus determine the total count and the percentages of the five major white cell types. In normal individuals, there are a majority of neutrophils (50–60%), followed by lymphocytes (20–40%), then monocytes (2–9%), with a few eosinophils (1–4%) and basophils (0.5–2%).

Within the category of lymphocytes there are further sub-types of cells. For example, lymphocytes can be broadly divided into T-cells (thymus-derived lymphocytes) and B-cells (bursal-equivalent lymphocytes), which are largely responsible for cell-mediated and humoral immunity respectively. Although morphological characteristics have been used to classify groups within the leukocytes, morphology alone has proved inadequate in distinguishing the many functional capabilities of lymphocyte sub-types. To distinguish lymphocytes with various functions, techniques including analysis by rosetting, immuno-fluorescence microscopy, enzyme histochemistry, and recently, monoclonal antibodies against unique cell surface markers have been developed.

T-cells are often further distinguished by the presence of one of two major cell surface antigens such as CD4 and CD8. Type CD4+ cells are referred to as helper T-cells and are involved in antibody-mediated immunity. These T-cells bind to antigens presented by B-cells and cause the development of a clone of plasma cells which secrete antibodies against the antigenic material. The CD4+ T-cells are also essential for cell-mediated immunity. It is understood that CD4+ T-cells bind to antigen presented by antigen-presenting cells (APCs) such as phagocytic macrophages and dendritic cells, and release lymphokines that attract other immune system cells to the area. The result is inflammation, and the accumulation of cells and molecules that attempt to wall off and destroy the antigenic material.

Type CD8+ T-cells are referred to as cytotoxic or killer T-cells. These T-cells secrete molecules that destroy the cell to which they have bound. This is important in fighting viral infections, since the CD8+ T-cells destroy the infected cells before they can release a fresh crop of viruses that are able to infect other cells.

Human immunodefiency virus is a retrovirus with high affinity for CD4+ T cells and therefore CD4+ T cells are potent targets for the virus. Acquired immune deficiency syndrome (AIDS) provides a vivid and tragic illustration of the importance of CD4+ T cells in immunity. The human immunodeficiency virus (HIV) binds to CD4+ molecules and invades and infects CD4+ T cells. As the disease progresses, the number of CD4+ T cells declines below its normal range of about 1000 per microliter (ul). One of the explanations may be the unceasing effort of the patient's CD8+ T cells to destroy the infected CD4+ cells. Alternately, uninfected CD4+ cells may be induced to commit suicide (apoptosis).

When the number of CD4+ T cells drop below 400 per microliter, the ability of the patient to mount an immune response declines dramatically. Not only does the patient become hypersusceptible to infections from pathogens that invade the body including microorganisms, especially viruses and fungi that normally inhabit our tissues without harming us. Eventually the patient dies of opportunistic infections like Candidiasis, Cytomegalovirus, Herpes simplex viruses, Pneumocystis carinii, pneumonia, Toxoplasmosis, Tuberculosis and others.

In addition to CD4 and CD8, there are many other cell surface antigens (for example, CD3, CD16, CD19, CD45, and CD56) which can be used to identify sub-types of lymphocytes. The ability to detect these cell surface antigens by antibody techniques has added a new dimension to diagnostic pathology, and a variety of techniques are available for the study of immunophenotypes of hematolymphoid disorders (e.g., AIDS, leukemias, and lymphomas). Conventional microimmuno-assays such as radio-immunoassays (RIA), enzyme-immunoassay (EIA), fluorescence-immunoassay (FIA) use an isotope, an enzyme, or a fluorescent substance in order to detect the presence or absence of corresponding antibodies or antigens, respectively, that react specifically therewith.

The number of platelets in a standard sample of blood typically is 133,000 to 333,000 platelets per microliter (μl). An excess number of platelets is called thrombocythemia. Above normal platelet counts may be due to a reactive response or bone marrow failure. Reactive responses are typically caused by bleeding, infection, neoplasia, and myeloproliferative disorders. Bone marrow failure usually involves loss of blood cells known as pancytopenia. On the other hand, decreased platelet counts are due to immune thrombocytopenia. Thrombocytopenia occurs if the platelet count fall below 30,000, which results in abnormal bleeding. Counts below 5000 are considered life threatening.

A number of therapeutic approaches are used to treat AIDS including protease inhibitors, reverse transcriptase inhibitors, Integrase inhibitors and others. Estimation of CD4+ and CD8+ T lymphocyte numbers and their ratio (CD4+/CD8+ T-lymphocytes) are critical to assess immune health of human patients with immune-compromised diseases and to assess the effectiveness of treatment.

The ability to detect cell-associated antigens by antibody techniques has added a new dimension to diagnostic pathology. A variety of techniques are available for the study of immunophenotypes of hematolymphiod disorders. Conventional microimmunoassays like radio-immunoassays (RIA), enzyme-immunoassay (EIA), fluorescence-immunoassay (FIA) use an isotope, an enzyme or a fluorescent substance in order to detect the presence or absence of corresponding antibodies or antigens, respectively, that react specifically therewith. However the above methods have limitations and disadvantages. RIA requires special installations, precautions, limited half-life and various other factors. Methods using enzyme or fluorescence substances as labels is measured by determining coloring or luminescence require sensitive, sophisticated instruments to detect the calorimetric or fluorescent reactions in addition to requiring several washing steps to remove excess, unbound, un-reacted reagents. Furthermore, application of the above methods of detection for cells particularly lymphocytes and cancer cells and the like specimens, needs improvement in technology for the preparation, detection and analysis in high efficiency.

A tool developed around the use of fluorescent antibody specific for cell-surface antigens is the technique of fluorescence-activated cell sorting (FACS) of flow cytometry. This is a very reliable, fast and sensitive method. Flow cytometric analysis is performed on whole blood sample that is subjected to RBC lysis leaving the leukocytes intact. White cells of interest are then labeled with fluorescent markers for identification with the FACS scanner. The foremost requirement of a sample for flow cytometric analysis is that the sample is in a monodisperse suspension and desired cells are labeled with fluorescent markers. It is very high-priced test and the whole system requires handling by a trained technician in a clinical analysis laboratory and an expensive instrument. Another disadvantage with flow cytometry is that the cells once analyzed are no longer available for repeated analysis or additional investigation for example microscopic examinations of rare event cells.

Surface marker analysis is a very useful laboratory tool, which has been particularly very useful in studying leukemias, lymphomas and immunodeficiency diseases. Antibody-based micro-array technologies certainly are the state-of-the art technology, particularly in clinical diagnostics, for identification of specific antigens in a sample. Most diagnostic tests require determination of only a limited panel of analytes (such as in of cancers, leukemia, lymphoma, thyroid disease, etc.). Therefore, the requirements by a miniaturized technology for only a very small amount of blood sample and the savings in time and cost of laboratory personnel, upon simultaneous measurement of all the clinically relevant parameters in a single test are likely to prove compelling attractive to hospital laboratories and point-of-care facilities due to its cost-effectiveness, labor effective and its simplicity.

We have developed a simple, inexpensive system for analyzing specific cell surface antigens and performing data analysis in a fraction of time and cost compared to conventional methods. This system employs specially prepared optical bio-discs, related detection assemblies, and supporting software and processing methods.

Blood samples require processing prior to analysis similar to the protocol used for FACS scanner. Erythrocytes (red cells) due to their abundant numbers can interfere with specific binding of leukocytes (white cells). Therefore, prior to analyzing a sample with FACS scanner, blood samples are incubated with RBC lysing buffer that destroys red cells excluding the white cells.

In commonly assigned U.S. Provisional Application No. 60/308,197 filed Jul. 27, 2001, we describe a method developed and designed to perform helper/inducer-suppressor/cytotoxic assay on an optical bio-disc by isolating mononuclear cells from the whole blood using a density gradient protocol. In the present invention, we described a microfluidic chamber or circuit that can be used to perform the lysis procedure on the disc and the leukocyte material left over is dispelled into the assay or analysis chambers that have been layered with specific capture antibodies for helper/inducer-suppressor/cytotoxic assay. This particular chamber design may include two interconnected chambers. Chamber one contains the lysis buffer. Blood sample to be analyzed is injected into the "lysis" chamber. Incubated for 15 minutes for the lysis to be complete. Once the lysis is complete, the disc is spun to enable the remaining leukocytes to pass into the analysis chamber that has been coated with specific capture antibodies. Following incubation of chemistry with the cell sample for 30 minutes, the disc is read and imaged with the laser optics and the images analyzed with an appropriate software.

SUMMARY OF THE INVENTION

This invention relates in general to clinical diagnostic assays and related optical bio-discs. More specifically, but without restriction to the particular embodiments hereinafter described in accordance with the best mode of practice, this invention relates to cell typing, including CD (cluster designation) marker assays. The CD marker assay of the present invention is a cell capture assay for determination of the number of CD4+ and CD8+ T-lymphocytes in a sample. The present invention is further directed to RBC lyses, cell separation, and evaluations of helper/inducer-suppressor/cytotoxic t-lymphocytes using whole blood and related optical bio-discs.

Improved methods and apparatus for carrying out analyses on samples, such as blood, cerebrospinal fluid, sputum, urine, colonocytes, or any other biological source, in a timely, cost efficient, and technically relevant way are provided. In particular, there is a need for easier, more efficient ways to quantify the relative levels of various types of white blood cells, or other cell types, parasites, pathogens, and biological matter. The present invention responds to this need. In addition, this invention relates to imaging blood cells, performing differential white cell counts, and related processing methods and software.

The test is based upon the principle of localized cell capture on specific locations on the disc. Several specific cell capture fields are created on disc by localized application of capture chemistries based upon monoclonal or polyclonal antibodies to particular lymphocyte (white blood cells) antigens.

The assay is performed within a bio-disc that includes a flow chamber having specific antibodies attached to the solid phase. The CD marker assay or helper-inducer/suppressor-cytotoxic test determines the absolute numbers of target cells including CD4+, CD8+, CD3+ and CD45+ lymphocytes captured by specific antibodies in capture or target zones.

An optical disc drive assembly is employed to rotate the disc, read, and process any encoded information stored on the disc, and analyze the cell capture zones in the flow chamber of the bio-disc. The optical disc drive is provided with a motor for rotating the bio-disc, a controller for controlling the rate of rotation of the disc, a processor for processing return signals from the disc, and analyzer for analyzing the processed signals. The rotation rate is variable and may be closely controlled both as to speed and time of rotation. The optical disc drive may also be utilized to write information to the bio-disc either before or after the test material in the flow chamber and target zones are interrogated by a read beam of the drive and analyzed by an analyzer. The bio-disc may include encoded information for controlling the rotation of the disc, providing processing information specific to the type of immunotyping assay to be conducted and for displaying the results on a monitor associated with the drive.

It is an aspect of the invention to provide methods and apparatus for conducting an assay in association with an optical analysis disc to detect and count cells. A further aspect of the invention is to provide methods and apparatuses for conducting assays in association with an optical analysis disc to detect lymphocytes.

According to another aspect of the present invention, there is provided a method that includes providing a sample in or on a disc surface, the disc having encoded information which is readable by an optical reader. This information can be used to control the scanning of the reader relative to the disc.

The disc is loaded into the optical reader, and an incident beam of electromagnetic radiation from a radiation source is directed to the disc. The beam is scanned over the disc by rotating the disc about a central axis and by moving the incident beam in a direction radial to the axis. A beam of electromagnetic radiation either transmitted through or reflected from the disc is detected and analyzed to extract information characteristic of the sample.

Embodiments of the invention also include a disc with a substrate and cap spaced to form a chamber. A sample of material, such as blood with cells, is provided in the chamber. When the disc is rotated, the sample moves past capture zones. The capture zones include capture layers with antibodies or other specific binding partners that bind to antigens such as CD4 and CD8 that are cell surface markers on the cell types of interest. Preferably one test can be used to image CD4 and CD8 and other antigens in a blood sample. According to another aspect of the present invention, there is provided a disc reader for directing light to viewing windows where the capture zones are located, and detecting transmitted or reflected light to identify and count captured cells. These CD4 and CD8 counts, and the ratio between them, are useful for monitoring conditions such as AIDS.

The test sample is preferably provided to a chamber within the disc. A single chamber preferably has multiple capture areas, each of which may have one or more antibodies. In one embodiment, a single channel has multiple capture zones, each with a different type of antibody, and may have capture zones that serve as control zones. These capture zones can be aligned along one or more radii of the disc. Detection methods include detecting transitions in the feature, or imaging the viewing window and using image recognition software to count captured cells. Counting may be direct, such as counting a desired cell; or indirect, such as counting a collection of desired and non-desired cells, counting non-desired cells, and subtracting to obtain a count of desired cells. The capture zone may have one or more layers of antibodies.

When a sample of cells is provided to the disc, the disc can be rotated in one or more stages to move the cells to the capture zones, then to move unbound cells away from the capture zones. The sample may be processed in other ways, e.g., incubated or heated with the light source that is used for detection. Microfluidics can be used to add stain or any other liquids that may be desired for on-disc processing of the sample. This processing is preferably specified in encoded information on the disc in information storage areas. The stored information may be advantageously employed to cause the drive and reader to rotate at desired speeds and for desired times with intermediate other steps, such as incubation.

Micro technologies are particularly valuable in clinical diagnostics for identification of cell types, parasites, pathogens, and other biological matter. The present invention utilizes micro technologies to perform differential white cell counts in whole blood on optical bio-discs. In addition, this invention is directed to imaging blood cells, performing differential white cell counts, and related processing methods and software.

Another test or assay according to the present invention may be performed in at least two ways. The first method is based upon the principle of optical imaging of blood cells in special channels located on the optical bio-disc. Approximately 5 to 20 microliters of whole blood is injected into specially designed channels on the disc. The images are analyzed with cell recognition software that identifies the various leukocyte sub-types and generates a white cell differential count. The second method is based on specific cell capture using cell specific antibodies against specific cell. In this particular embodiment, antibodies are directed against lymphocytes (CD2, CD19), monocytes (CD14), and eosinophils (CD15), for example. As with the related assay discussed above, these leukocyte sub-type specific antibodies are assembled/attached to a solid surface within the bio-disc that includes a flow chamber.

A bio-disc drive assembly is employed to rotate the disc, read and process any encoded information stored on the disc, and analyze the cell capture zones in the flow chamber of the bio-disc. The bio-disc drive is provided with a motor for rotating the bio-disc, a controller for controlling the rate of rotation of the disc, a processor for processing return signals from the disc, and analyzer for analyzing the processed signals. The rotation rate is variable and may be closely controlled both as to speed, time of rotation, and direction of rotation. The bio-disc may also be utilized to write information to the bio-disc either before, during, or after the test material in the flow chamber and target zones is interrogated by the read beam of the drive and analyzed by the analyzer. The bio-disc may include encoded information for controlling the rotation of the disc, providing processing information specific to the type of immunotyping assay to be conducted and for displaying the results on a monitor associated with the bio-drive.

The differential cell count protocols in general and in particular differential white blood cell counting protocols are developed for CD, CD-R, or DVD formats, modified versions of these formats, and alternatives thereto. The read or interrogation beam of the drive detects the various cells in the analysis sample and generates images that can be analyzed with differential cell counter software.

Microscopic methods or sophisticated cell counters are essential to perform these tedious and laborious cell-counting assays. The present method uses optical bio-discs and related assemblies. Optical images of the various leukocyte sub-types free in the analysis chamber or those captured by a specific antibody method are generated and analyzed by cell recognition software programs that identify the various cellular elements in the blood or other body fluids by their light scattering properties. This return light is detected after the light/matter interaction between the incident bean and the sample of interest. The detected return light signal is processed to provide discernable signal signatures or digital IDs. While prior art methods typically require preparation such as cell staining, RBC elimination, or other laborious protocols, embodiments of the present methods do not require any pre-processing of the sample. These methods include microscopic analysis or cell detection in a CD-type or optical disc reader using a top-detector, bottom-detector, event counter, or cell counter.

The following paragraphs provide a summary of the principal method steps according to certain specific preferred embodiments of the present invention directed to bio-disc manufacturing.

Disc Preparation: Gold reflective discs or transmissive discs are cleaned using an air gun to remove any dust particles. The disc is rinsed twice with iso-propanol, using the spin coater. A 2% polystyrene is spin coated on the disc to give a very thick coating throughout.

Deposition of Chemistry: One embodiment includes a three step deposition protocol that incubates: streptavidin, 30 minute incubated; biotinylated first antibody incubated for 60 minutes; and second capture antibody incubated for 30 minutes. All the steps are done at room temperature in a humidity chamber using stringent washing and drying steps between depositions.

Briefly, 1 µl of 1 mg/ml streptavidin in phosphate buffered saline is layered over each window and incubated for 30 minutes. Excess streptavidin is rinsed off using distilled water and the disc is dried. Biotinylated IgG-dextran complex is prepared by combining equal volumes of biotinylated IgG (125 µg/ml in PBS) and aldehyde-activated dextran (200 µg/ml). Dextran-aldehyde biotinylated-IgG complex is layered over streptavidin in each capture window and incubated for 60 minutes or overnight in a refrigerator. Excess reagent is rinsed off and the disc spun-dry. Specific barcode capture patterns are created by layering capture antibodies on designated spots on the bio-disc slot. For a differential count, anti-neutrophil (CD128 or others), anti-lymphocyte (CD2, CD19, CD56, and others), anti-eosinophil (CD15), anti-monocyte (CD14), anti-basophil (CD63), and anti-platelets (CD32 and CD151) are layered in designated spot of each slot, for example. Table 1 below lists examples of variations of capture patterns for capture layer assembly. Incubate for 30 minutes or overnight in the refrigerator. Assemble the disc using a 25 µm, 50 µm, or 100 µm (50 µm channel requires twice the volume of sample as that needed for 25 µm chamber), straight, U-shaped, or other channel formats and a clear cover disc (for use with a top detector) or reflective cover disc (for use with a bottom detector).

TABLE 1

| | Capture Layer Assembly and Variations | | | | | |
|---|---|---|---|---|---|---|
| Window | 1 | 2 | 3 | 4 | 5 | 6 |
| 1st Layer (Active Layer) | Polystyrene | Polystyrene | Polystyrene | Polystyrene | Polystyrene | Polystyrene |
| 2nd Layer | | Streptavidin | Streptavidin | Streptavidin | Streptavidin | Streptavidin |
| Secondary Antibody | | B-anti-Mouse IgG + DCHO | B-anti-Mouse IgG + DCHO | B-anti-Mouse IgG + DCHO | B-anti-Mouse IgG + DCHO | B-anti-Mouse IgG + DCHO |

TABLE 1-continued

Capture Layer Assembly and Variations

| Window | 1 | 2 | 3 | 4 | 5 | 6 |
|---|---|---|---|---|---|---|
| Primary Antibody | Reference Dot | Lymphocyte Specific antibody | Neutrophil Specific antibody | Eosinophil Specific antibody | Basophil Specific antibody | Monocyte Specific antibody |

Disc Leak-Checking and Blocking Non Specific Binding of Undesired Cells: Since blood, a biohazardous material, is being analyzed, the discs are leak checked, as part of the quality control manufacturing aspects of the present invention, to make sure none of the chambers leak during spinning of the disc with the sample in situ. Each channel is preferably filled with StabilGuard, a commercially available blocking agent, and blocked for at an hour. The disc is spun at 5000 rpm for 5 minutes and inspected for leaks and disc stability. After checking for leaks, the disc is placed in a vacuum chamber for 24 hours. After vacuuming, the chambers filled with PBS buffer or empty are placed in a vacuum pouch and stored in refrigerator until use.

Isolation of Buffy-coat Layer from Whole Blood: Buffy coat is prepared by centrifuging defibrinated venous blood in a centrifuge tube for 25 minutes at 2800 rpm. The supernatant plasma is carefully removed with a fine pipette. Then pipette the underlying white layer that contains the leukocytes and the platelets. An alternate method to obtain the buffy coat from the blood without centrifugation is to allow the blood to sediment with sedimentation-enhancing agents such as fibrinogen, dextran, gum acacia, Ficoll, or methylcellulose. Boyum's reagent (methylcellulose and sodium metrizoate) is particularly suitable for obtaining leukocyte preparation without any red cell contamination. Alternatively the lymphocytes may be isolated form whole blood by positive or negative selection, or lysis methods.

Assay on Disc—Description of Base Technology: One preferred embodiment of the differential white cell count disc test includes three individual components, (1) base disc including the chemistry, (2) channel layer, and (3) cover disc.

Buffy coat, preferably diluted in PBS, is injected into the disc chamber, the inlet and outlet ports of the chamber are sealed with tape and the disc is incubated for a desired time preferably at room temperature. In other related commonly assigned cellular assays using bio-discs, whole blood is directly added in to fluidic circuits in the bio-disc and analysis is performed on whole blood samples. In the current invention, however, purified T lymphocyte cell samples are preferably used for the reasons stated below. For both purified sample and whole blood methods, a given area (e.g., one millimeter square in area) on the disc is scanned using the standard 780 nm laser of the optical drive with the top or bottom detector. Related cell recognition software developed by assignee and disclosed in U.S. Provisional Application Ser. No. 60/363,949 entitled "Methods for Differential Cell Counts Including Leukocytes and Use of Optical Bio-Disc for Performing Same" filed Mar. 12, 2002 and U.S. Provisional Application Ser. No. 60/404,921 entitled "Methods For Differential Cell Counts Including Related Apparatus and Software For Performing Same" filed Aug. 21, 2002, is automated to give a differential count from the captured image which is preferably equal to a millimeter square, for example. For the second method, the disc is scanned using the standard 780 nm laser to image the capture zone which may include lymphocytes, neutrophils, basophils, eosinophils, monocytes, and platelets. The cell recognition software developed by assignee is automated to perform the following routines: (a) centrifuge the disc to spin off excess unbound cells, (b) image an specific area or specific capture zones, and (c) data processing that includes counting the specifically captured cells in each capture zone and deriving the numbers of different sub-sets of leukocytes.

During the processing step, the recognition software reads across each capture zone and marks cells it encounters. Following processing data from each capture zone, the software displays the number of lymphocytes, neutrophils, basophils, eosinophils, monocytes, and platelets zones per micro liter volume of blood. The entire process takes about 10–15 minutes from inserting the disc into the optical drive to displaying to results of interest.

Related disclosure associated with the present invention is also presented in U.S. Provisional Application Ser. No. 60/307,262 entitled "Capture Layer Assemblies and Optical Bio-Discs for Immunophenotyping" filed Jul. 23, 2001; U.S. Provisional Application Ser. No. 60/307,264 entitled "Methods for Imaging Blood Cells, Blood-Borne Parasites and Pathogens, and Other Biological Matter Including Related Optical Bio-Discs and Drive Assemblies" filed Jul. 23, 2001; U.S. Provisional Application Ser. No. 60/307,562 entitled "Optical Analysis Discs Including Fluidic Circuits for Optical Imaging and Quantitative Evaluation of Blood Cells Including Lymphocytes" filed Jul. 23, 2001; and U.S. Provisional Application Ser. No. 60/307,487 entitled "Methods for Differential Cell Counts Including Leukocytes and Use of Optical Bio-Disc for Performing Same" filed Jul. 24, 2001, all of which are herein incorporated by reference.

The following paragraphs provided a summary of the principal elements of the disc specifications according to certain specific preferred embodiments of the present.

Tracking Design: In one preferred embodiment of the present invention, the disc is a forward Wobble Set FDL21: 13707 or FDL21:1270 coating with 300 nm of gold. On this reflective disc, oval data windows of size 2×1 mm are etched out by Lithography. "U" shaped channels are used to create chambers that are 25 µm in height. It takes about 7 µl of sample to fill the entire chamber including the inlet and outlet ports. A 4-window/4-channel format may be preferably used. However on the transmissive disc, no data windows are etched, and the entire disc is available for use.

Adhesive and Bonding: In one preferred embodiment, the adhesive or channel layer including the present "U" shaped fluidic circuits is made from Fraylock adhesive DBL 201 Rev C 3M94661. Alternatively straight channels are used to create the chambers.

Cover Disc: Clear disc, fully reflective with 48 sample inlets with a diameter of 0.040 inches location equidistant at radius 26 mm are used in one specific embodiment of the present disc assembly.

Data Capture and Processing: The data disc is scanned and read with the software at a preferred speed of ×4 and a sample rate of 2.67 MHz using assignee's cell recognition software.

Software: The present invention further includes processing methods and related cell recognition and imaging software. This software is directed to conducting and displaying cell counts and differential cell counts. The present software may be stored on the optical bio-disc, in the optical disc drive reader device, or alternatively only accessible by the optical reader from a secured server. This server may be implemented in a computing network such as a Local Area Network (LAN), a Wide Area Network (WAN), or otherwise made available over the Internet under prescribed terms and conditions. Such distribution methods are disclosed in commonly assigned U.S. Provisional Application No. 60/246,824 entitled "Interactive Method and System for Analyzing Biological Samples and Processing Related Medical Information Using Specially Prepared Bio-Optical Disc, Optical Disc Drive, and Internet Connections" filed Nov. 8, 2000 and related U.S. patent application Ser. No. 09/986,078 entitled "Interactive System for Analyzing Biological Samples and Processing Related Information and the Use Thereof" filed Nov. 7, 2001, both of which are herein incorporated by reference in their entireties.

Materials: The materials employed to practice different preferred embodiments disclosed herein include a forward wobble gold metalized photo-resist disc, a transmissive gold metalized disc, pipettes and tips, spin coater, centrifuge, swing-out rotor, Vacutainer™ CPT tubes with an anti-coagulant such as sodium citrate or ethylene diamine tetra acetic acid (EDTA), humidity chamber, disc press, adhesive, cover disc, clear cover disc, tape or equivalent, vacuum apparatus, yellow tips, and vacuum chamber.

Reagents: The reagents employed in performing the cell counts according to certain methods of the present invention include phosphate buffered saline, isopropyl alcohol, distilled water, and StabilGuard.

It is an object of the present invention to overcome limitations in the known art. Another object of the present invention is to adapt a known optical disc system to perform differential white cell counts in whole blood on optical bio-discs. It is a further object of the present invention to image blood cells and perform differential white cell counts.

These and other objects and advantages of the present invention are achieved in an optical disc and drive system for performing a cluster designation count that includes an optical assay disc, a light source, a photo detector circuit of an optical disc drive, and a processor. The optical assay disc includes a substrate, an active layer disposed over the substrate, and a cover disc or cap portion integrally attached to the active layer by an adhesive or channel member. The adhesive member has one or more portions removed therefrom thereby forming chambers in which one or more capture agents are immobilized. The capture agents, being immobilized on the active layer, and within the chambers, define discrete capture zones. The light source directs light to the disc at the capture zones. The photo detector circuit of the optical disc drive is configured to detect light reflected from, or transmitted through the disc and provide an information-carrying signal from an optical disc assembly. The processor is coupled to the photo detector circuit to obtain from the information-carrying signal, operational information used to operate the optical disc system and count items in the sample bound to the capture agents.

According to one particular aspect of this system, the processor includes image recognition software for detecting and imaging cells. In one embodiment, the photo detector is on the same side of the disc as the light source for detecting light reflected from the capture zones. In an alternate embodiment, the photo detector is on the opposite side of the disc as the light source for detecting light transmitted through the capture zones.

The present invention is also directed to a method of performing a cluster designation count with an optical disc and disc drive. The method includes the steps of providing a blood sample in a first tube containing a separation gradient, rotating the first tube at a time and speed sufficient to separate the blood sample into layers, resuspending a MNC layer that contains T-cells to form a MNC suspension, providing a sample of the MNC suspension on a disc surface that includes at least one capture zone containing at least one capture agent, loading the disc into an optical reader, rotating the disc, directing an incident beam of electromagnetic radiation to the capture zone, detecting a beam of electromagnetic radiation formed after interacting with the disc at the capture zone, converting the detected beam into an output signal, and analyzing the output signal to extract information relating to the number of cells captured at the capture zone. In one embodiment of this method, the optical disc is constructed with a reflective layer such that light directed to the capture zone and not striking a cell is reflected. In another embodiment of this method, the optical disc is constructed such that light directed to the capture zone and not striking a cell is transmitted through the optical disc. Other related aspects pertaining to determining concentrations of cell populations in a sample is disclosed in commonly assigned and co-pending U.S. Provisional Application Ser. No. 60/384,205 entitled "Optical Disc Systems For Determining The Concentration Of Cells or Particles In A Sample And Methods Relating Thereto" filed May 30, 2002. This application is herein incorporated by reference in its entirety.

According to another aspect of this method, the disc surface is coated with a first group of capture agents. In one embodiment of thereof, the capture agents are immobilized on the disc surface by a cross-linking system. In an alternative embodiment, the capture agents are immobilized directly on the disc surface.

According to yet another aspect of this method, the capture agents define one or more discrete capture zones. In one particular embodiment thereof, the one or more capture zones are located within one or more chambers within the optical disc. In another embodiment of this method, the capture agents have a selective affinity for cell surface antigens. In an alternative embodiment, the capture agents are for binding with primary capture agents having a selective affinity for cell surface antigens. In a preferred embodiment, the cell surface antigens are independently selected from the CD family of antigens. In a more preferred embodiment, the cell surface antigens are selected from the group consisting of CD3, CD4, CD8, and CD45.

According to still another aspect of this method, the rotating includes rotating for a sufficient period of time at a sufficient speed so that the cells have an opportunity to bind with the capture agents. In an embodiment of this aspect of this method, the rotating further includes rotating for a sufficient period of time at a sufficient speed so that unbound cells are moved away from the capture zones. In a preferred embodiment of this aspect of this method, the rotating is done at a single speed.

The embodiments of the method according to these aspects of the present invention may advantageously further include the steps of directing the sample of MNC cells into proximity with the capture agents, incubating the cells in the presence of the capture agents, and allowing the cells to specifically bind to the capture agents. An embodiment of this method further includes the step of analyzing the number of cells captured to thereby determine a cell concentration in the sample. In one aspect of this embodiment, the analyzing includes detecting sufficiently large changes in the level of light reflected from or transmitted through the disc. In another aspect of this embodiment, the analyzing includes using image recognition to count the captured cells. In a preferred embodiment of this method, the image recognition distinguishes one type of white blood cell from another.

Another embodiment of this method further includes the steps of counting the captured cells in each of the capture zones and providing an output including cell counts. In an aspect of this embodiment, the output includes counts for CD4 cells and CD8 cells, and a ratio of CD4 to CD8 cells.

In accordance with yet another principal aspect of this invention, there is provided an alternate method of performing a cluster designation count. This alternate method includes the steps of (1) providing a blood sample in a tube containing a separation gradient, (2) rotating the tube at a time and speed sufficient to separate the blood sample into layers, (3) resuspending a MNC layer containing T-cells to form a MNC suspension, (4) adding a primary antibody to the MNC suspension to form a primary antibody-T-cell complex, (5) providing a sample of the primary antibody-T-cell complex on a disc surface that includes at least one capture zone containing at least one capture agent, (6) loading the disc into an optical reader, (7) directing an incident beam of electromagnetic radiation to the capture zone, (8) detecting a beam of electromagnetic radiation formed after interacting with the disc at the capture zone, (9) converting the detected beam into an output signal, and (10) analyzing the output signal to extract information relating to the number of cells captured at the capture zone.

Similarly in one embodiment of this alternate method, the optical disc is constructed with a reflective layer such that light directed to the capture zone and not striking a cell is reflected. In another embodiment of this method, the optical disc is constructed such that light directed to the capture zone and not striking a cell is transmitted through the optical disc.

According to an aspect of this method, the disc surface is coated with a first group of capture agents. In one embodiment thereof, the capture agents are immobilized on the disc surface by a cross-linking system. In an alternative embodiment, the capture agents are immobilized directly on the disc surface.

According to yet another aspect of this method, the capture agents define one or more discrete capture zones. In one particular embodiment thereof, the one or more capture zones are located within one or more chambers within the optical disc. In another embodiment of this method, the capture agents are for binding with cell surface antigens. In an alternative embodiment, the capture agents are for binding with a second group of capture agents having a selective affinity for cell surface antigens. In a preferred embodiment, the cell surface antigens are independently selected from the CD family of antigens. In a more preferred embodiment, the cell surface antigens are selected from the group consisting of CD3, CD4, CD8, and CD45.

According to yet another aspect of this method, the rotating includes rotating for a sufficient period of time at a sufficient speed so that the cells have an opportunity to bind with the capture agents. In an embodiment of this aspect of this method, the rotating further includes rotating for a sufficient period of time at a sufficient speed so that unbound cells are moved away from the capture zones. In a preferred embodiment of this aspect of this method, the rotating is done at a single speed.

The embodiments of the method according to these aspects of the present invention may advantageously further include the steps of directing the sample of primary antibody-T-cell complex into proximity with the capture agents, incubating the complexes in the presence of the capture agents, and allowing the complexes to specifically bind to the capture agents. An embodiment of this method further includes the step of analyzing the number of complexes captured to thereby determine a cell concentration in the sample. In one aspect of this embodiment, the analyzing includes detecting sufficiently large changes in the level of light reflected from or transmitted through the disc. In another aspect of this embodiment, the analyzing includes using image recognition to count the captured complexes. In a preferred embodiment of this method, the image recognition distinguishes one type of white blood cell from another.

Another embodiment of this method further includes the steps of counting the captured cells in each of the capture zones and providing an output including cell counts. In an aspect of this embodiment, the output includes counts for CD4 cells and CD8 cells, and a ratio of CD4 to CD8 cells.

In any of the above methods, the tube may further contain an anticoagulant. Further, in many of the specific implementations and embodiments of these methods, the surface on which the capture agent is immobilized is internal to the disc and is bounded on opposite sides by a substrate and cap.

According to the manufacturing aspects of this invention, there is provided a method of making an optical assay disc for performing a cluster designation count. This method of making an optical assay disc includes the steps of providing a cross-linker in a tube, adding a capture agent to the tube, allowing the cross-linker and the capture agent to combine (forming a complex), providing a substrate, coating the substrate with an active layer, depositing the complex onto the active layer, and attaching a cover disc or cap portion to the active layer using an adhesive member. In this embodiment, the cross-linker is aldehyde-activated dextran. The capture agents are for binding with cell surface antigens.

According to an aspect of this method, the depositing involves depositing the complexes are predefined locations, thereby forming capture zones. In one embodiment thereof, the attaching involves attaching a cover disc or cap portion having a reflective layer such that light directed to the capture zone and not striking a cell is reflected. In an alternative embodiment thereof, the attaching involves attaching a cover disc or cap portion having a semi-reflective layer such that light directed to the capture zone and not striking a cell is transmitted through the optical disc.

In an alternate embodiment, the capture agents include primary and secondary capture antibodies. The secondary antibodies are bound to the disc surface and have specific affinity for the primary capture antibodies. In this embodiment, the primary capture antibodies have a selective affinity for cell surface antigens of interest. In a preferred embodiment thereof, the cell surface antigens are selected from the CD family of antigens. In a more preferred embodiment, the cell surface antigens are selected from the group consisting of CD3, CD4, CD8, and CD45.

Also according to the manufacturing aspects of this invention, there is provided an alternate method of making an optical assay disc for performing a cluster designation count. This alternate method of making an optical assay disc includes the steps of providing a substrate, coating the substrate with an active layer, depositing a capture agent onto the active layer (forming a capture zone), incubating the substrate, rotating the substrate, and attaching a cover disc or cap portion to the active layer using an adhesive member. In one particular embodiment of this method, the step of incubating involves incubating for a sufficient period of time, at a sufficient temperature to allow immobilization of the capture agent onto the active layer. In another embodiment of this method, the step of rotating involves rotating for a sufficient period of time at a sufficient speed so that non-immobilized capture agents are moved away from the capture zones.

In accordance with another aspect of this method, the capture agent is selected from the group consisting of IgG, biotinylated-IgG, anti-CD3 antibody, biotinylated-anti-CD3 antibody, anti-CD4 antibody, biotinylated-anti-CD4 antibody, anti-CD8 antibody, biotinylated-anti-CD8 antibody, anti-CD45 antibody, and biotinylated-anti-CD45 antibody. In one embodiment of this aspect, the capture agent is a primary capture agent. In an alternative embodiment, the capture agent is a secondary capture. According to one aspect of this alternative embodiment, the method further includes the step of depositing a primary capture agent onto the secondary capture agent after the step of rotating. In another aspect of this alternative embodiment, the method further includes the steps of incubating the substrate and rotating the substrate following depositing the primary capture agent on the secondary capture agent.

According to yet another principal aspect of this invention, there is provided an optical assay disc for performing a cluster designation count. The optical assay disc includes a substrate, an active layer disposed over the substrate, a cover disc or cap portion integrally attached to the active layer by an adhesive member (having one or more portions removed to form one or more chambers defined therebetween), and one or more capture agents immobilized on the active layer. The capture agents define discrete capture zones within the one or more chambers. In one embodiment of this assay disc, the capture agents are immobilized by a cross-linking system. In an alternative embodiment of this assay disc, the capture agents are immobilized by the active layer.

In one particular embodiment of this optical assay disc, the capture agents are antibodies having a selective affinity for cell surface antigens. In a preferred embodiment, the capture agents are selected from the group consisting of antibodies for CD3, CD4, CD8, and CD45. In another embodiment of this optical assay disc, the capture agents are antibodies having a selective affinity for primary antibodies that have a selective affinity for cell surface antigens. Similarly, in a preferred embodiment of this aspect of the optical assay disc, the primary antibodies are selected from the group consisting of antibodies for CD3, CD4, CD8, and CD45. In this embodiment of the optical assay disc, the primary capture agents are anti-human produced in mice, and the secondary capture agents are anti-mouse produced in goats.

Technical aspects related to the present invention are also in U.S. Provisional Application Ser. No. 60/307,489 entitled "Optical Analysis Discs Including Microfluidic Circuits for Performing Cell Counts" filed Jul. 24, 2001; U.S. Provisional Application Ser. No. 60/307,825 entitled "Methods for Reducing Non-Specific Binding of Cells on Optical Bio-Discs Utilizing Charged Matter Including Heparin, Plasma, or Poly-Lysine" filed Jul. 25, 2001; U.S. Provisional Application Ser. No. 60/307,762 entitled "Methods for Reducing Non-Specific Binding of Cells on Optical Bio-Discs Utilizing Blocking Agents" filed Jul. 25, 2001; U.S. Provisional Application Ser. No. 60/307,764 entitled "Methods for Reducing Bubbles in Fluidic Chambers Using Polyvinyl Alcohol and Related Techniques for Achieving Same in Optical Bio-Discs" filed Jul. 25, 2001; U.S. Provisional Application Ser. No. 60/308,214 entitled "Sealing Methods for Containment of Hazardous Biological Materials within Optical Analysis Disc Assemblies" filed Jul. 27, 2001; and U.S. Provisional Application Ser. No. 60/308,197 entitled "Methods for Calculating Qualitative and Quantitative Ratios of Helper/Inducer-Suppressor/Cytotoxic T-Lymphocytes Using Optical Bio-Disc Platform" filed Jul. 27, 2001, all of which are herein incorporated by reference in their entireties. More specifically now, the present invention is further directed to an optical bio-disc for conducting a cellular assay. The optical bio-disc of the present invention may include the following components: a rotatable substrate, a cap portion associated with the substrate, and a fluidic circuit formed between said substrate and said cap portion. The fluidic circuit may include a mixing chamber associated with the substrate which includes an inlet port, a purification chamber in fluid communication with the mixing chamber, a filter means associated the said purification chamber, an analysis chamber having a capture zone in fluid communication with the purification chamber, and a vent port associated with the analysis chamber. The filter means may be made from microspheres or a cellular sieve. The microspheres may be coated with a purification agent. The purification agent may include monoclonal antibodies, polyclonal antibodies, oligonucleotides, ligands, receptors, and binding agents; wherein the monoclonal antibodies may be anti-CD56, anti-CD14, anti-CD19, anti-CD9, anti-CD31, anti-CD41, anti-CD13, anti-CD31, and anti-CD43 antibodies. The capture zone is coated with a capture agent which may be a monoclonal antibody, a polyclonal antibody, an oligonucleotide, a ligand, a receptor, or a binding agent. The monoclonal antibody may be an anti-CD4, anti-CD8, and anti-CD2 anitbody.

The optical bio-disc may also have a lysis buffer reservoir and a lysis buffer valve between a fluidic channel connecting the lysis buffer reservoir with the mixing chamber. The lysis buffer reservoir may be pre-filled with a lysis buffer. The optical bio-disc may also include an analysis buffer reservoir and an analysis buffer valve between a fluidic channel connecting the analysis buffer reservoir with the purification chamber. The analysis buffer reservoir may be pre-filled with an analysis buffer. The optical bio-disc may further include a waste chamber in fluid communication with the analysis chamber and the vent port. The optical bio-disc can also have a sample mix valve located in the fluidic circuit connecting the mixing chamber and the purification chamber. Further details relating to the above-mentioned optical bio-disc of the present invention is discussed below in conjunction with FIGS. 59 and 60.

The optical bio-disc described above may also include a RBC capture zone connecting the mixing chamber and the purification chamber such that when a sample is loaded into the mixing chamber, the sample flows through the RBC capture zone prior to entering the purification chamber. The RBC capture zone may include pier posts distributed throughout the RBC capture zone. The RBC capture zone can be a straight channel. It may also be serpentine, wavy, or sinusoidal. The RBC capture zone may be coated with a RBC capture agent including lectin. Examples of this type of fluidic circuit is described below in conjunction with FIGS. 61A, 61B, and 61C.

The present invention is also directed to a method of using the optical bio-disc described above which may include the following steps: loading a whole blood sample into the mixing chamber through the inlet port, loading the bio-disc into an optical reader, rotating the bio-disc at a first speed sufficient to open the lysis buffer valve and release the lysis buffer into the mixing chamber containing the blood sample, incubating the sample in said lysis buffer for a sufficient time to allow lysis of red blood cells in the sample, and rotating the bio-disc at a second speed sufficient to open the sample mix valve and allow movement of the sample into and through the purification chamber, where unwanted cells are captured, and through the analysis chamber where specific cells are captured on the capture zone. Once the cells move through the analysis chamber, an incident beam of electromagnetic radiation may then be directed to the capture zone. The beam of electromagnetic radiation formed after interacting with the disc at the capture zone may then be detected and the signal collected is then converted into an output signal and analyzed to extract therefrom information relating to the number of cells captured at the capture zone.

The present invention is also directed to another method for conducting a cellular assay which includes the following steps: loading a whole blood sample into the mixing chamber through the inlet port of the optical bio-disc described above, loading the bio-disc into an optical reader, rotating the bio-disc at a sufficient speed and time to move the sample through the RBC capture zone where red blood cells in the sample are captured, through the purification zone where unwanted cells in the sample are captured, and through the analysis chamber where specific cells are captured on the capture zone, directing an incident beam of electromagnetic radiation to the capture zone, detecting a beam of electromagnetic radiation formed after interacting with the disc at the capture zone, converting the detected beam into an output signal, and analyzing the output signal to extract therefrom information relating to the number of cells captured at the capture zone.

Another embodiment of the optical bio-disc of the present invention includes a rotatable substrate, a microfluidic cassette attached to the substrate, and fluidic circuits formed within the microfluidic cassette. The microfluidic cassette may be formed from plates having various cut-out sections to form the various components of the fluidic circuits including an inlet port, mixing chamber, flow channel, and purification chamber when the plates are assembled to form the microfluidic cassette. Further details regarding the microfluidic cassette is discussed below in conjunction with FIGS. 62A, 62B, 62C, and 63.

The present invention further discloses an optical disc and drive system for receiving a sample which includes a bio-disc which has a substrate, a cap parallel to the substrate, a mixing chamber, purification chamber, and analysis chamber defined between the analysis chamber having capture zones, and a capture layer over the substrate at the capture zones such that a first capture zone has a first cell capture agent and a second capture zone has a second cell capture agent. The system includes an optical disc drive having a light source for directing light to the disc at the capture zones, a detector for detecting light reflected from or transmitted through the disc at the capture zones and providing a signal, and a processor for using the signal to count items in the sample bound to the capture molecules.

Yet another aspect of the present invention includes a method of making an optical bio-disc for use in cellular assays. This method of making the bio disc includes the following steps: forming a rotatable optical disc substrate, forming a cover disc with similar dimensions to the substrate, forming a channel layer with cut out portions to form fluidic circuits wherein the fluidic circuits includes an inlet port, a mixing chamber, a purification chamber, an analysis chamber, and a vent port; said analysis chamber including capture zones. The present method further includes the steps of binding capture probes onto the capture zones, attaching the channel layer to the substrate, loading a filter means into the purification chamber, and attaching the cover disc to the channel layer to thereby form the optical bio-disc. The attaching of the cover disc, channel layer, and substrate may be achieved using adhesives and plastic welding. The filter means may be made of microspheres and cellular sieves coated with a purification agent.

The above methods and apparatuses can have one or more advantages which include, but are not limited to, simple and quick on-disc processing without the necessity of an experienced technician to run the test, small sample volumes, use of inexpensive materials, and use of known optical disc formats and drive manufacturing. These and other features and advantages will be better understood by reference to the following detailed description when taken in conjunction with the accompanying drawing figures and technical examples.

BRIEF DESCRIPTION OF THE DRAWINGS

Further objects of the present invention together with additional features contributing thereto and advantages accruing therefrom will be apparent from the following description of the preferred embodiments of the invention which are shown in the accompanying drawing figures with like reference numerals indicating like components throughout, wherein:

FIG. 13 is a partial longitudinal cross sectional view of the reflective optical bio-disc shown in FIGS. 2, 3, and 4 illustrating a wobble groove formed therein;

FIG. 14 is a partial longitudinal cross sectional view of the transmissive optical bio-disc illustrated in FIGS. 5, 8, and 9 showing a wobble groove formed therein and a top detector;

FIG. 15 is a view similar to FIG. 11 showing the entire thickness of the reflective disc and the initial refractive property thereof;

FIG. 16 is a view similar to FIG. 12 showing the entire thickness of the transmissive disc and the initial refractive property thereof;

FIGS. 20A–20I are cross-sectional side views showing embodiments of a first implementation of a method of depositing capture agents onto the capture zones of a reflective bio-disc using a cross-linking system according to the present invention;

FIGS. 24A–24L are cross-sectional side views showing embodiments of a second implementation of a method of depositing capture agents onto the capture zones of a reflective bio-disc using primary and secondary capture antibodies and a cross-linking system according to the present invention;

FIG. 25 is an alternate embodiment of the reflective disc shown in FIGS. 24A–24L without use of the cross-linking system;

FIG. 26 shows the capture chemistries utilized in FIGS. 24A–24L as implemented in a transmissive disc format;

FIGS. 27A and 27B are pictorial representations showing cell capture by a, primary antibody that is bound to a secondary antibody, which is bound to a substrate by a strand of DCHO in a second implementation of the invention;

FIGS. 27C and 27D are pictorial representations showing cell capture by a primary antibody that is bound directly to a substrate by a strand of DCHO in a second implementation of the invention;

FIGS. 32A–32I are cross-sectional side views showing embodiments of a third implementation of a method of depositing capture agents onto the capture zones of a reflective bio-disc using a cross-linking system;

FIG. 33 is an alternate embodiment of the reflective disc shown in FIGS. 32A–32I without use of the cross-linking system;

FIG. 34 shows the capture chemistries utilized in FIGS. 32A–32I as implemented in a transmissive disc format;

FIG. 39 is an alternate embodiment of the reflective disc shown in FIGS. 38A, 38B, and 38C without use of the cross-linking system;

FIG. 40 shows the capture chemistries utilized in FIGS. 38A, 38B, and 38C as implemented in a transmissive disc format;

FIGS. 44B, 44C, and 44D are cross-sectional side views of a reflective optical bio-disc showing embodiments of a fourth implementation of a method of blood sample analysis using primary and secondary capture antibodies and a cross-linking system;

FIG. 45 is an alternate embodiment of the reflective disc shown in FIGS. 44B, 44C, and 44D without use of the cross-linking system;

FIG. 46 shows the capture chemistries utilized in FIGS. 44B, 44C, and 44D as implemented in a transmissive disc format;

FIG. 49 shows a larger view of corresponding microscope and disc images to illustrate the results obtainable from the methods and apparatus of the present invention;

FIG. 57 is a graphical representation illustrating the relationship between FIGS. 57A, 57B, 57C, and 57D;

FIGS. 57A, 57B, 57C, and 57D, when taken together, form a pictorial graphical representation of transformation of the signature traces from FIG. 56B into digital signals that are stored as one-dimensional arrays and combined into a two-dimensional array for data input;

FIG. 64 is a bar graph illustration of results from a CD marker assay using the optical bio-disc of the present invention.

DETAILED DESCRIPTION OF THE INVENTION

The present invention is directed to disc drive systems, optical bio-discs, cellular assays and related cell counting methods, image processing techniques, and related software. Each of these aspects of the present invention is discussed below in further detail.

Aspects of the present invention relating to the disc drive systems, optical bio-discs, cellular assays and related cell counting methods, image processing techniques, and related software disclosed herein are also presented in U.S. Provisional Application Ser. No. 60/338,679 entitled "Quantitative and Qualitative Methods for Cell Isolation and Typing Including Immunophenotyping" filed Nov. 13, 2001; U.S. Provisional Application Ser. No. 60/332,001 entitled "Capture Layer Assemblies and Optical Bio-Discs for Immunophenotyping" filed Nov. 14, 2001; U.S. Provisional Application Ser. No. 60/334,131 entitled "Methods for Calculating Qualitative and Quantitative Ratios of Helper/Inducer-Suppressor/Cytotoxic T-Lymphocytes Using Optical Bio-Disc Platform" filed Nov. 30, 2001; U.S. Provisional Application Ser. No. 60/353,300 entitled "Methods for Differential Cell Counts Including Leukocytes and Use of Optical Bio-Disc for Performing Same" filed Jan. 31, 2002; U.S. Provisional Application Ser. No. 60/363,949 entitled. "Methods for Differential Cell Counts Including Leukocytes and Use of Optical Bio-Disc for Performing Same" filed Mar. 12, 2002; and U.S. Provisional Application Ser. No. 60/404,921 entitled "Methods For Differential Cell Counts Including Related Apparatus and Software For Performing Same" filed Aug. 21, 2002, all of which are herein incorporated by reference.

Drive System and Related Discs

Figure 1:
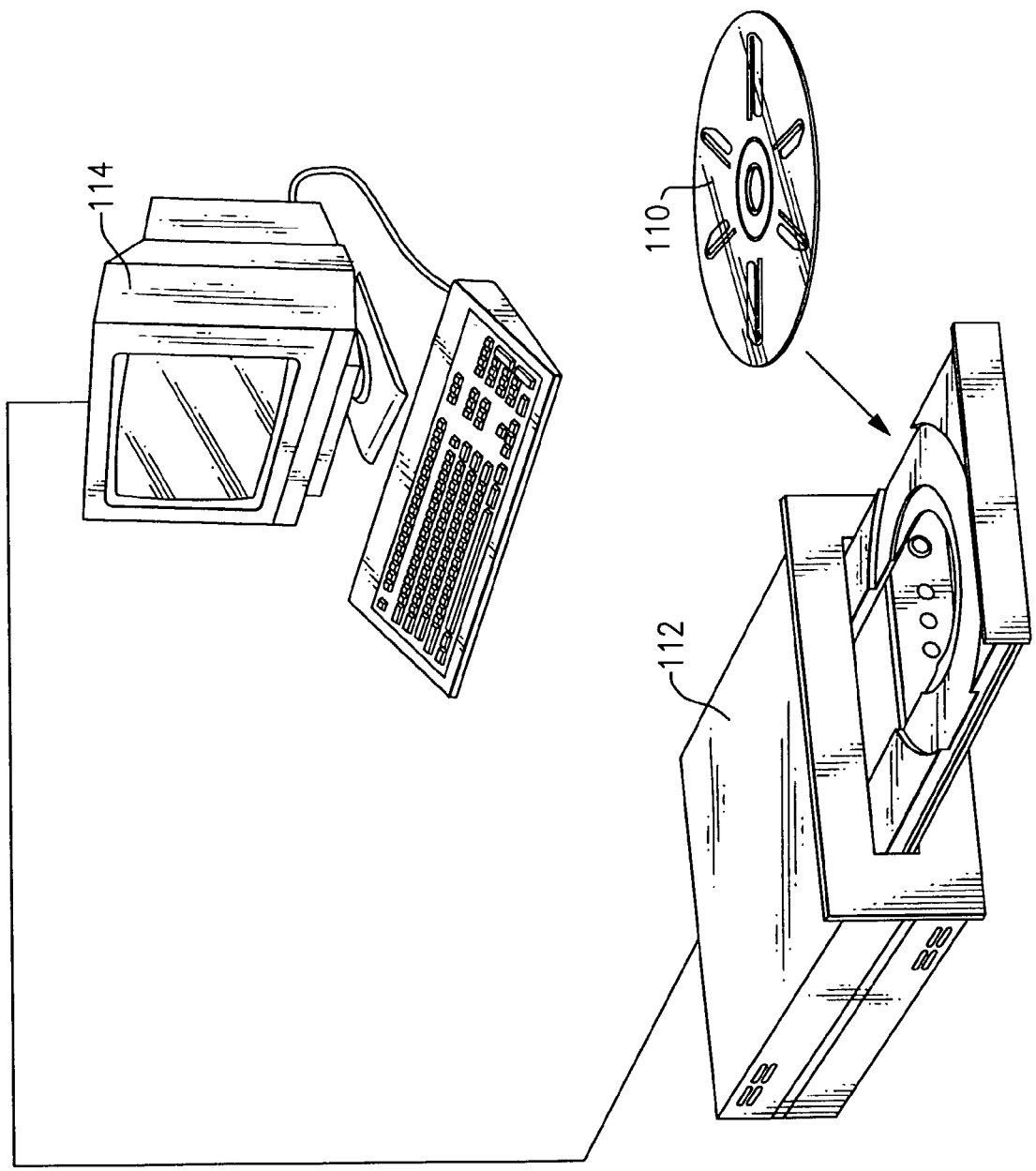
FIG. 1 is a pictorial representation of a bio-disc system according to the present invention.

FIG. 1 is a perspective view of an optical bio-disc 110 according to the present invention as implemented to conduct the cell counts and differential cell counts disclosed herein. The present optical bio-disc 110 is shown in conjunction with an optical disc drive 112 and a display monitor 114. Further details relating to this type of disc drive and disc analysis system are disclosed in commonly assigned and co-pending U.S. patent application Ser. No. 10/008,156 entitled "Disc Drive System and Methods for Use with Bio-discs" filed Nov. 9, 2001; U.S. patent application Ser. No. 10/043,688 entitled "Optical Disc Analysis System Including Related Methods For Biological and Medical Imaging" filed Jan. 10, 2002; and U.S. patent application Ser. No. 10/279,677 entitled "Segmented Area Detector for Biodrive and Methods Relating Thereto" filed Oct. 24, 2002, all of which are herein incorporated by reference in their entireties.

Figure 2:
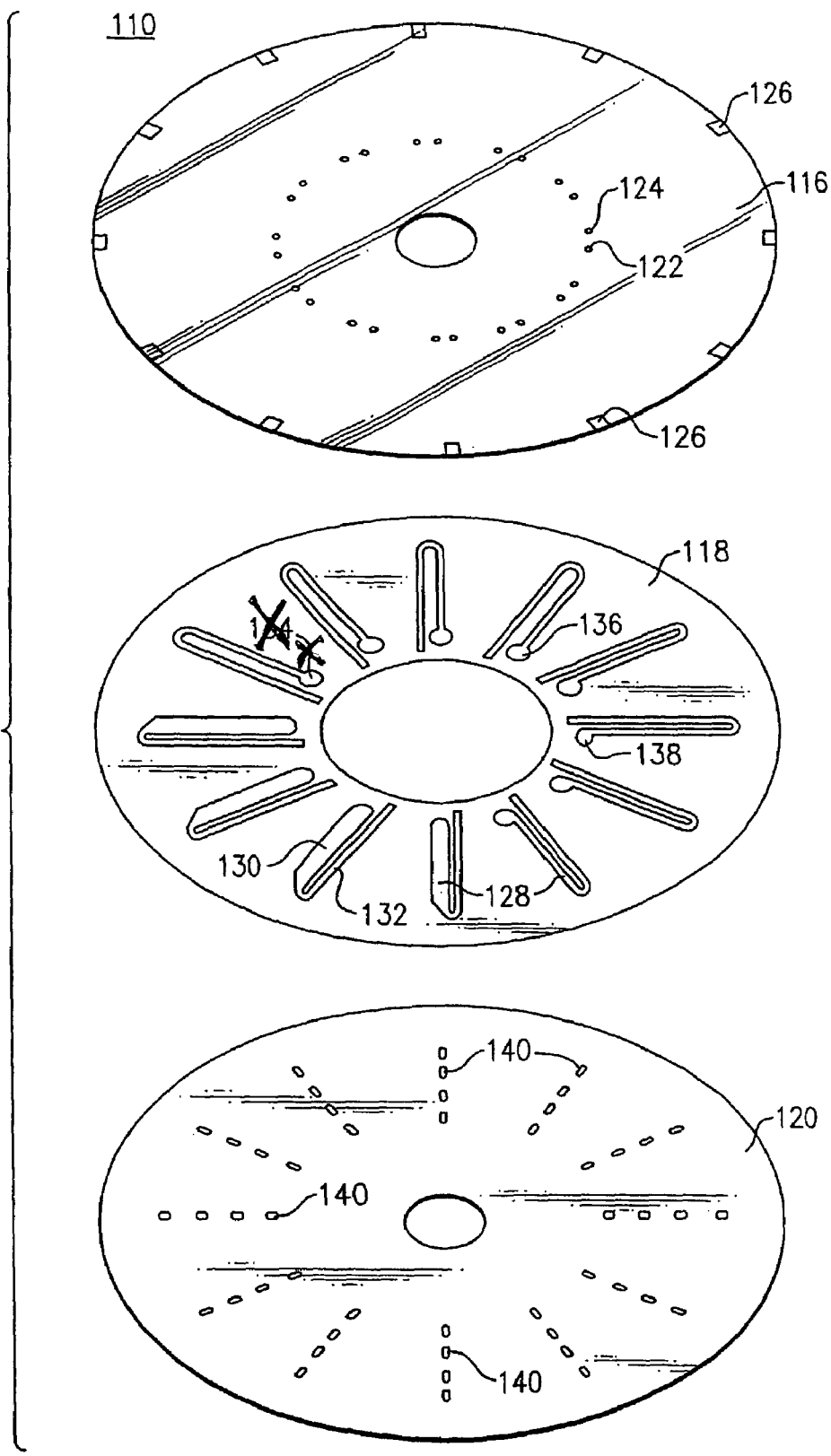
FIG. 2 is an exploded perspective view of a reflective bio-disc as utilized in conjunction with the present invention.
Figure 4:
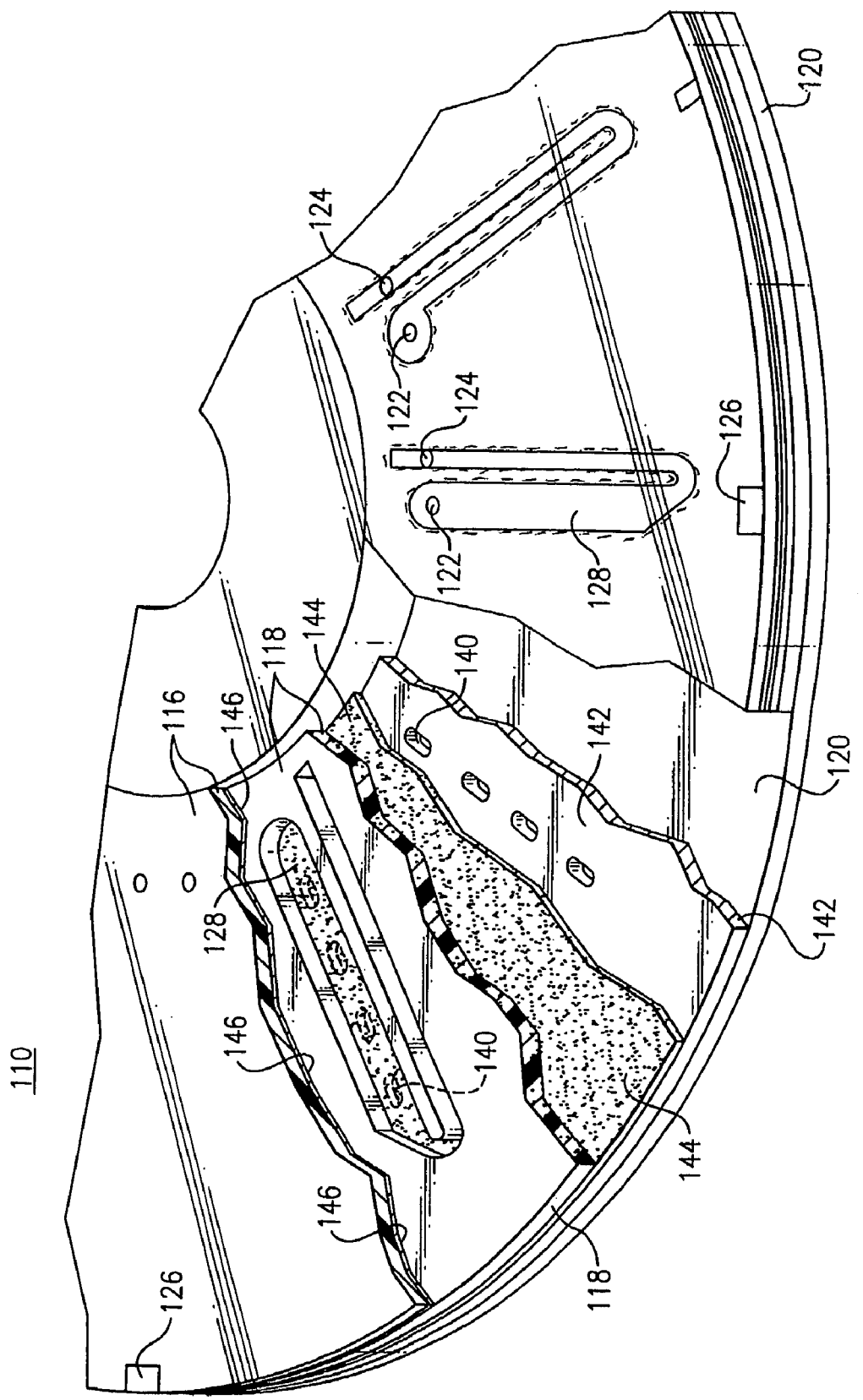
FIG. 4 is a perspective view of the disc illustrated in FIG. 2 with cut-away sections showing the different layers of the disc.

FIG. 2 is an exploded perspective view of the principal structural elements of one embodiment of the optical bio-disc 110. FIG. 2 is an example of a reflective zone optical bio-disc 110 (hereinafter "reflective disc") that may be used in the present invention. The principal structural elements include a cover disc or cap portion 116, an adhesive member or channel layer 118, and a substrate 120. The cover disc 116 includes one or more inlet ports 122 and one or more vent ports 124. The cover disc 116 may be formed from polycarbonate and is preferably coated with a reflective surface 146 (FIG. 4) on the bottom thereof as viewed from the perspective of FIG. 2. In the preferred embodiment, trigger marks or markings 126 are included on the surface of the reflective layer 142 (FIG. 4). Trigger markings 126 may include a clear window in all three layers of the bio-disc, an opaque area, or a reflective or semi-reflective area encoded with information that sends data to a processor 166, as shown FIG. 10, that in turn interacts with the operative functions of the interrogation or incident beam 152, FIGS. 6 and 10.

The second element shown in FIG. 2 is an adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes a flow channel or analysis chamber 130 and a return channel 132. Some of the fluidic circuits 128 illustrated in FIG. 2 include a mixing chamber. Two different types of mixing chambers are illustrated. The first is a symmetric mixing chamber 136 that is symmetrically formed relative to the flow channel or analysis chamber 130. The second is an off-set mixing chamber 138. The off-set mixing chamber 138 is formed to one side of the flow channel or analysis chamber 130 as indicated.

The third element illustrated in FIG. 2 is a substrate 120 including target or capture zones 140. The substrate 120 is preferably made of polycarbonate and has a reflective layer 142 deposited on the top thereof, FIG. 4. The target zones 140 are formed by removing the reflective layer 142 in the indicated shape or alternatively in any desired shape. Alternatively, the target zone 140 may be formed by a masking technique that includes masking the target zone 140 area before applying the reflective layer 142. The reflective layer 142 may be formed from a metal such as aluminum or gold.

Figure 3:
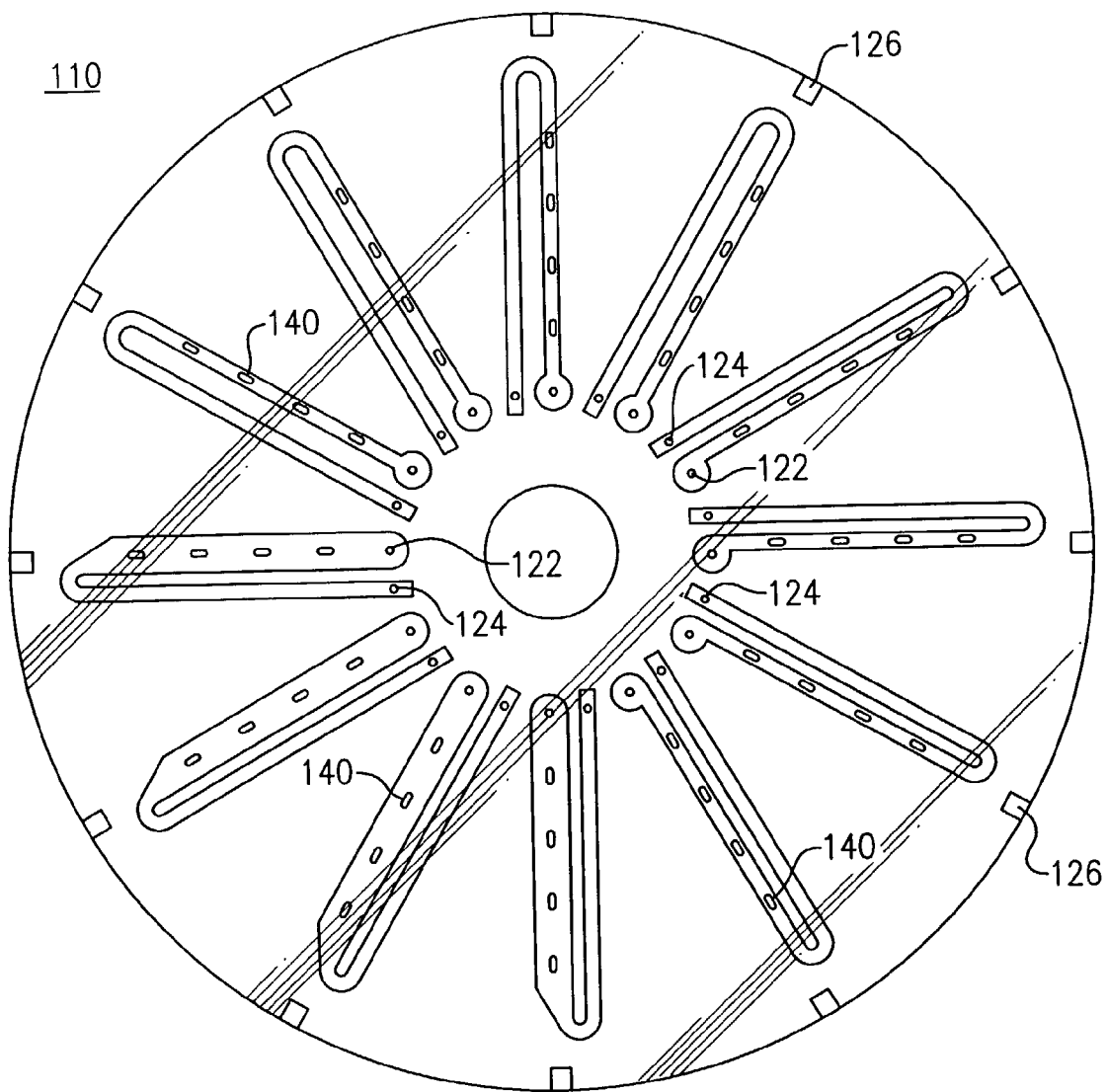
FIG. 3 is a top plan view of the disc shown in FIG. 2.

FIG. 3 is a top plan view of the optical bio-disc 110 illustrated in FIG. 2 with the reflective layer 142 on the cover disc or cap portion 116 shown as transparent to reveal the fluidic circuits 128, the target zones 140, and trigger markings 126 situated within the disc.

FIG. 4 is an enlarged perspective view of the reflective zone type optical bio-disc 110 according to one embodiment of the present invention. This view includes a portion of the various layers thereof, cut away to illustrate a partial sectional view of each principal layer, substrate, coating, or membrane. FIG. 4 shows the substrate 120 that is coated with the reflective layer 142. An active layer 144 is applied over the reflective layer 142. In the preferred embodiment, the active layer 144 may be formed from polystyrene. Alternatively, polycarbonate, gold, activated glass, modified glass, or modified polystyrene, for example, polystyrene-co-maleic anhydride, may be used. In addition, hydrogels can be used. Alternatively as illustrated in this embodiment, the plastic adhesive member 118 is applied over the active layer 144. The exposed section of the plastic adhesive member 118 illustrates the cut out or stamped U-shaped form that creates the fluidic circuits 128. The final principal structural layer in this reflective zone embodiment of the present bio-disc is the cover disc or cap portion 116. The cover disc 116 includes the reflective surface 146 on the bottom thereof. The reflective surface 146 may be made from a metal such as aluminum or gold.

Figure 5:
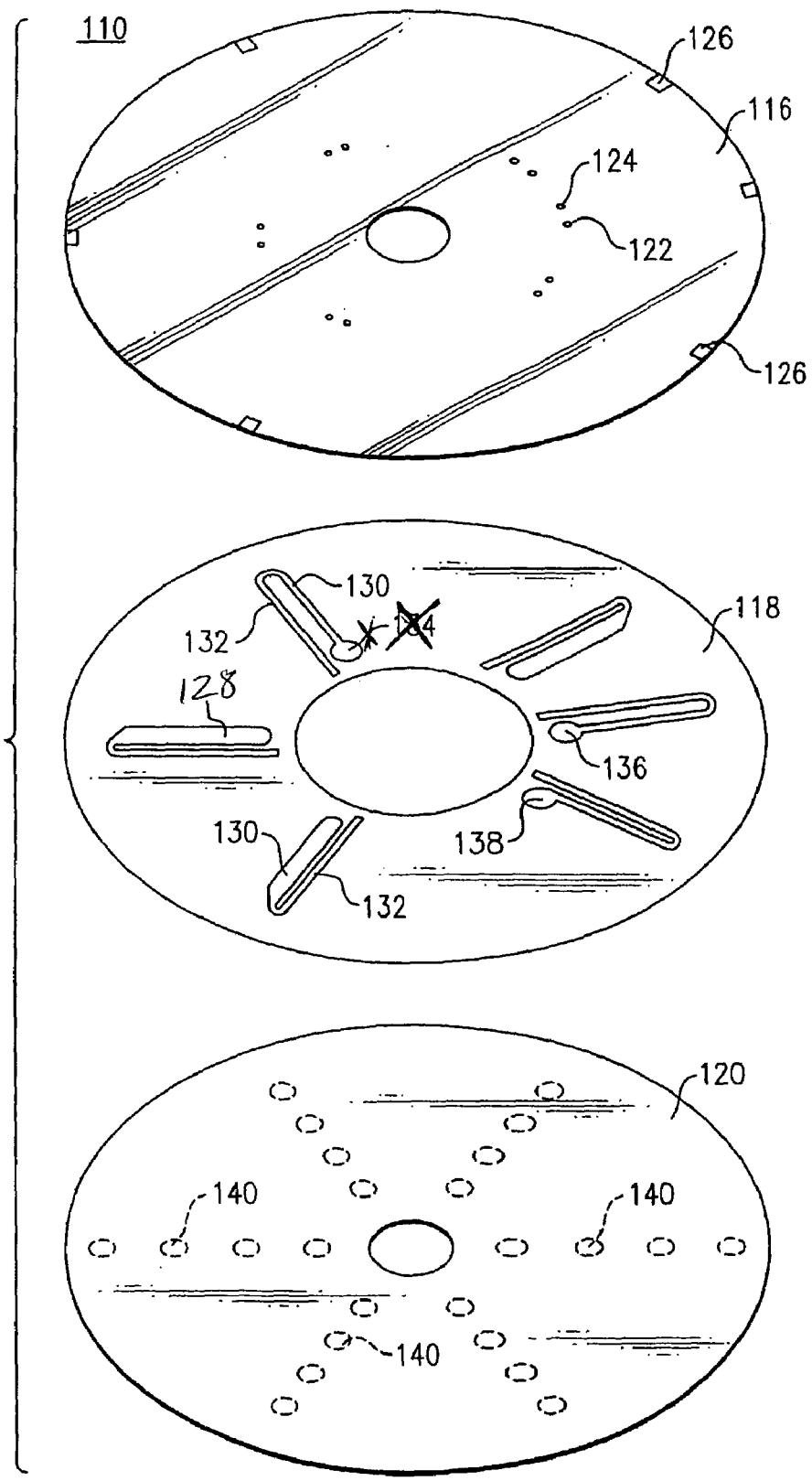
FIG. 5 is an exploded perspective view of a transmissive bio-disc as employed in conjunction with the present invention.
Figure 6:
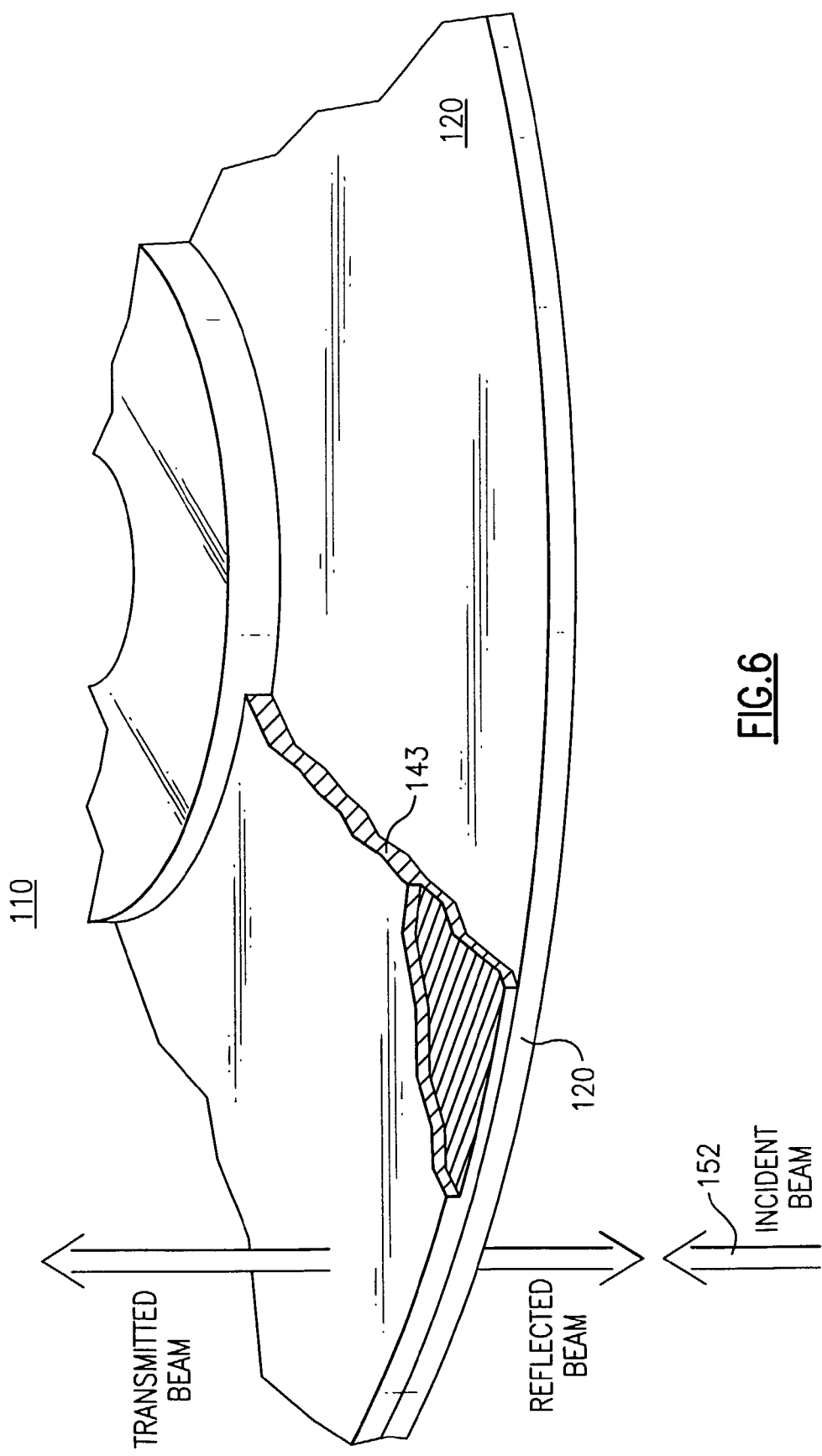
FIG. 6 is a perspective view representing the disc shown in FIG. 5 with a cut-away section illustrating the functional aspects of a semi-reflective layer of the disc.
Figure 9:
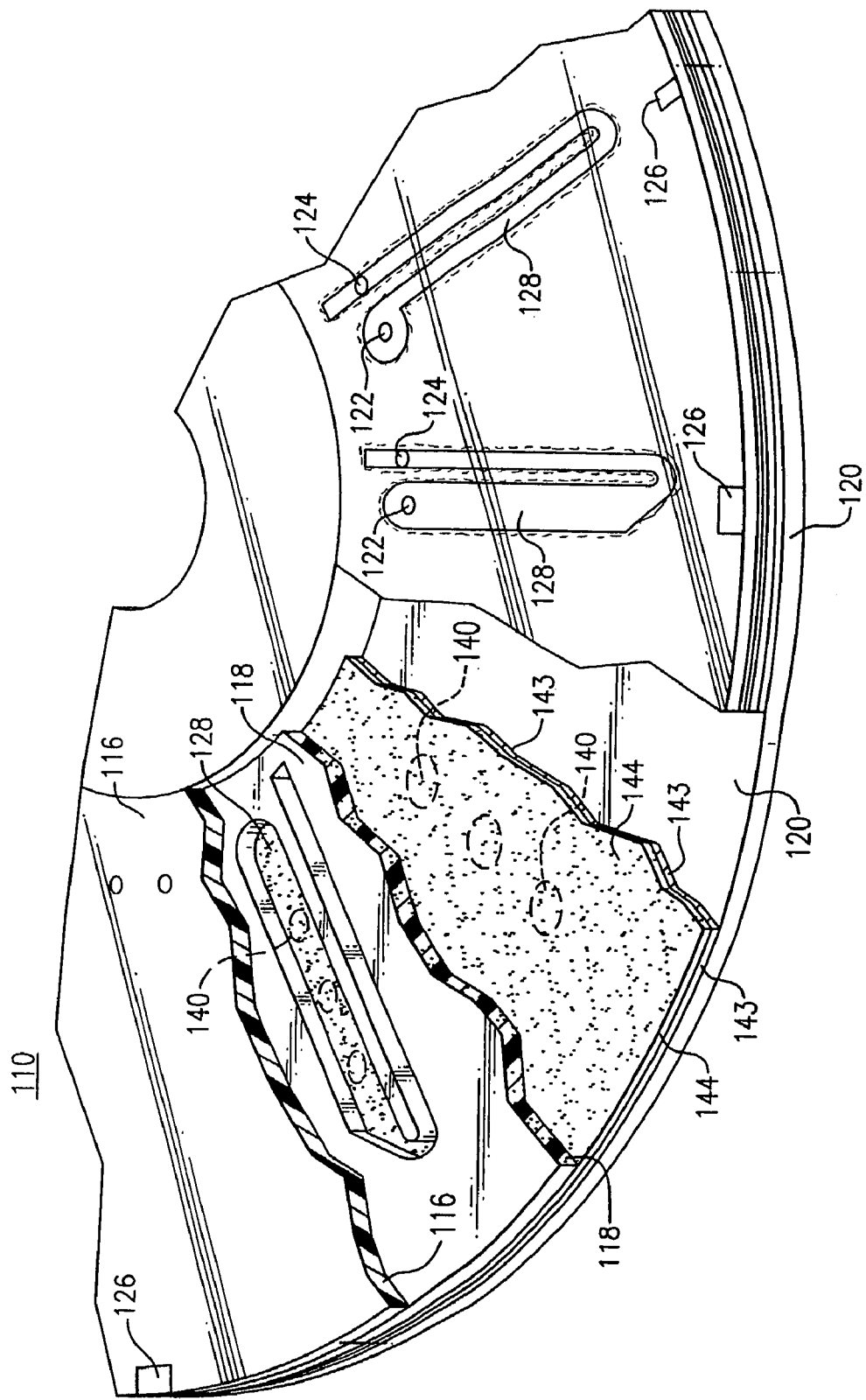
FIG. 9 is a perspective view of the disc illustrated in FIG. 5 with cut-away sections showing the different layers of the disc including the type of semi-reflective layer shown in FIG. 6.

Referring now to FIG. 5, there is shown an exploded perspective view of the principal structural elements of a transmissive type of optical bio-disc 110 according to the present invention. The principal structural elements of the transmissive type of optical bio-disc 110 similarly include the cover disc or cap portion 116, the adhesive or channel member 118, and the substrate 120 layer. The cover disc 116 includes one or more inlet ports 122 and one or more vent ports 124. The cover disc 116 may be formed from a polycarbonate layer. Optional trigger markings 126 may be included on the surface of a thin semi-reflective layer 143, as best illustrated in FIGS. 6 and 9. Trigger markings 126 may include a clear window in all three layers of the bio-disc, an opaque area, or a reflective or semi-reflective area encoded with information that sends data to the processor 166, FIG. 10, which in turn interacts with the operative functions of the interrogation beam 152, FIGS. 6 and 10.

The second element shown in FIG. 5 is the adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes the flow channel or analysis chamber 130 and the return channel 132. Some of the fluidic circuits 128 illustrated in FIG. 5 include a mixing chamber. Two different types of mixing chambers are illustrated. The first is the symmetric mixing chamber 136 that is symmetrically formed relative to the flow channel or analysis chamber 130. The second is the off-set mixing chamber 138. The off-set mixing chamber 138 is formed to one side of the flow channel or analysis chamber 130 as indicated.

Figure 12:
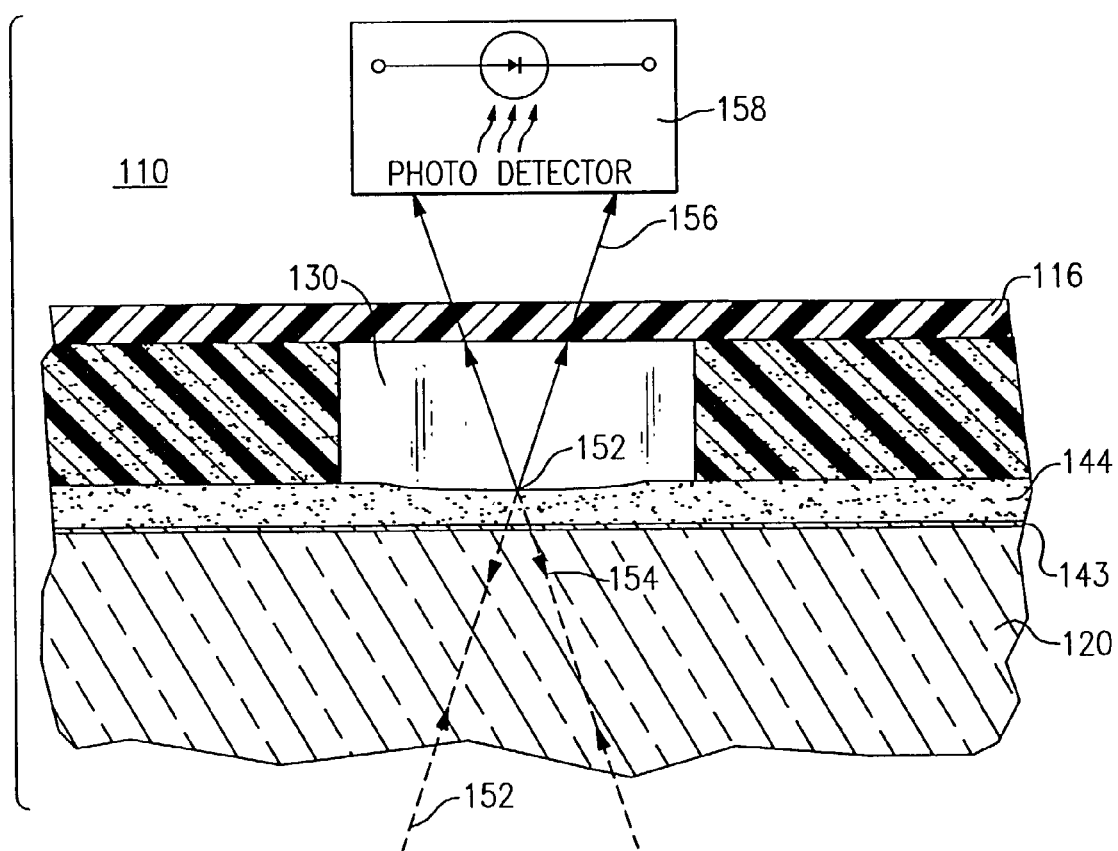
FIG. 12 is a partial cross sectional view taken perpendicular to a radius of the transmissive optical bio-disc illustrated in FIGS. 5, 8, and 9 showing a flow channel formed therein and a top detector.

The third element illustrated in FIG. 5 is the substrate 120 which may include the target or capture zones 140. The substrate 120 is preferably made of polycarbonate and has the thin semi-reflective layer 143 deposited on the top thereof, FIG. 6. The semi-reflective layer 143 associated with the substrate 120 of the disc 110 illustrated in FIGS. 5 and 6 is significantly thinner than the reflective layer 142 on the substrate 120 of the reflective disc 110 illustrated in FIGS. 2, 3 and 4. The thinner semi-reflective layer 143 allows for some transmission of the interrogation beam 152 through the structural layers of the transmissive disc as shown in FIGS. 6 and 12. The thin semi-reflective layer 143 may be formed from a metal such as aluminum or gold.

FIG. 6 is an enlarged perspective view of the substrate 120 and semi-reflective layer 143 of the transmissive embodiment of the optical bio-disc 110 illustrated in FIG. 5. The thin semi-reflective layer 143 may be made from a metal such as aluminum or gold. In the preferred embodiment, the thin semi-reflective layer 143 of the transmissive disc illustrated in FIGS. 5 and 6 is approximately 100–300 Å thick and does not exceed 400 Å. This thinner semi-reflective layer 143 allows a portion of the incident or interrogation beam 152 to penetrate and pass through the semi-reflective layer 143 to be detected by a top detector 158, FIGS. 10 and 12, while some of the light is reflected or returned back along the incident path. As indicated below, Table 2 presents the reflective and transmissive characteristics of a gold film relative to the thickness of the film. The gold film layer is fully reflective at a thickness greater than 800 Å. While the threshold density for transmission of light through the gold film is approximately 400 Å.

Figure 7:
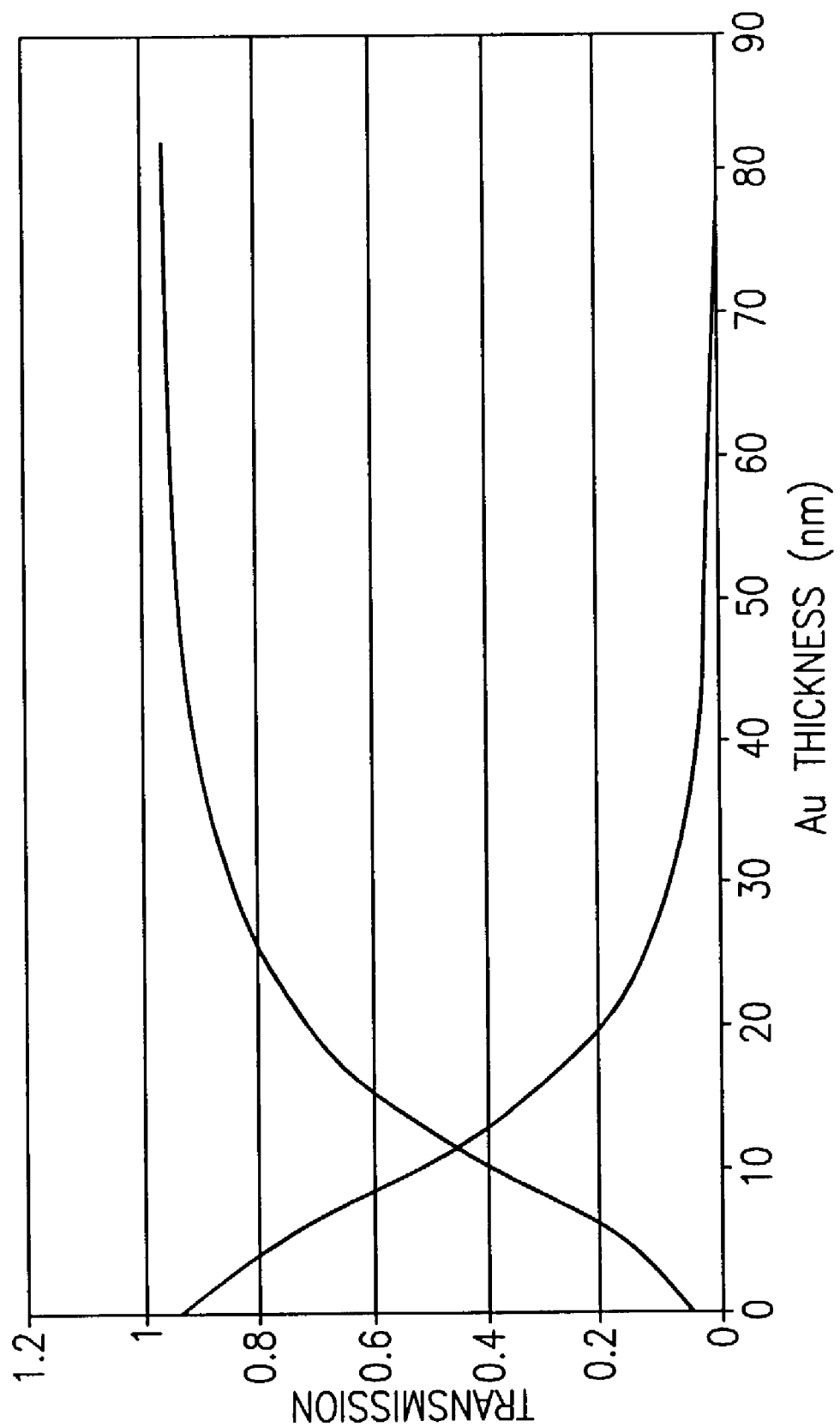
FIG. 7 is a graphical representation showing the relationship between thickness and transmission of a thin gold film.

In addition to Table 2, FIG. 7 provides a graphical representation of the inverse relationship of the reflective and transmissive nature of the thin semi-reflective layer 143 based upon the thickness of the gold. Reflective and transmissive values used in the graph illustrated in FIG. 7 are absolute values.

TABLE 2

Au film Reflection and Transmission (Absolute Values)

| Thickness (Angstroms) | Thickness (nm) | Reflectance | Transmittance |
|---|---|---|---|
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |
| 450 | 45 | 0.9222 | 0.0244 |
| 500 | 50 | 0.9328 | 0.0163 |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

Figure 8:
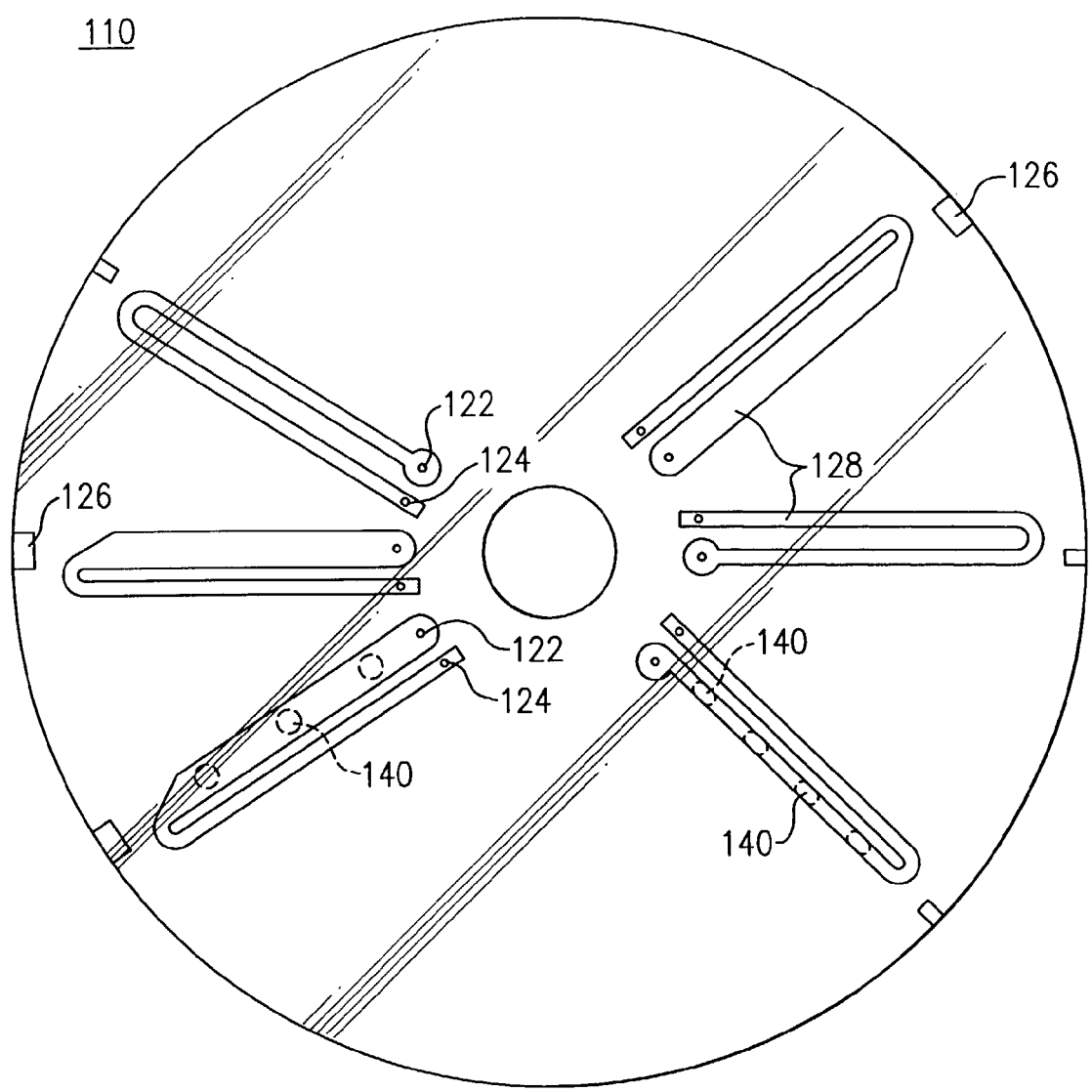
FIG. 8 is a top plan view of the disc shown in FIG. 5.

With reference next to FIG. 8, there is shown a top plan view of the transmissive type optical-disc 110 illustrated in FIGS. 5 and 6 with the transparent cover disc or cap portion 116 revealing the fluidic channels, the trigger markings 126, and the target zones 140 as situated within the disc.

FIG. 9 is an enlarged perspective view of the optical bio-disc 110 according to the transmissive disc embodiment of the present invention. The disc 110 is illustrated with a portion of the various layers thereof cut away to show a partial sectional view of each principal layer, substrate, coating, or membrane. FIG. 9 illustrates a transmissive disc format with the clear cover disc or cap portion 116, the thin semi-reflective layer 143 on the substrate 120, and trigger markings 126. In this embodiment, trigger markings 126 include opaque material placed on the top portion of the cap. Alternatively the trigger marking 126 may be formed by clear, non-reflective windows etched on the thin reflective layer 143 of the disc, or any mark that absorbs or does not reflect the signal coming from the trigger detector 160, FIG. 10. FIG. 9 also shows, the target zones 140 formed by marking the designated area in the indicated shape or alternatively in any desired shape. Markings to indicate target zone 140 may be made on the thin semi-reflective layer 143 on the substrate 120 or on the bottom portion of the substrate 120 (under the disc). Alternatively, the target zones 140 may be formed by a masking technique that includes masking the entire thin semi-reflective layer 143 except the target zones 140. In this embodiment, target zones 140 may be created by silk screening ink onto the thin semi-reflective layer 143. In the transmissive disc format illustrated in FIGS. 5, 8, and 9, the target zones 140 may alternatively be defined by address information encoded on the disc. In this embodiment, target zones 140 do not include a physically discernable edge boundary.

With continuing reference to FIG. 9, an active layer 144 is illustrated as applied over the thin semi-reflective layer 143. In the preferred embodiment, the active layer 144 is a 40 to 200 μm thick layer of 2% polystyrene. Alternatively, polycarbonate, gold, activated glass, modified glass, or modified polystyrene, for example, polystyrene-co-maleic anhydride, may be used. In addition, hydrogels can be used. As illustrated in this embodiment, the plastic adhesive member 118 is applied over the active layer 144. The exposed section of the plastic adhesive member 118 illustrates the cut out or stamped U-shaped form that creates the fluidic circuits 128.

The final principal structural layer in this transmissive embodiment of the present bio-disc 110 is the clear, non-reflective cover disc or cap portion 116 that includes inlet ports 122 and vent ports 124.

Figure 10:
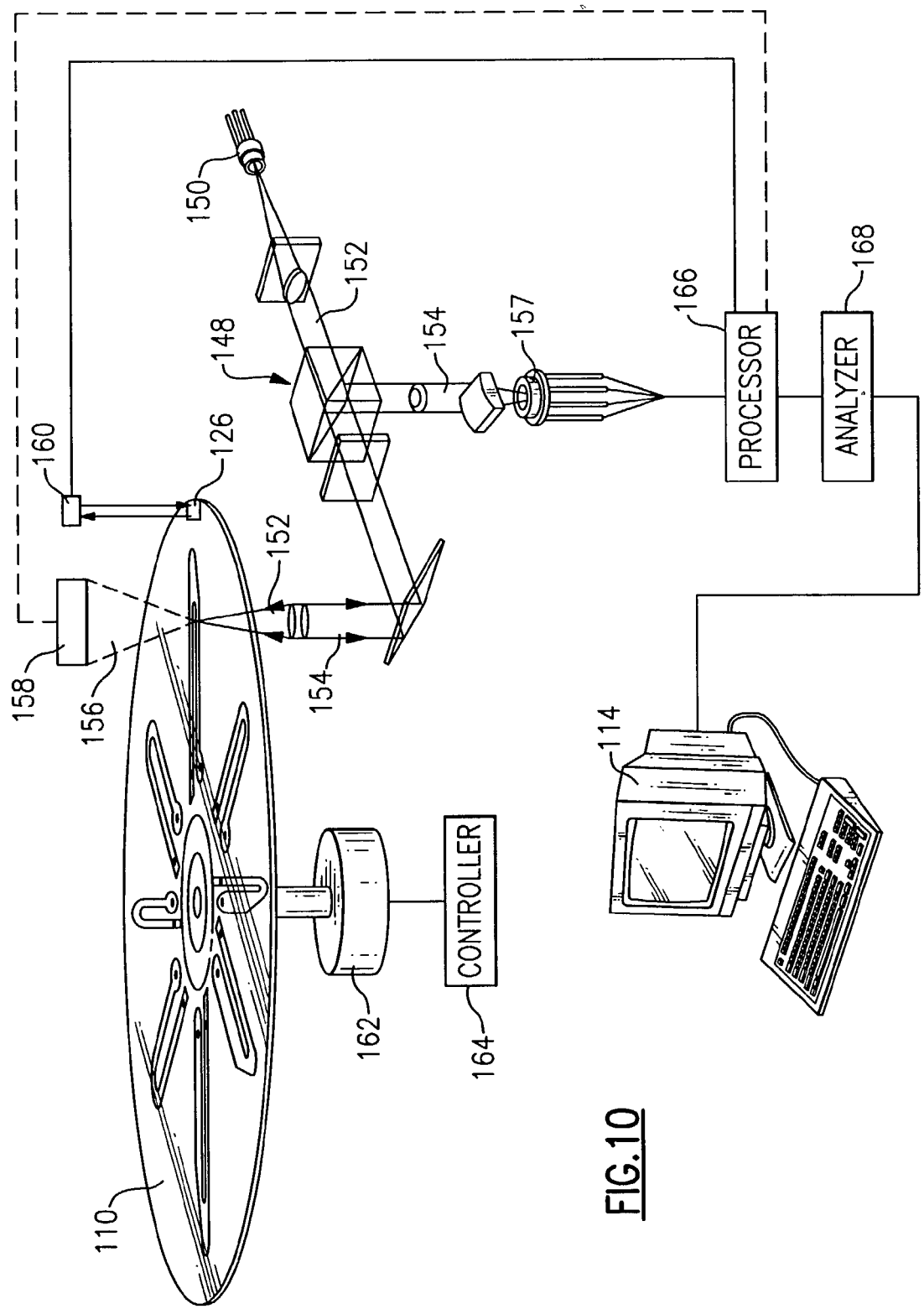
FIG. 10 is a perspective and block diagram representation illustrating the system of FIG. 1 in more detail.

Referring now to FIG. 10, there is a representation in perspective and block diagram illustrating optical components 148, a light source 150 that produces the incident or interrogation beam 152, a return beam 154, and a transmitted beam 156. In the case of the reflective bio-disc illustrated in FIG. 4, the return beam 154 is reflected from the reflective surface 146 of the cover disc 116 of the optical bio-disc 110. In this reflective embodiment of the present optical bio-disc 110, the return beam 154 is detected and analyzed for the presence of signal elements by a bottom detector 157. In the transmissive bio-disc format, on the other hand, the transmitted beam 156 is detected, by a top detector 158, and is also analyzed for the presence of signal elements. In the transmissive embodiment, a photo detector may be used as a top detector 158.

FIG. 10 also shows a hardware trigger mechanism that includes the trigger markings 126 on the disc and a trigger detector 160. The hardware triggering mechanism is used in both reflective bio-discs (FIG. 4) and transmissive bio-discs (FIG. 9). The triggering mechanism allows the processor 166 to collect data only when the interrogation beam 152 is on a respective target zone 140. Furthermore, in the transmissive bio-disc system, a software trigger may also be used. The software trigger uses the bottom detector to signal the processor 166 to collect data as soon as the interrogation beam 152 hits the edge of a respective target zone 140. FIG. 10 further illustrates a drive motor 162 and a controller 164 for controlling the rotation of the optical bio-disc 110. FIG. 10 also shows the processor 166 and analyzer 168 implemented in the alternative for processing the return beam 154 and transmitted beam 156 associated the transmissive optical bio-disc.

Figure 11:
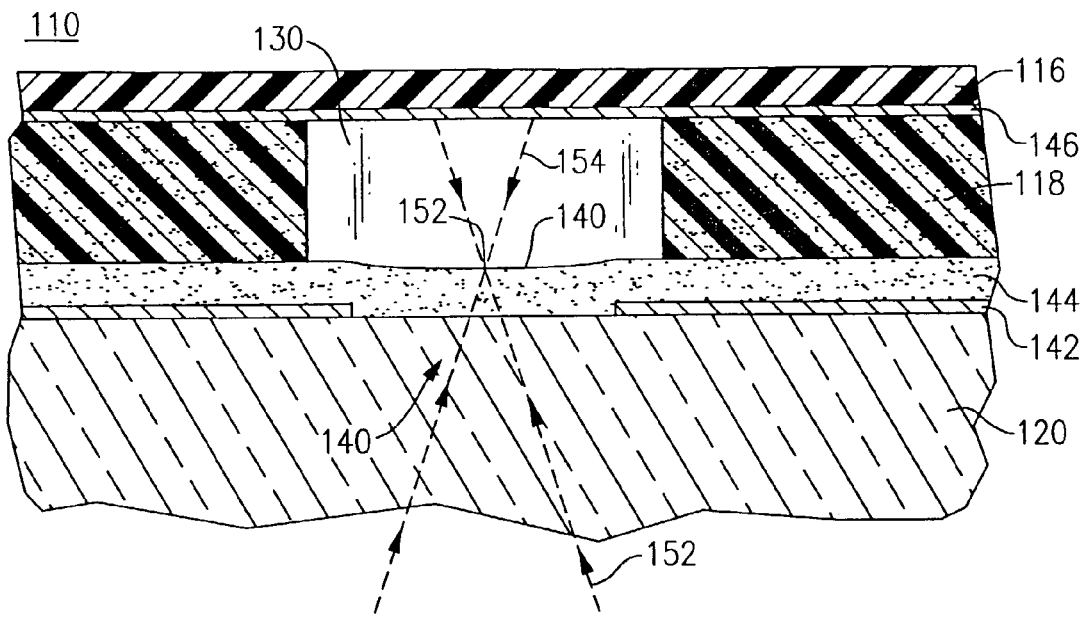
FIG. 11 is a partial cross sectional view taken perpendicular to a radius of the reflective optical bio-disc illustrated in FIGS. 2, 3, and 4 showing a flow channel formed therein.

As shown in FIG. 11, there is presented a partial cross sectional view of the reflective disc embodiment of the optical bio-disc 110 according to the present invention. FIG. 11 illustrates the substrate 120 and the reflective layer 142. As indicated above, the reflective layer 142 may be made from a material such as aluminum, gold or other suitable reflective material. In this embodiment, the top surface of the substrate 120 is smooth. FIG. 11 also shows the active layer 144 applied over the reflective layer 142. As also shown in FIG. 11, the target zone 140 is formed by removing an area or portion of the reflective layer 142 at a desired location or, alternatively, by masking the desired area prior to applying the reflective layer 142. As further illustrated in FIG. 11, the plastic adhesive member 118 is applied over the active layer 144. FIG. 11 also shows the cover disc 116 and the reflective surface 146 associated therewith. Thus when the cover disc 116 is applied to the plastic adhesive member 118 including the desired cutout shapes, flow channel or analysis chamber 130 is thereby formed. As indicated by the arrowheads shown in FIG. 11, the path of the incident beam 152 is initially directed toward the substrate 120 from below the disc 110. The incident beam then focuses at a point proximate the reflective layer 142. Since this focusing takes place in the target zone 140 where a portion of the reflective layer 142 is absent, the incident continues along a path through the active layer 144 and into the flow channel or analysis chamber 130. The incident beam 152 then continues upwardly traversing through the flow channel to eventually fall incident onto the reflective surface 146. At this point, the incident beam 152 is returned or reflected back along the incident path and thereby forms the return beam 154.

FIG. 12 is a partial cross sectional view of the transmissive embodiment of the bio-disc 110 according to the present invention. FIG. 12 illustrates a transmissive disc format with the clear cover disc 116 and the thin semi-reflective layer 143 on the substrate 120. FIG. 12 also shows the active layer 144 applied over the thin semi-reflective layer 143. In the preferred embodiment, the transmissive disc has the thin semi-reflective layer 143 made from a metal such as aluminum or gold approximately 100–300 Angstroms thick and does not exceed 400 Angstroms. This thin semi-reflective layer 143 allows a portion of the incident or interrogation beam 152, from the light source 150, FIG. 10, to penetrate and pass upwardly through the disc to be detected by a top detector 158, while some of the light is reflected back along the same path as the incident beam but in the opposite direction. In this arrangement, the return or reflected beam 154 is reflected from the semi-reflective layer 143. Thus in this manner, the return beam 154 does not enter into the flow channel or analysis chamber 130. The reflected light or return beam 154 may be used for tracking the incident beam 152 on pre-recorded information tracks formed in or on the semi-reflective layer 143 as described in more detail in conjunction with FIGS. 13 and 14. In the disc embodiment illustrated in FIG. 12, a physically defined target zone 140 may or may not be present. Target zone 140 may be created by direct markings made on the thin semi-reflective layer 143 on the substrate 120. These marking may be formed using silk screening or any equivalent method. In the alternative embodiment where no physical indicia are employed to define a target zone (such as, for example, when encoded software addressing is utilized) the flow channel or analysis chamber 130 in effect may be employed as a confined target area in which inspection of an investigational feature is conducted.

FIG. 13 is a cross sectional view taken across the tracks of the reflective disc embodiment of the bio-disc 110 according to the present invention. This view is taken longitudinally along a radius and flow channel of the disc. FIG. 13 includes the substrate 120 and the reflective layer 142. In this embodiment, the substrate 120 includes a series of grooves 170. The grooves 170 are in the form of a spiral extending from near the center of the disc toward the outer edge. The grooves 170 are implemented so that the interrogation beam 152 may track along the spiral grooves 170 on the disc. This type of groove 170 is known as a "wobble groove". A bottom portion having undulating or wavy sidewalls forms the groove 170, while a raised or elevated portion separates adjacent grooves 170 in the spiral. The reflective layer 142 applied over the grooves 170 in this embodiment is, as illustrated, conformal in nature. FIG. 13 also shows the active layer 144 applied over the reflective layer 142. As shown in FIG. 13, the target zone 140 is formed by removing an area or portion of the reflective layer 142 at a desired location or, alternatively, by masking the desired area prior to applying the reflective layer 142. As further illustrated in FIG. 13, the plastic adhesive member 118 is applied over the active layer 144. FIG. 13 also shows the cover disc or cap portion 116 and the reflective surface 146 associated therewith. Thus, when the cover disc 116 is applied to the plastic adhesive member 118 including the desired cutout shapes, the flow channel or analysis chamber 130 is thereby formed.

FIG. 14 is a cross sectional view taken across the tracks of the transmissive disc embodiment of the bio-disc 110 according to the present invention as described in FIG. 12, for example. This view is taken longitudinally along a radius and flow channel of the disc. FIG. 14 illustrates the substrate 120 and the thin semi-reflective layer 143. This thin semi-reflective layer 143 allows the incident or interrogation beam 152, from the light source 150, to penetrate and pass through the disc to be detected by the top detector 158, while some of the light is reflected back in the form of the return beam 154. The thickness of the thin semi-reflective layer 143 is determined by the minimum amount of reflected light required by the disc reader to maintain its tracking ability. The substrate 120 in this embodiment, like that discussed in FIG. 13, includes the series of grooves 170. The grooves 170 in this embodiment are also preferably in the form of a spiral extending from near the center of the disc toward the outer edge. The grooves 170 are implemented so that the interrogation beam 152 may track along the spiral. FIG. 14 also shows the active layer 144 applied over the thin semi-reflective layer 143. As further illustrated in FIG. 14, the plastic adhesive member or channel layer 118 is applied over the active layer 144. FIG. 14 also shows the cover disc or cap portion 116 without a reflective surface 146. Thus, when the cap is applied to the plastic adhesive member 118 including the desired cutout shapes, the flow channel or analysis chamber 130 is thereby formed and a part of the incident beam 152 is allowed to pass therethrough substantially unreflected.

FIG. 15 is a view similar to FIG. 11 showing the entire thickness of the reflective disc and the initial refractive property thereof. FIG. 16 is a view similar to FIG. 12 showing the entire thickness of the transmissive disc and the initial refractive property thereof. Grooves 170 are not seen in FIGS. 15 and 16 since the sections are cut along the grooves 170. FIGS. 15 and 16 show the presence of the narrow flow channel or analysis chamber 130 that is situated perpendicular to the grooves 170 in these embodiments. FIGS. 13, 14, 15, and 16 show the entire thickness of the respective reflective and transmissive discs. In these figures, the incident beam 152 is illustrated initially interacting with the substrate 120 which has refractive properties that change the path of the incident beam as illustrated to provide focusing of the beam 152 on the reflective layer 142 or the thin semi-reflective layer 143.

Cellular Assays

A generic homogeneous solid phase cell capture assay for the rapid determination of absolute number of $CD4^+$ and $CD8^+$ T-lymphocyte populations and ratio of $CD4^+/CD8^+$ lymphocytes in blood samples may be performed utilizing the methods of the invention. The test, which is run within small flow channels incorporated into a bio-disc, determines the number of $CD4^+$, $CD8^+$, $CD2^+$, $CD3^+$, $CD19^+$, and $CD45^+$ cells captured by the specific antibodies on the capture zones in 7–15 μl of mononuclear cells (MNC) isolated from whole blood. The test is based upon the principle of localized cell capture on specific locations on the disc. Several specific cell capture zones are created on the disc by localized application of capture chemistries based upon monoclonal or polyclonal antibodies to particular blood cell surface antigens. Upon flooding the 25–100 μl chambers with the MNC blood (10,000–30,000 cells/μl), cells expressing CD4, CD8, CD2, CD3, CD19, and CD45 antigens are captured in the capture zones within the disc. Also incorporated within the capture zones are defined negative control areas. Other related aspects directed to sorting and analyzing cells in a sample is disclosed in commonly assigned and co-pending U.S. Provisional Application Ser. No. 60/398,464 entitled "Optical Bio-disc Cell Sorter and Analyser" filed Jul. 25, 2002. This application is herein incorporated by reference in its entirety.

Figure 17A:
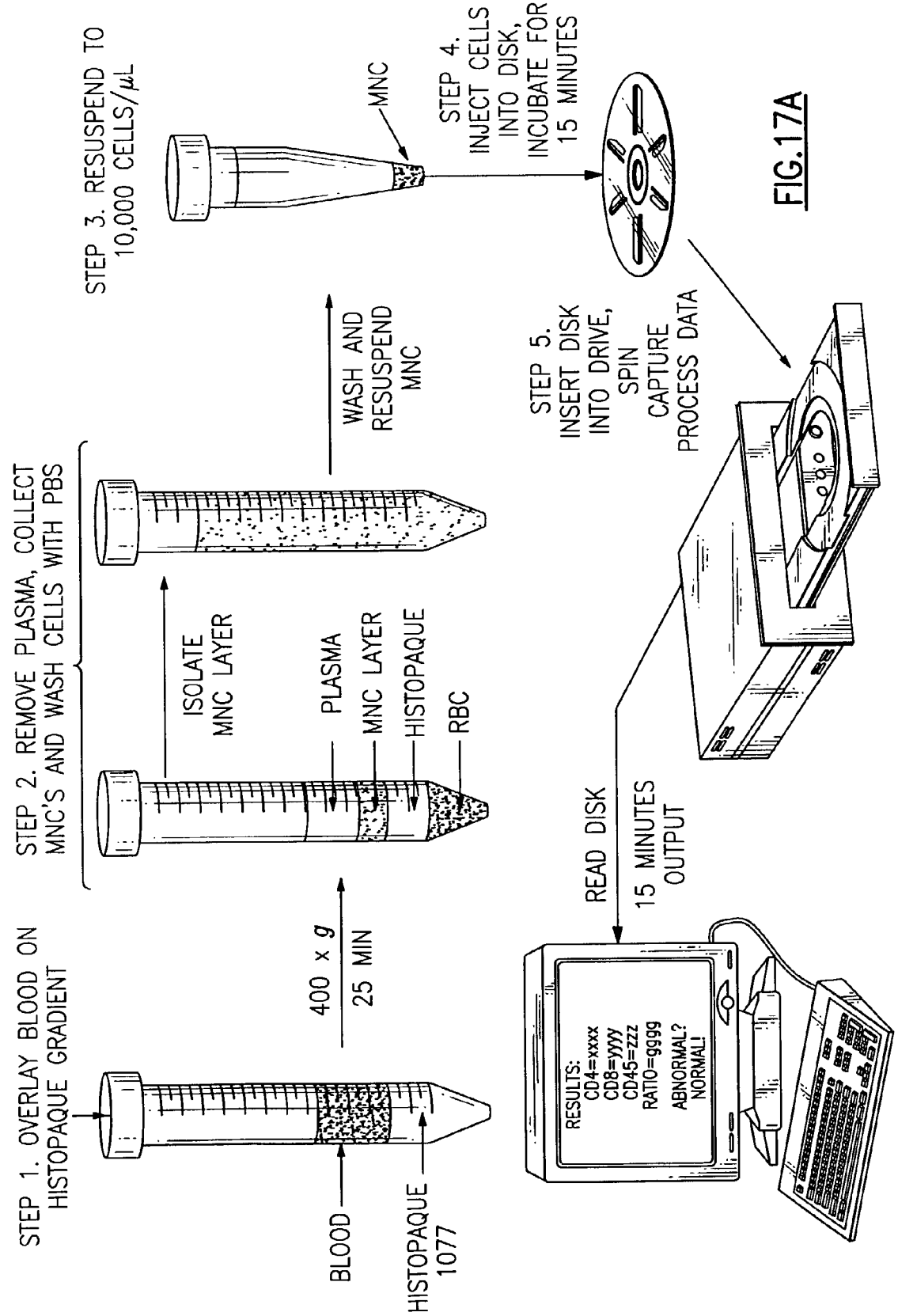
FIG. 17A is a pictorial flow chart showing the analysis of a blood sample using methods of the invention.

FIG. 17A is a pictorial flow chart showing the analysis of a blood sample. In step 1, blood (4–8 ml) is collected directly into a 4 or 8 ml Becton Dickinson CPT Vacutainer™ and an anticoagulant such as EDTA, acid citrate dextrose (ACD), or heparin. In an equivalent step of another embodiment of the invention, 3 ml of blood in anticoagulant is overlayed into a tube 172 containing a separation gradient 176 such as Histopaque® 1077. In any case, the blood sample 174 is preferably used within two hours of collection. The tube 172 containing the separation gradient 176 with blood sample 174 overlay is centrifuged at 400×g in a biohazard centrifuge with horizontal rotor and swing out buckets for 30 minutes at room temperature. After centrifugation, the plasma layer 178 is removed (step 2), leaving about 2 mm of plasma above the mononuclear cell (MNC) fraction 180. The MNC layer 180 is collected and washed with phosphate buffer saline (PBS). Cells are pelleted by centrifugation at 250×g for 10 minutes at room temperature to remove any remaining platelets. The supernatant is removed and the MNC pellet 180 is re-suspended in PBS by tapping the tube gently. The final pellet 180 is re-suspended (step 3) to a cell count of 10,000–30,000 cells/μl depending upon the height of the flow channel or analysis chamber 130 of the bio-disc 110.

The flow channel or analysis chamber 130 of a bio-disc 110 is flooded with 7 μl of the MNC suspension, and the inlet ports 122 and vent ports 124 (FIGS. 3 and 8) of the chamber are sealed with an adhesive tab or other suitable sealing member (step 4). The bio-disc 110 is incubated for 15 minutes at room temperature, and then scanned using a 780 nm laser in an optical drive 112 to image the capture field (step 5). It should be understood that if a transmissive bio-disc 110 is used, optical drive 112 optionally includes a top detector 158 (FIG. 10) to image the capture field. Software is preferably encoded on the disc to instruct the drive to automatically perform the following tasks: (a) centrifuge the disc to spin off excess unbound cells in one or more stages; (b) image specific capture windows on a display monitor 114; and (c) process data. Data processing includes, but is not limited to, counting the specifically captured cells in each capture zone and deriving the ratio of $CD4^+/CD8^+$ or whichever ratio is programmed to be determined. Other desired ratios may be readily provided by alternative embodiments of the present invention.

As further illustrated in FIG. 17A, the present invention is directed to a method of performing a cluster designation count with an optical disc and disc drive system. The method includes the steps of providing a blood sample in a first tube containing a separation gradient, rotating the first tube at a time and speed sufficient to separate the blood sample into layers, resuspending a MNC layer that contains T-cells to form a MNC suspension, providing a sample of the MNC suspension on a disc surface that includes at least one capture zone containing at least one capture agent, loading the disc into an optical reader, rotating the disc, directing an incident beam of electromagnetic radiation to the capture zone, detecting a beam of electromagnetic radiation formed after interacting with the disc at the capture zone, converting the detected beam into an output signal, and analyzing the output signal to extract information relating to the number of cells captured at the capture zone. In one embodiment of this method, the optical disc is constructed with a reflective layer such that light directed to the capture zone and not striking a cell is reflected. In another embodiment of this method, the optical disc is constructed such that light directed to the capture zone and not striking a cell is transmitted through the optical disc.

During the analyzing/processing step, the software reads across each capture zone image and marks cell images as it encounters them. For example, following counting of the number of captured $CD4^+$ and $CD8^+$ cells, the software calculates the ratio of $CD4^+/CD8^+$ cells and displays both the absolute numbers of cells in $CD4^+$, $CD8^+$, $CD3^+$ and $CD45^+$ capture zones per microliter of whole blood and also the $CD4^+/CD8^+$ ratio. The entire process takes about 12 minutes from inserting the disc into the optical drive to obtaining the numbers and ratios. Other related aspects regarding quantitating specific cell populations in a sample are disclosed in commonly assigned and co-pending U.S. Provisional Application Ser. No. 60/382,319 entitled "Methods For Calculating Specific Populations Of Cells Captured In An Optical Bio-Disc" filed May 22, 2002; and U.S. Provisional Application Ser. No. 60/382,944 entitled "Methods and Apparatus for Use in Detection and Quantitation of Cell Populations and Use of Optical Bio-Disc for Performing Same" filed May 24, 2002. These applications are herein incorporated by reference in their entireties.

In one embodiment, the disc is a forward Wobble Set FDL21:13707 or FDL21:1270 CD-R disc coated with 300 nm of gold as the encoded information layer. On a reflective disc, viewing windows of size 2×1 mm oval are etched out of the reflective layer by known lithography techniques. In some designs of transmissive disc, no separate viewing windows are etched, and the entire disc is available for use. In one specific embodiment, the adhesive layer is Fraylock adhesive DBL 201 Rev C 3M94661. The cover is a clear disc with 48 sample inlets with a diameter of 0.040 inches located equidistantly at radius 26 mm. The data disc is scanned and read with the software at speed 4× and sample rate 2.67 MHz using $CD4^+/CD8^+$ counting software.

Figure 17B:
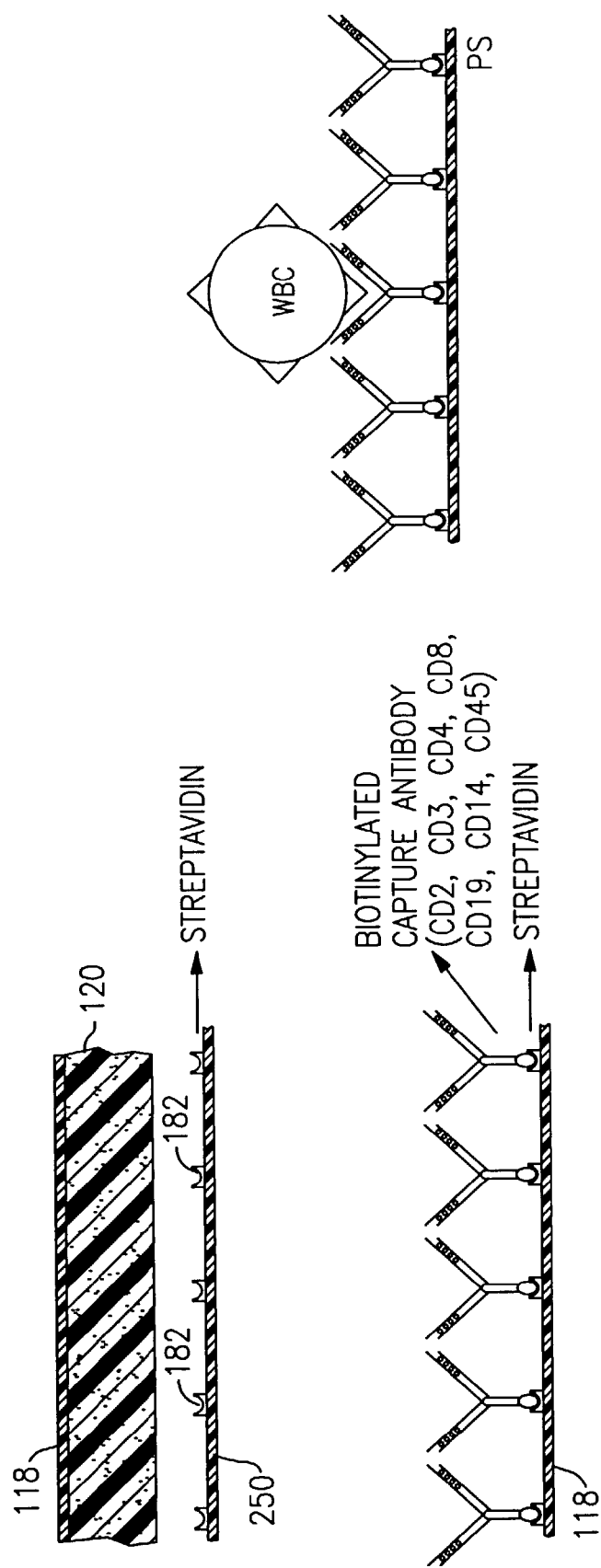
FIG. 17B is a pictorial detail view showing the attachment of antibodies to a white blood cell for use with the disc illustrated in FIG. 17A.

Referring to FIG. 17B, in one embodiment of the present invention, a thick layer of polystyrene 118 is formed over a substrate 120 and is (optionally) layered with streptavidin 182. Cell capture antibodies are attached to the strepavidin 182 through biotin. These antibodies can include biotinylated antibodies attached to Dextran-activated aldehyde coated over the streptavidin to create an ample number of binding sites for the capture antibody. This creates a strong capture chemistry that can specifically form robust bonds with white blood cells (WBCs).

Figure 18A:
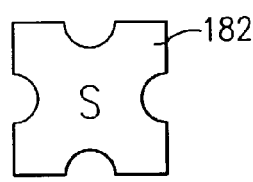
FIG. 18A is a pictorial representation of streptavidin.
Figure 18B:
FIG. 18B is a pictorial representation of biotin.
Figure 18C:
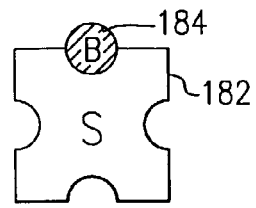
FIG. 18C is a pictorial representation of the cross-linking system consisting of streptavidin and biotin.

FIGS. 18A, 18B, and 18C are pictorial representations of a cross-linking or binding system used in an embodiment of the present invention. It should be understood that a cross-linking system involves one or more cross-linking agents, receptor-ligand agents, or conjugates, to cross-link one or more macromolecular moieties to another. A cross-link may be a covalent or non-covalent interaction between two, usually formed when two macromolecular free radicals combine. Chemical modifications or conjugation processes to achieve cross-links involve the reaction of one functional group with another, resulting in the formation of a bond. The creation of bioconjugate reagents with reactive or selectively reactive functional groups forms the basis for simple and reproducible cross-linking or tagging of target molecules ("*Bioconjugate Techniques*," Greg T. Hermanson, Academic Press, San Diego, Calif., (1996)).

Cross-linking agents include, but are not limited to homobifunctional linkers, heterobifunctional linkers, and zero-length cross-linkers. Homobifunctional linkers are linkers with two reactive sites of the same functionality, such as glutaraldehyde. These reagents could tie one protein to another by covalently reacting with the same common groups on both molecules. Heterobifunctional conjugation reagents contain two different reactive groups that can couple to two different functional targets on proteins and other macromolecules. For example, one part of a cross-linker may contain an amine-active group, while another portion may consist of a sulfhydryl-active group. The result is the ability to direct the cross-linking reaction to selected parts of target molecules, thus garnering better control over the conjugation process. Zero-length cross-linkers mediate the conjugation of two molecules by forming a bond containing no additional atoms. Thus, one atom of a molecule is covalently attached to an atom of a second molecule with no intervening linker or spacer. One of ordinary skill in the art may refer to "*Bioconjugate Techniques*," Greg T. Hermanson, Academic Press, San Diego, Calif., (1996), for a detailed description of cross-linking agents.

In the present invention, cross-linking agents are bound to the surface of a bio-disc to immobilize capture agents within the target zones. A preferred cross-linking or binding system is the heterobifunctional group consisting of biotin and avidin, i.e. biotinylated capture agents bound to an avidin-coupled substrate. FIG. 18A is a pictorial representation of avidin 182. Without limitation, avidin includes streptavidin, neutravidin and modifications, thereof. As shown, the protein comprises four subunits, each of which contains one binding site for biotin (Hermanson). Avidin 182 can be coupled to plastics such as polystyrene by various chemistries. Ideally, avidin 182 is attached to the active layer 144 (FIGS. 4 and 9) of the bio-disc, binding essentially irreversibly to biotinylated sensing elements (e.g. antibodies).

FIG. 18B is a pictorial representation of biotin 184. Biotin (or vitamin H) is a naturally occurring growth factor present in small amounts within every cell. Biotin's interaction with the proteins avidin, neutravidin, and streptavidin is among the strongest non-covalent bond known. A biotin molecule 184 may be attached directly to a protein via its valeric acid side chain or derivitized with other organic components to create spacer arms and various reactive groups. Amines, carboxylates, sulfhydryls, and carbohydrate groups can be specifically targeted for biotinylation through the appropriate choice of biotin derivative (Hermanson). FIG. 18C is a pictorial representation of the cross-linking system consisting of biotin 184 interacting with avidin 182.

Implementations of the embodiments of the invention utilize capture agents to perform the assays described herein. It should be understood that a capture agent refers to any macromolecule for detecting an analyte. The capture agents of the invention include macromolecules preferentially selective, or having a selective binding affinity, for an analyte of interest. Capture agents include, but are not limited to, synthetic or biologically produced nucleic acid and synthetic or biologically produced proteins. Examples of capture agents that can be employed by this invention, include, but are not restricted to, deoxyribonucleic acid (DNA), ribonucleic acid (RNA), oligonucleotides, polymerase chain reaction products, or a combination of these nucleotides (chimera), antibodies (monoclonal or polyclonal), cell membrane receptors, and anti-sera reactive with specific antigenic determinants (such as on viruses, cells, or other materials), drugs, peptides, co-factors, lectins, polysaccharides, cells, cellular membranes, and organelles. Preferably, capture agents of the invention are antibodies.

Antibodies include, but are not limited to polyclonal, monoclonal, and recombinantly created antibodies. Antibodies of the invention can be produced in vivo or in vitro. Methods for the production of antibodies are well known to those skilled in the art. For example, see Antibody Production: Essential Techniques, Peter Delves (Ed.), John Wiley & Son Ltd, ISBN: 0471970107 (1997), which is incorporated herein in its entirely by reference. Alternatively, antibodies may be obtained from commercial sources, e.g., Research Diagnostics Inc., Pleasant Hill Road, Flanders, N.J. 07836. Antibodies of the invention are not meant to be limited to antibodies of any one particular species; for example, antibodies of humans, mice, rats, and goats are all contemplated by the invention. Preferably, the primary antibodies of the invention are anti-human produced in mice, and the secondary antibodies of the invention are anti-mouse produced in goats.

The term "antibody" is also inclusive of any class or subclass of antibodies, as any or all antibody types may be used to bind to cell surface antigens. The use of antibodies in the art of medical diagnostics is well known to those skilled in the art. For example, see Diagnostic and Therapeutic Antibodies (Methods in Molecular Medicine), Andrew J. T. George and Catherine E. Urch (Eds.), Humana Press; ISBN: 0896037983 (2000) and Antibodies in Diagnosis and Therapy: Technologies, Mechanisms and Clinical Data (Studies in Chemistry Series), Siegfried Matzku and Rolf A. Stahel (Eds.), Harwood Academic Pub.; ISBN: 9057023105 (1999), which are incorporated entirely herein by reference.

Figure 18D:
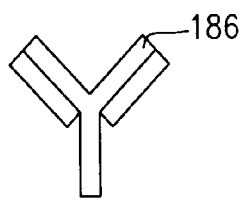
FIG. 18D is a pictorial representation of a secondary antibody.
Figure 18E:
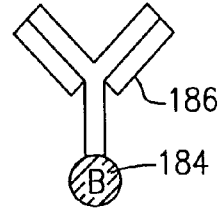
FIG. 18E is a pictorial representation of a biotinylated secondary antibody.

In at least some embodiments of the invention, a plurality of capture agents is used to detect analytes of interest. FIG. 18D is a pictorial representation of the IgG class of antibodies used in the methods of the invention as a secondary capture agent 186. It should be understood that secondary capture agents of the invention include, but are not limited to, agents having an affinity for another capture agents, which have an affinity for the analyte of interest. FIG. 18E shows the secondary capture agent IgG 186 bound to a biotin molecule 184 hereinafter referred to as biotinylated-IgG.

Figures 18F, 18G:
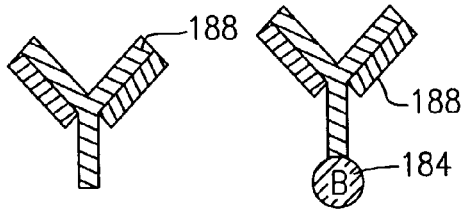
FIG. 18F is a pictorial representation of a primary antibody.
FIG. 18G is a pictorial representation of a biotinylated primary antibody.

FIG. 18F is a pictorial representation of a primary capture agent 188. It should be understood that a primary capture agent 188 of the invention has a selective affinity for the analyte of interest. Preferably, a primary capture agent is an antibody having an affinity for leukocytes. More specifically, these antibodies are directed against lymphocytes (CD2, CD19), monocytes (CD14), eosinophils (CD15), and other cell surface markers of interest. FIG. 18G shows the primary capture agent 188 bound to a biotin molecule 184. In addition to CD4 and CD8, there are antibodies against many other cell surface antigens (e.g., CD3, CD16, CD19, CD45, CD56), which can be used to identify sub-types of lymphocytes.

Figure 18H:
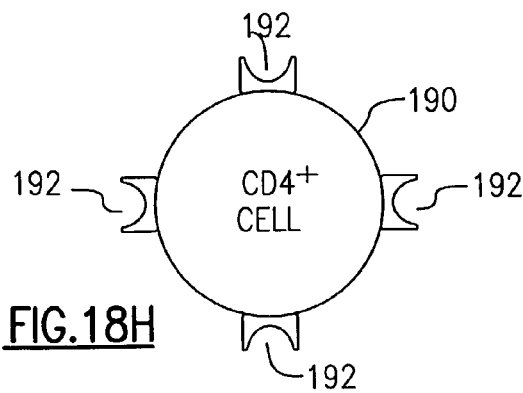
FIG. 18H is a pictorial representation of a $CD4^+$ cell showing four CD4 surface antigens.

FIG. 18H is a pictorial representation of a $CD4^+$ T-cell 190. $CD4^+$ T-cells bind to specific antigens expressed by antigen-presenting cells (APCs) such as phagocytic macrophages and dendritic cells, and release lymphokines that attract other immune system cells to the area. The result is inflammation, and the accumulation of cells and molecules that attempt to wall off and destroy the antigenic material. It should be understood that CD4+ T-cells have a multitude of antigens 192 over the entire cell surface. However, FIG. 18H shows the CD4+ T-cell 190 having four antigens 192 for illustrative purposes only.

Figure 18I:
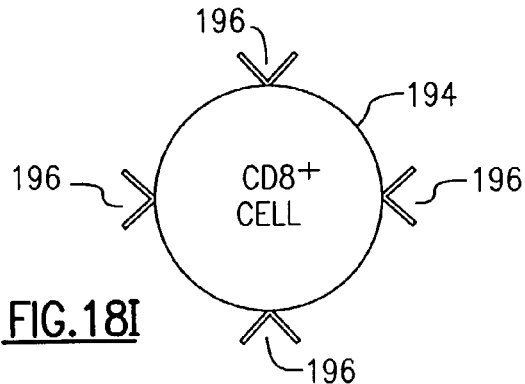
FIG. 18I is a pictorial representation of a $CD8^+$ cell showing four CD8 surface antigens.

FIG. 18I is a pictorial representation of a CD8+ T-cell 194. These T-cells secrete molecules that destroy the cell to which they have bound. This is important in fighting viral infections, as the CD8+ T-cells destroy the infected cells before they can release a fresh crop of viruses able to infect other cells. It should be understood that CD8+ T-cells have a multitude of antigens 196 over the entire cell surface. However, FIG. 18I shows the CD8+ T-cell 194 having four antigens 196 for illustrative purposes only.

Figure 18J:
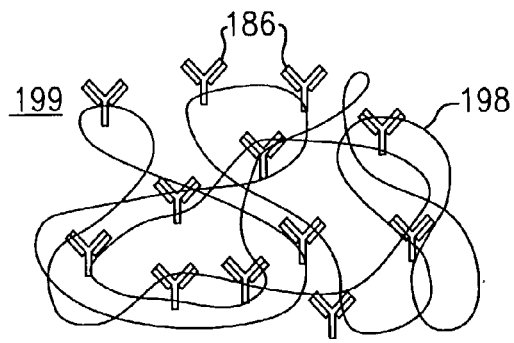
FIG. 18J is a pictorial representation showing secondary antibodies bound to aldehyde-activated dextran.
Figure 18K:
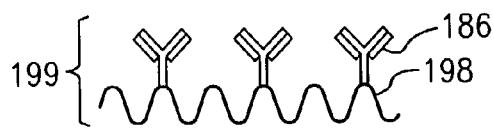
FIG. 18K is a cross-sectional pictorial representation of FIG. 18J.

FIG. 18J is a pictorial representation showing secondary antibodies 186 bound to a 3-Dimentional matrix of aldehyde-activated dextran (DCHO) 198, thereby forming a DCHO-antibody complex 199. Dextran is mainly a linear polysaccharide consisting of repeating units of D-glucose linked together by glycosidic bonds. Used extensively as a cross-linking agent, dextran is multivalent in nature, which allows molecules to be attached at numerous sites along the polymer chain (Hermanson). For illustrative purposes only, antibodies 186 bound to dextran 198 will be depicted as shown in FIG. 18K.

Aspects relating the cellular assays of the present invention are also disclosed in U.S. Provisional Application Ser. No. 60/308,176 entitled "Quantitative and Qualitative Methods for Characterizing Cancerous Blood Cells Including Leukemic Blood Samples Using Optical Bio-Disc Platform" filed Jul. 27, 2001; U.S. Provisional Application Ser. No. 60/312,248 entitled "Methods for Quantitative and Qualitative Characterization of Cancerous Blood Cells Including Lymphoma Blood Samples Using Optical Bio-Disc Platform" filed Aug. 15, 2001; U.S. Provisional Application Ser. No. 60/313,514 entitled "Methods for Specific Cell Capture by Off-Site Incubation of Primary Antibodies with Sample and Subsequent Capture by Surface-Bound Secondary Antibodies and Optical Bio-Disc Including Same" filed Aug. 20, 2001; U.S. Provisional Application Ser. No. 60/313,715 entitled "RBC Lysis Protocol Evaluations of Helper/Inducer-Suppressor/Cytotoxic T-Lymphocytes Using Whole Blood and Related Optical Bio-Disc" filed Aug. 20, 2001; U.S. Provisional Application Ser. No. 60/313,536 entitled "RBC Sieving Protocol Evaluations of Helper/Inducer-Suppressor/Cytotoxic T-Lymphocytes Using Whole Blood and Related Optical Bio-Disc" filed Aug. 20, 2001; and U.S. Provisional Application Ser. No. 60/315,937 entitled "Quantitative and Qualitative Methods for Cell Isolation and Typing Including Immunophenotyping" filed Aug. 30, 2001, all of which are herein incorporated by reference.

Implementation I

Figure 19A:
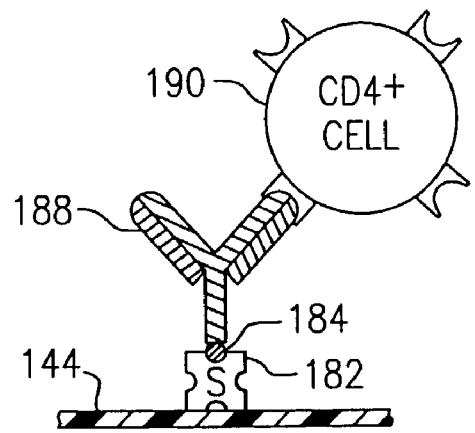
FIGS. 19A and 19B are pictorial representations showing cell capture by a primary antibody that is bound to a substrate by a cross-linking system in a first implementation of the invention.
Figure 19B:
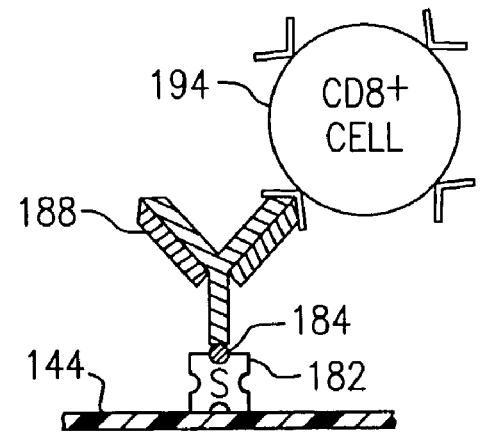
Figure 19C:
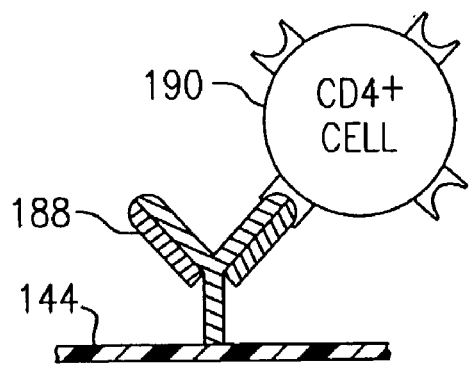
FIGS. 19C and 19D are pictorial representations showing cell capture by a primary antibody that is directly bound to a substrate in a first implementation of the invention.
Figure 19D:
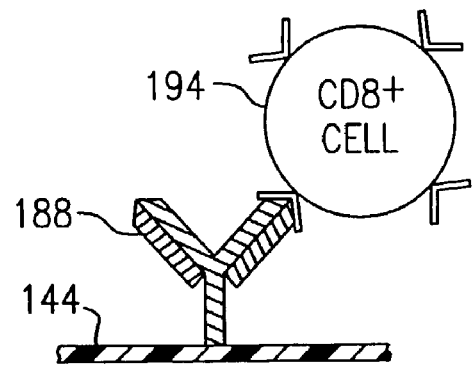

FIGS. 19A–19D are pictorial representations of analyte capture in a first implementation of the invention. FIGS. 19A and 19B show capture of CD4+ T-cells 190 and CD8+ T-cells 194 by biotinylated primary antibodies (FIG. 18G). The antibodies 188 are immobilized on the active layer 144 of the bio-disc 110 (FIGS. 4 and 9) by the cross-linking agent streptavidin 182. FIGS. 19C and 19D show another embodiment of the same implementation of the invention without a cross-linking system. In this embodiment, primary antibodies 188 are immobilized directly on the active layer 144 of the bio-disc 110.

Figure 20D:
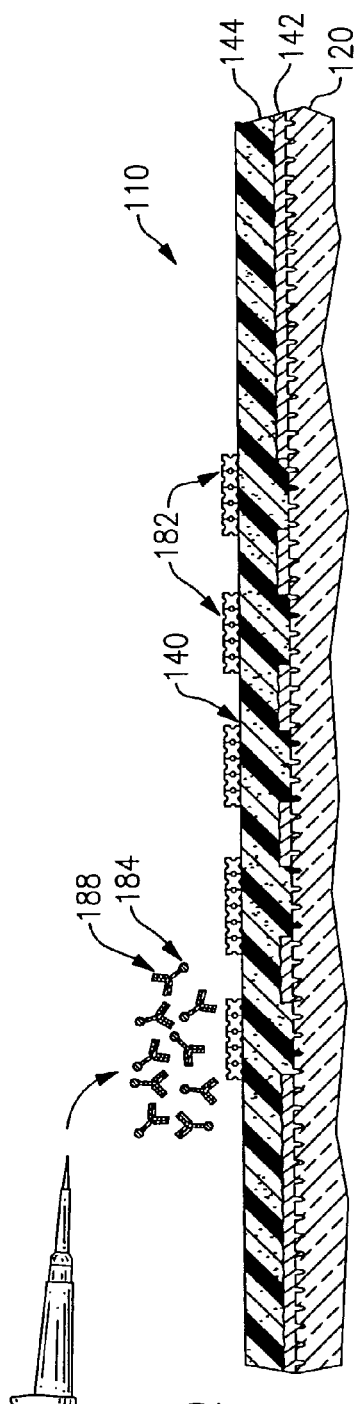
Figure 20E:
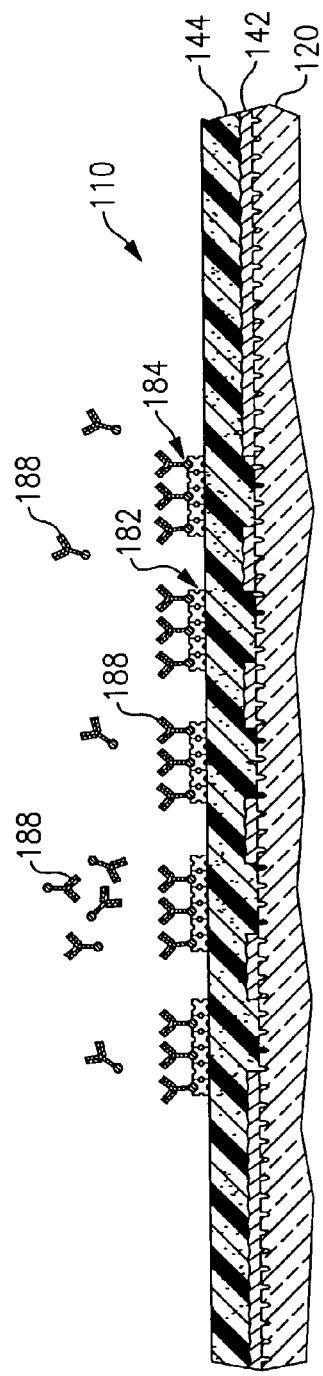
Figure 20F:
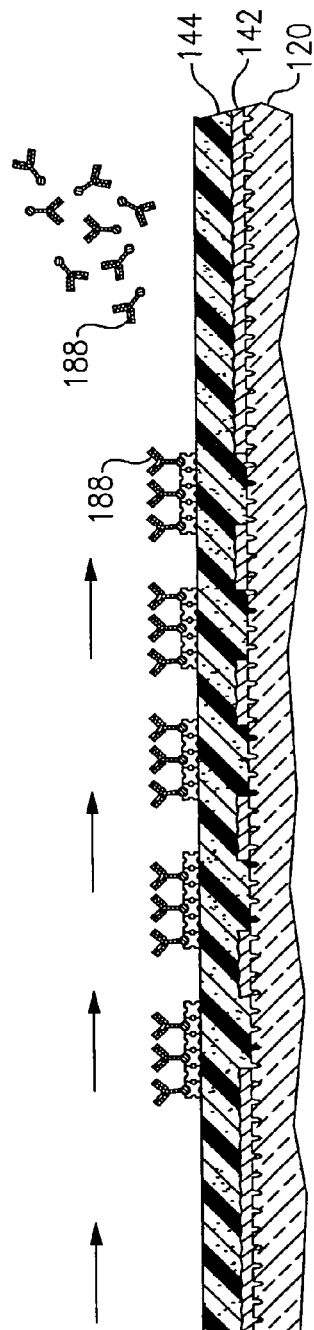
Figure 20G:
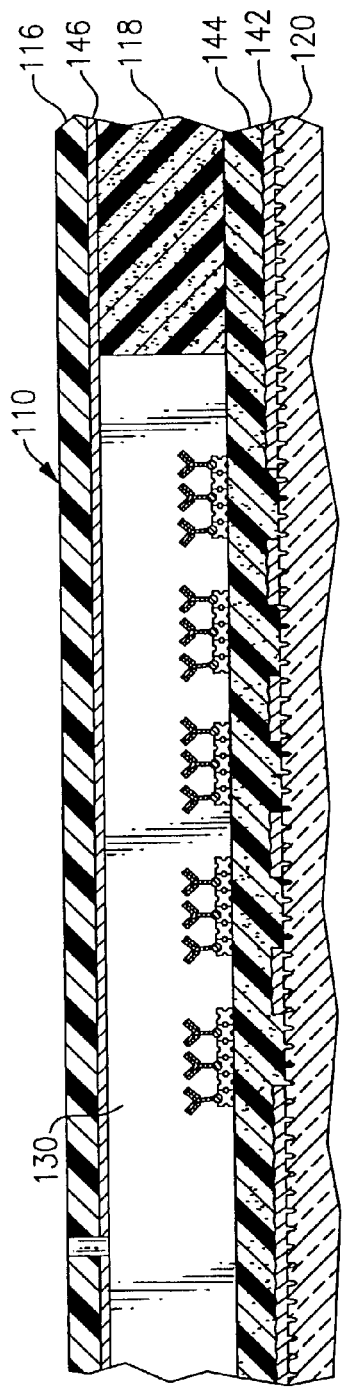
Figure 20H:
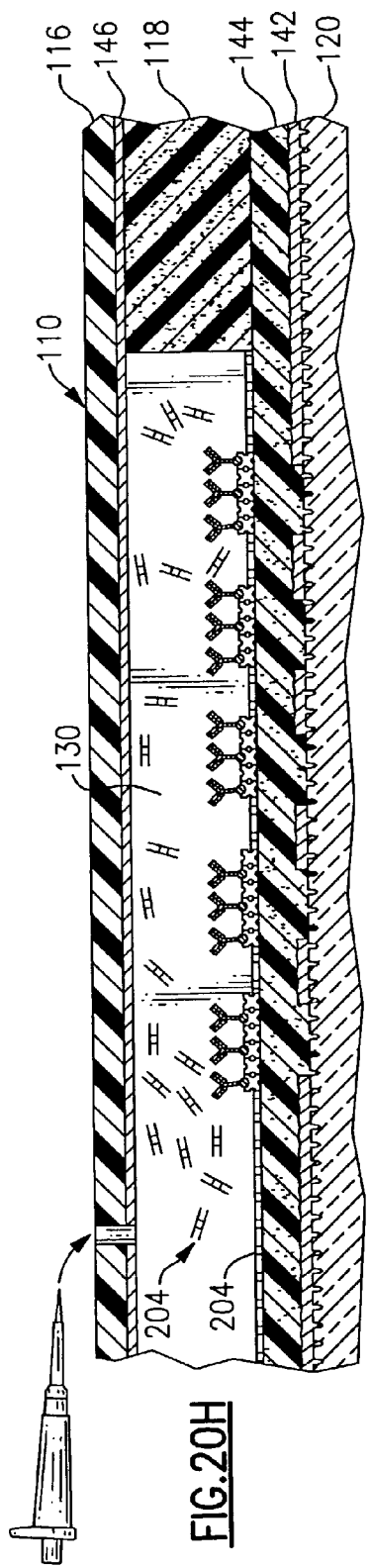
Figure 20I:
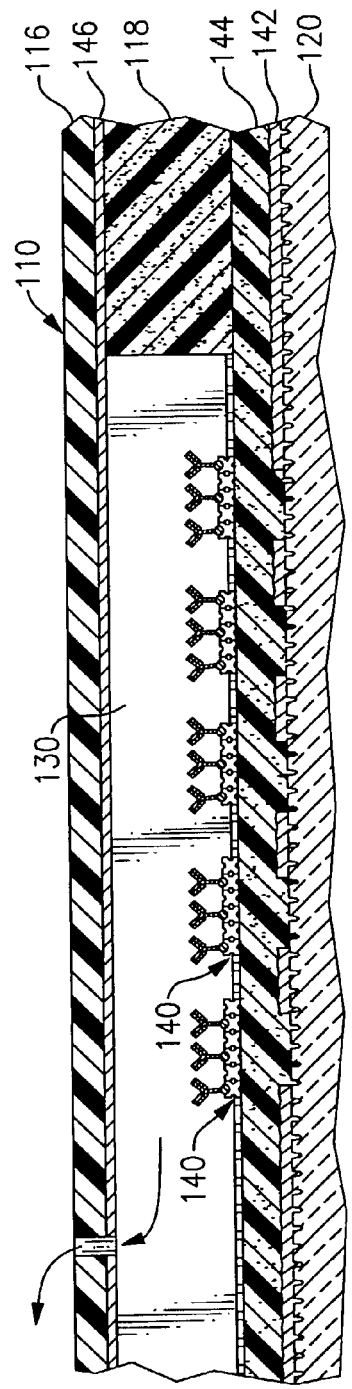

FIGS. 20A–20I are cross-sectional views showing construction of an embodiment of the first implementation of the invention. The first embodiment involves construction of a reflective disc utilizing a cross-linking system to immobilize the capture agents within the flow channels of the bio-disc. Referring to FIG. 20A, a light-transparent substrate 120, a reflective layer 142, and an active layer 144 of an optical bio-disc 110 are shown. Portions of reflective layer 142 are removed (or openings were created when deposited) to produce viewing windows 200 through which light can be directed at the locations of capture zones 140 where the antibodies are to be affixed. FIG. 20A shows five such capture zones 140, the first thereof indicated as capture zone 141. The active layer 144 is preferably polystyrene, which is spin-coated, or otherwise deposited by methods known in the art, over the reflective layer 142 to form a smooth surface with a thickness of about 40 to 300 microns. Streptavidin 182 is then deposited over each capture zone 140 and 141, and the disc 110 is incubated at room temperature in a humidity chamber for 30 minutes (FIG. 20B). The disc 110 is washed to remove unbound streptavidin 182, and then spin-dried to completely remove moisture from the surface of the disc 110 (FIG. 20C). A reference mark or calibration dot 202 is deposited over the first capture zone 141 and biotinylated primary antibodies 188 are deposited over each successive capture zone 140 (FIGS. 20D and 20E). The disc 110 is then incubated at room temperature in a humidity chamber for 30 minutes. Unbound antibodies 188 are removed with a PBS wash, and the disc 110 is spin-dried to remove surface moisture (FIG. 20F). An adhesive member 118 is attached to the active layer 144 (FIG. 20G). A cover disc or cap portion 116 (FIG. 2) may be formed from polycarbonate and is preferably coated with a reflective surface 146 on the bottom as best shown in FIG. 4. The cover disc 116 is integrally attached to adhesive member 118 thereby forming flow channels 130 within the disc (FIG. 20G). A blocking agent 204, such as StabilGuard®, is injected into each flow channel or analysis chamber 130 to quickly and effectively block any remaining nonspecific binding sites of the active layer 144 (FIG. 20H). The disc 110 is incubated at room temperature in a humidity chamber for a predetermined time of preferably 30 minutes, and any remaining solution is completely removed via vacuum (FIG. 20I).

Figure 21:
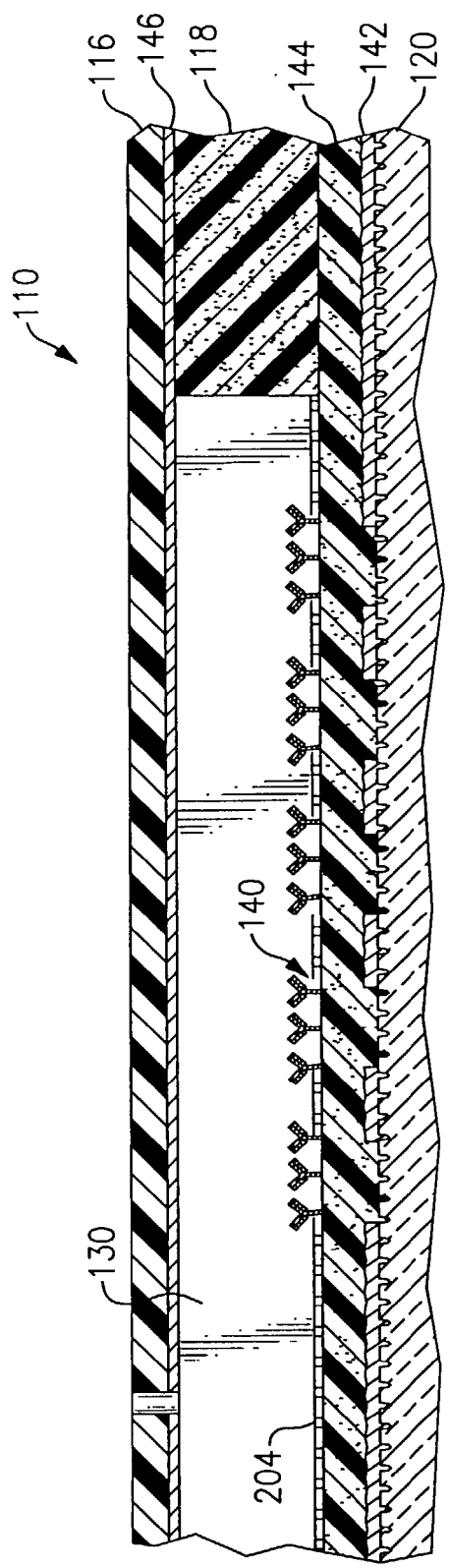
FIG. 21 is an alternate embodiment of the reflective disc shown in FIGS. 20A–20I without use of the cross-linking system.

A second embodiment of the first implementation of the invention involves construction of a reflective disc 110 without the use of a cross-linking system to immobilize the capture agents within the flow channels 130 of the bio-disc 110. In this embodiment, a reference mark or calibration dot 202 is deposited over the first window 141 and non-biotinylated primary antibodies 188 (FIG. 18F) are deposited directly onto the active layer 144 (FIG. 20A) over each successive capture zone 140. The disc 110 is then incubated at room temperature in a humidity chamber for preferably 30 minutes (FIG. 20E). Unbound antibodies 188 are removed with a PBS wash, and the disc 110 is spin-dried to remove surface moisture (FIG. 20F). The adhesive member 118 is attached to the active layer 144. A cover disc or cap portion 116 (FIG. 2) may be formed from polycarbonate and is preferably coated with a reflective surface 146 on the bottom as best shown in FIG. 4. The cover disc 116 is integrally attached to adhesive member 118 thereby forming flow channels 130 within the disc (FIG. 20G). A blocking agent 204, such as StabilGuard®, is injected into each flow channel or analysis chamber 130 to quickly and effectively block any remaining nonspecific binding sites of the active layer 144 (FIG. 20H). The disc is incubated at room temperature in a humidity chamber for 30 minutes, and any remaining solution is completely removed via vacuum (FIG. 20I). FIG. 21 shows a cross-sectional view of the completed reflective bio-disc 110 without use of a cross-linking system.

Figure 22:
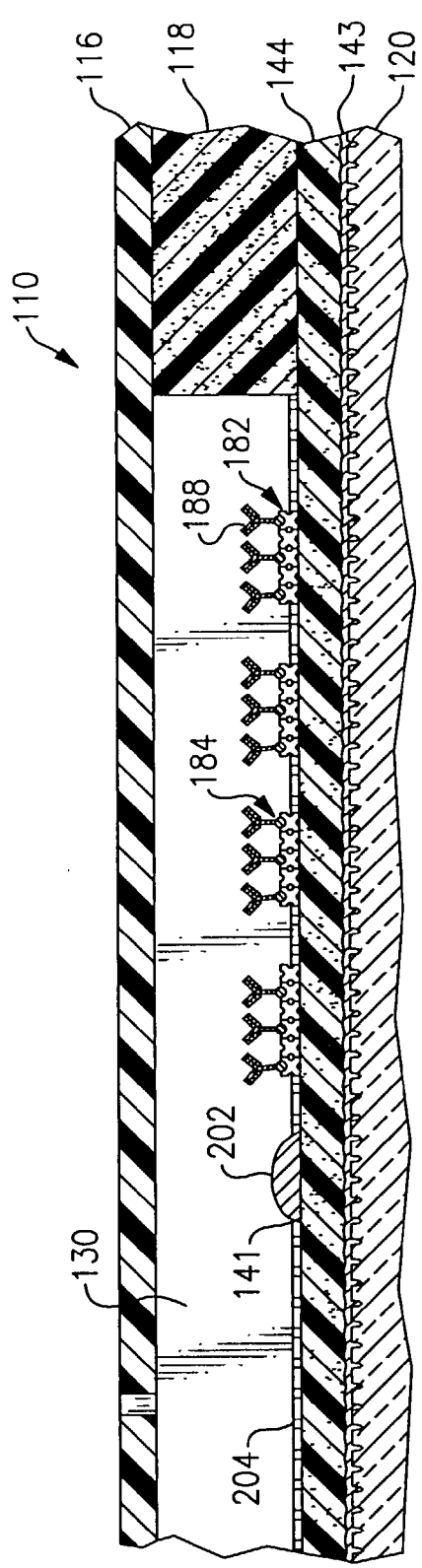
FIG. 22 shows the capture chemistries utilized in FIGS. 20A–20I as implemented in a transmissive disc format.

A third embodiment of the first implementation of the invention involves construction of a transmissive disc 110 utilizing a cross-linking system to immobilize the capture agents within the flow channels 130 of the bio-disc 110. In this embodiment, the substrate 120, semi-reflective layer 143 without viewing windows 200 (FIG. 20A), and active layer 144 are presented as shown in FIG. 5. Deposition of streptavidin 182, biotinylated primary antibodies 188, reference dot 202, and blocking agent 204 are as described above, and as shown in FIGS. 20B–20H. A respective adhesive member 118 is attached to the active layer 144. An optically transparent cover disc or cap portion 116 (FIG. 5) may be formed from polycarbonate. The cover disc 116 is integrally attached to adhesive member 118 thereby forming flow channels 130 within the disc 110 (FIG. 20G). FIG. 22 shows a cross-sectional view of the completed transmissive bio-disc 110 utilizing a cross-linking system. It should be understood that a fourth embodiment of the first implementation may be constructed by those skilled in the art. The fourth embodiment involves construction of a transmissive disc 110 without the use of a cross-linking system to immobilize the capture agents within the flow channels of the bio-disc 110 (FIGS. 21 and 22).

Implementation II

Figure 23A:
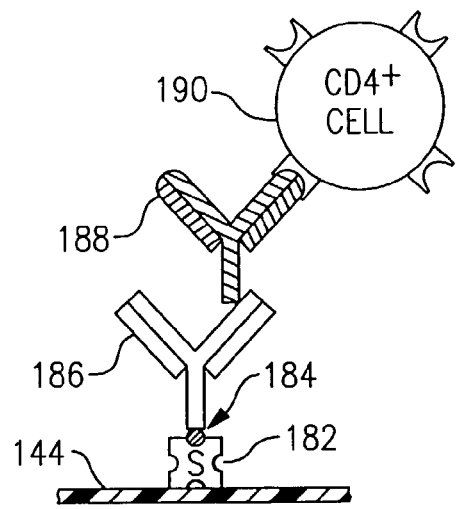
FIGS. 23A and 23B are pictorial representations showing cell capture by a primary antibody that is bound to a secondary antibody, which is bound to a substrate by a cross-linking system in a second implementation of the invention.
Figure 23B:
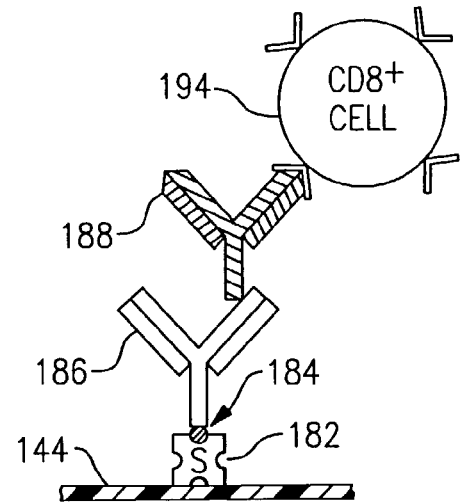
Figure 23C:
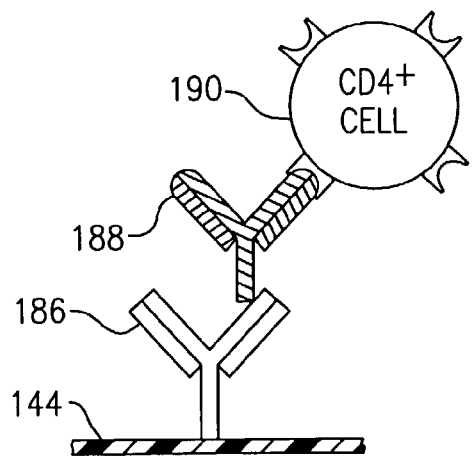
FIGS. 23C and 23D are pictorial representations showing cell capture by a primary antibody that is bound to a secondary antibody, which is directly bound to a substrate in a second implementation of the invention.
Figure 23D:
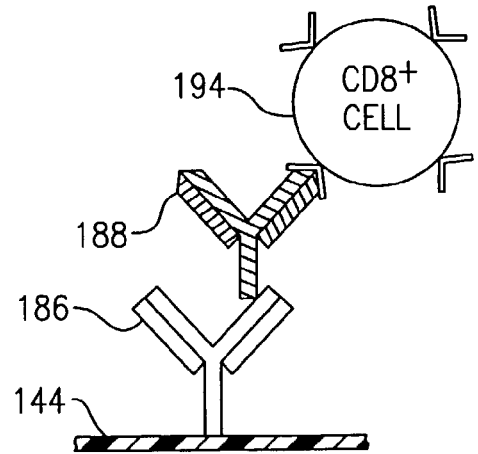

FIGS. 23A–23D are pictorial representations of analyte capture in a second implementation of the invention. FIGS. 23A and 23B show capture of CD4+ T-cells 190 and CD8+ T-cells 194 by primary antibodies 188 (FIG. 18F). The primary antibodies 188 are bound to biotinylated secondary antibodies 186 (FIG. 18E) immobilized on the active layer 144 of the bio-disc 110 (FIGS. 4 and 9) by the cross-linking agent streptavidin 182. FIGS. 23C and 23D show another embodiment of the same implementation of the invention without a cross-linking system. In this embodiment, the secondary antibodies 186 are immobilized directly on the active layer 144 of the bio-disc 110.

Figure 24A:
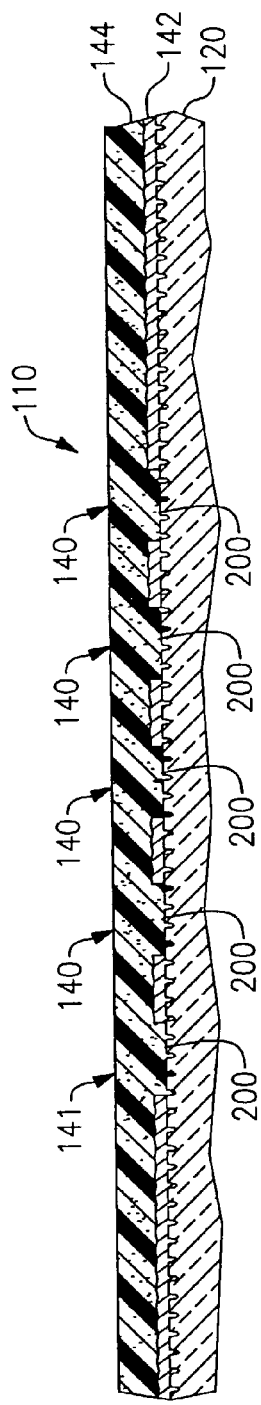
Figure 24B:
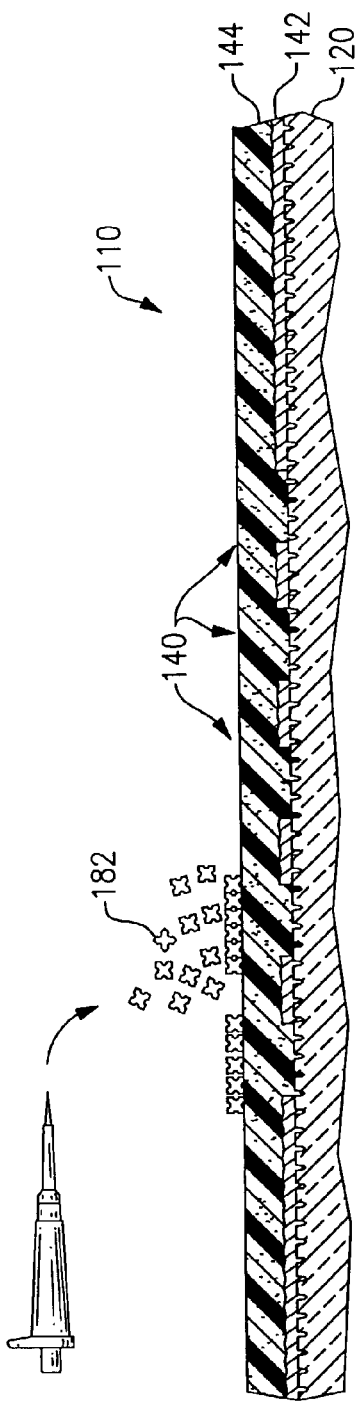
Figure 24C:
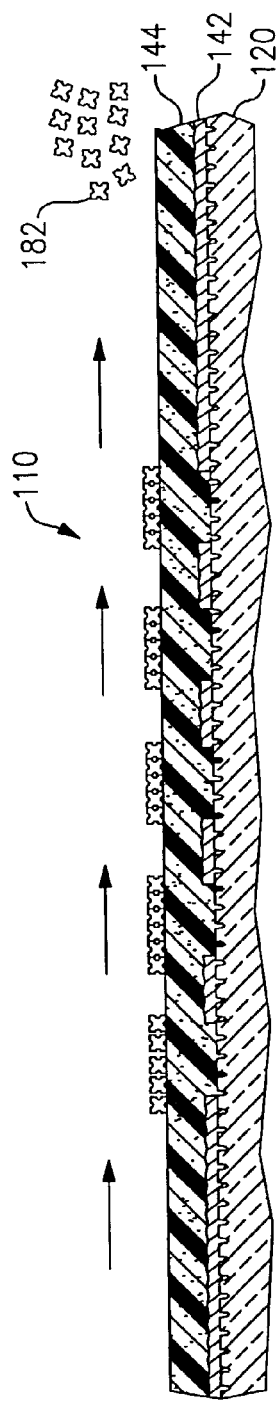
Figure 24D:
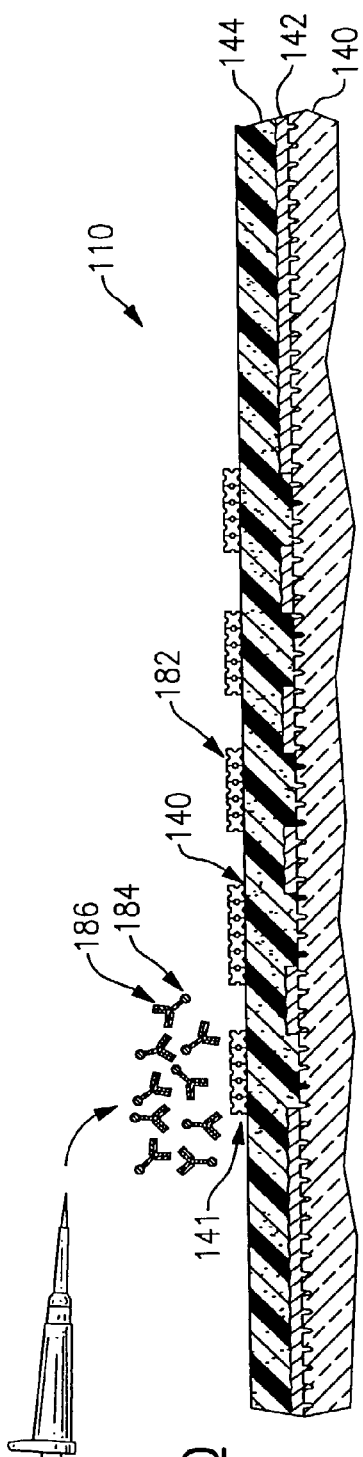
Figure 24E:
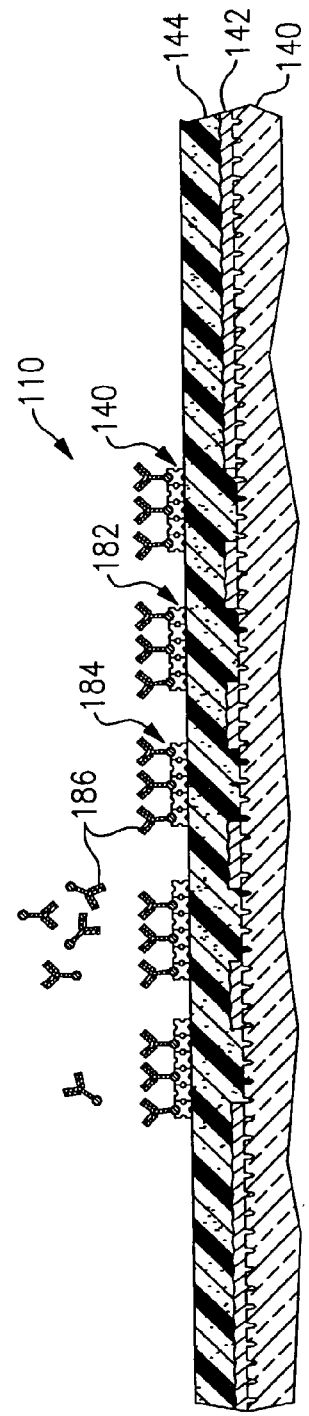
Figure 24F:
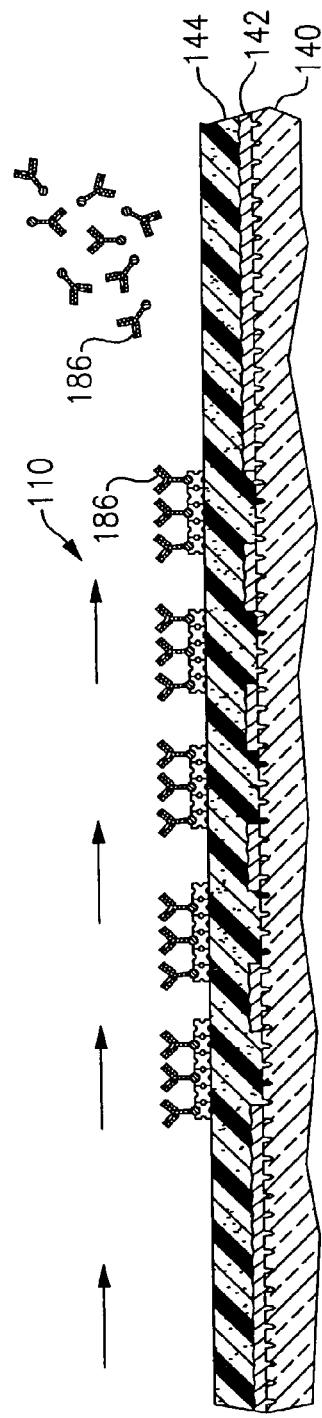
Figure 24J:
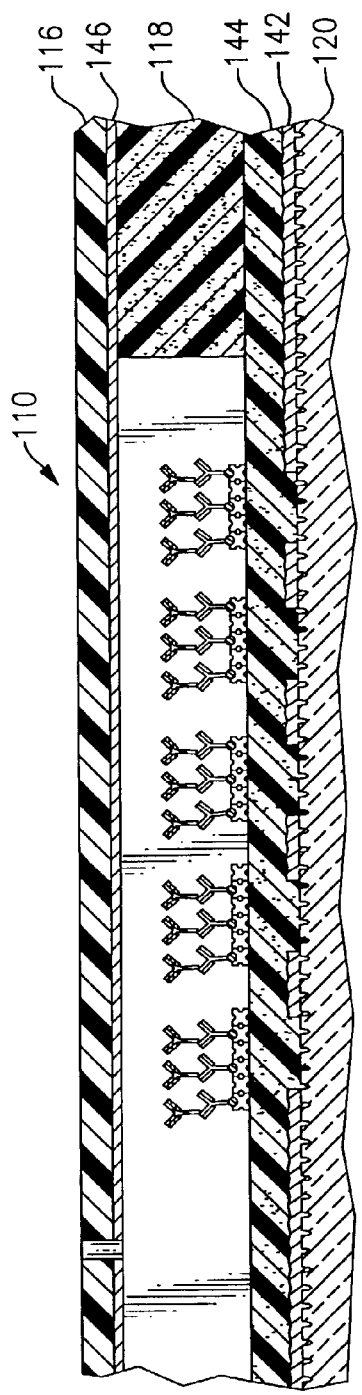
Figure 24K:
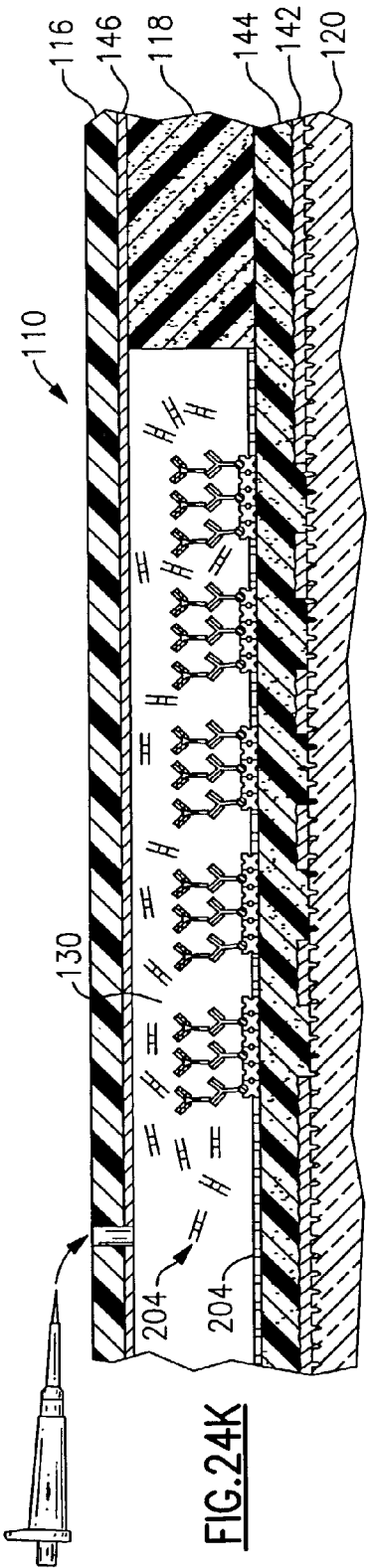
Figure 24L:
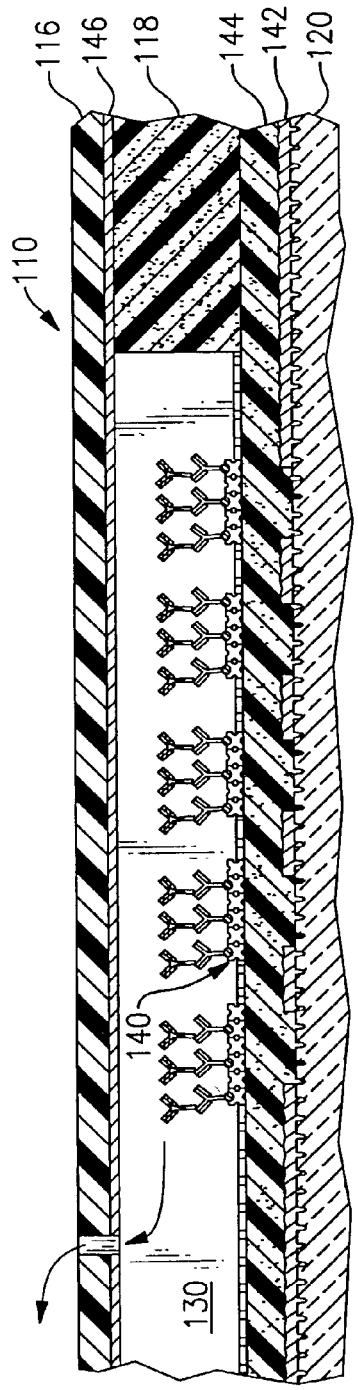

FIGS. 24A–24L are cross-sectional views showing construction of an embodiment of the second implementation of the invention. The first embodiment involves construction of a reflective disc utilizing a cross-linking system to immobilize the capture agents within the flow channels 130 of the bio-disc 110. Referring to FIG. 24A, a light-transparent substrate 120, a reflective layer 142, and an active layer 144 of an optical bio-disc 110 are shown. Portions of reflective layer 142 are removed (or openings were created when deposited) to produce viewing windows 200 through which light can be directed at the locations of capture zones 140 where the antibodies are to be affixed. FIG. 24A shows five such capture zones 140, the first thereof being designated as capture zone 141. The active layer 144 is preferably polystyrene, which is spin-coated over the reflective layer 142 to form a smooth surface with a thickness of about 40 to 300 microns. Streptavidin 182 is then deposited over each capture zone 140 and 141, and the disc 110 is incubated at room temperature in a humidity chamber for approximately 30 minutes (FIG. 24B). The disc 110 is washed to remove unbound streptavidin 182, and then spin-dried to completely remove moisture from the surface of the disc 110 (FIG. 24C). A reference mark or calibration dot 202 is deposited over the first capture zone 141 and biotinylated secondary antibodies 186 are deposited over each successive capture zone 140 (FIGS. 24D and 24E). The disc 110 is then incubated at room temperature in a humidity chamber for preferably 30 minutes (FIG. 24E). Unbound secondary antibodies 186 are removed with a PBS wash, and the disc 110 is spin-dried to remove surface moisture (FIG. 24F). Primary antibodies 188 (FIG. 18F) then are deposited over each capture zone 140 (FIG. 24G). The disc 110 is then incubated at room temperature in a humidity chamber for approximately 30 minutes (FIG. 24H). Unbound primary antibodies 188 are removed with a PBS wash, and the disc 110 is spin-dried to remove surface moisture (FIG. 24I). A respective adhesive member 118 is attached to the active layer 144. The cover disc or cap portion 116 (FIG. 2) may be similarly formed from polycarbonate and is preferably coated with the reflective surface 146 on the bottom as best shown in FIG. 4. The cover disc 116 is integrally attached to adhesive member 118 thereby forming flow channels 130 within the disc (FIG. 24J). A blocking agent 204, such as StabilGuard®, is injected into each flow channel or analysis chamber 130 to quickly and effectively block any remaining nonspecific binding sites of the active layer 144 (FIG. 24K). The disc 110 is incubated at room temperature in a humidity chamber for 30 minutes, and any remaining solution is completely removed via vacuum (FIG. 24L).

A second embodiment of the second implementation of the invention involves construction of a reflective disc 110 without the use of a cross-linking system to immobilize capture agents within the flow channels 130 of the bio-disc 110. In this embodiment, a reference mark or calibration dot 202 is deposited over the first window 141 and non-biotinylated secondary antibodies 186 (FIG. 18D) are deposited directly onto the active layer 144 (FIG. 24A) over each successive capture zone 140. The disc 110 is then incubated at room temperature in a humidity chamber for 30 minutes (FIG. 24E). Unbound secondary antibodies 186 are removed with a PBS wash, and the disc 110 is spun-dried to remove surface moisture (FIG. 24F). Primary antibodies 188 (FIG. 18F) then are deposited over each capture zone 140 (FIG. 24G). The disc 110 is then incubated at room temperature in a humidity chamber for 30 minutes (FIG. 24H). Unbound primary antibodies 188 are removed with a PBS wash, and the disc 110 is spin-dried to remove surface moisture (FIG. 24I). An adhesive member 118 is attached to the active layer 144. As with the prior embodiments, the cover disc or cap portion 116 of this embodiment may be formed from polycarbonate and is preferably coated with a reflective surface 146 on the bottom as best shown in FIG. 4. The cover disc or cap portion 116 is integrally attached to adhesive member 118 thereby forming flow channels 130 within the disc (FIG. 24J). A blocking agent 204, such as StabilGuard®), is injected into each flow channel or analysis chamber 130 to quickly and effectively block any remaining nonspecific binding sites of the active layer 144 (FIG. 24K). The disc is incubated at room temperature in a humidity chamber for preferably 30 minutes in this embodiment, and any remaining solution is completely removed via vacuum (FIG. 24L). FIG. 25 shows a cross-sectional view of the completed reflective bio-disc 110 without use of a cross-linking system.

A third embodiment of the second implementation of the invention involves construction of a transmissive disc 110 utilizing a cross-linking system to immobilize the capture agents within the flow channels 130 of the bio-disc 110. In this embodiment, the substrate 120, semi-reflective layer 143 without viewing windows 200 (FIG. 24A), and active layer 144 are presented as shown in FIG. 5. Deposition of streptavidin 182, biotinylated secondary antibodies 186, primary antibodies 188, reference dot 202, and blocking agent 204 are as described above, and as shown in FIGS.

24B–24K. The adhesive member 118 is attached to the active layer 144 in a similar manner. The optically transparent cover disc or cap portion 116 (FIG. 5) may be formed from polycarbonate. The cover disc 116 is integrally attached to adhesive member 118 thereby forming flow channels 130 within the disc 110 (FIG. 24J). FIG. 26 shows a cross-sectional view of the completed transmissive bio-disc 110 utilizing a cross-linking system. It should be understood that a fourth embodiment of this second implementation may be constructed by those skilled in the art. The fourth embodiment involves construction of a transmissive disc 110 without the use of a cross-linking system to immobilize the capture agents within the flow channels of the bio-disc 110 (FIGS. 21 and 22).

Implementation III

FIGS. 27A–27D are pictorial representations of analyte capture according to a third implementation of the present invention. FIGS. 27A and 27B show capture of $CD4^+$ T-cells 190 and $CD8^+$ T-cells 194 by primary antibodies 188 (FIG. 18F). The primary antibodies 188 are bound to secondary antibodies 186 (FIG. 18D), which are bound to a strand of DCHO 198 to form a DCHO-antibody complex 199 as shown below in FIG. 28A. The DCHO-antibody complex 199 may contain one or more antibodies cross-linked by the DCHO 198. The DCHO-antibody complex 199 is immobilized on the active layer 144 through binding of some of the secondary antibodies 186 to the active layer 144 of the bio-disc 110 (FIGS. 4 and 9). FIGS. 27C and 27D show another embodiment of the same implementation of the invention without the secondary antibodies 186. In this embodiment, the primary antibodies 188 are bound directly to the DCHO to form the DCHO-antibody complex 199, which is immobilized on the active layer 144 of the bio-disc 110.

Figure 28A:
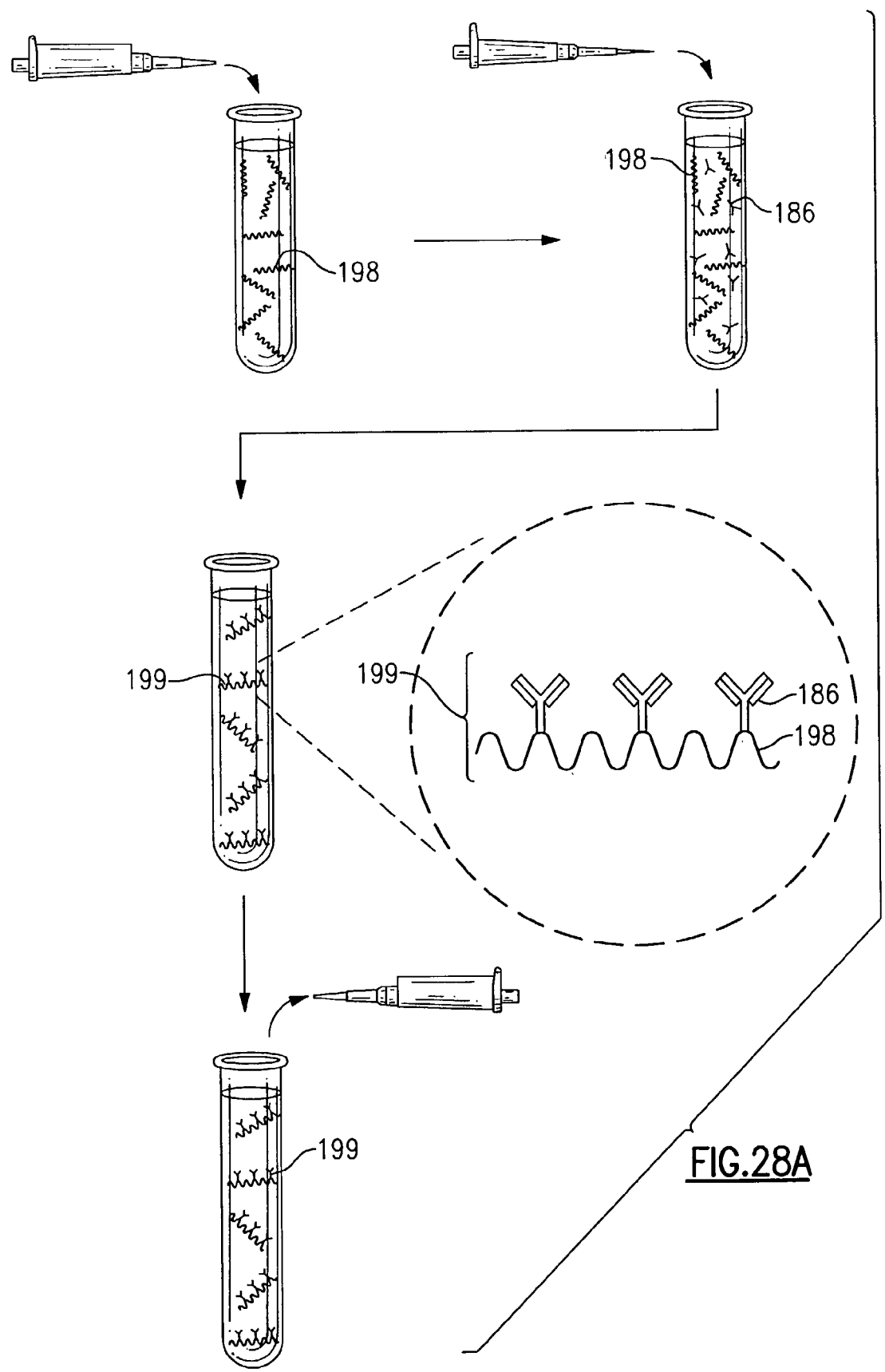
FIG. 28A is a pictorial flow diagram showing preparation of antibody-DCHO complexes.
Figure 28B:
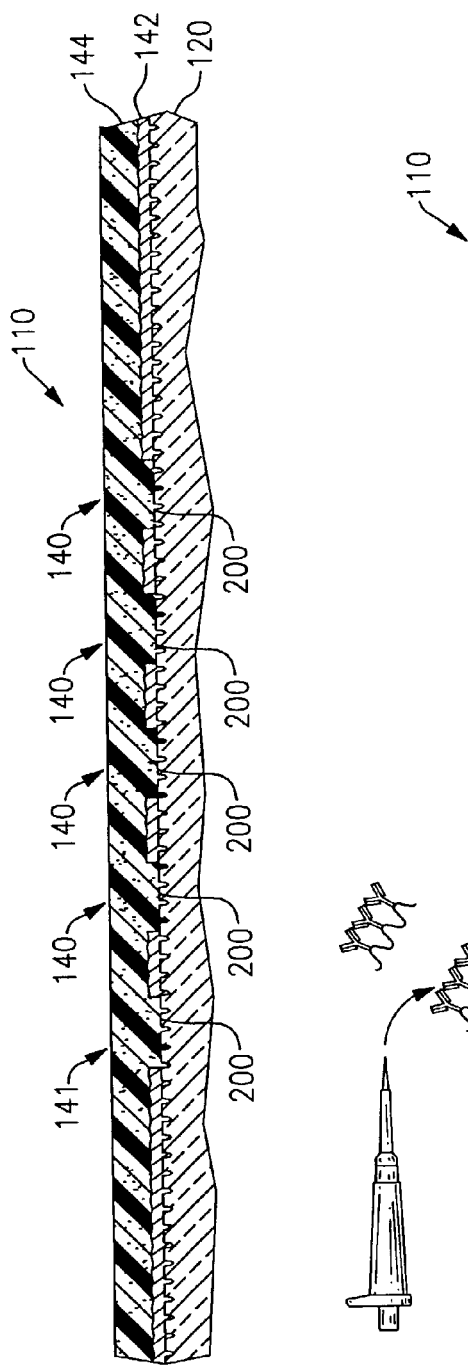
FIGS. 28B–28J are cross-sectional side views showing embodiments of a second implementation of a method of depositing capture agents onto the capture zones of a reflective bio-disc using primary and secondary antibodies and a strand of DCHO.
Figure 28C:
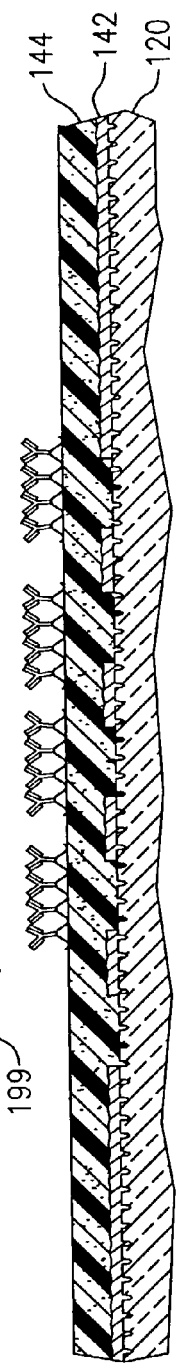
Figure 28D:
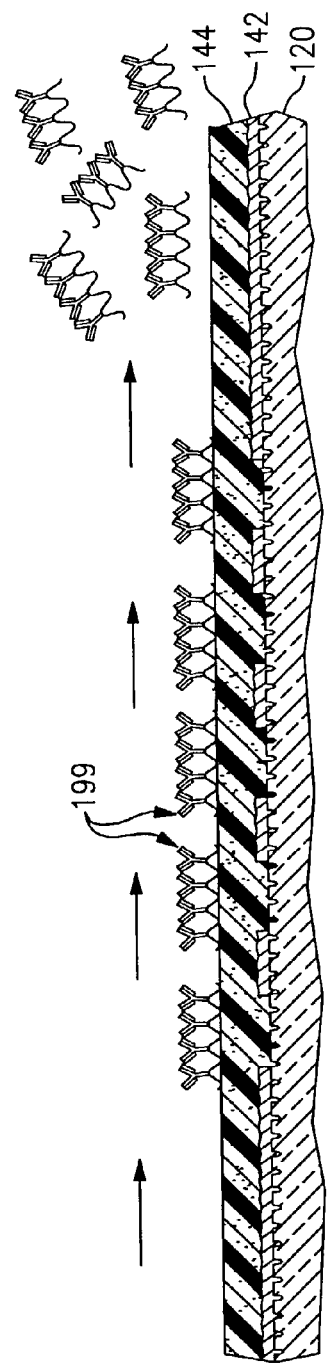
Figure 28E:
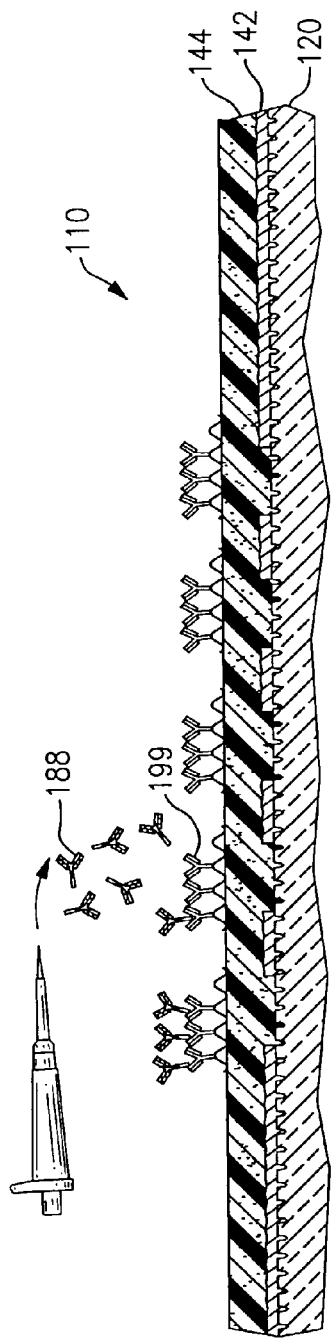
Figure 28F:
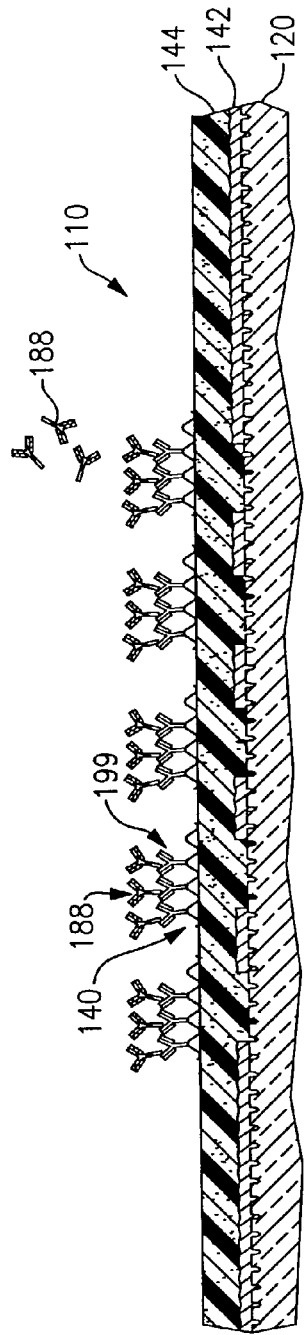
Figure 28G:
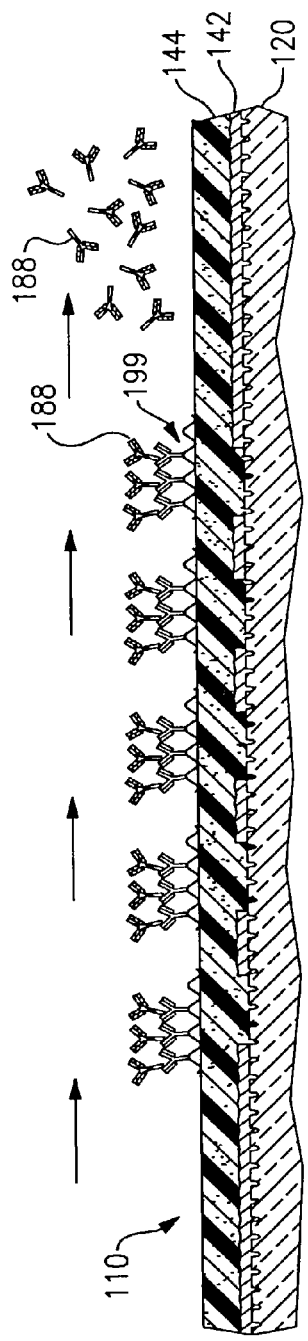
Figure 28H:
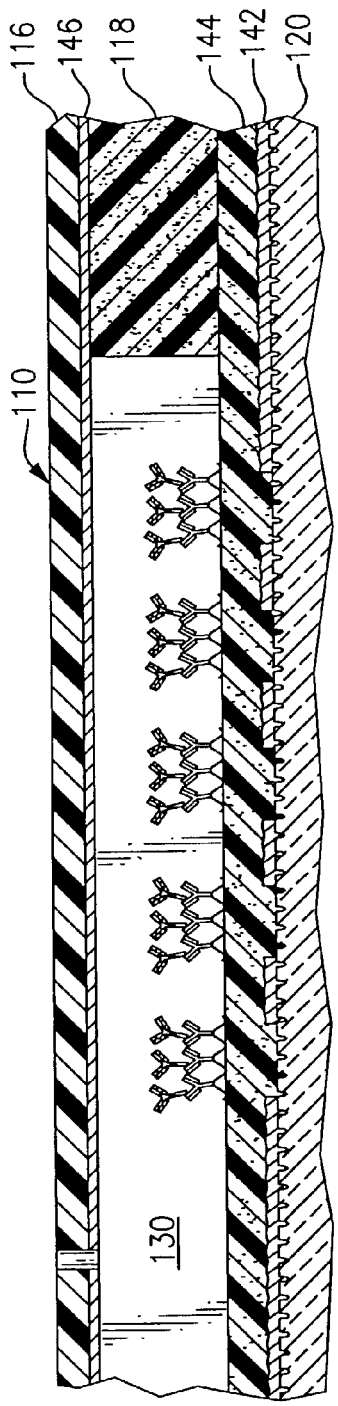
Figure 28I:
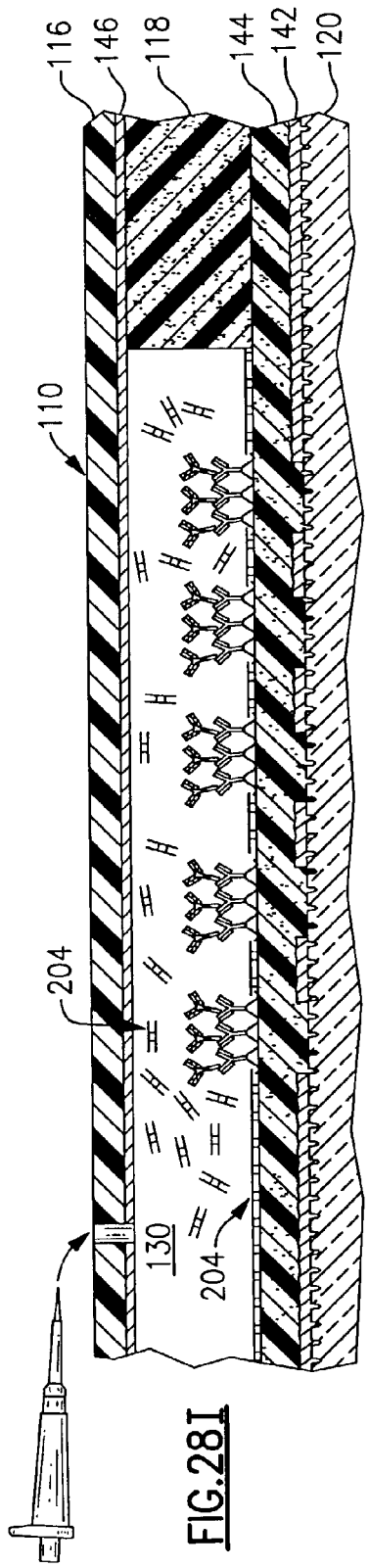
Figure 28J:
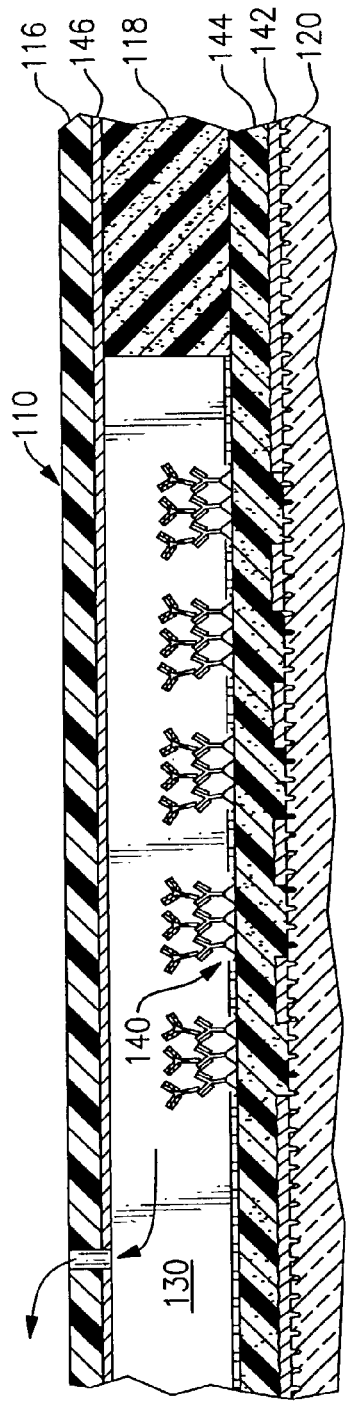

FIG. 28A is a pictorial flow diagram showing preparation of antibody-DCHO complexes while FIGS. 28B–28J are multiple views showing construction of an embodiment of the third implementation of the invention. The first embodiment of this third implementation involves construction of a reflective disc utilizing the cross-linking agent DCHO to cross-link two or more capture agents. FIG. 28A shows preparation of the DCHO-antibody complex 199. Equal concentrations of DCHO 198 and secondary antibodies 186 are mixed and allowed to combine, thereby forming the DCHO-antibody (secondary) complex 199. Referring to FIG. 28B, a light-transparent substrate 120, a reflective layer 142, and an active layer 144 of an optical bio-disc 110 are shown. Portions of reflective layer 142 are removed (or opening created when deposited) to produce viewing windows 200 through which light can be directed at the locations of capture zones 140 where the antibodies are to be affixed. FIG. 28B shows five such capture zones 140, the first thereof indicated as capture zone 141. The active layer 144 is preferably polystyrene, which is spin-coated over the reflective layer 142 to form a smooth surface with a thickness of about 40 to 300 microns. DCHO-antibody complex (secondary) 199 is then deposited over each capture zone 140, and the disc 110 is incubated at room temperature in a humidity chamber for 30 minutes in this specific embodiment (FIG. 28C). The disc 110 is washed to remove unbound DCHO-antibody complex (secondary) 199, and then spin-dried to completely remove moisture from the surface of the disc 110 (FIG. 28D). A reference dot 202 is deposited over the first capture zone 141 and primary antibodies 188 are deposited over each successive capture zone 140 (FIG. 28E). The disc 110 is then incubated at room temperature in a humidity chamber for 30 minutes (FIG. 28F). Unbound primary antibodies 188 are removed with a PBS wash, and the disc 110 is spin-dried to remove surface moisture (FIG. 28G). The adhesive member or channel layer 118 is attached to the active layer 144. As with the above embodiments, the cover disc or cap portion 116 generally shown in FIG. 2 may be formed from polycarbonate and is preferably coated with a reflective surface 146 on the bottom as best shown in FIG. 4. In the present embodiment, the cover disc or cap portion 116 is integrally attached to adhesive member 118 thereby forming flow channels 130 within the disc as illustrated in FIG. 28H. A blocking agent 204, such as StabilGuard®, is injected into each flow channel or analysis chamber 130 to quickly and effectively block any remaining nonspecific binding sites of the active layer 144. This step is shown in FIG. 28I. The disc 110 is incubated at room temperature in a humidity chamber for approximately 30 minutes in this embodiment, and any remaining solution is completely removed via vacuum as represented in FIG. 28J.

According to the manufacturing aspects of this invention, FIGS. 28A–28J also show a method of making an optical assay disc for performing a cluster designation count. This method of making an optical assay disc includes the steps of providing a cross-linker in a tube, adding a capture agent to the tube, allowing the cross-linker and the capture agent to combine (forming a complex), providing a substrate, coating the substrate with an active layer, depositing the complex onto the active layer, and attaching a cover disc or cap portion to the active layer using an adhesive member. In this embodiment, the cross-linker is aldehyde-activated dextran. The capture agents are for binding with cell surface antigens. In an alternate embodiment, the capture agents are for binding with primary capture agents having a selective affinity for cell surface antigens. In a preferred embodiment, the cell surface antigens are independently selected from the CD family of antigens. In a more preferred embodiment, the cell surface antigens are independently selected from the group consisting of CD3, CD4, CD8, and CD45.

Figure 29:
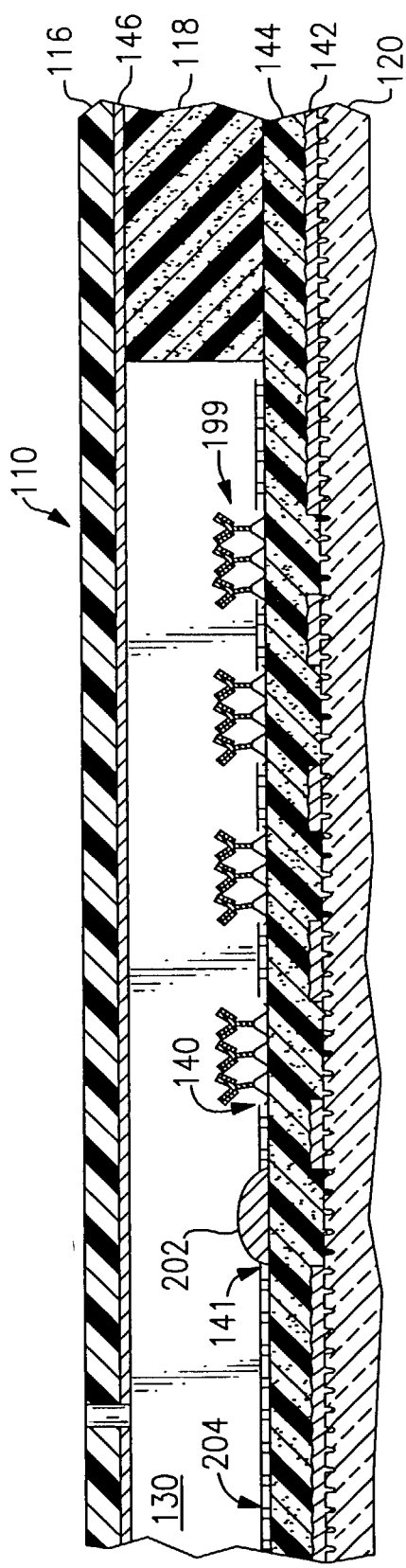
FIG. 29 is an alternate embodiment of the reflective disc shown in FIGS. 28B–28J without use of secondary antibodies.

A second embodiment of the third implementation of the invention involves construction of a reflective disc 110 without the use of a secondary antibody to immobilize the primary capture agents within the flow channels 130 of the bio-disc 110. In this embodiment, equal concentrations of DCHO 198 and primary antibodies 188 are mixed and allowed to combine, thereby forming the DCHO-antibody (primary) complex 199 represented in FIG. 28A. A reference or calibration mark 202 is deposited over the first window 141 and the DCHO-antibody (primary) complex 199 are deposited onto the active layer 144 (FIG. 28C) over each successive capture zone 140. The disc 110 is then incubated at room temperature in a humidity chamber for preferably 30 minutes and unbound DCHO-antibody (primary) complex 199 is removed with a PBS wash. The disc 110 is spin-dried to remove surface moisture as illustrated in FIG. 28D. The adhesive member or channel layer 118 is similarly attached to the active layer 144. The cover disc or cap portion 116 may be formed from polycarbonate and is preferably coated with a reflective surface 146 on the bottom as best shown in FIG. 4. The cover disc 116 is integrally attached to adhesive member 118 thereby forming flow channels 130 within the disc as shown in FIG. 28H. A blocking agent 204, such as StabilGuard®, is injected into each flow channel or analysis chamber 130 to quickly and effectively block any remaining nonspecific binding sites of the active layer 144 (FIG. 28I). The disc is incubated at room temperature in a humidity chamber for approximately 30 minutes, and any remaining solution is completely removed via vacuum as illustrated in FIG. 28J. FIG. 29 shows a cross-sectional view of the completed reflective bio-disc 110 without use of secondary antibodies.

Figure 30:
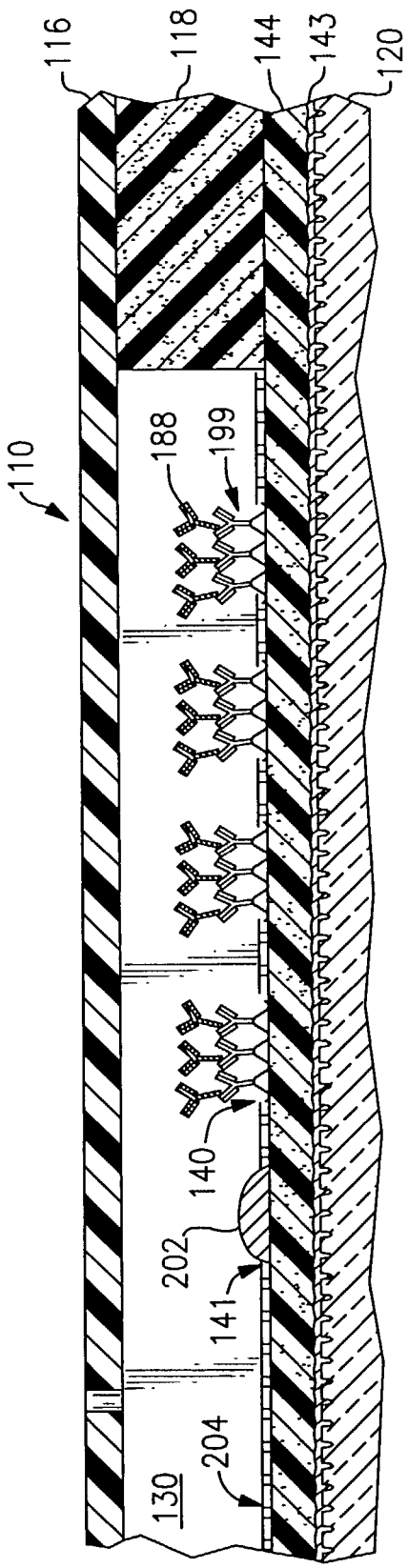
FIG. 30 shows the capture chemistries utilized in FIGS. 28B–28J as implemented in a transmissive disc format.

A third embodiment of the third implementation of the invention involves construction of a transmissive disc 110 utilizing the cross-linker DCHO to immobilize the capture agents within the flow channels 130 of the bio-disc 110. In this embodiment, the substrate 120, semi-reflective layer 143 without viewing windows 200 (FIG. 28B), and active layer 144 are presented as shown in FIG. 5. Deposition of DCHO-antibody (secondary) complex 199, primary antibodies 188, reference mark or dot 202, and blocking agent 204 are as described above, and as shown in FIGS. 28C–28I. The adhesive member or channel layer 118 is attached to the active layer 144. An optically transparent cover disc or cap portion 116 (FIG. 5) may be formed from polycarbonate. The cover disc or cap portion 116 is integrally attached to adhesive member 118 thereby forming flow channels 130 within the disc 110. FIG. 30 shows a cross-sectional view of the completed transmissive bio-disc 110 utilizing a DCHO-antibody (secondary) complex 199 and primary antibodies 188. It should be understood that a fourth embodiment of the third implementation may be constructed by those skilled in the art. The fourth embodiment involves construction of a transmissive disc 110 without the use of secondary antibodies to immobilize the primary capture agents within the flow channels of the bio-disc 110 (FIGS. 29 and 30). Other embodiments may involve use of streptavidin 182 (FIG. 18A) and biotin 184 (FIG. 18B) to immobilize primary or secondary antibodies to the active layer 144 of the bio-disc 110. Immobilized antibodies (both primary and secondary) can thereafter be complexed with DCHO 198 for increased concentrations of capture agents within the flow channels 130 of the bio-disc 110.

Implementation IV

Figure 31A:
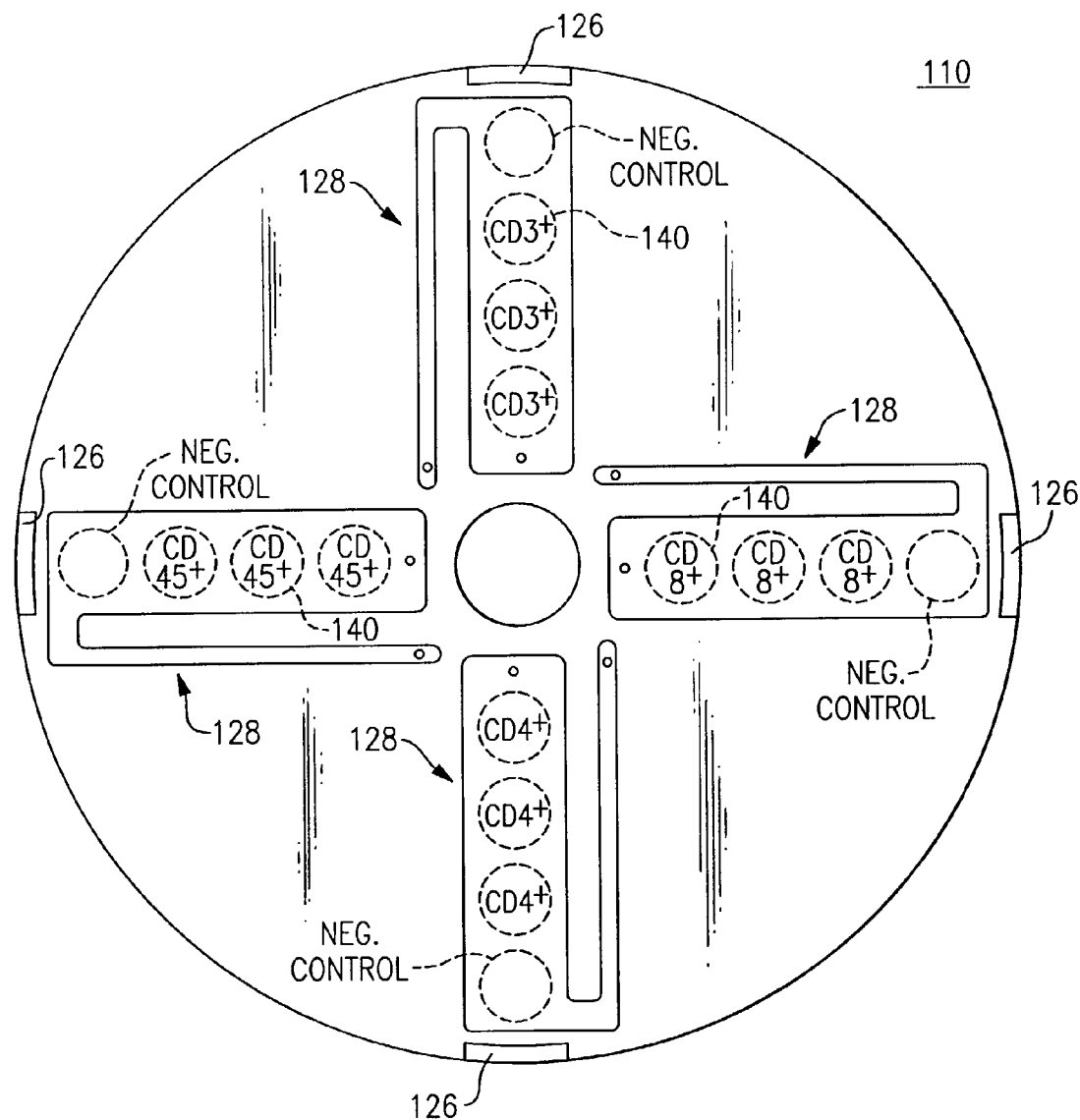
FIG. 31A is a top plan view of an optical bio-disc showing four fluidic circuits each having several capture zones for a specific cell surface marker and a negative control zone.

FIG. 31A is a top plan view of an optical bio-disc 110 showing four fluidic circuits 128 each having several capture zones 140 for a specific cell surface marker and a negative control zone. As shown, each fluidic circuit is dedicated to having capture zones 140 specifically directed to CD3, CD4, CD8, and CD45. Any other desired pattern or combination of cell surface antigens such as, for example, other CD markers or cell surface markers may be employed. In this particular implementation, for each individual fluidic circuit it is necessary to have only a single common capture agent in each of the capture zones 140. The disc shown in FIG. 31A is specifically suited for use with the cell capture chemistries and methods described below in FIGS. 31B-31E, 44A-44D, 45, and 46. The bio-disc 110 represented in FIG. 31A may be either a reflective or transmissive disc.

Figure 31B:
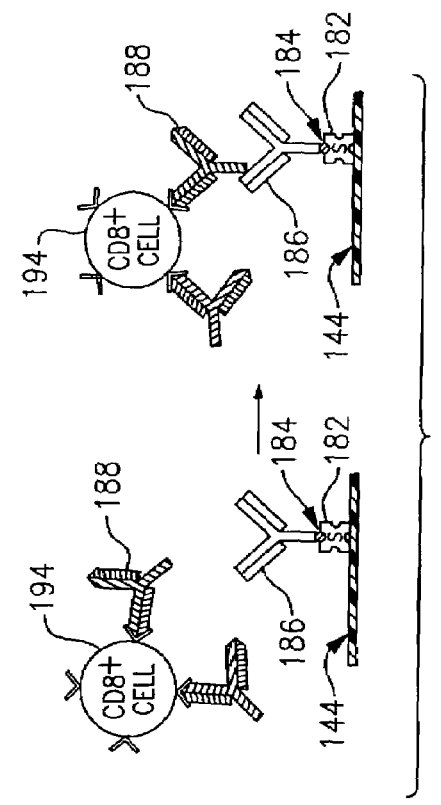
FIGS. 31B and 31C are pictorial representations showing capture of a primary antibody-cell complex by a secondary antibody that is bound to a substrate by a cross-linking system in a third implementation of the invention.
Figure 31C:
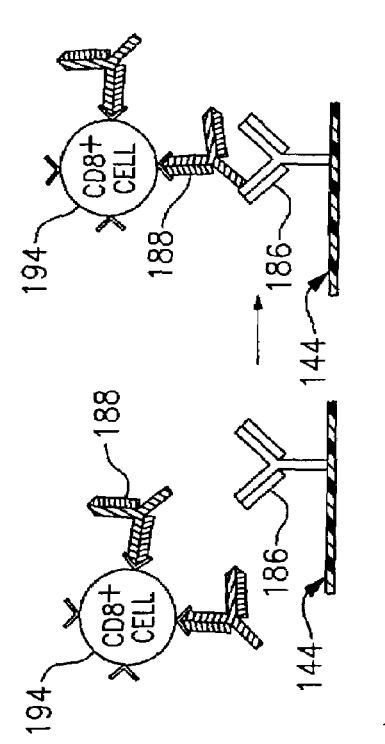
Figure 31D:
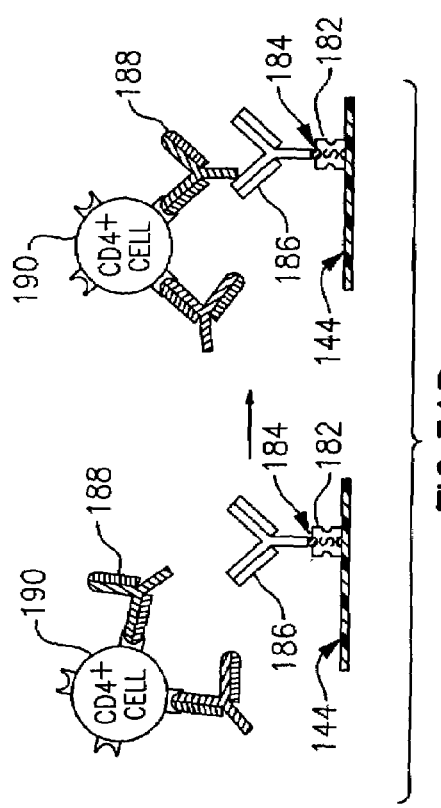
FIGS. 31D and 31E are pictorial representations showing capture of a primary antibody-cell complex by a secondary antibody that is directly bound to a substrate in a third implementation of the invention.
Figure 31E:
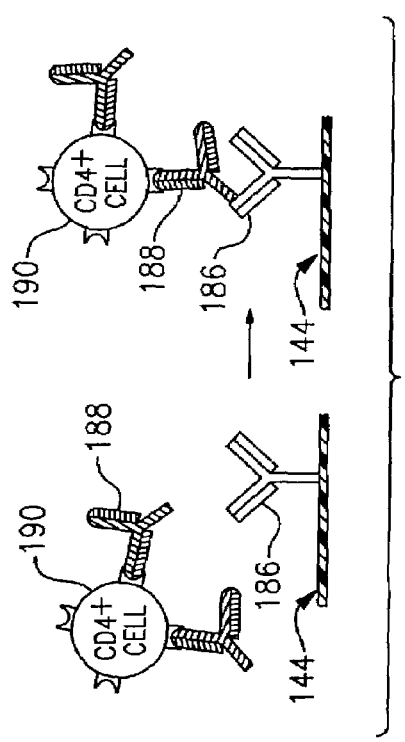

Turning now to FIGS. 31B–31E, there is shown pictorial representations of analyte capture in a fourth implementation of the present invention. FIGS. 31B and 31C show capture by secondary antibodies 186 of CD4+ cells 190 and CD8+ cells 194 that were previously combined with primary antibodies 188 (FIG. 18F) to form primary antibody-cell complexes. The primary antibodies 188 are bound to biotinylated secondary antibodies 186 (FIG. 18E) immobilized on the active layer 144 of the bio-disc 110 (FIGS. 4 and 9) by the cross-linking agent streptavidin 182. FIGS. 31D and 31E show another embodiment of the same implementation of the invention without a cross-linking system. In this embodiment, the secondary antibodies 186 are immobilized directly on the active layer 144 of the bio-disc 110.

Figure 32A:
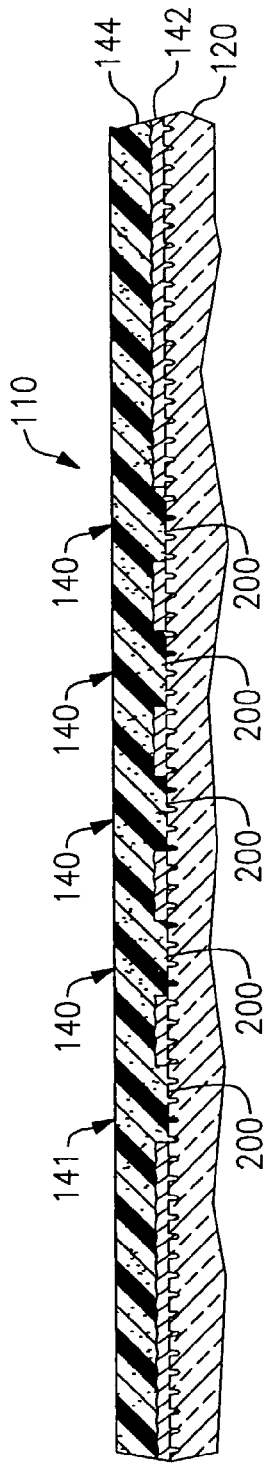
Figure 32B:
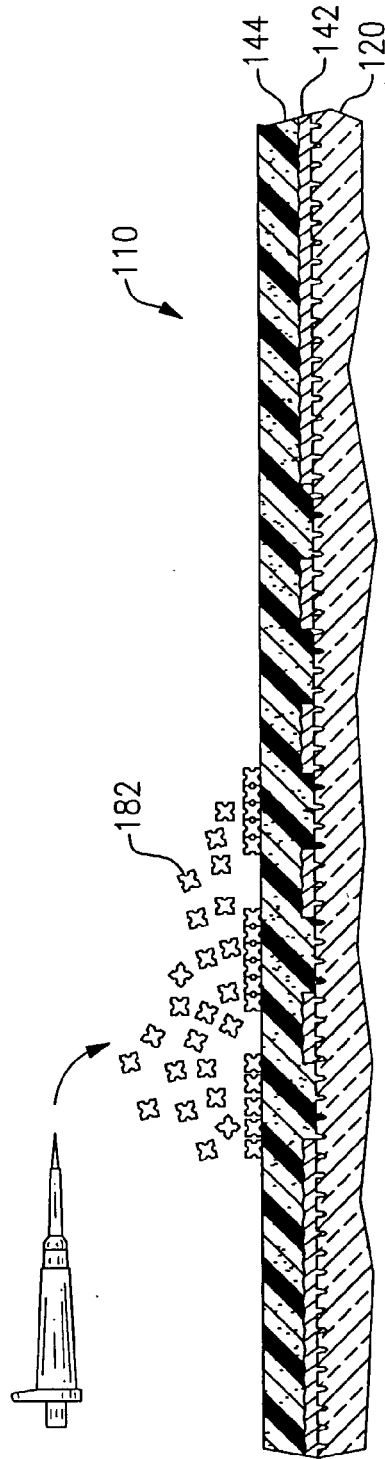
Figure 32C:
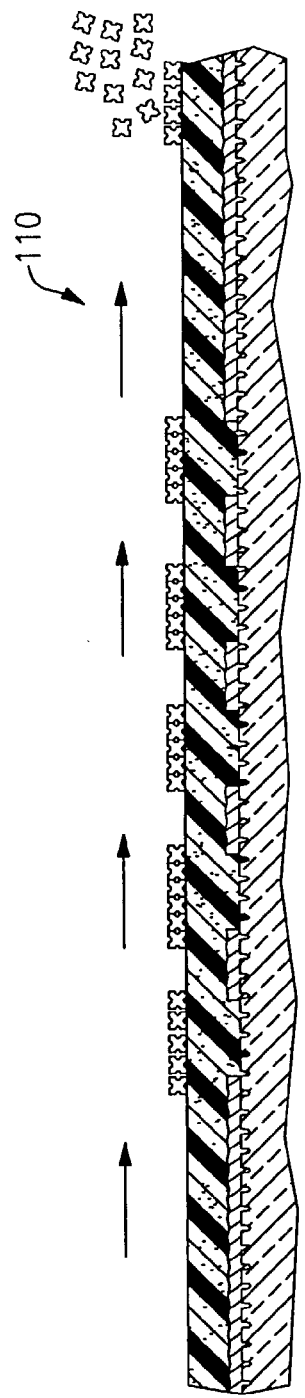
Figure 32G:
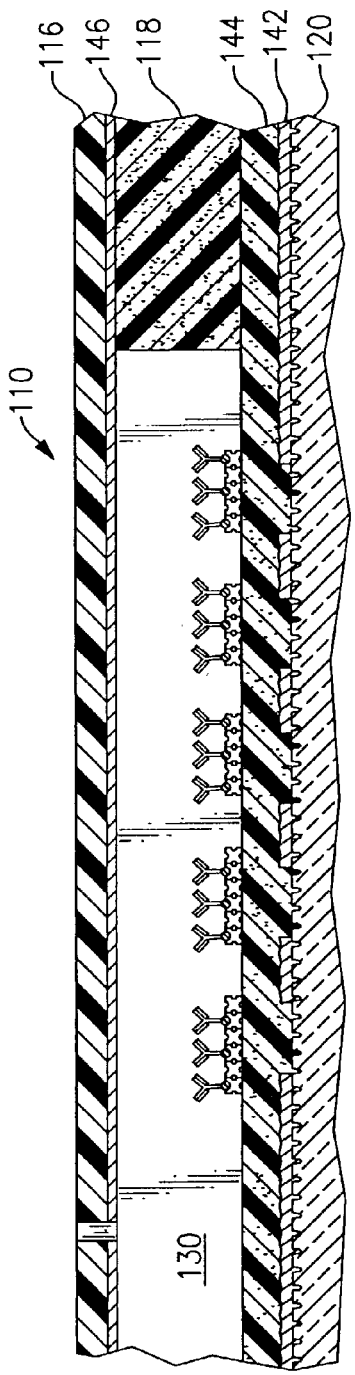
Figure 32H:
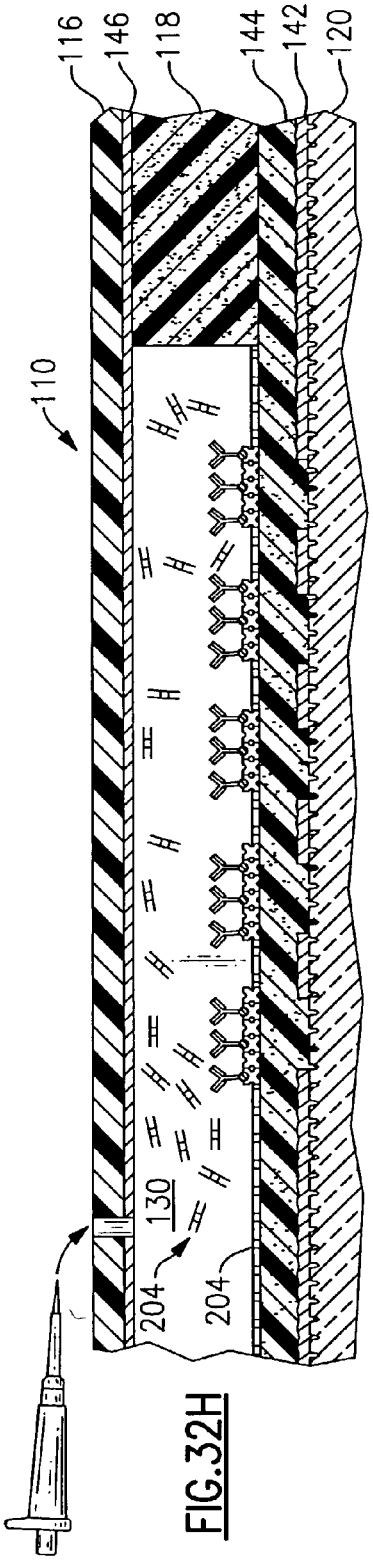
Figure 32I:
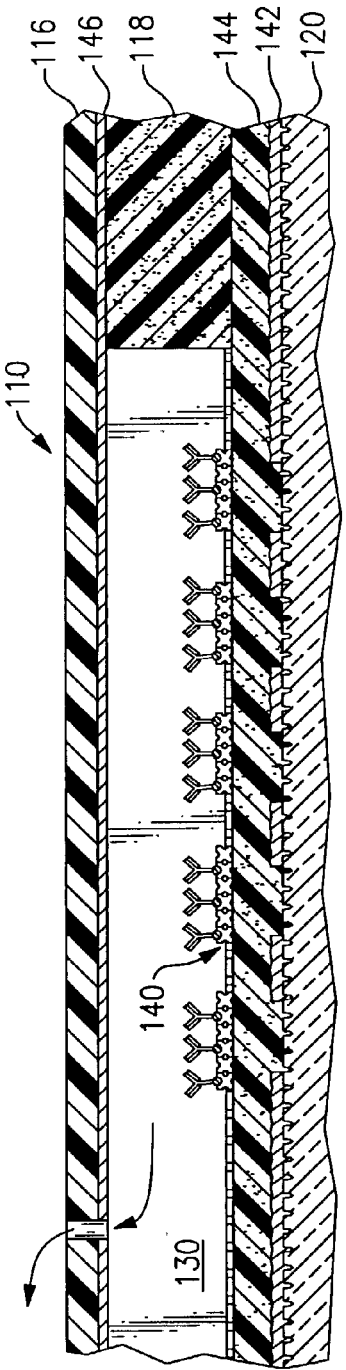

FIGS. 32A–32I are cross-sectional views showing construction of an embodiment of the fourth implementation of the invention. The first embodiment involves construction of a reflective disc utilizing a cross-linking system to immobilize the capture agents within the flow channels of the bio-disc. Referring to FIG. 32A, a light-transparent substrate 120, a reflective layer 142, and an active layer 144 of an optical bio-disc 110 are shown. Portions of reflective layer 142 are removed (or openings were created when deposited) to produce viewing windows 200 through which light can be directed at the locations of capture zones 140 where the antibodies are to be affixed. FIG. 32A shows five such capture zones 140, the first thereof designated as capture zone 141. The active layer 144 is preferably polystyrene, which is spin-coated over the reflective layer 142 to form a smooth surface with a thickness of about 40 to 300 microns. Streptavidin 182 is then deposited over each capture zone 140 and 141, and the disc 110 is incubated at room temperature in a humidity chamber for approximately 30 minutes as represented in FIG. 32B. The disc 110 is washed to remove unbound streptavidin 182, and then spin-dried to completely remove moisture from the surface of the disc 110 as illustrated in FIG. 32C. A reference mark or calibration dot 202 is deposited over the first capture zone 141 and biotinylated secondary antibodies 186 are deposited over each successive capture zone 140 as shown in FIGS. 32D and 32E. The disc 110 is then incubated at room temperature in a humidity chamber for approximately 30 minutes in this embodiment. This step is illustrated in FIG. 32E. Unbound secondary antibodies 186 are removed with a PBS wash, and the disc 110 is spin-dried to remove surface moisture. This step of the present method is represented in FIG. 32F. An adhesive member or channel layer 118 is similarly applied to the active layer 144. A respective cover disc or cap portion 116 is preferably formed from polycarbonate and coated with a reflective surface 146 on the bottom as best shown in FIG. 4. The cover disc 116 is integrally attached to adhesive member 118 thereby forming flow channels 130 within the disc as shown in FIG. 32G. A blocking agent 204, such as StabilGuard®, is injected into each flow channel or analysis chamber 130 to quickly and effectively block any remaining nonspecific binding sites of the active layer 144. This step is shown in FIG. 32H. The disc 110 is incubated at room temperature in a humidity chamber for preferably 30 minutes, and any remaining solution is completely removed via vacuum as represented in FIG. 32I.

A second embodiment of the fourth implementation of the invention involves construction of a reflective disc 110 without the use of a cross-linking system to immobilize the capture agents within the flow channels 130 of the bio-disc 110. In this embodiment, a reference mark or calibration dot 202 is deposited over the first window 141 and non-biotinylated secondary antibodies 186, shown generally in FIG. 18D, are deposited directly onto the active layer 144 over each successive capture zone 140. The disc 110 is then incubated at room temperature in a humidity chamber for 30 minutes. Unbound secondary antibodies 186 are removed with a PBS wash, and the disc 110 is spin-dried to remove surface moisture. An adhesive member 118 is attached to the active layer 144. A cover disc or cap portion 116 may be formed from polycarbonate and is preferably coated with a reflective surface 146 on the bottom as best shown in FIG. 4. The cover disc 116 is integrally attached to adhesive member 118 thereby forming flow channels 130 within the disc. A blocking agent 204, such as StabilGuard®, is injected into each flow channel or analysis chamber 130 to quickly and effectively block any remaining nonspecific binding sites of the active layer 144. The disc is incubated at room temperature in a humidity chamber for approximately 30 minutes, and any remaining solution is completely removed via vacuum. FIG. 33 shows a cross-sectional view of the completed reflective bio-disc 110 without use of a cross-linking system.

A third embodiment of the fourth implementation of the invention involves construction of a transmissive disc 110 utilizing a cross-linking system to immobilize the capture agents within the flow channels 130 of the bio-disc 110. In this embodiment, the substrate 120, semi-reflective layer 143 without viewing windows 200 (FIG. 32A), and active layer 144 are presented as shown in FIG. 5. Deposition of streptavidin 182, biotinylated primary antibodies 188, reference mark 202, and blocking agent 204 are as described above, and as shown in FIGS. 32B–32H. An adhesive member 118 is attached to the active layer 144. An optically transparent cover disc or cap portion 116 (FIG. 5) may be formed from polycarbonate. The cover disc 116 is integrally attached to adhesive member 118 thereby forming flow channels 130 within the disc 110 (FIG. 32G). FIG. 34 shows a cross-sectional view of the completed transmissive bio-disc 110 utilizing a cross-linking system. It should be understood that a fourth embodiment of the fourth implementation may be constructed by those skilled in the art. The fourth embodiment involves construction of a transmissive disc 110 without the use of a cross-linking system to immobilize the secondary capture agents within the flow channels of the bio-disc 110 (FIGS. 33 and 34).

Cluster Designation Count—Implementation I

Figure 35A:
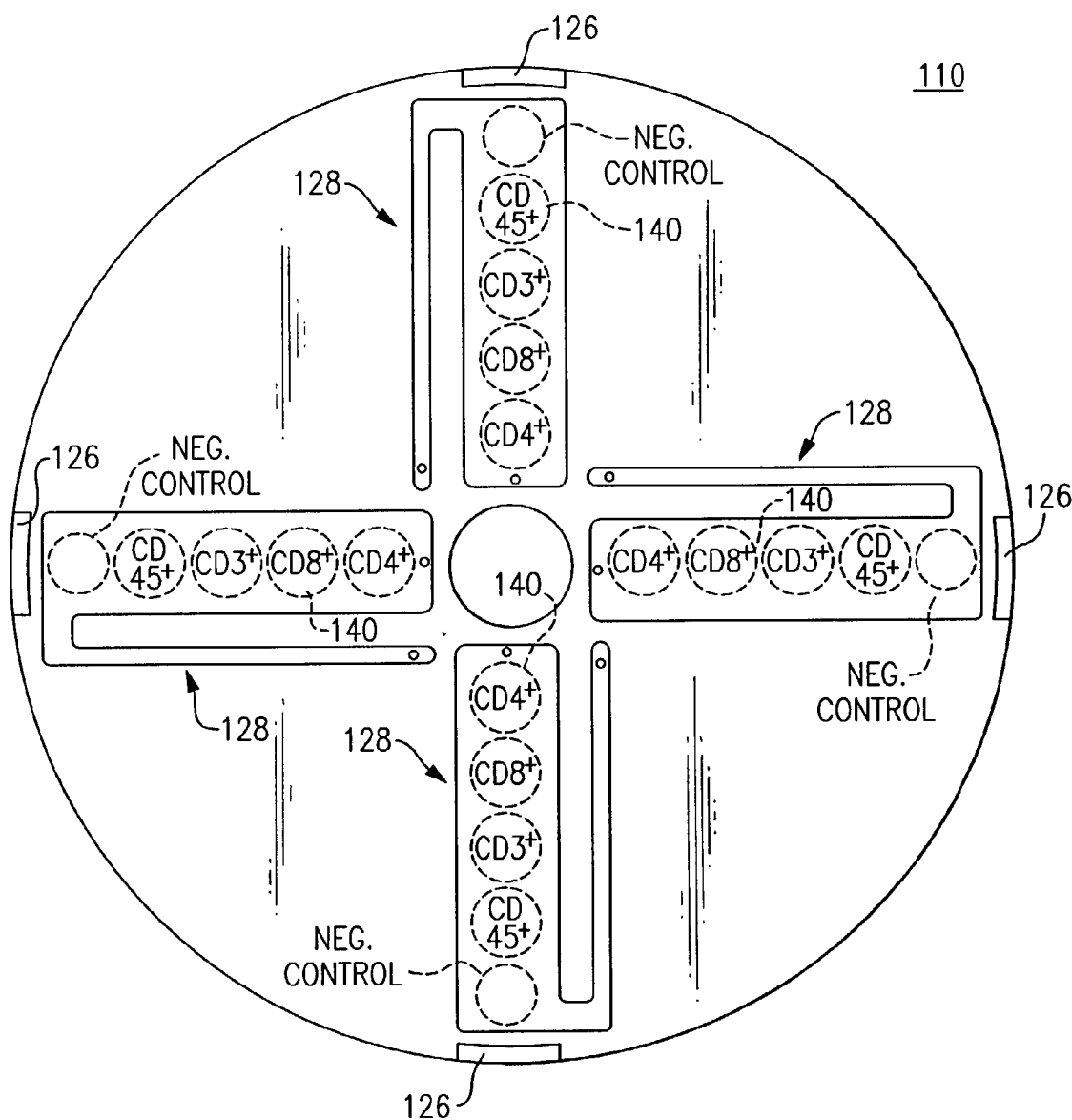
FIG. 35A is a top plan view of an optical bio-disc showing four fluidic circuits each having several capture zones for different cell surface markers and a negative control zone.

FIG. 35A is a top plan view of an optical bio-disc 110 showing four fluidic circuits 128 each having several capture zones 140 for four different specific cell surface markers and a negative control zone. As shown, each fluidic circuit is dedicated to having four capture zones 140 each one specifically directed to CD4, CD8, CD3, and CD45. Any other desired pattern or combination of cell surface antigens such as, for example, other CD markers or cell surface markers may be employed. In this particular implementation, there is no restriction that for each individual fluidic circuit it is necessary to have only a single common capture agent in each of the capture zones 140. On the contrary, in this implementation, it is desirable to have capture zones with different capture agents. These capture zones may be arranged, for example, in an array format having at least a 2-by-2 matrix. The disc shown in FIG. 35A is specifically suited for use with the cell capture chemistries and methods described below in FIGS. 35B–35D, 36, 37, 38A–38C, 39, 40, 41A–41C, 42, and 43. The bio-disc 110 represented in FIG. 35A may be either a reflective or transmissive disc.

Figures 35B, 35C, 35D:
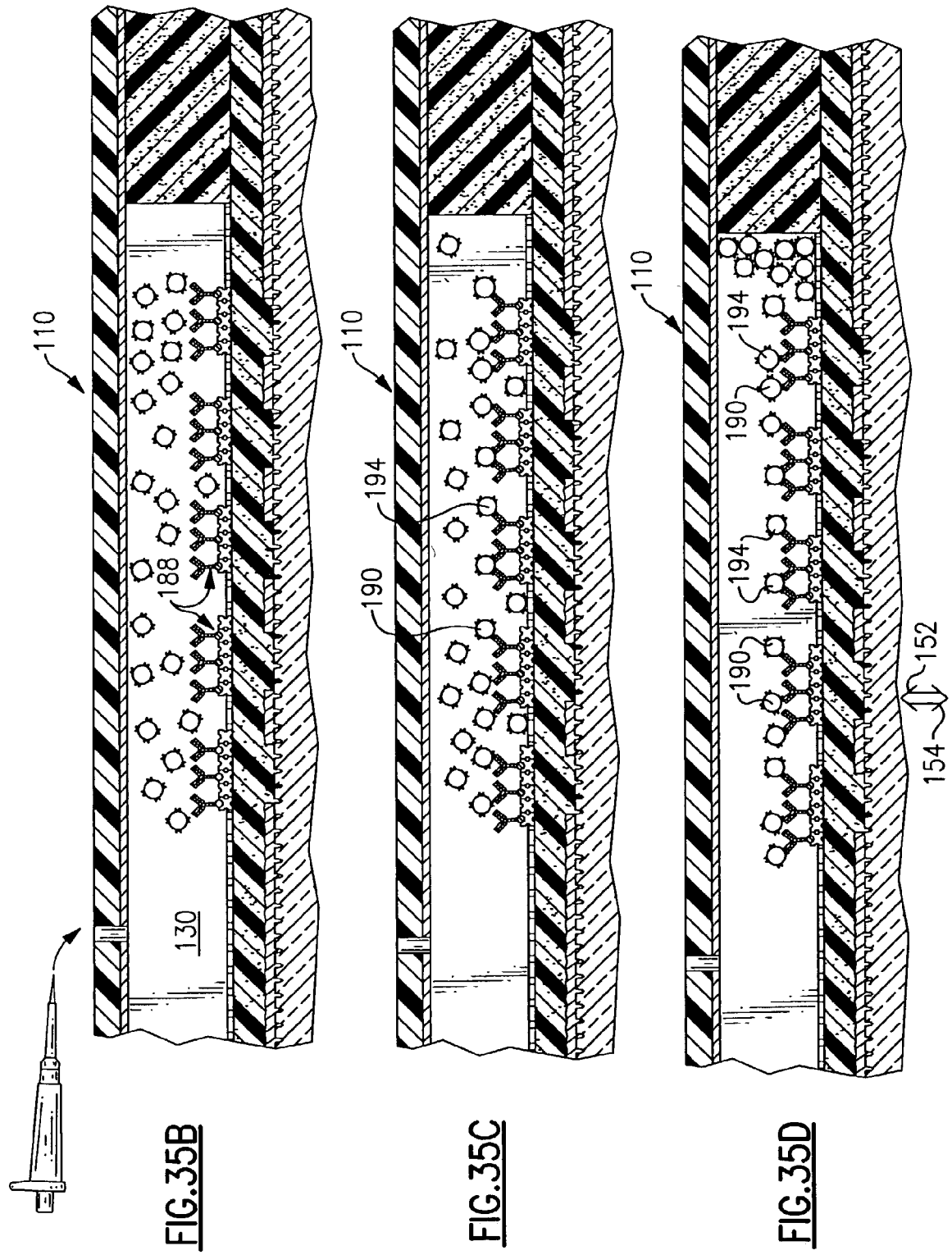
FIGS. 35B, 35C, and 35D are cross-sectional side views of a reflective optical bio-disc showing embodiments of a first implementation of a method of blood sample analysis using a cross-linking system.

Referring next to FIGS. 35B–35D, analysis of a purified and washed MNC sample (FIG. 17A) using a bio-disc of the first implementation of the invention is shown. The flow channels 130 of a bio-disc 110 are flooded with the MNC sample as represented in FIG. 35B. Capillary action, pressure applied with an external applicator, and/or centrifugal force (i.e., the force on a body in curvilinear motion directed away from the center or curvature or axis of rotation) act upon the test sample to achieve contact with the primary antibodies 188. As shown in FIG. 35C, the primary antibodies come into contact with and then capture any CD4$^+$ cells 190 and CD8$^+$ cells 194 present within the test sample. The optical drive motor 162 (FIG. 10) spins the disc, which clears the capture zones 140 (FIG. 20I) of unbound T-cells. The incident beam 152 of an optical disc drive 112 (FIG. 1) interacts with the captured CD4$^+$ cells 190 and CD8$^+$ cells 194, FIG. 35D, and the return beam 154 is reflected to the detector 157 (FIG. 10) for processing and analysis.

Figure 36:
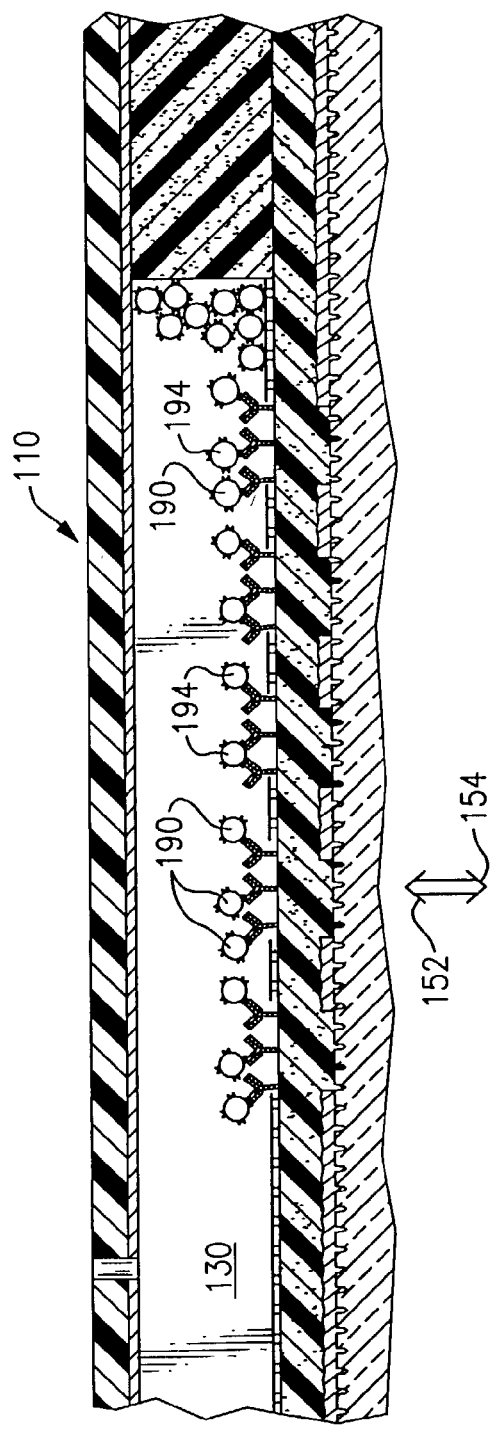
FIG. 36 is an alternate embodiment of the reflective disc shown in FIGS. 35B, 35C, and 35D without use of the cross-linking system.

FIG. 36 shows analysis of the same test sample from FIGS. 35B–35D, using the second embodiment of the first implementation of the invention. The flow channels 130 of a bio-disc 110 are flooded with the MNC sample (FIG. 35B). Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with, and capture any CD4$^+$ T-cells 190 and CD8$^+$ T-cells 194 present within the test sample (FIG. 35C). The optical drive motor 162 (FIG. 10) spins the disc, which clears the capture zones 140 (FIG. 20I) of unbound T-cells. The incident beam 152 of an optical disc drive 112 (FIG. 1) interacts with the captured CD4$^+$ T-cells 190 and CD8$^+$ T-cells 194 (FIG. 35D) and the return beam 154 is reflected to the detector 157 (FIG. 10) for processing and analysis.

Figure 37:
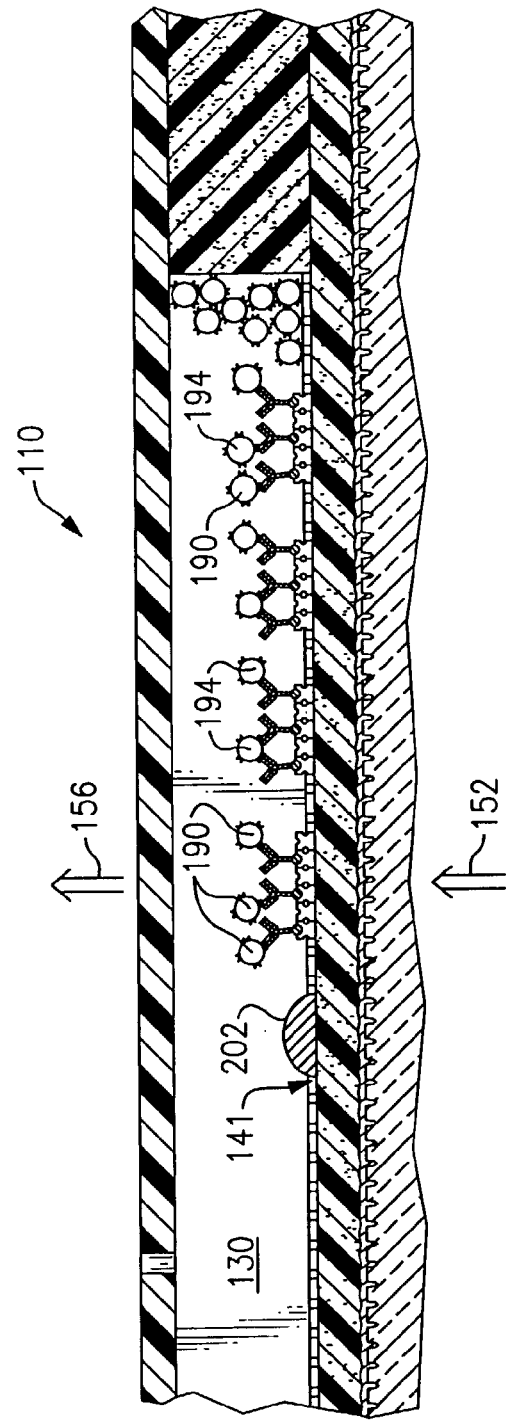
FIG. 37 shows the capture chemistries utilized in FIGS. 35B, 35C, and 35D as implemented in a transmissive disc format.

FIG. 37 shows analysis of the same test sample from FIGS. 35B–35D, using the third embodiment of the first implementation of the invention. The flow channels 130 of a bio-disc 110 are flooded with the MNC sample (FIG. 35B). Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with and then capture any CD4$^+$ T-cells 190 and CD8$^+$ T-cells 194 present within the test sample (FIG. 35C). The optical drive motor 162 (FIG. 10) spins the disc, which clears the capture zones 140 (FIG. 20I) of unbound T-cells. The incident beam 152 of an optical disc drive 112 (FIG. 1) interacts with the captured CD4$^+$ T-cells 190 and CD8$^+$ T-cells 194 (FIG. 35D) and the transmitted beam 156 is passed to the detector 157 (FIG. 10) for processing and analysis.

Cluster Designation Count—Implementation II

Figure 38:
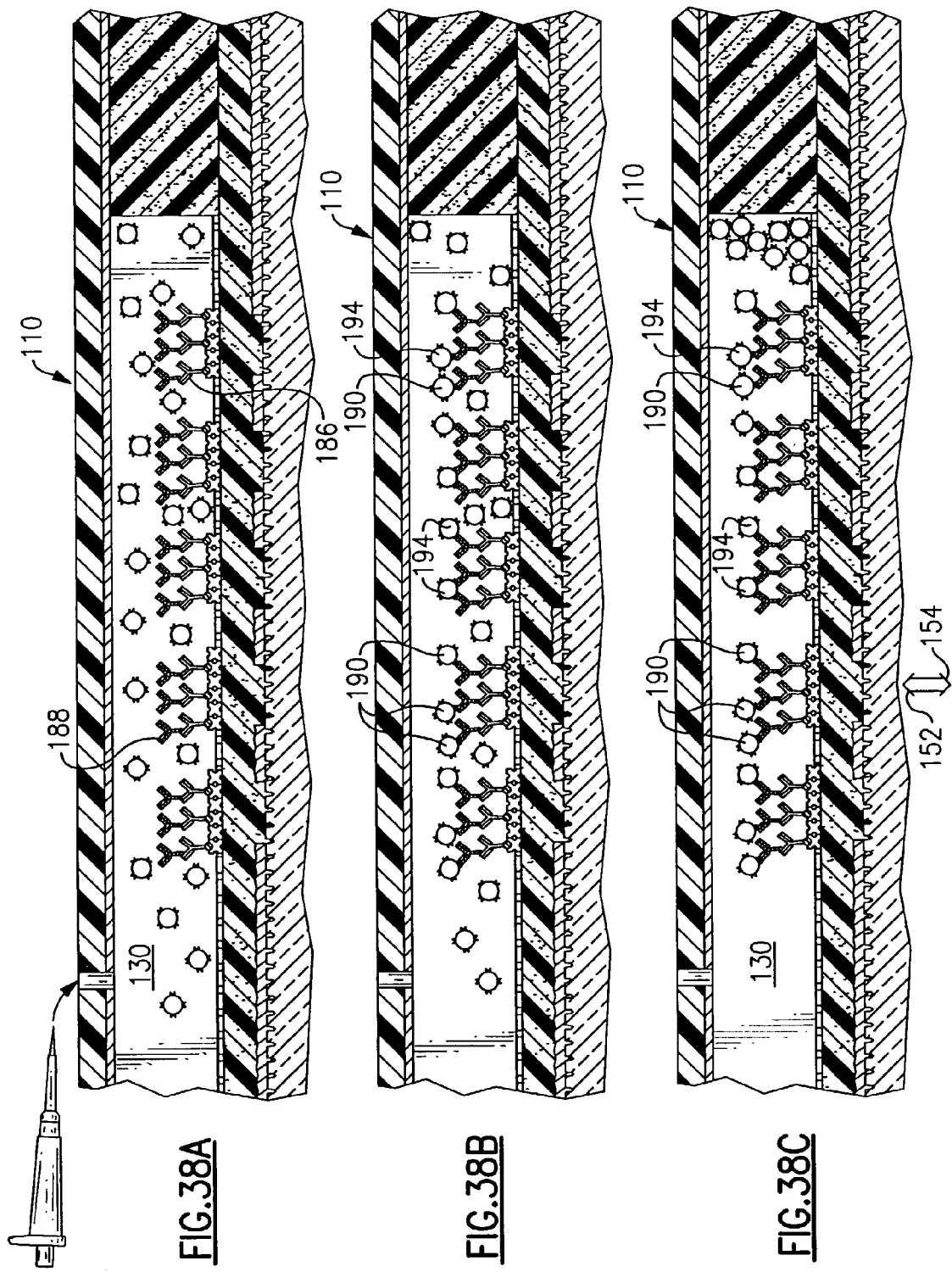
FIGS. 38A, 38B, and 38C are cross-sectional side views of a reflective optical bio-disc showing embodiments of a second implementation of a method of blood sample analysis using primary and secondary capture antibodies and a cross-linking system.

With reference now to FIGS. 38A–38C, analysis of a purified and washed MNC sample (FIG. 17A) using a bio-disc of the second implementation of the invention is shown. The flow channels 130 of a bio-disc 110 are flooded with the MNC sample as shown in FIG. 38A. Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with, and capture any CD4$^+$ T-cells 190 and CD8$^+$ T-cells 194 present within the test sample. This step is illustrated in FIG. 38B. The optical drive motor 162 (FIG. 10) spins the disc, which clears the capture zones 140 (FIG. 24L) of unbound T-cells. The incident beam 152 of an optical disc drive 112 (FIG. 1) interacts with the captured CD4$^+$ T-cells 190 and CD8$^+$ T-cells 194, FIG. 38C, and the return beam 154 is reflected to the detector 157 (FIG. 10) for processing and analysis.

FIG. 39 shows analysis of the same test sample from FIGS. 38A–38C, using the second embodiment of the second implementation of the invention. The flow channels 130 of a bio-disc 110 are flooded with the MNC sample (FIG. 38A). Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with, and capture any CD4+ T-cells 190 and CD8+ T-cells 194 present within the test sample (FIG. 38B). The optical drive motor 162 (FIG. 10) spins the disc, which clears the capture zones 140 (FIG. 24L) of unbound T-cells. The incident beam 152 of an optical disc drive 112 (FIG. 1) interacts with the captured CD4+ T-cells 190 and CD8+ T-cells 194 and (FIG. 38C) the return beam 154 is reflected to the detector 157 (FIG. 10) for processing and analysis.

FIG. 40 shows analysis of the same test sample from FIGS. 38A–38C, using the third embodiment of the second implementation of the invention. The flow channels 130 of a bio-disc 110 are flooded with the MNC sample (FIG. 38A). Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with, and capture any CD4+ T-cells 190 and CD8+ T-cells 194 present within the test sample (FIG. 38B). The optical drive motor 162 (FIG. 10) spins the disc, which clears the capture zones 140 (FIG. 24L) of unbound T-cells. The incident beam 152 of an optical disc drive 112 (FIG. 1) interacts with the captured CD4+ T-cells 190 and CD8+ T-cells 194 (FIG. 38C) and the transmitted beam 156 is passed to the detector 157 (FIG. 10) for processing and analysis.

Cluster Designation Count—Implementation III

Figure 41:
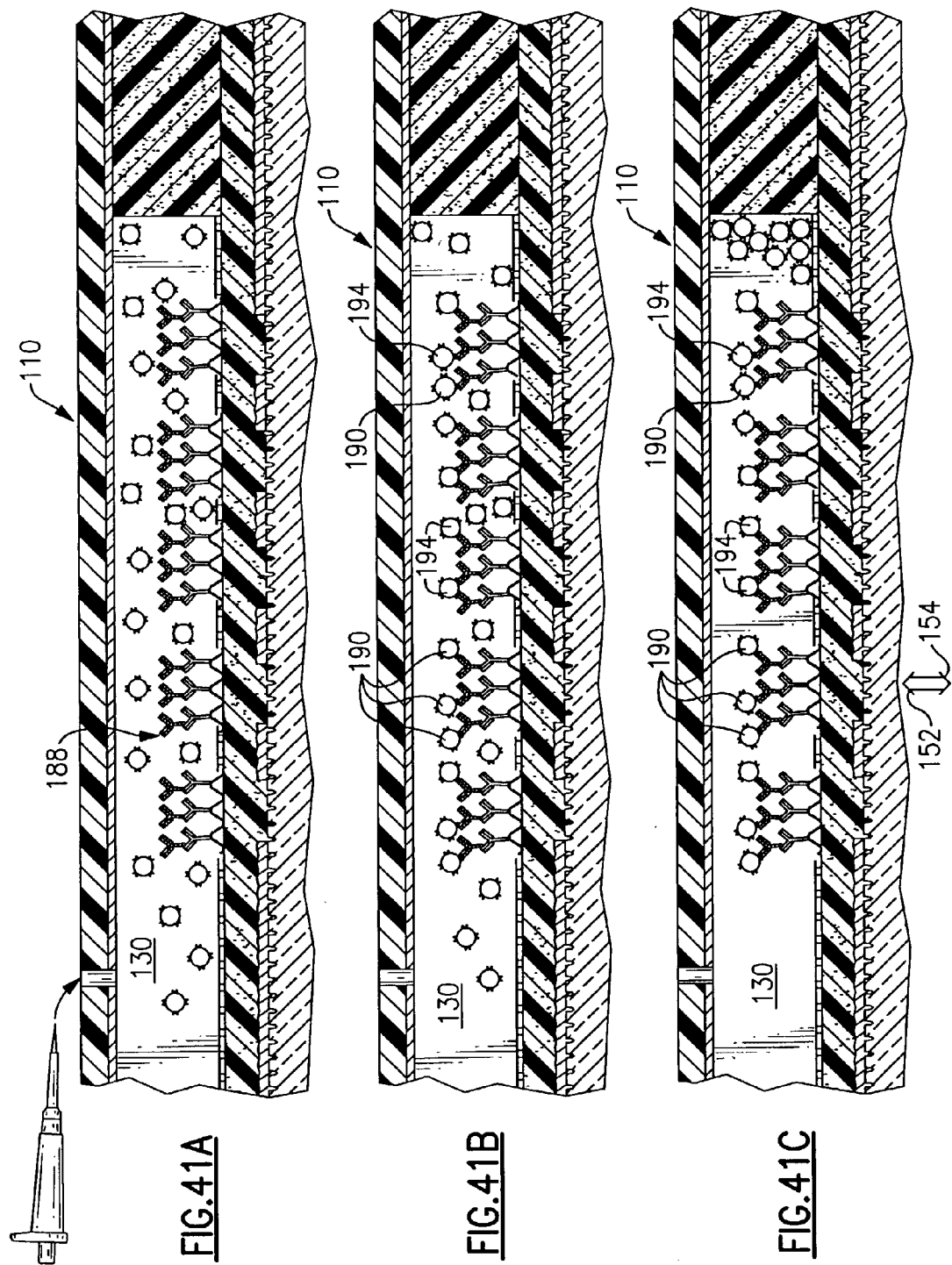
FIGS. 41A, 41B, and 41C are cross-sectional side views of a reflective optical bio-disc showing embodiments of a third implementation of a method of blood sample analysis using primary and secondary antibodies and a strand of DCHO.

Turning next to FIGS. 41A–41C, analysis of a purified and washed MNC sample (FIG. 17A) using a bio-disc of the third implementation of the invention is shown. The flow channels 130 of a bio-disc 110 are flooded with the MNC sample as illustrated in FIG. 41A. Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with and then capture any CD4+ T-cells 190 and CD8+ T-cells 194 present within the test sample. This step of the present method is shown FIG. 41B. The optical drive motor 162 (FIG. 10) spins the disc, which clears the capture zones 140 (FIG. 28J) of unbound T-cells. The incident beam 152 of an optical disc drive 112 (FIG. 1) interacts with the captured CD4+ T-cells 190 and CD8+ T-cells 194, FIG. 41C, and the return beam 154 is reflected to the detector 157 (FIG. 10) for processing and analysis.

Figure 42:
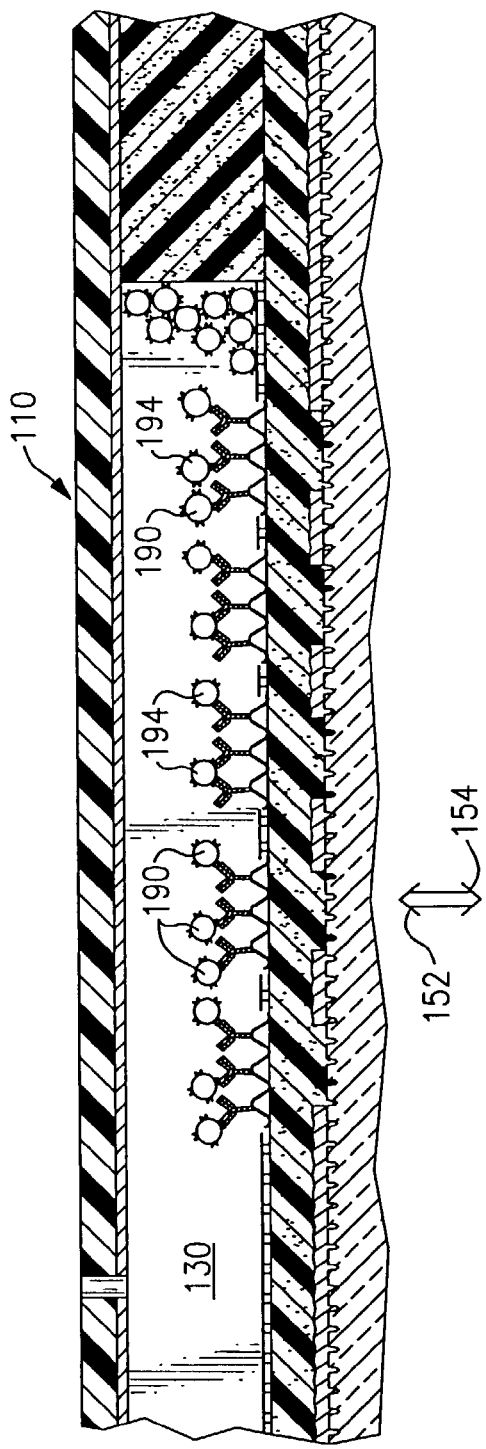
FIG. 42 is an alternate embodiment of the reflective disc shown in FIGS. 41A, 41B, and 41C without use of secondary antibodies.

FIG. 42 shows analysis of the same test sample from FIGS. 41A–41C, using the second embodiment of the third implementation of the invention. The flow channels 130 of a bio-disc 110 are flooded with the MNC sample (FIG. 41A). Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with, and capture any CD4+ T-cells 190 and CD8+ T-cells 194 present within the test sample, (FIG. 41B). The optical drive motor 162 (FIG. 10) spins the disc, which clears the capture zones 140 (FIG. 28J) of unbound T-cells. The incident beam 152 of an optical disc drive 112 (FIG. 1) interacts with the captured CD4+ T-cells 190 and CD8+ T-cells 194 (FIG. 41C) and the return beam 154 is reflected to the detector 157 (FIG. 10) for processing and analysis.

Figure 43:
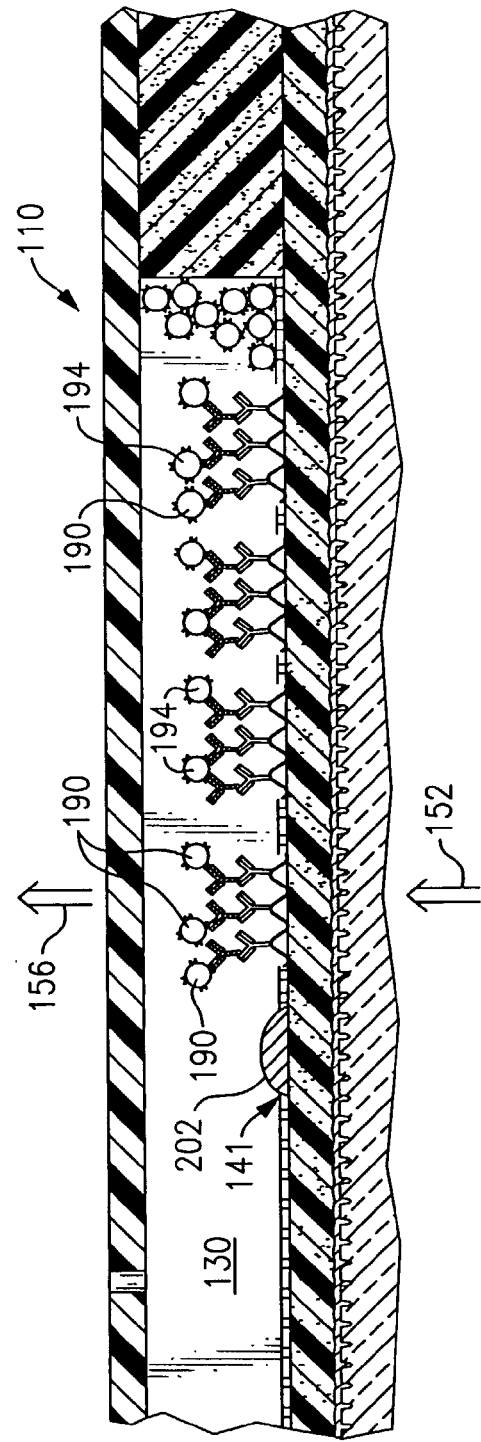
FIG. 43 shows the capture chemistries utilized in FIGS. 41A, 41B, and 41C as implemented in a transmissive disc format.

FIG. 43 shows analysis of the same test sample from FIGS. 41A–41C, using the third embodiment of the third implementation of the invention. The flow channels 130 of a bio-disc 110 are flooded with the MNC sample (FIG. 41A). Capillary action, pressure applied with an external applicator, and/or centrifugal force (i.e., the force on a body in curvilinear motion directed away from the center or curvature or axis of rotation) act upon the test sample to achieve contact with the primary antibodies 188. The primary antibodies come into contact with, and capture any CD4+ T-cells 190 and CD8+ T-cells 194 present within the test sample (FIG. 41B). The optical drive motor 162 (FIG. 10) spins the disc, which clears the capture zones 140 (FIG. 28J) of unbound T-cells. The incident beam 152 of an optical disc drive 112 (FIG. 1) interacts with the captured CD4+ T-cells 190 and CD8+ T-cells 194 (FIG. 41C) and the transmitted beam 156 is passed to the detector 157 (FIG. 10) for processing and analysis.

Cluster Designation Count—Implementation IV

Figure 44A:
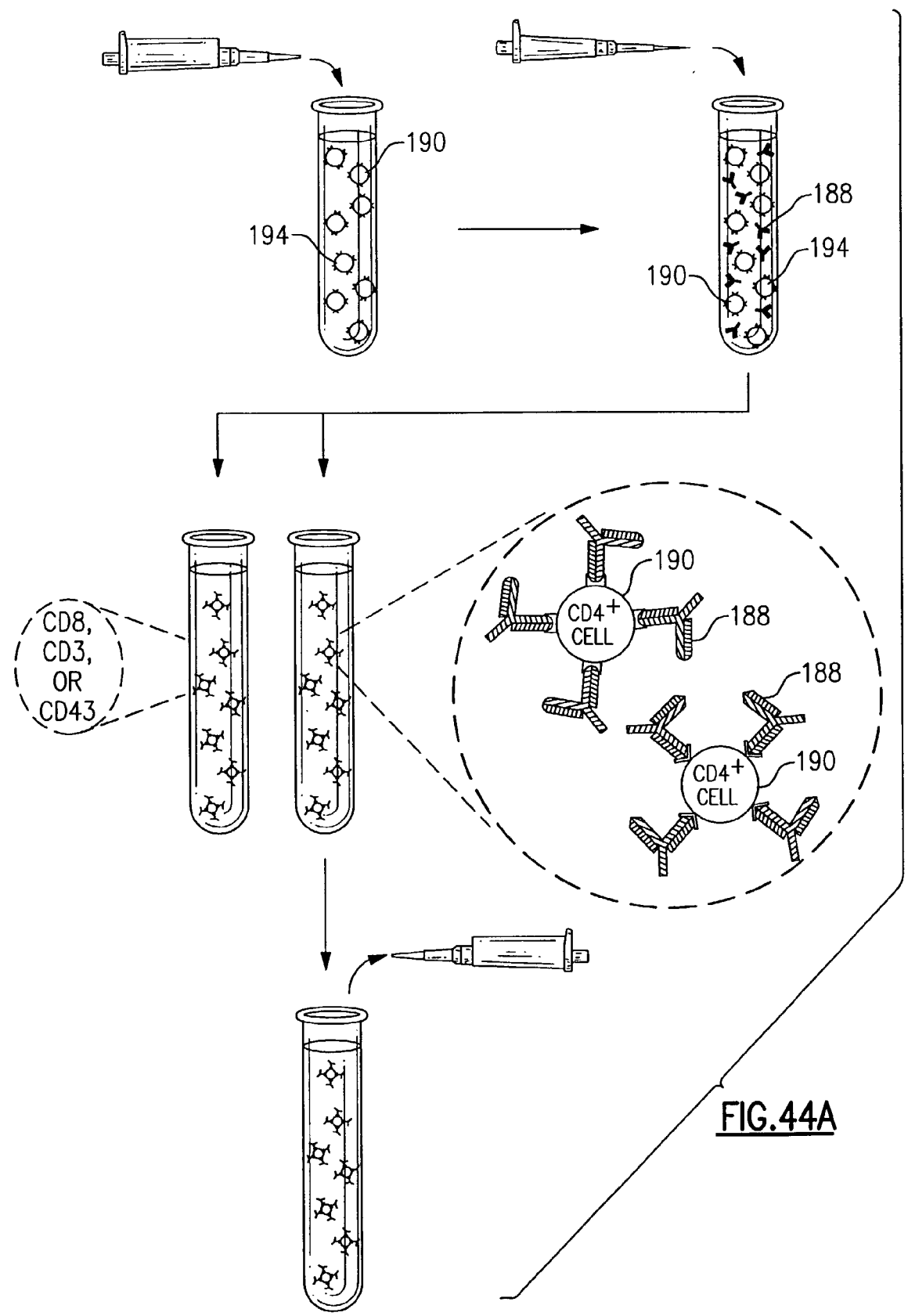
FIG. 44A is a pictorial flow diagram showing preparation of primary antibody-cell complexes.

Referring now to FIGS. 44A–44D, analysis of a purified and washed MNC sample (FIG. 17A) using a bio-disc of the fourth implementation of the invention is shown. FIG. 44A is a pictorial flow diagram showing preparation of the primary antibody-T-cell complex. The MNC suspension containing both CD4+ T-cells 190 and CD8+ T-cells 194 is mixed with primary antibodies 188, and allowed to bind, thereby forming the primary antibody-T-cell complexes. As would be apparent to one of skill in the art, other cells with different surface markers may also be tagged using the current implementation. As shown in FIG. 44B, the flow channels 130 of a bio-disc 110 are flooded with the primary antibody-T-cell complexes. Capillary action, pressure applied with an external applicator, and/or centrifugal force (i.e., the force on a body in curvilinear motion directed away from the center or curvature or axis of rotation) act upon the test sample to achieve contact with the secondary antibodies 188 immobilized on the active layer 144 of the bio-disc 110. The secondary antibodies 186, having an affinity for the primary antibody-T-cell complexes capture the complexes as shown in FIG. 44C. The optical drive motor 162 (FIG. 10) spins the disc, which clears the capture zones 140 (FIG. 32I) of unbound complexes. The incident beam 152 of the optical disc drive 112 (FIG. 1) interacts with the captured complexes, FIG. 44D, and the return beam 154 is reflected to the detector 157 (FIG. 10) for processing and analysis.

FIGS. 44A–44D also show another principal aspect of the methods of this invention. In conjunction with FIG. 17A, there is provided another method of performing a cluster designation count. This method includes the steps of (1) providing a blood sample in a tube containing a separation gradient, (2) rotating the tube at a time and speed sufficient to separate the blood sample into layers, (3) resuspending a MNC layer containing T-cells to form a MNC suspension, (4) adding a primary antibody to the MNC suspension to form a primary antibody-T-cell complex, (5) providing a sample of the primary antibody-T-cell complex on a disc surface that includes at least one capture zone containing at least one capture agent, (6) loading the disc into an optical reader, (7) directing an incident beam of electromagnetic radiation to the capture zone, (8) detecting a beam of electromagnetic radiation formed after interacting with the disc at the capture zone, (9) converting the detected beam into an output signal, and (10) analyzing the output signal to extract information relating to the number of cells captured at the capture zone. In one embodiment of this method, the optical disc is constructed with a reflective layer such that light directed to the capture zone and not striking a cell is reflected. In another embodiment of this method, the optical disc is constructed such that light directed to the capture zone and not striking a cell is transmitted through the optical disc.

FIG. 45 shows analysis of the same test sample from FIGS. 44A–44D, using the second embodiment of the fourth implementation of the invention. The flow channels 130 of a bio-disc 110 are flooded with the primary antibody-T-cell complexes (FIG. 44B). Capillary action, pressure applied with an external applicator, and/or centrifugal force (i.e., the force on a body in curvilinear motion directed away from the center or curvature or axis of rotation) act upon the test sample to achieve contact with the secondary antibodies 188 immobilized on the active layer 144 of the bio-disc 110. The secondary antibodies 186, having an affinity for the primary antibody-T-cell complexes capture the complexes (FIG. 44C). The optical drive motor 162 (FIG. 10) spins the disc, which clears the capture zones 140 (FIG. 32I) of unbound complexes. The incident beam 152 of the optical disc drive 112 (FIG. 1) interacts with the captured complexes (FIG. 44D) and the return beam 154 is reflected to the detector 157 (FIG. 10) for processing and analysis.

FIG. 46 shows analysis of the same test sample from FIGS. 44A–44D, using the third embodiment of the fourth implementation of the invention. The flow channels 130 of a bio-disc 110 are flooded with the primary antibody-T-cell complexes (FIG. 44B). Capillary action, pressure applied with an external applicator, and/or centrifugal force (i.e., the force on a body in curvilinear motion directed away from the center or curvature or axis of rotation) act upon the test sample to achieve contact with the secondary antibodies 188 immobilized on the active layer 144 of the bio-disc 110. The secondary antibodies 186, having an affinity for the primary antibody-T-cell complexes capture the complexes (FIG. 44C). The optical drive motor 162 (FIG. 10) spins the disc, which clears the capture zones 140 (FIG. 32I) of unbound complexes. The incident beam 152 of an optical disc drive 112 (FIG. 1) interacts with the captured complexes (FIG. 44D) and the transmitted beam 156 is passed to the detector 157 (FIG. 10) for processing and analysis.

Those skilled in the art will appreciate in light of these teachings that one or more embodiments of one or more implementations of the methods of the invention may be combined without departing from the scope and spirit of this invention.

Cell Detection and Related Software

Figure 47:
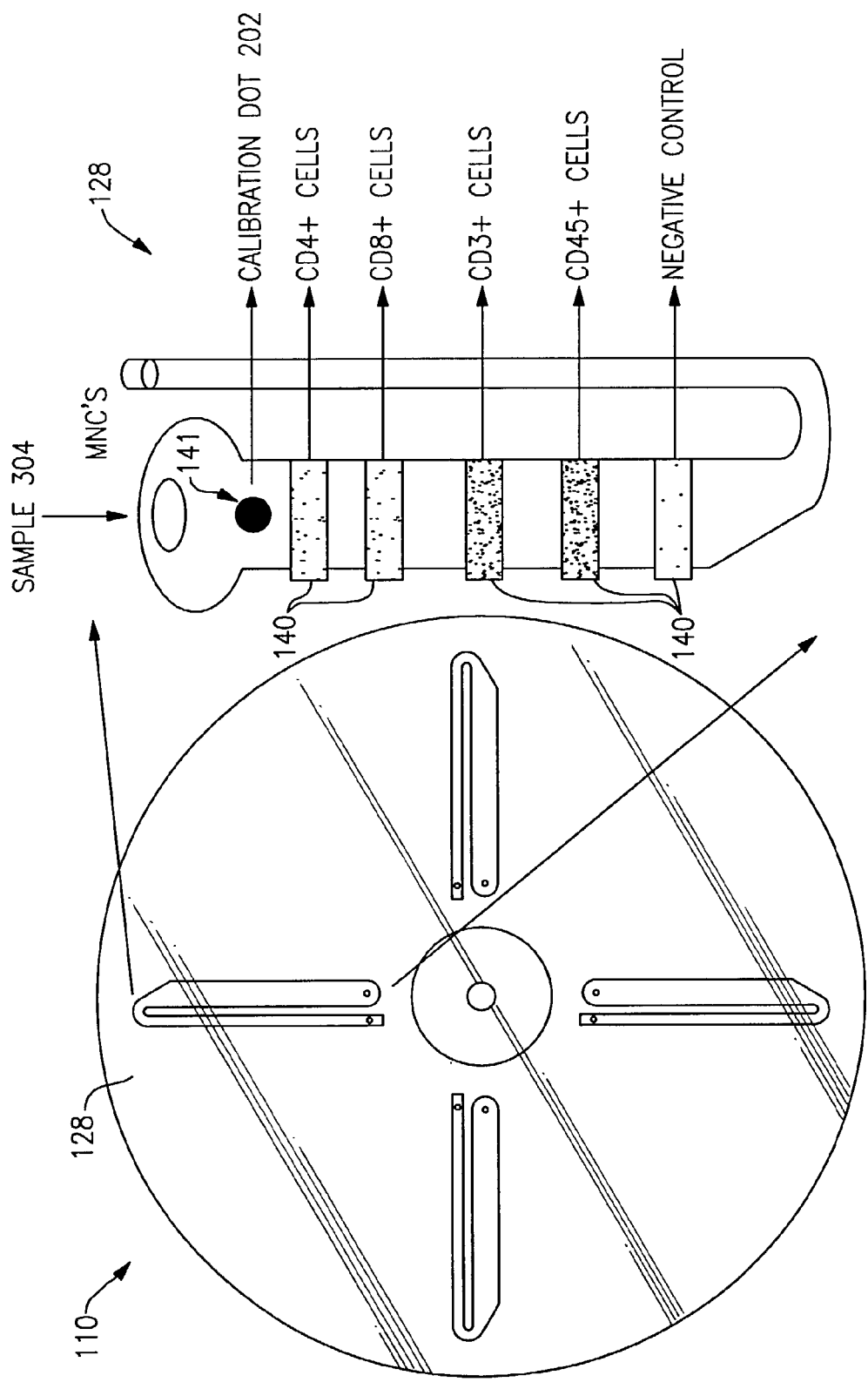
FIG. 47 is a pictorial diagram of an optical disc having chambers to illustrate a bar code technique according to an embodiment of the present invention.

Referring now to FIG. 47, there is shown the optical bio-disc 110 including a fluid circuit 128 for holding a sample. FIG. 47 also shows the fluidic circuit 47 enlarged to illustrate different capture or target zones 140 and the target zone 141 including the reference mark or calibration dot 202. In this specific embodiment, five capture zones 140 are employed, each respectively implemented to capture CD4+ cells, CD8+ cells, CD3+ cells, CD45+ cells, and myoglobin as the negative control.

Figure 48A:
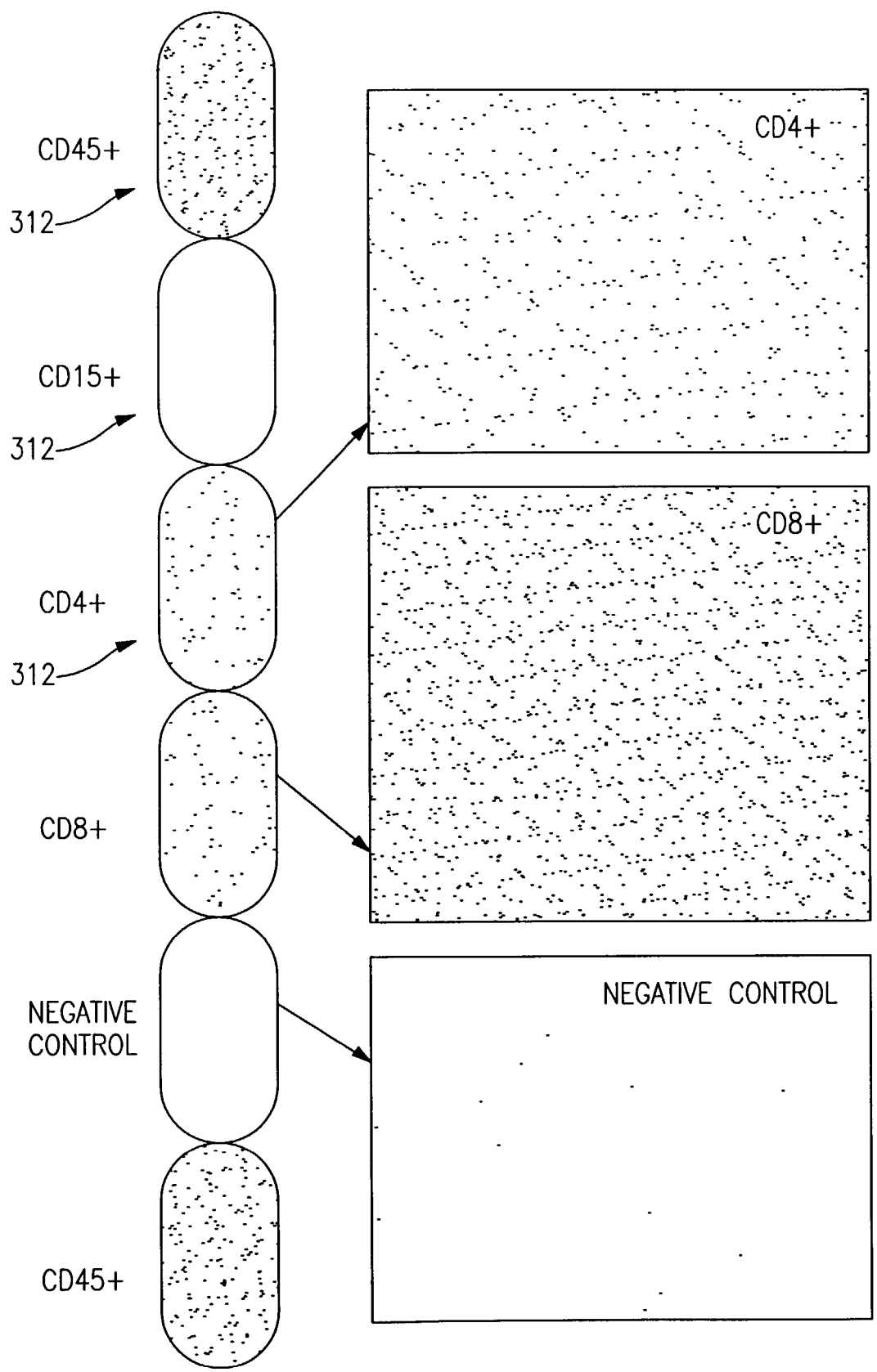
FIG. 48A is an illustration of results obtained from an assay using the bar code format according to an embodiment of the present invention.
Figure 48B:
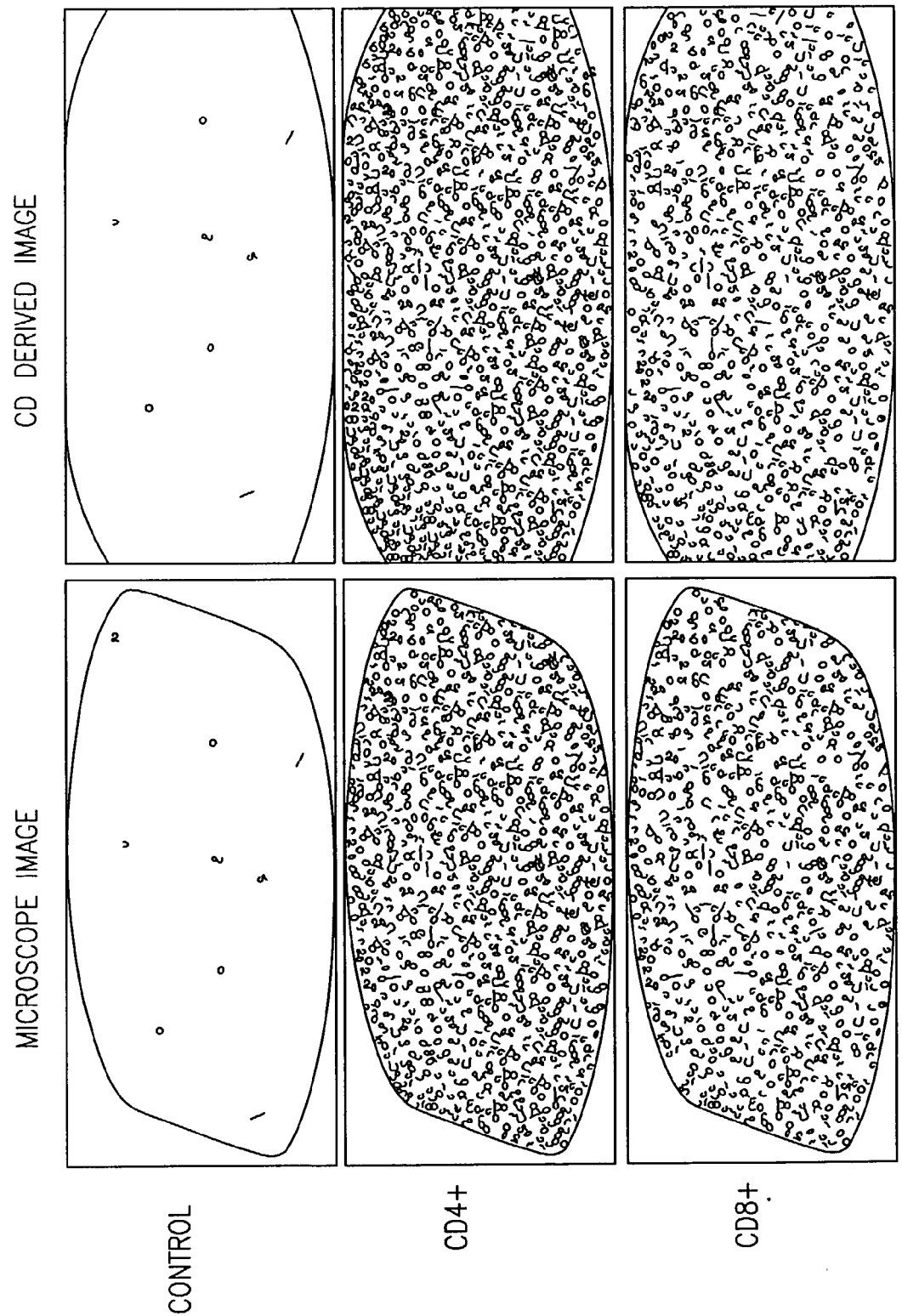
FIG. 48B shows corresponding microscope and disc images for CD4, CD8, and control regions.

FIG. 48A an image obtained from a different embodiment including six capture zones 140 each implemented, respectively, to capture CD45+ cells, CD15+ cells, CD4+ cells CD8+ cells, a second capture zone for CD15+ cells, and a second capture zone for CD45+ cells. In this embodiment, the two CD45 and CD15 capture zones may be used as a validation control or check to verify that the capture efficiency and expected count results are in agreement. FIG. 48A also shows a series of cell surface antigens with enlarged views for CD4, CD8, and a control. As indicated here, the image is of a number of cells shown against a background field. FIG. 48B represents a close up view of the control, CD4, and CD8 capture zones from an actual microscope image compared to a bio-disc derived image according to the present invention. FIG. 49 illustrates another comparison in greater detail of an actual microscope image and a corresponding bio-disc image according to the present invention. As represented in FIGS. 48B and 49, the inventors have found that the bio-disc images are of equal quality and resolution compared to those obtainable from a microscope. These images thus demonstrate that individual cells can be made visible against a background using the apparatus and methods of the present invention. Methods for detecting investigational features are described in more detail in commonly assigned U.S. Provisional Application Ser. Nos. 60/270,095 and 60/292,108 each entitled "Signal Processing Apparatus and Methods for Obtaining Signal Signatures of Investigational Features Detected on a Surface of an Optical Disc Assembly" respectively filed on Feb. 2, 2001 and May 18, 2001, and in commonly assigned U.S. patent application Ser. No. 10/043,688 entitled "Optical Disc Analysis System Including Related Methods For Biological and Medical Imaging" as filed on Jan. 10, 2002, all of which are incorporated herein by reference.

These cells can be detected through one of a variety of different methods including, for example, using edge detection hardware or software to detect and count sufficiently large changes in the level of transmitted or reflected light and thus count the transitions and hence the cells. Another method, described in more detail below, uses image or pattern recognition software to identify cells against the background. Image recognition can distinguish WBCs from RBCs, and also distinguish neutrophils, monocytes, basophils, eosinophils, granulocytes, and lymphocytes.

An optical disc with tracks on the order of 1.6 microns apart can be used to image cells or aggregates on the disc. For example, a white blood cell would typically have a diameter of at least 5 and as many as 12 tracks, and therefore an image of that white blood cell can be obtained.

To obtain such an image, a transmissive disc of the type shown in FIGS. 2, 3 and 4 may be used (although a reflective disc would be operable), and a disc drive system of the type shown in FIG. 10 including trigger sensor 160 and top detector 158. Trigger detector 158 detects a trigger mark 126 in a transmissive disc and provides a signal to a computer that data is to be collected and/or processed when that mark is detected. As the light source passes across the tracks in the viewing window, an image is obtained for the received transmitted light. The top detector in this case can be a single detector, or an array of multiple detector elements oriented in the radial and/or circumferential direction. Such detectors and detection methods are described, for example, in commonly assigned U.S. Provisional Application Ser. No. 60/247,465 entitled "Optical Disc Drive For Bio-Optical Disc" filed Nov. 9, 2000; U.S. Provisional Application Ser. No. 60/293,093 entitled "Disc Drive Assembly For Optical Bio-Discs" filed May 22, 2001; and U.S. patent application Ser. No. 10/008,156 entitled "Disc Drive System and Methods for Use with Bio-discs" filed Nov. 9, 2001, each of which is incorporated herein by reference in its entirety.

After images such as those in FIGS. 48A, 48B and 49 are obtained, the image data can be processed further with image recognition software designed to identify desired features. It is further desirable that the image recognition software not only have the ability to distinguish cells from background, but also one type of cell from another.

Figure 50:
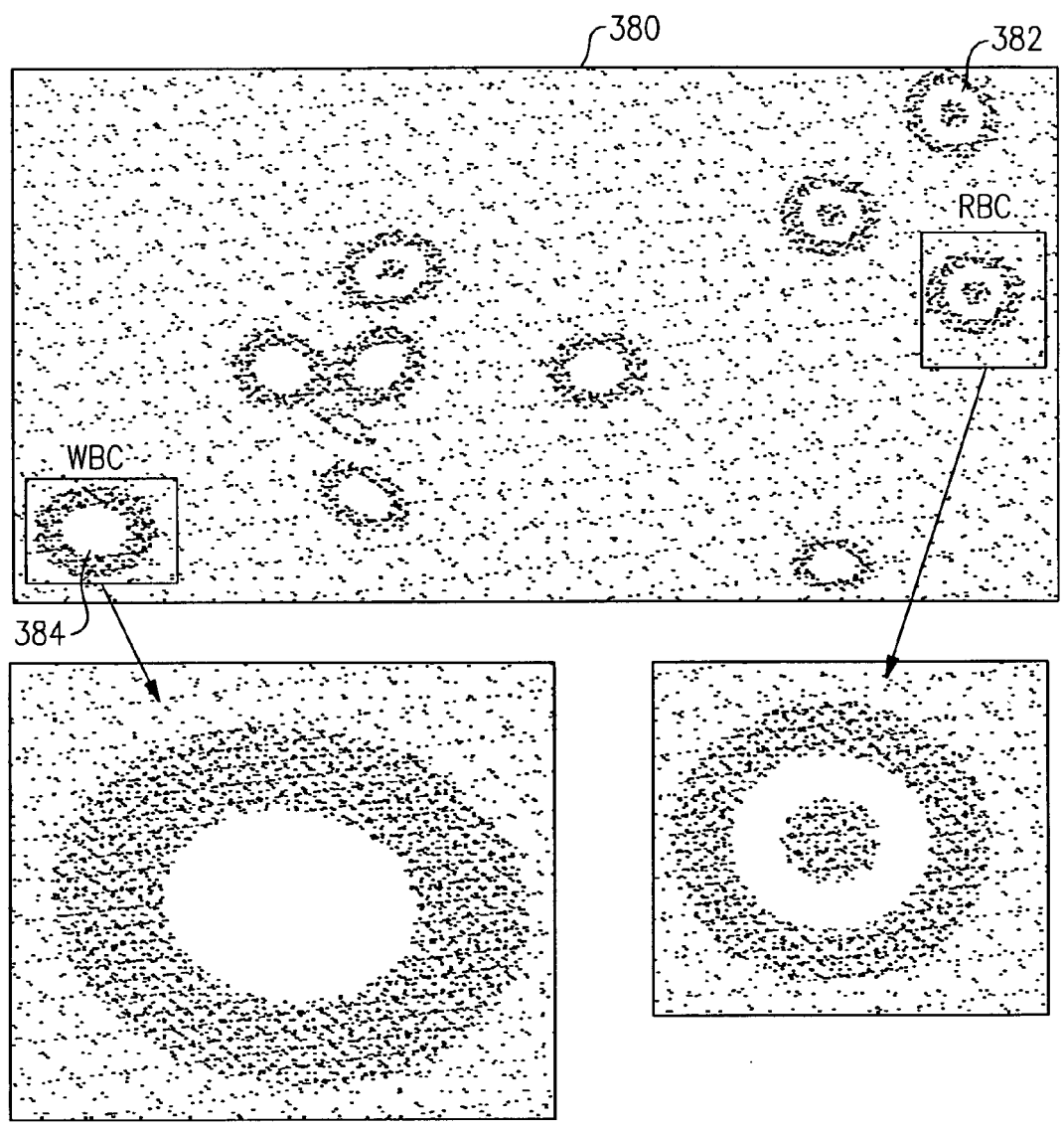
FIGS. 50 and 51 illustrate the use of image recognition according to an embodiment of the present invention.

With reference now to FIG. 50, there is shown an image derived from investigational data that includes both red blood cells and white blood cells. As indicated in the enlarged views, these white and red cells have clearly distinct characteristics and thus can be detected against the background and can also be distinguished from each other with image recognition. In addition, it is also possible to distinguish types of white blood cells from each other, including lymphocytes, monocytes, neutrophils, eosinophils, granulocytes, and basophils.

Figure 51:
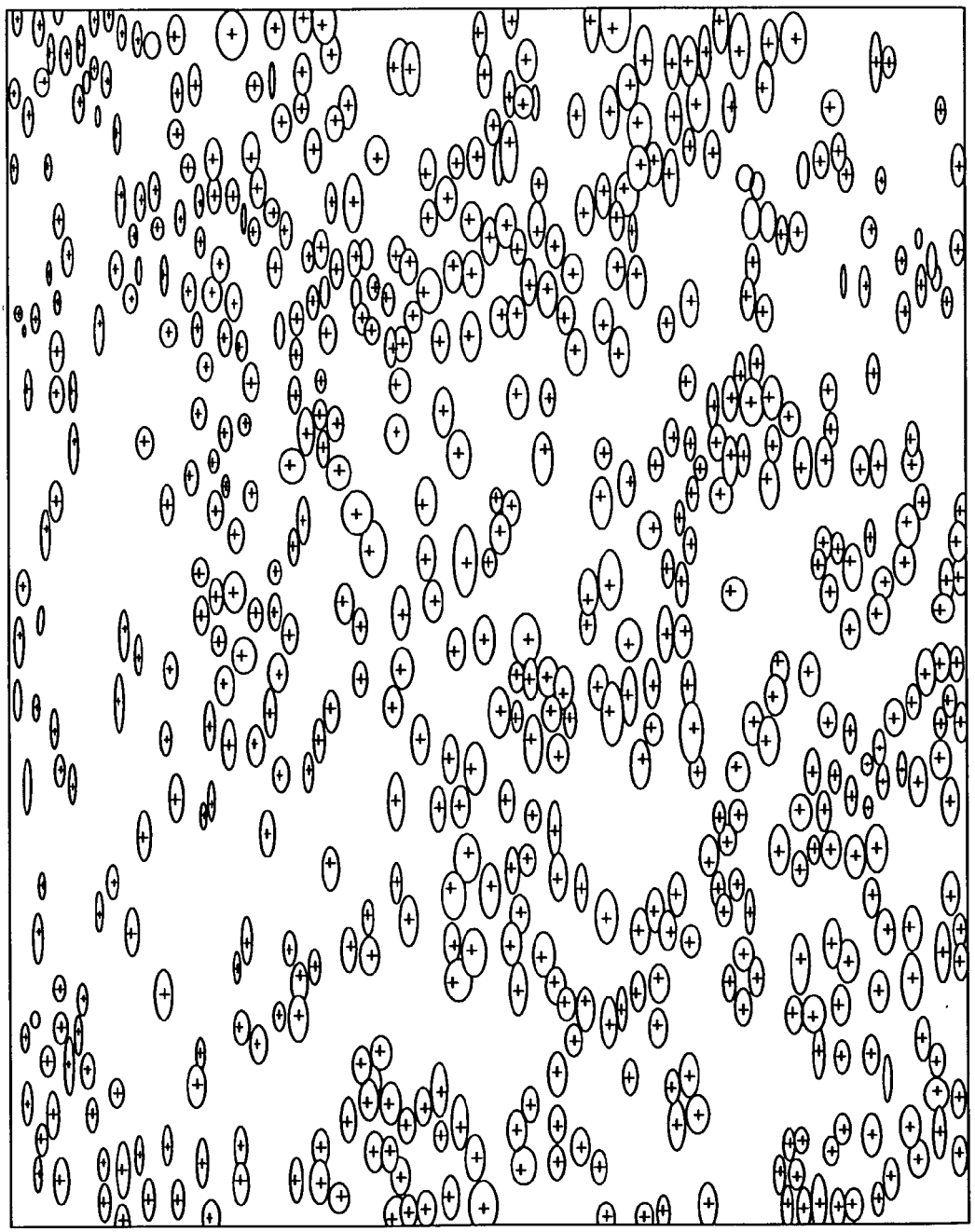
Figure 52:
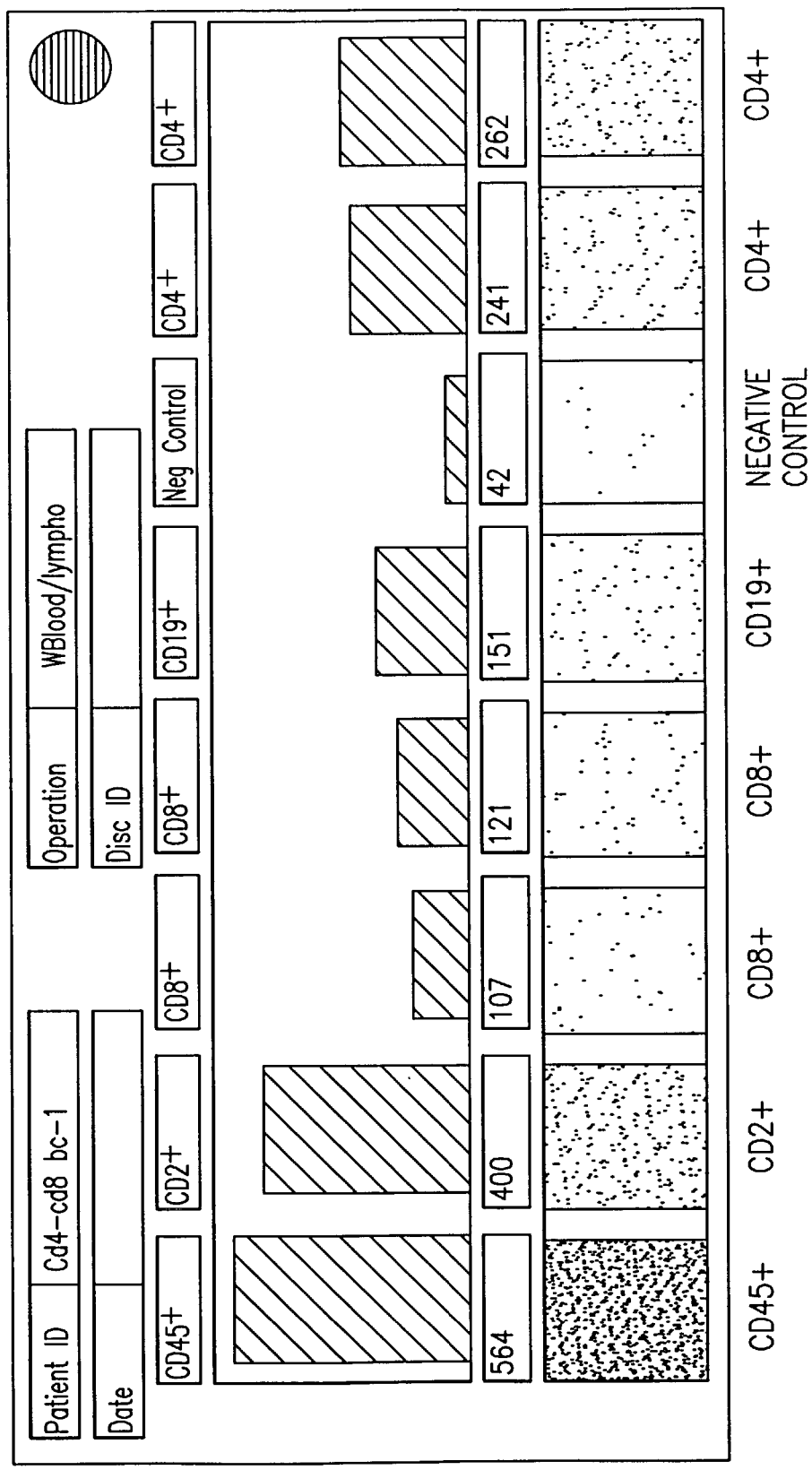
FIG. 52 is illustrative screen shot of expected output from the bar code according to an embodiment of the present invention.
Figure 53:
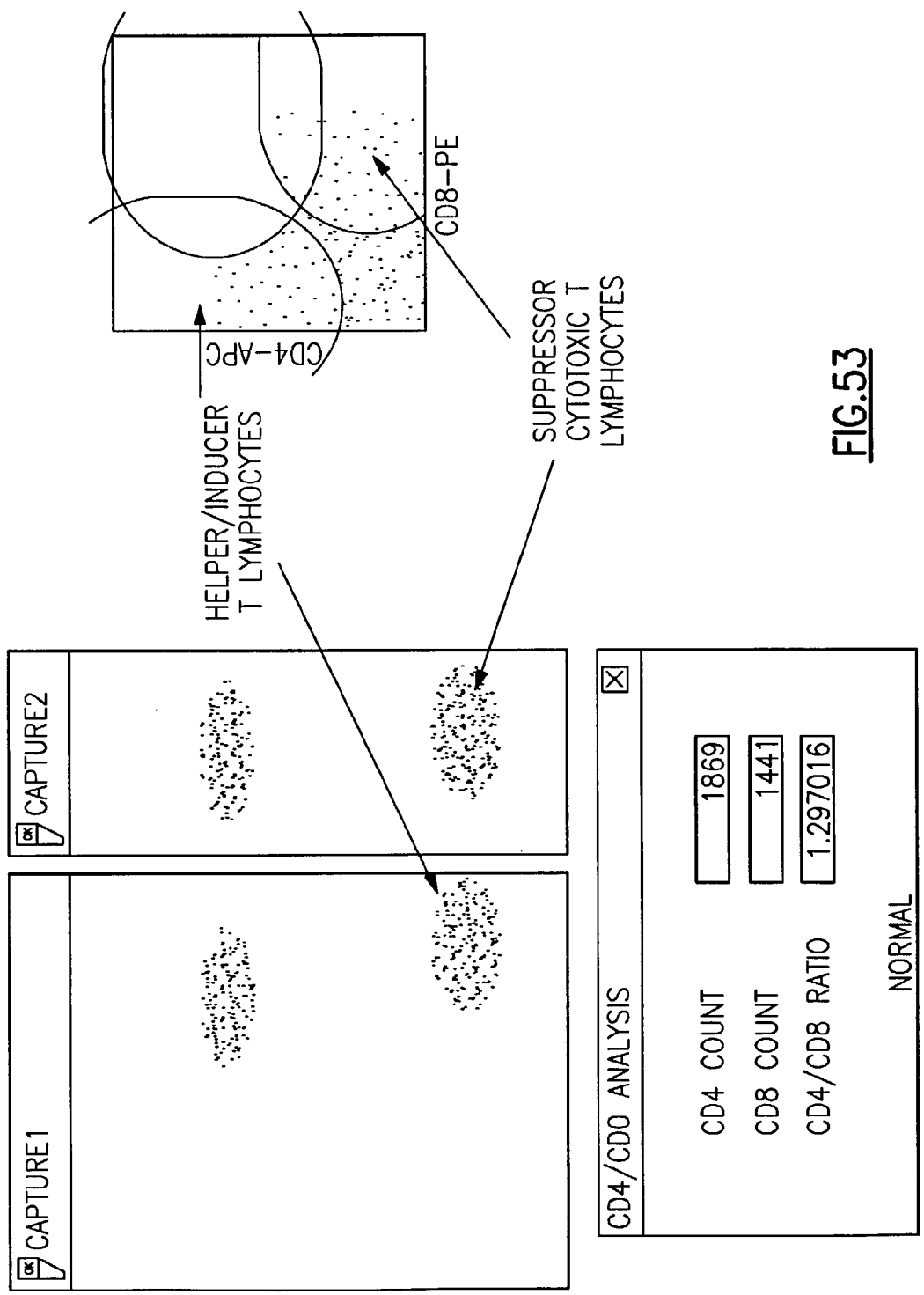
FIG. 53 shows a method for going from captured cells to usable output according to an embodiment of the present invention.

FIG. 51 shows a sample field with a number of cells with a plus sign indicating each object that is identified as a cell. After the number of cells have been detected for every zone or any number of desired zones, resulting cell count data can be displayed in a single screen that provides an easy to view representation such as that shown in FIG. 52. As depicted in FIG. 52, the specific cell counts are provided along with a bar graph to demonstrate relative numbers of cells. In the case of a CD4/CD8 analysis, the system can also produce a CD4/CD8 ratio as well as any other desired mathematical calculation or comparison. FIG. 53 provides a different view of the process showing cells in an image field being converted to a CD4 count, a CD8 count, and a ratio, with the output indicating that the ratio is in a normal range.

Aspects of the present invention relating to cell detection and associated processing methods are also disclosed in U.S. Provisional Application Ser. No. 60/316,273 entitled "Capture Layer Assemblies and Optical Bio-Discs for Immunophenotyping" filed Aug. 31, 2001; U.S. Provisional Application Ser. No. 60/318,026 entitled "Methods for Imaging Blood cells, Blood-Borne Parasites and Pathogens, and Other Biological Matter Including Related Optical Bio-Discs and Drive Assemblies" filed Sep. 7, 2001; U.S. Provisional Application Ser. No. 60/322,527 entitled "Optical Analysis Discs Including Microfluidic Circuits for Performing Cell Counts" filed Sep. 14, 2001; U.S. Provisional Application Ser. No. 60/322,040 entitled "Optical Analysis Discs Including Fluidic Circuits for Optical Imaging and Quantitative Evaluation of Blood Cells Including Lymphocytes" filed Sep. 11, 2001; U.S. Provisional Application Ser. No. 60/322,863 entitled "Methods for Differential Cell Counts Including Leukocytes and Use of Optical Bio-Disc for Performing Same" filed Sep. 12, 2001; and U.S. Provisional Application Ser. No. 60/322,793 entitled "Methods for Reducing Non-Specific Binding of Cells on Optical Bio-Discs Utilizing Charged Matter Including Heparin, Plasma, or Poly-Lysine" filed Sep. 17, 2001, all of which are herein incorporated by reference.

Differential Cell Count Methods and Related Software

A number of methods and related algorithms for white blood cell counting using optical disc data are herein discussed in further detail. These methods and related algorithms are not limited to counting white blood cells, but may be readily applied to conducting counts of any type of cellular matter including, but not limited to, red blood cells, white blood cells, beads, and any other objects, both biological and non-biological, that produce similar optical signatures that can be detected by an optical reader.

For the purposes of illustration, the following description of the methods and algorithms related to the present invention as described with reference to FIGS. 54–58, are directed to white blood cell counting. With some modifications, these methods and algorithms can be applied to counting other types of cells, or objects similar in size to white blood cells. The data evaluation aspects of the cell counting methods and algorithms are described generally herein to provide related background for the methods and apparatus of the present invention. Methods and algorithms for capturing and processing investigational data from the optical bio-disc has general broad applicability and has been disclosed in further detail in commonly assigned U.S. Provisional Application No. 60/291,233 entitled "Variable Sampling Control For Rendering Pixelation of Analysis Results In Optical Bio-Disc Assembly And Apparatus Relating Thereto" filed May 16, 2001 which is herein incorporated by reference and the above incorporated U.S. Provisional Application No. 60/404,921 entitled "Methods For Differential Cell Counts Including Related Apparatus And Software For Performing Same". In the following discussion, the basic scheme of the methods and algorithms with a brief explanation is presented. As illustrated in FIG. 10, information concerning attributes of the biological test sample is retrieved from the optical bio-disc 110 in the form of a beam of electromagnetic radiation that has been modified or modulated by interaction with the test sample. In the case of the reflective optical bio-disc discussed in conjunction with FIGS. 2, 3, 4, 11, 13, and 15, the return beam 154 carries the information about the biological sample. As discussed above, such information about the biological sample is contained in the return beam essentially only when the incident beam is within the flow channel or analysis chamber 130 or target zones 140 and thus in contact with the sample. In the reflective embodiment of the bio-disc 110, the return beam 154 may also carry information encoded in or on the reflective layer 142 or otherwise encoded in the wobble grooves 170 illustrated in FIGS. 13 and 14. As would be apparent to one of skill in the art, pre-recorded information is contained in the return beam 154 of the reflective disc with target zones, only when the corresponding incident beam is in contact with the reflective layer 142. Such information is not contained in the return beam 154 when the incident beam 152 is in an area where the information bearing reflective layer 142 has been removed or is otherwise absent. In the case of the transmissive optical bio-disc discussed in conjunction with FIGS. 5, 6, 8, 9, 12, 14, and 16, the transmitted beam 156 carries the information about the biological sample.

With continuing reference to FIG. 10, the information about the biological test sample, whether it is obtained from the return beam 154 of the reflective disc or the transmitted beam 156 of the transmissive disc, is directed to a processor 166 for signal processing. This processing involves transformation of the analog signal detected by the bottom detector 157 (reflective disc) or the top detector 158 (transmissive disc) to a discrete digital form.

Figure 54:
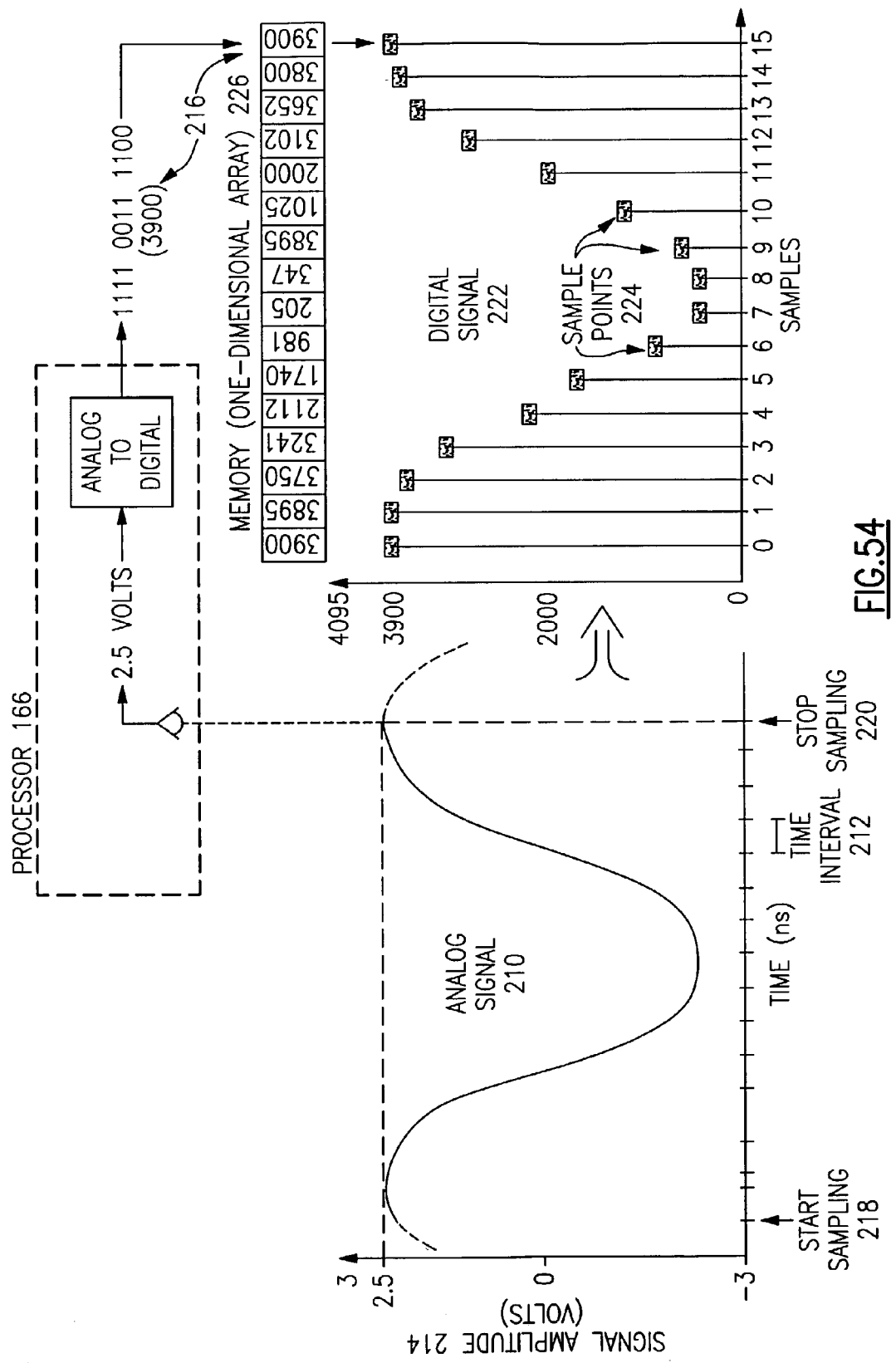
FIG. 54 is a pictorial graphical representation of the transformation of a sampled analog signal to a corresponding digital signal that is stored as a one-dimensional array.

Referring next to FIG. 54, the signal transformation involves sampling the analog signal 210 at fixed time intervals 212, and encoding the corresponding instantaneous analog amplitude 214 of the signal as a discrete binary integer 216. Sampling is started at some start time 218 and stopped at some end time 220. The two common values associated with any analog-to-digital conversion process are sampling frequency and bit depth. The sampling frequency, also called the sampling rate, is the number of samples taken per unit time. A higher sampling frequency yields a smaller time interval 212 between consecutive samples, which results in a higher fidelity of the digital signal 222 compared to the original analog signal 210. Bit depth is the number of bits used in each sample point to encode the sampled amplitude 214 of the analog signal 210. The greater the bit depth, the better the binary integer 216 will approximate the original analog amplitude 214. In the present embodiment, the sampling rate is 8 MHz with a bit depth of 12 bits per sample, allowing an integer sample range of 0 to 4095 (0 to $(2^n-1)$), where n is the bit depth. This combination may change to accommodate the particular accuracy necessary in other embodiments. By way of example and not limitation, it may be desirable to increase sampling frequency in embodiments involving methods for counting beads, which are generally smaller than cells. The sampled data is then sent to processor 166 for analog-to-digital transformation.

During the analog-to-digital transformation, each consecutive sample point 224 along the laser path is stored consecutively on disc or in memory as a one-dimensional array 226. Each consecutive track contributes an independent one-dimensional array, which yields a two-dimensional array 228 (FIG. 57A) that is analogous to an image.

Figure 55:
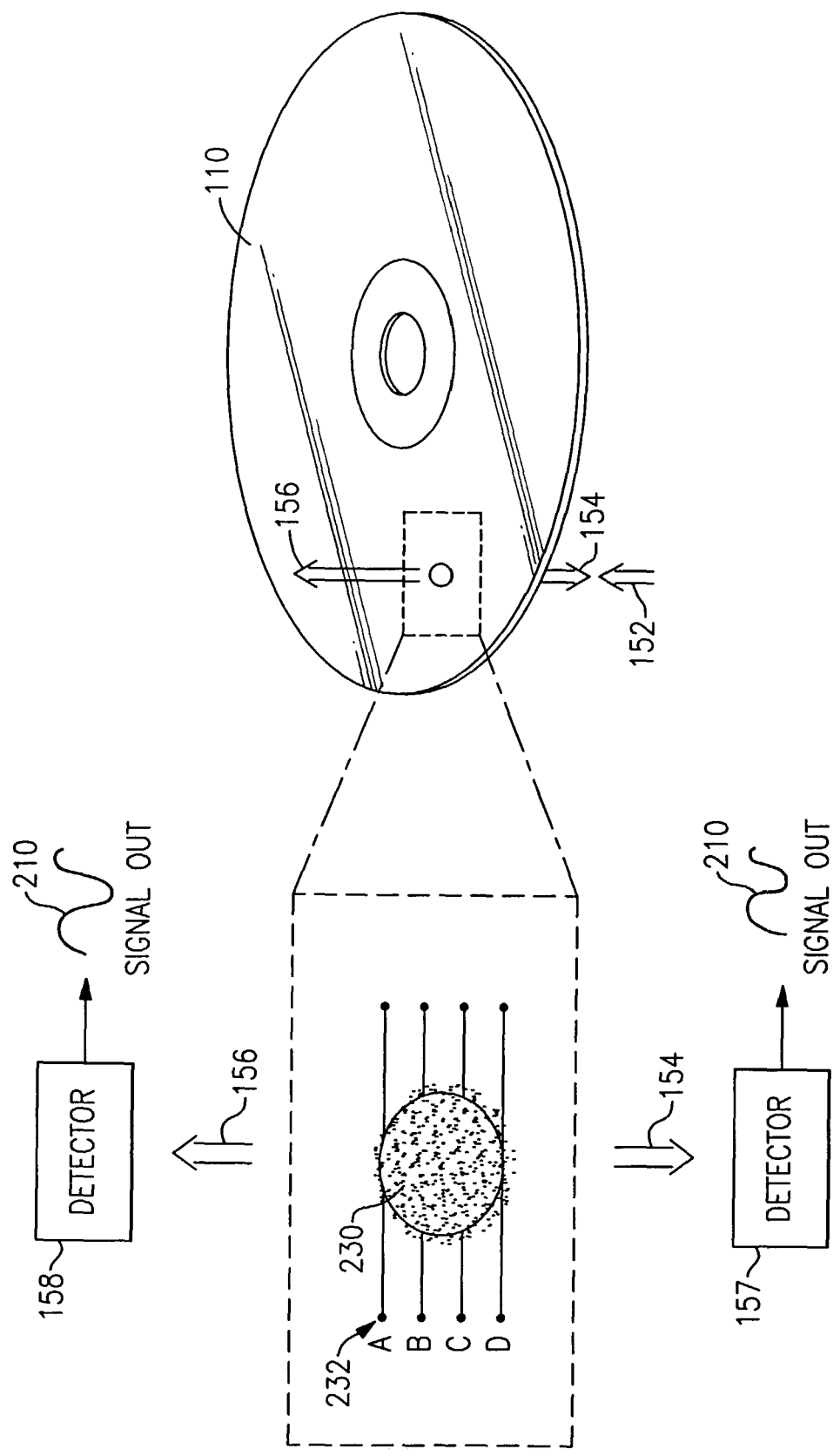
FIG. 55 is a perspective view of an optical disc with an enlarged detailed view of an indicated section showing a captured white blood cell positioned relative to the tracks of the bio-disc yielding a signal-containing beam after interacting with an incident beam.

FIG. 55 is a perspective view of an optical bio-disc 110 of the present invention with an enlarged detailed perspective view of the section indicated showing a captured white blood cell 230 positioned relative to the tracks 232 of the optical bio-disc. As shown, the interaction of incident beam 152 with white blood cell 230 yields a signal-containing beam, either in the form of a return beam 154 of the reflective disc or a transmitted beam 156 of the transmissive disc, which is detected by either of detectors 157 or 158.

Figure 56A:
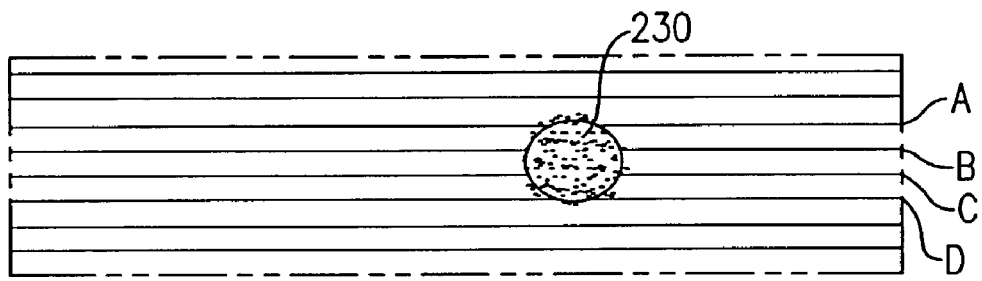
FIG. 56A is a graphical representation of a white blood cell positioned relative to the tracks of an optical bio-disc according to the present invention.
Figure 56B:
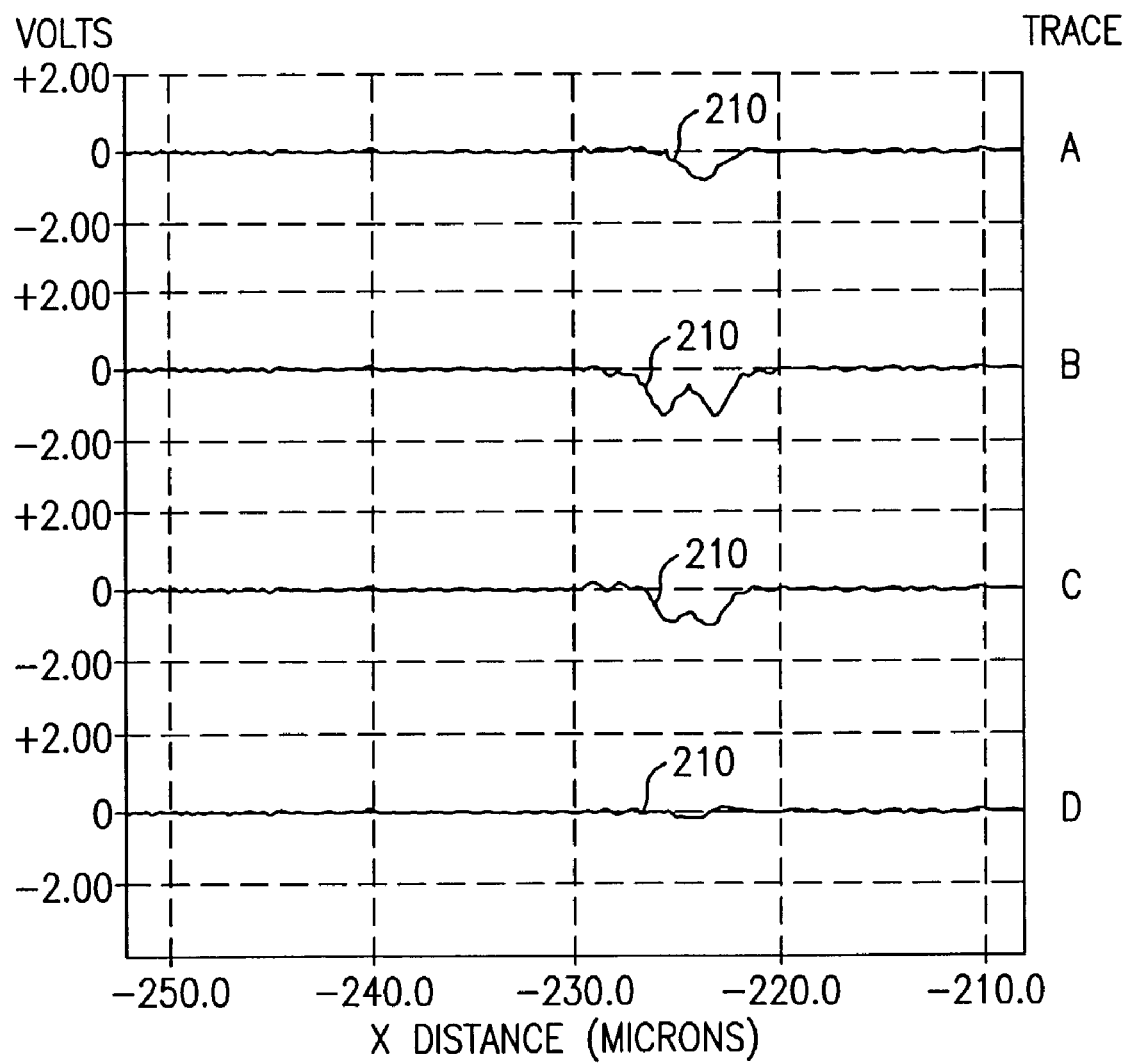
FIG. 56B is a series of signature traces derived from the white blood cell of FIG. 56A according to the present invention.

FIG. 56A is another graphical representation of the white blood cell 230 positioned relative to the tracks 232 of the optical bio-disc 110 shown in FIG. 55. As shown in FIGS. 55 and 56A, the white blood cell 230 covers approximately four tracks A, B, C, and D. FIG. 56B shows a series of signature traces derived from the white blood cell 210 of FIGS. 55 and 56A. As indicated in FIG. 56B, the detection system provides four analogue signals A, B, C, and D corresponding to tracks A, B, C, and D. As further shown in FIG. 56B, each of the analogue signals A, B, C, and D carries specific information about the white blood cell 230. Thus as illustrated, a scan over a white blood cell 230 yields distinct perturbations of the incident beam that can be detected and processed. The analog signature traces (signals) 210 are then directed to processor 166 for transformation to an analogous digital signal 222 as shown in FIGS. 57A and 57C as discussed in further detail below.

Figure 57A:
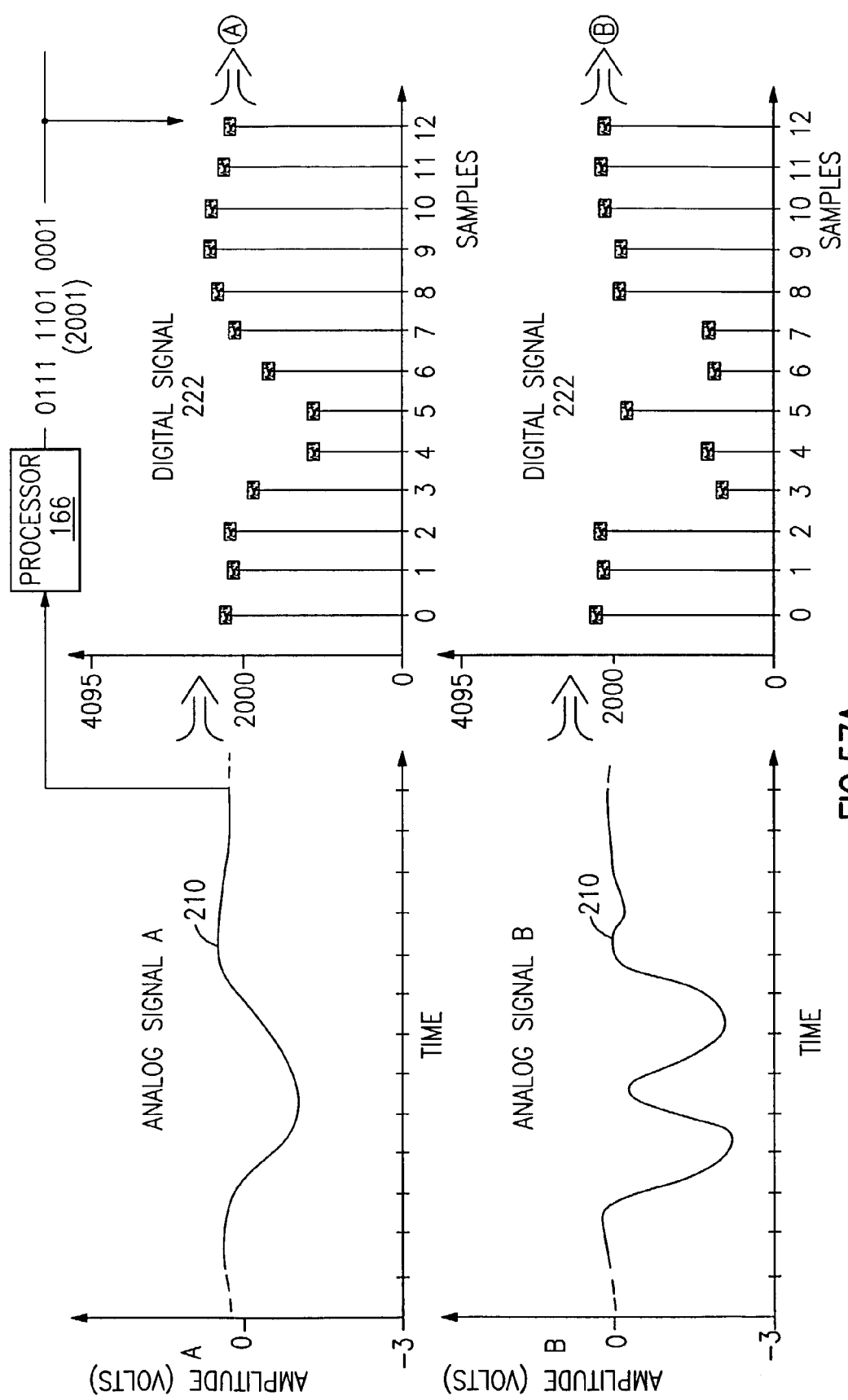
Figure 57B:
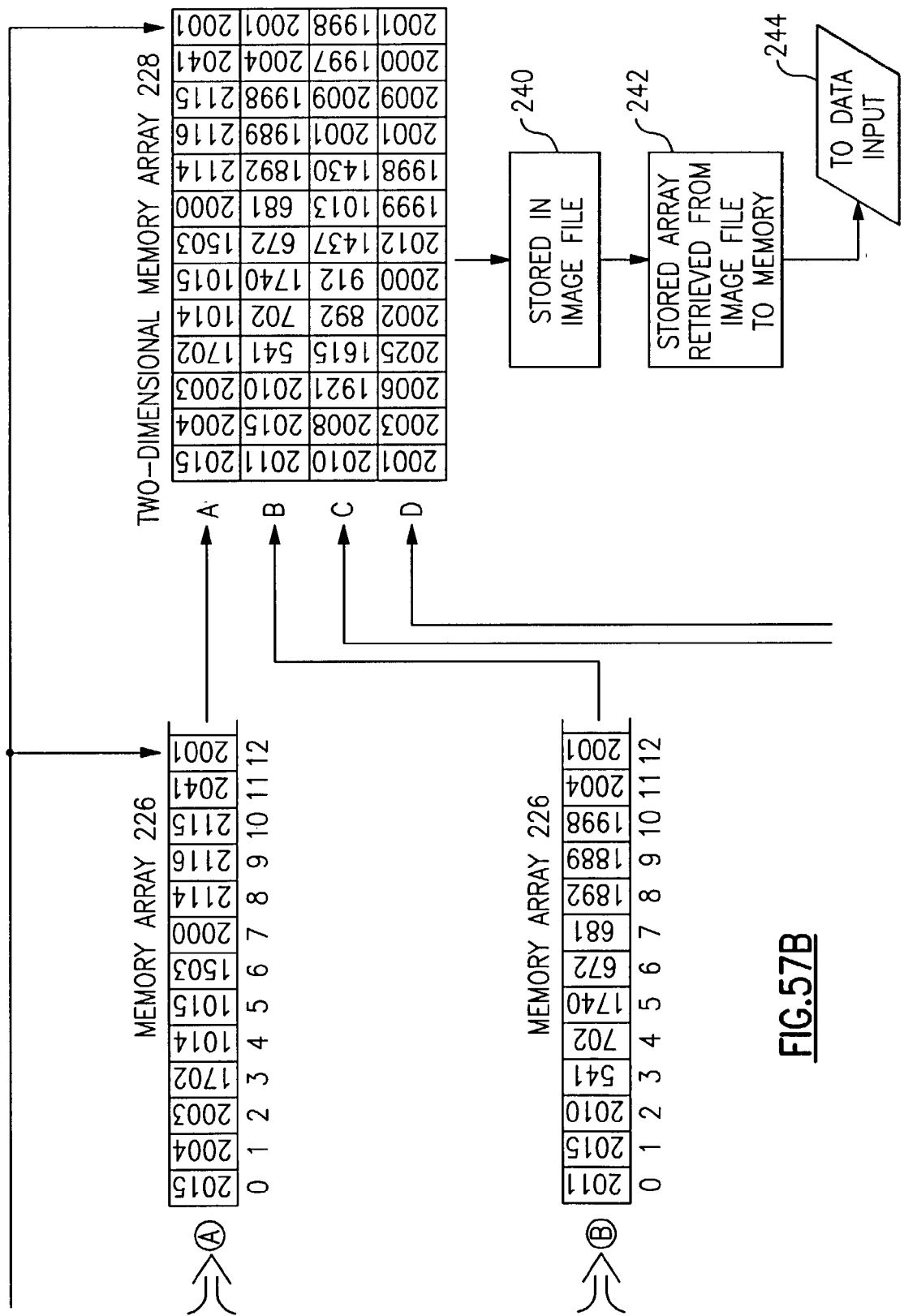
Figure 57C:
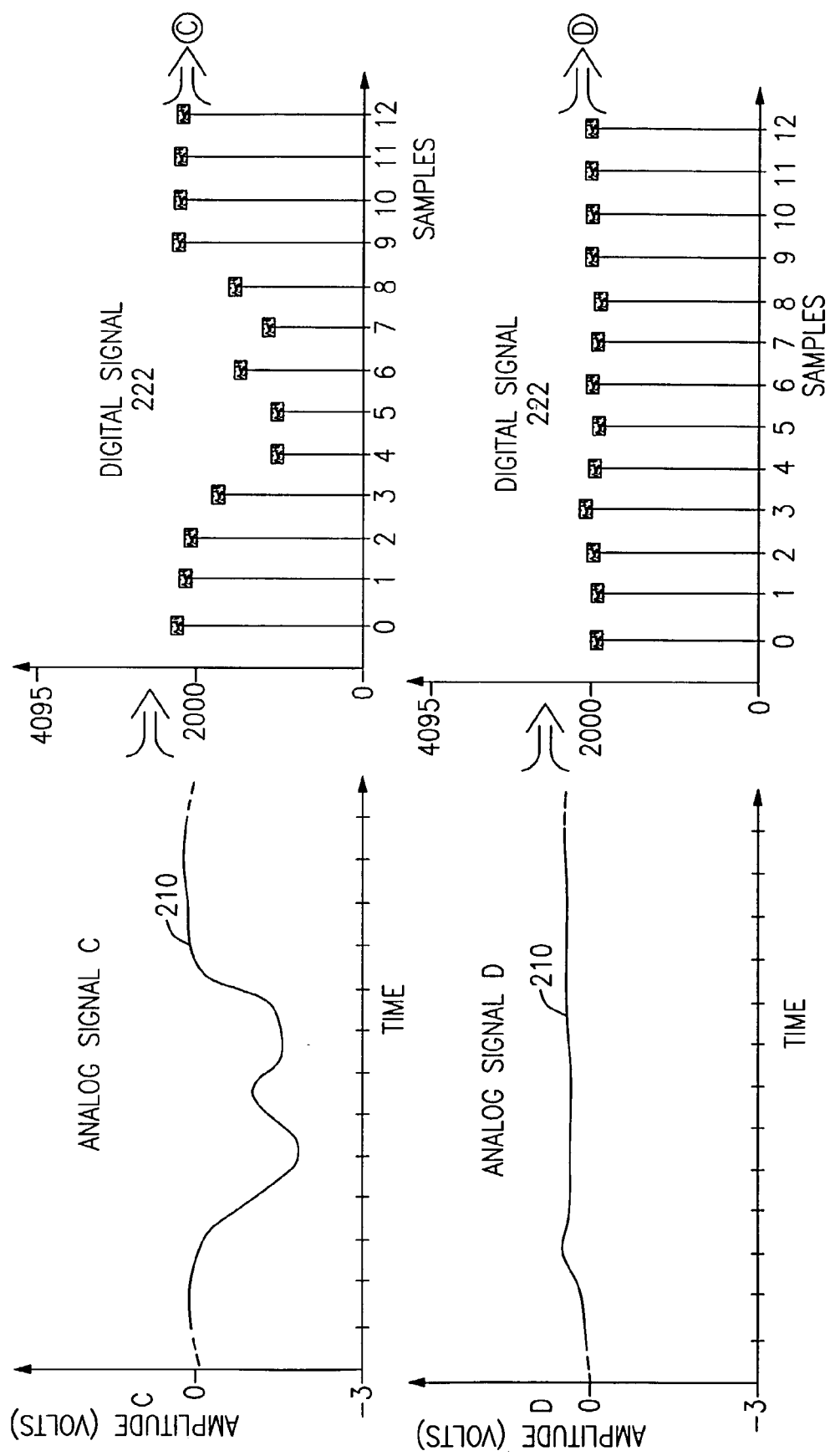

FIG. 57 is a graphical representation illustrating the relationship between FIGS. 57A, 57B, 57C, and 57D. FIGS. 57A, 57B, 57C, and 57D are pictorial graphical representations of transformation of the signature traces from FIG. 56B into digital signals 222 that are stored as one-dimensional arrays 226 and combined into a two-dimensional array 228 for data input 244.

With particular reference now to FIG. 57A, there is shown sampled analog signals 210 from tracks A and B of the optical bio-disc shown in FIGS. 55 and 56A. Processor 166 then encodes the corresponding instantaneous analog amplitude 214 of the analog signal 210 as a discrete binary integer 216 (see FIG. 54). The resulting series of data points is the digital signal 222 that is analogous to the sampled analog signal 210.

Referring next to FIG. 57B, digital signal 222 from tracks A and B (FIG. 57A) is stored as an independent one-dimensional memory array 226. Each consecutive track contributes a corresponding one-dimensional array, which when combined with the previous one-dimensional arrays, yields a two-dimensional array 228 that is analogous to an image. The digital data is then stored in memory or on disc as a two-dimensional array 228 of sample points 224 (FIG. 54) that represent the relative intensity of the return beam 154 or transmitted beam 156 (FIG. 55) at a particular point in the sample area. The two-dimensional array is then stored in memory or on disc in the form of a raw file or image file 240 as represented in FIG. 57B. The data stored in the image file 240 is then retrieved 242 to memory and used as data input 244 to analyzer 168 shown in FIG. 10.

FIG. 57C shows sampled analog signals 210 from tracks C and D of the optical bio-disc shown in FIGS. 55 and 56A. Processor 166 then encodes the corresponding instantaneous analog amplitude 214 of the analog signal 210 as a discrete binary integer 216 (FIG. 54). The resulting series of data points is the digital signal 222 that is analogous to the sampled analog signal 210.

Referring now to FIG. 57D, digital signal 222 from tracks C and D is stored as an independent one-dimensional memory array 226. Each consecutive track contributes a corresponding one-dimensional array, which when combined with the previous one-dimensional arrays, yields a two-dimensional array 228 that is analogous to an image. As above, the digital data is then stored in memory or on disc as a two-dimensional array 228 of sample points 224 (FIG. 54) that represent the relative intensity of the return beam 154 or transmitted beam 156 (FIG. 55) at a particular point in the sample area. The two-dimensional array is then stored in memory or on disc in the form of a raw file or image file 240 as shown in FIG. 57B. As indicated above, the data stored in the image file 240 is then retrieved 242 to memory and used as data input 244 to analyzer 168 FIG. 10.

Figure 58:
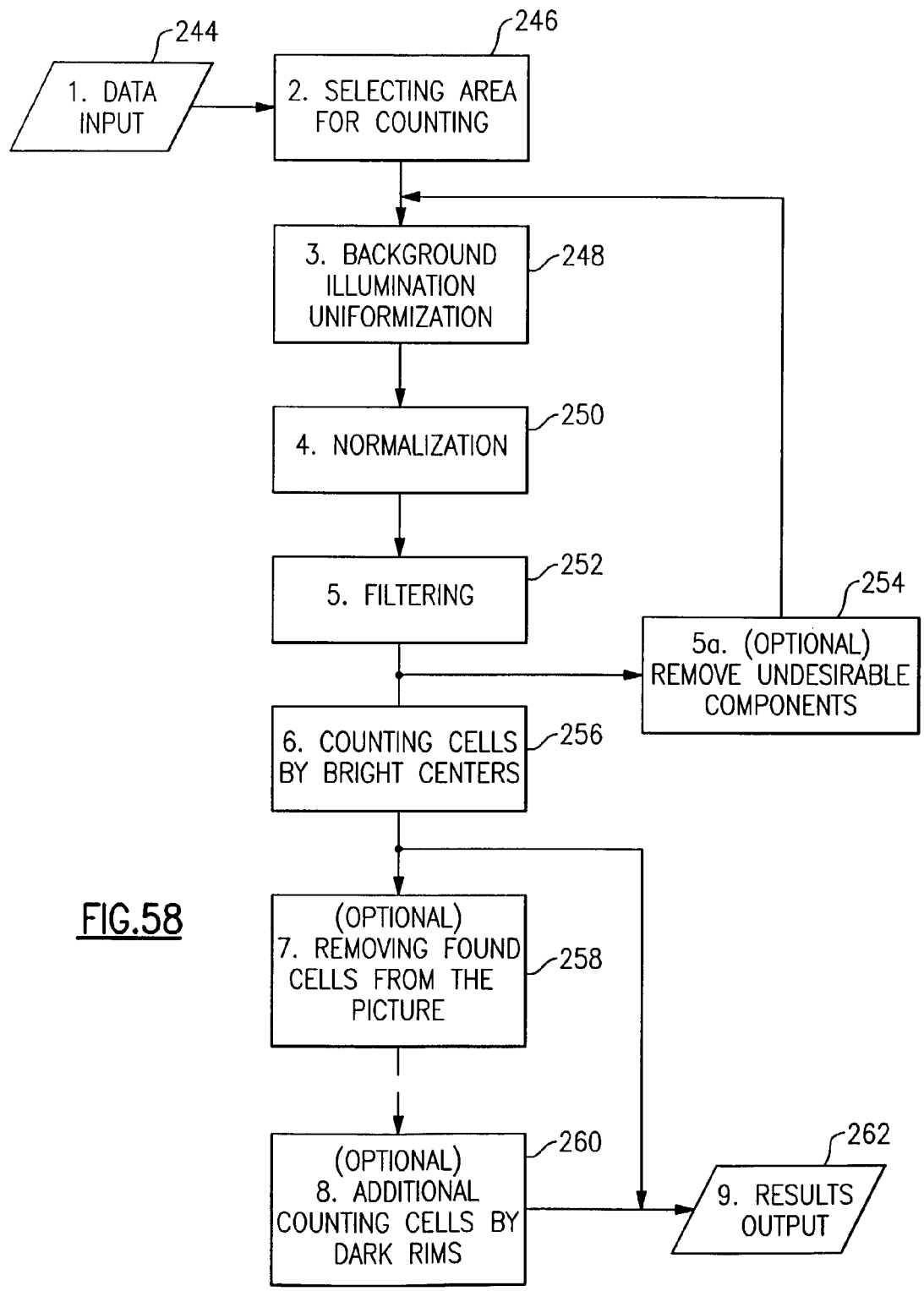
FIG. 58 is a logic flow chart depicting the principal steps for data evaluation according to processing methods and computational algorithms related to the present invention.

The computational and processing algorithms of the present invention are stored in analyzer 168 (FIG. 10) and applied to the input data 244 to produce useful output results 262 (FIG. 58) that may be displayed on the display monitor 114 (FIG. 10). With reference now to FIG. 58 there is shown a logic flow chart of the principal steps for data evaluation according to the processing methods and computational algorithms of the present invention. A first principal step of the present processing method involves receipt of the input data 244. As described above, data evaluation starts with an array of integers in the range of 0 to 4096.

The next principle step 246 is selecting an area of the disc for counting. Once this area is defined, an objective then becomes making an actual count of all white blood cells contained in the defined area. The implementation of step 246 depends on the configuration of the disc and user's options. By way of example and not limitation, embodiments of the invention using discs with windows such as the target zones 140 shown in FIGS. 2 and 5, the software recognizes the windows and crops a section thereof for analysis and counting. In one preferred embodiment, such as that illustrated in FIG. 2, the target zones or windows have the shape of 1×2 mm rectangles with a semicircular section on each end thereof. In this embodiment, the software crops a standard rectangle of 1×2 mm area inside a respective window. In an aspect of this embodiment, the reader may take several consecutive sample values to compare the number of cells in several different windows.

In embodiments of the invention using a transmissive disc without windows, as shown in FIGS. 5, 6, 8, and 9, step 246 may be performed in one of two different manners. The position of the standard rectangle is chosen either by positioning its center relative to a point with fixed coordinates, or by finding reference mark 202 (see for example FIGS. 24L, 25, and 26), which is a spot of dark dye. In the case where a reference mark 202 is employed, a dye with a desired contrast is deposited in a specific position 141 (FIG. 20E for example) on the disc with respect to two clusters of cells. The optical disc reader is then directed to skip to the center of one of the clusters of cells and the standard rectangle is then centered around the selected cluster.

As for the user options mentioned above in regard to step 246, the user may specify a desired sample area shape for cell counting, such as a rectangular area, by direct interaction with mouse selection or otherwise. In the present embodiment of the software, this involves using the mouse to click and drag a rectangle over the desired portion of the optical bio-disc-derived image that is displayed on a monitor 114. Regardless of the evaluation area selection method, a respective rectangular area is evaluated for counting in the next step 248.

The third principal step in FIG. 58 is step 248, which is directed to background illumination uniformization. This process corrects possible background uniformity fluctuations caused in some hardware configurations. Background illumination uniformization offsets the intensity level of each sample point such that the overall background, or the portion of the image that is not cells, approaches a plane with an arbitrary background value $V_{background}$. While $V_{background}$ may be decided in many ways, such as taking the average value over the standard rectangular sample area, in the present embodiment, the value is set to 2000. The value V at each point P of the selected rectangular sample area is replaced with the number ($V_{background}$+(V−average value over the neighborhood of P)) and truncated, if necessary, to fit the actual possible range of values, which is 0 to 4095 in a preferred embodiment of the present invention. The dimensions of the neighborhood are chosen to be sufficiently larger than the size of a cell and sufficiently smaller than the size of the standard rectangle.

The next step in the flow chart of FIG. 58 is a normalization step 250. In conducting normalization step 250, a linear transform is performed with the data in the standard rectangular sample area so that the average becomes 2000 with a standard deviation of 600. If necessary, the values are truncated to fit the range 0 to 4096. This step 250, as well as the background illumination uniformization step 248, makes the software less sensitive to hardware modifications and tuning. By way of example and not limitation, the signal gain in the detection circuitry, such as top detector 158 (FIG. 55), may change without significantly affecting the resultant cell counts.

As shown in FIG. 58, a filtering step 252 is next performed. For each point P in the standard rectangle, the number of points in the neighborhood of P, with dimensions smaller than indicated in step 248, with values sufficiently distinct from $V_{background}$ is calculated. The points calculated should approximate the size of a cell in the image. If this number is large enough, the value at P remains as it was; otherwise it is assigned to $V_{background}$. This filtering operation is performed to remove noise, and in the optimal case only cells remain in the image while the background is uniformly equal $V_{background}$.

An optional step 254 directed to removing bad components may be performed as indicated in FIG. 58. Defects such as scratches, bubbles, dirt, and other similar irregularities may pass through filtering step 252. These defects may cause cell counting errors either directly or by affecting the overall distribution in the images histogram. Typically, these defects are sufficiently larger in size than cells and can be removed in step 254 as follows. First a binary image with the same dimensions as the selected region is formed. A in the binary image is defined as white, if the value at the corresponding point of the original image is equal to $V_{background}$, and black otherwise. Next, connected components of black points are extracted. Then subsequent erosion and expansion are applied to regularize the view of components. And finally, components that are larger than a defined threshold are removed. In one embodiment of this optional step, the component is removed from the original image by assigning the corresponding sample points in the original image with the value $V_{background}$. The threshold that determines which components constitute countable objects and which are to be removed is a user-defined value. This threshold may also vary depending on the investigational feature being counted i.e. white blood cells, red blood cells, or other biological matter. After optional step 254, steps 248, 250, and 252 are preferably repeated.

The next principal processing step shown in FIG. 58 is step 256, which is directed to counting cells by bright centers. The counting step 256 consists of several substeps. The first of these substeps includes performing a convolution. In this convolution substep, an auxiliary array referred to as a convolved picture is formed. The value of the convolved picture at point P is the result of integration of a picture after filtering in the circular neighborhood of P. More precisely, for one specific embodiment, the function that is integrated, is the function that equals v−2000 when v is greater than 2000 and 0 when v is less than or equal to 2000. The next substep performed in counting step 256 is finding the local maxima of the convolved picture in the neighborhood of a radius about the size of a cell. Next, duplicate local maxima with the same value in a closed neighborhood of each other are avoided. In the last substep in counting step 256, the remaining local maxima are declared to mark cells.

In some hardware configurations, some cells may appear without bright centers. In these instances, only a dark rim is visible and the following two optional steps 258 and 260 are useful.

Step 258 is directed to removing found cells from the picture. In step 258, the circular region around the center of each found cell is filled with the value 2000 so that the cells with both bright centers and dark rims would not be found twice.

Step 260 is directed to counting additional cells by dark rims. Two transforms are made with the image after step 258. In the first substep of this routine, substep (a), the value v at each point is replaced with (2000−v) and if the result is negative it is replaced with zero. In substep (b), the resulting picture is then convolved with a ring of inner radius R1 and outer radius R2. R1 and R2 are, respectively, the minimal and the maximal expected radius of a cell, the ring being shifted, subsequently, in substep (d) to the left, right, up and down. In substep (c), the results of four shifts are summed. After this transform, the image of a dark rim cell looks like a four petal flower. Finally in substep (d), maxima of the function obtained in substep (c) are found in a manner to that employed in counting step 256. They are declared to mark cells omitted in step 256.

After counting step 256, or after counting step 260 when optionally employed, the last principal step illustrated in FIG. 58 is a results output step 262. The number of cells found in the standard rectangle is displayed on the monitor 114 shown in FIGS. 1 and 5, and each cell identified is marked with a red cross on the displayed optical bio-disc-derived image.

Other related aspects regarding processing data collected from an optical bio-disc assay is disclosed in commonly assigned and co-pending U.S. patent application Ser. No. 10/241,512 entitled "Methods for Differential Cell Counts Including Related Apparatus and Software Performing Same" filed Sep. 11, 2002. This application is incorporated by reference in its entirety as if fully repeated herein.

Methods for Isolating T-Lymphocytes from Whole Blood

There is a need for a method for isolating T cells or T lymphocytes from a cell sample including whole blood or mononuclear cell samples prepared using the gradient method described above in conjunction with FIG. 17. One method for isolating T lymphocytes, for example, is the use of bio-active reagents that causes agglutination and precipitation of unwanted cells. A non-limiting example of such a method is the "Biological Enrichment and Separation Technology" (BEST) method for isolating T-cells. The bio-active reagent used in the BEST method is called Prepacyte (BioE, St. Paul, Minn.). Prepacyte allows for the isolation of T cells from a cell sample including whole blood and mononuclear cells by selective removal of unwanted cells including granulocytes, platelets, monocytes, B cells, and NK cells. The percent recovery yield and purity of T cells isolated using the Prepacyte method is significantly higher than that of the gradient method. The selective removal of unwanted cells is mediated by the use of antibodies having specific affinity to the unwanted cells.

Cell preparation using Prepacyte takes about 30 minutes. For example, T cells may be isolated from whole blood by the following procedure. First, anticoagulated blood is mixed with an equal volume of Prepacyte. For the cell prepartion for the CD marker case of the present invention, for example, 1 ml of whole blood is mixed with 1 ml of Prepacyte to create an assay solution. The assay solution is then mixed gently for about 15 mins. to allow agglutination of unwanted cells. Then the assay solution is placed upright on a test tube rack for about 15 minutes to allow precipitation of the now agglutinated unwanted cells. After precipitation of unwanted cells, the supernatant containing the T cells are then removed and placed in a new container. The T cells are then washed in PBS. The washed T cells are then counted and resuspended in PBS to a pre-determined cell concentration. The T lymphocyte suspension is then loaded into the optical bio-disc for analysis.

Alternatively, isolation of specific cell populations including T cells from a cell sample including whole blood, for example, may be carried out using cell capture methods. In the cell capture method, antibodies directed against unwanted cells are bound to a solid phase including beads, a bio-matrix, or membranes. The cell sample is then passed through and allowed to interact with the solid phase where the unwanted cells are bound and only the desired cells pass through. Further details relating to other aspects associated with the use of a bio-matrix for cell separation and purification is disclosed in, for example, commonly assigned co-pending U.S. Provisional Application Ser. No. 60/365,462 entitled "Methods and Apparatus for Separating Whole Blood Components in an Optical Bio-disc Analysis Chamber for use in Biomedical Assays" filed Mar. 18, 2002, which is incorporated by reference in its entirety herein.

Yet another alternative for separating cells of interest from a sample including whole blood and mononuclear cells is the use of magnetic bead separation. In this method cells of interest may be positively or negatively selected from the sample. In negative selection method, magnetic beads are coated with antibodies specific to unwanted cells. The beads are mixed with the sample and incubated to allow the beads to bind to unwanted cells. The unwanted cells are then removed by exposing the sample to a magnetic field. The removal of unwanted cells may be carried out inside the fluidic circuit of the bio-disc and/or using a magneto-optical bio-disc. In contrast, positive selection uses magnetic beads having specific antibodies to the cell type/s of interest. The beads are mixed with the sample and incubated to allow the beads to bind to cells of interest. The magnetically tagged desired cell types are then isolated from the rest of the sample by exposing the sample to a magnetic field. The isolation of cells of interest may be carried out inside the fluidic circuit of the bio-disc and/or using a magneto-optical bio-disc. Further details relating to magneto-optical bio discs is disclosed in, for example, commonly assigned co-pending U.S. patent applications Ser. No. 10/099,256 entitled "Dual Bead Assays using Cleavable Spacers and/or Ligation to Improve Specificity including Related Methods and Apparatus" filed Mar. 14, 2002; and Ser. No. 10/099,266 entitled "Use of Restriction Enzymes and other Chemical Methods to Decrease Non-Specific Binding in Dual Bead Assays and Related Bio-Discs, Methods, and System Apparatus for Detecting Medical Targets" filed Mar. 14, 2002, which are both incorporated by reference in their entireties. Details relating to separating cells tagged with magnetic particles is disclosed in commonly assigned co-pending U.S. Provisional Application Ser. No. 60/398,464 entitled "Optical Bio-disc Cell Sorter and Analyser" filed Jul. 25, 2002; which is herein incorporated in its entirety by reference.

Still another alternative for separating cells is using a microfluidic chamber that can be used to separate or remove red blood cells through a sieving device integrated into the microfluidic chamber. The sieve that has apertures that are approximately about 5 micrometer (um) allow red cells to pass through and are collected in the waste chamber. The larger (>5 um) white cells are expelled into the assay chamber that has been layered with specific capture antibodies for helper/inducer-suppressor/cytotoxic assay. This particular chamber design has two interconnected slots or chambers. Chamber one contains the sieve. Blood sample to be analyzed is injected into the "sieving" chamber. As the blood cells come in contact with the sieve, red cells pass through the sieve that allows objects 5 um or less to pass through. Red cells are eliminated by using optimal centrifugal force, white blood cells that remain over the sieve are propelled into the "assay" chamber, that has been coated with specific capture antibodies. Following 30 minutes incubation for the antibody-antigen interaction, disc is read and imaged with the laser optics and the images analyzed with the CD4CD8 software.

A further alternative for isolating cells of interest, like leukocytes from whole blood, is to perform RBC lysis in the biodisc 110. The leukocyte material left over after lysis is dispelled into analysis chambers that have been layered with specific capture antibodies for helper/inducer-suppressor/cytotoxic assay. This particular fluidic circuit may include two interconnected slots or chambers. Chamber one may contain a lysis buffer (lysis chamber). Blood sample to be analyzed is injected into the "lysis" chamber. Incubated for 15 minutes for complete lysis. Once the lysis is complete, the disc is spun to enable the remaining leukocytes to pass into an analysis chamber, that has been coated with specific capture antibodies. Following a pre-determined incubation period, the disc is read and imaged with the laser optics and the images analyzed with a cellular analysis system. Further details regarding related cellular analysis systems are disclosed in for example commonly assigned U.S. Provisional Application Ser. Nos. 60/356,982, 60/372,007, and 60/408,227, each entitled "Bio-disc and Bio-drive Analyser System including Methods Relating Thereto", respectively filed on Feb. 13, 2002, Apr. 11, 2002, and Sep. 9, 2002; and U.S. patent application Ser. No. 10/279,677 entitled "Segmented Area Detector for Biodrive and Methods Relating Thereto" filed on Oct. 24, 2002, and U.S. patent application Ser. No. 10/241,512 entitled "Methods for Differential Cell Counts Including Related Apparatus and Software Performing Same" filed on Sep. 11, 2002.

As mentioned above, the isolation of T cells may be carried out in a fluidic circuit in the optical bio-disc. FIGS.

59, 60, 61A, 61B, 61C, 62A, 62B, and 62C shows examples of different fluidic circuits that may be used to purify cells of interest from a sample.

Figure 59:
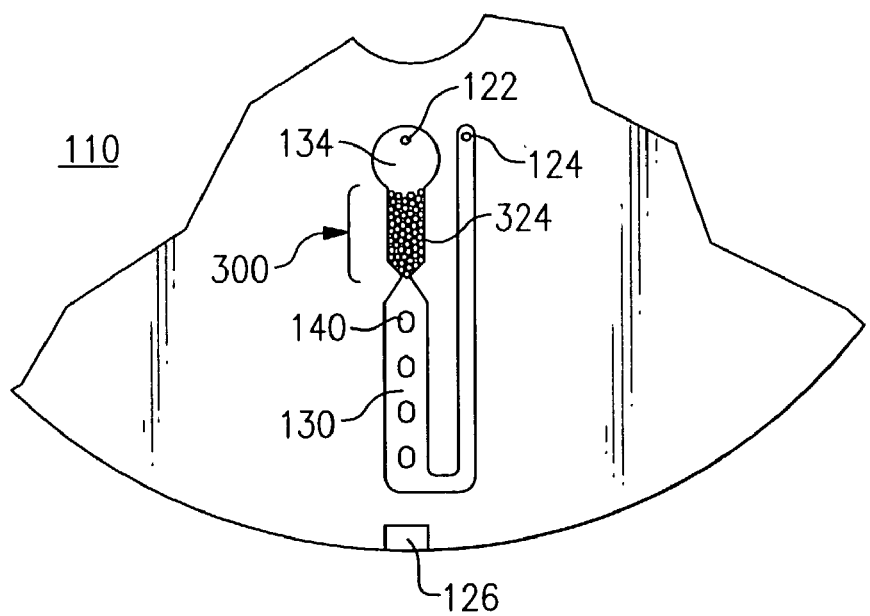
FIG. 59 shows a top plan view of a fluidic circuit used for isolating T cells from whole blood or MNC samples.

With reference to FIG. 59, there is illustrated a fluidic circuit for isolating T cells from whole blood or MNC samples. In this embodiment of the fluidic circuit, a whole blood or MNC sample is added into the mixing chamber 134 through the inlet port 122. The inlet port is then sealed and the disc is spun at a pre-determined speed to move the cells in the sample through the purification chamber 300 at a rate that allows sufficient time for unwanted cells to bind to the capture beads 324 in the purification chamber 300. The capture beads 324 have antibodies attached thereto that are directed against surface markers of unwanted cells. For example, the capture beads 324 may have anti-CD56 for NK cells, CD14 for monocytes, CD19 for B cells, CD9, CD31, or CD41 for platelets, and CD13, CD31, or CD43 for granulocytes attached thereto. Thus, a majority of unwanted cells are removed in the purification chamber 300 and T cells and red blood cells pass through the purification chamber 300 into the analysis chamber 130 where the different types of T cells are analyzed using the above mentioned methods. The red blood cells and excess buffer spin to the bottom of the channel and normally does not interfere with the assay.

Figure 60:
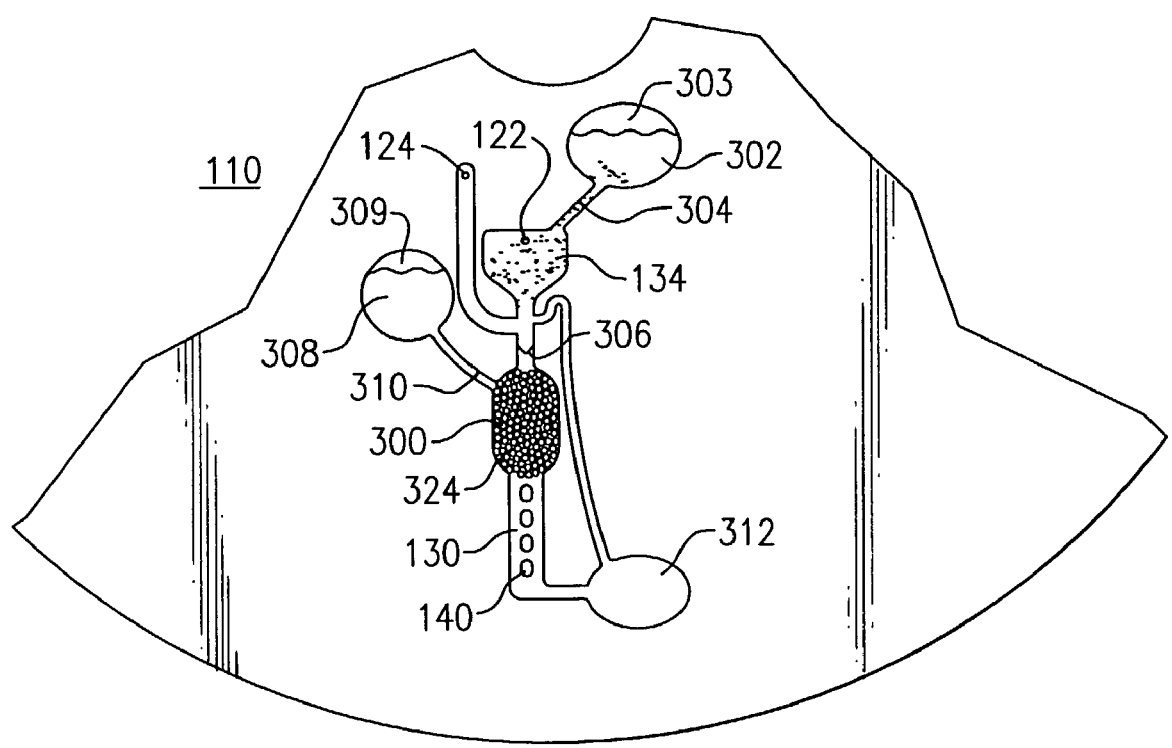
FIG. 60 shows another embodiment of a fluidic circuit for purifying and analyzing T cells including RBC lysis and white blood cell purification steps.

Referring next to FIG. 60, there is shown a fluidic circuit for purifying and analyzing T cells including RBC lysis and white blood cell purification steps. In this specific embodiment of a fluidic circuit, whole blood is added into the mixing chamber 134 through the inlet port 122. The inlet port is sealed and the disc is spun in a disc drive at a first speed such that the lysis valve 304 opens and the lysis buffer in the lysis buffer 302 in reservoir 303 moves into the mixing chamber 134 and mixes with the blood sample. The first speed should not cause valve 306 to open. The disc may then be agitated using the disc drive to increase the efficiency of lysis. After the lysing step, the disc is then spun at a second speed which is sufficient to open valves 306 and 310 thus moving the sample and allowing the analysis buffer 308 in the buffer reservoir 309 to mix with the sample. The disc is spun at a third speed to move the cells in the sample through the purification chamber 300 at a rate that allows sufficient time for unwanted cells to bind to the capture beads 324 in the purification chamber 300. The capture beads 324 have purification agents attached thereto that are directed against surface markers of unwanted cells. For example, the capture beads 324 may have purification agents including for example, DNA, ligands, receptors, and antibodies such as anti-CD56 for NK cells, CD14 for monocytes, CD19 for B cells, CD9, CD31, or CD41 for platelets, and CD13, CD31, or CD43 for granulocytes attached thereto. Thus, a majority of unwanted cells are removed in the purification chamber 300 and T cells pass through the purification chamber 300 into the analysis chamber 130 where the different types of T cells are analyzed using the above mentioned methods. Excess buffer and sample moves to the waste chamber 312. Further details relating to surface chemistries used to bind probes onto solid support such as beads and the surface of a disc, including gold and polycarbonate surfaces, are disclosed in, for example, commonly assigned U.S. Provisional Application Ser. No. 60/353,770 entitled "Capture Layer Assemblies Including Metal Layer for Immobilization of Receptor Molecules and Related Optical Assay Discs" filed Jan. 30, 2002; and U.S. Provisional Application Ser. No. 60/353,745 entitled "Capture Layer Assemblies Including Polymer Substrates for Immobilization of Receptor Molecules and Related Optical Assay Discs" filed Jan. 30, 2002; and U.S. patent application Ser. No. 10/194,396 entitled "Multi-Purpose Optical Analysis Disc For Conducting Assays And Various Reporting Agents For Use Therewith" filed Jul. 12, 2002. All of these applications are incorporated by reference in their entireties as if fully repeated herein.

The beads 324 may carry different chemical functionalities including, for example, carboxyl, amino, aldehyde, and hydrazine functional groups that facilitate binding of the purification agents. The purification agents may bind onto a solid phase through various chemical processes described below in detail. Thiol or amine active groups may be covalently bound to the purification agents to thereby produce a modified purification agent. This modified purification agent may then be directly bound through their attached active groups by covalent dative binding directly to metal surface such as gold, for example. If the purification agent is a protein, direct binding of the purification agent to the gold surface may carried out through dative binding of exposed cysteine and methionine residues on the protein without the need for thiol or amine modification. The bond between the purification agent and the surface of beads, for example, is sufficient so that the purification agent remains attached to the beads, when the disc 110 is rotated.

Several methods may be used to form functionally active biochemical layers on the surface of beads and the polycarbonate (PC) or gold surface of the disc substrate 120. Passive adsorption is one preferred method for achieving the linkage of a bio-chemical, chemical, binding reagent, or purification agent to the polymer or metal surface of the disc substrate 120 and to polymer surfaces of microspheres or beads. Large bio-molecules containing pockets of hydrophobic amino acids, carbohydrates, and similar components are easily linked to a non-polar polymer surface through passive adsorption. The hydrophobic forces exhibited by the polymer and the bio-molecule or purification agent, as well as the electrostatic interaction between the substrate and the purification agent, result in the formation of a stable linkage. The pH, salt concentration, and presence of competing substances will, among other factors, determine the extent to which various purification agents link non-covalently to the plain surface of the polymer or the metal covered polymer surface. If the purification agent is a protein, the pH of the coating buffer containing the purification agent affects the binding of the capture agent onto the polymer substrate or metal layer. A pH of the coating buffer solution close to the isoelectric point of the purification agent will increase the hydrophobicity of the protein thus leading to a stronger interaction of the protein with the substrate resulting in stronger bonding and most likely also to higher density of immobilized capture agent.

Alternatively, thiolated purification agents may be immobilized onto the gold or metallic surface through dative binding of thiol active groups on the purification agent. In one preferred embodiment of the present invention, the purification agents are proteins, these purification agents may be directly bound to a gold surface, of a colloidal gold particle, covalently by dative binding to form metalorganic bonds through cysteine or methionine residues of the purification agent or binding protein. The dative binding of the thiol or methionine active groups may be facilitated by a mild reducing agent such as sodium cyanoborohydride ($NaCNBH_3$). In yet another embodiment of the present invention, thiolated forms of affinity agents such as biotin, streptavidin, avidin, Neutravidin, and BSA-biotin may be initially bound to the gold surface by dative binding, either directly through cysteine and methionine residues on the surface of these proteins or through attached thiol active groups on thiolated proteins. Purification agents conjugated with an appropriate binding pair including biotin, streptavidin, Neutravidin, and avidin are then mixed with the beads or nano-particles and allowed to bind to the beads having the respective affinity agents. In still another embodiment, streptavidin or biotin may be used as a bridging agent to bind respectively, a biotinylated or streptavidinated, bead surface to its respective streptavidinated or biotinylated purification agent.

Passive adsorption of the purification agents may not work for a number of biopolymers that do not interact passively with the chemically inert surface of the polymer substrate or the metal covered polymer substrate. This is because there may be a lack of sites for non-covalent interaction. Proteins of low molecular weight, polypeptides, and molecules with predominantly ionic character, for example, do not link to polymer surfaces due to lack of, or the presence of only very weak, hydrophobic or electrostatic interaction.

Another critical aspect in immobilizing binding proteins or purification agents onto a solid support is the retention of functional activity of bound protein or purification agent. Frequently, the purification agents loose their biochemical properties due to denaturation in the process of immobilization involving structural reorganization followed by conformational changes and accompanying changes of functionally active sites. Enzymes, receptors, lectins, and antibodies are examples of such bio-polymers, binding proteins, or purification agents.

Situations where the lack of passive interaction with the support polymer substrate or the loss of functional activity due to the immobilization process, necessitate another approach. The approach taken in these cases leads to the functionalization of the chemically inert surface of the beads or disc substrate upon which the immobilization of the biochemical reagent is intended. Functionalization is a process by which the bead surface, disc substrate, or metal surface is modified by attaching specific molecules or polymers with functional groups to the surface. The functional groups are then used to bind recognition molecules such as binding proteins, capture antibodies, receptors, and other similar assay components. Structural changes of the binding protein at regions of the molecule known not to harbor vital biochemical function will augment the contribution derived from the modified substrate or metal surface.

Surfaces of polymeric materials have been modified previously. See for instance Braybrook et al., Prog. Polym. Sci. 15:715–734, 1990. Most of the modification procedures known in the art involve sequential treatment of surfaces with chemical reagents. Examples include sulfonation of polystyrene, Gibson et al., Macromolecules 13:34, 1980; base hydrolysis of polyimide, Lee et al., Macromolecules 23:2097, 1990; and base treatment of polyvinylidene fluoride, Dias et al., Macromolecules 17:2529, 1984. Another conventional method for modifying polymer surfaces includes exposing the surface of a hydrocarbon such as polyethylene with nitrene or carbene intermediates generated in a gas phase (Breslow in "Azides and Nitrenes", chapter 10, Academic Press, New York, 1984). Perfluorophenyl azides (PFPAs) have been shown to be efficient in the insertion in CH bonds over their non-fluorinated analogues (Keana et al., Fluorine Chem. 43:151, 1989). Recently, bis-(PFPA)s have been shown to be efficient cross-linking agents for Polystyrene (Cai et al., Chem. Mater. 2:631, 1990).

Chemical modification of the inert polymer surface is efficiently done through grafting procedures that allow the deposition of a thin interphase layer, active layer, or interlayer on the surface of beads, for example. Ideally, the interphase layer should make a stable linkage of the grafted material to the bead surface and contain a spacer molecule ending in a functional group or variety of chemically different functional groups. This allows the selection of specific surface chemistries for efficient covalent immobilization of a variety of purification agents with different demand for spatial orientation, including side directed attachment within the structure of the binding protein. The introduction of spacer molecules, especially hydrophilic spacers as part of the graft, contributes significantly to the flexibility and accessibility of the immobilized purification agents. By placing a spacer layer between the solid phase of the substrate modified or grafted with different functional groups and the binding protein, a potentially denaturing effect of the direct contact of the protein with the functional groups is eliminated.

Figure 61A:
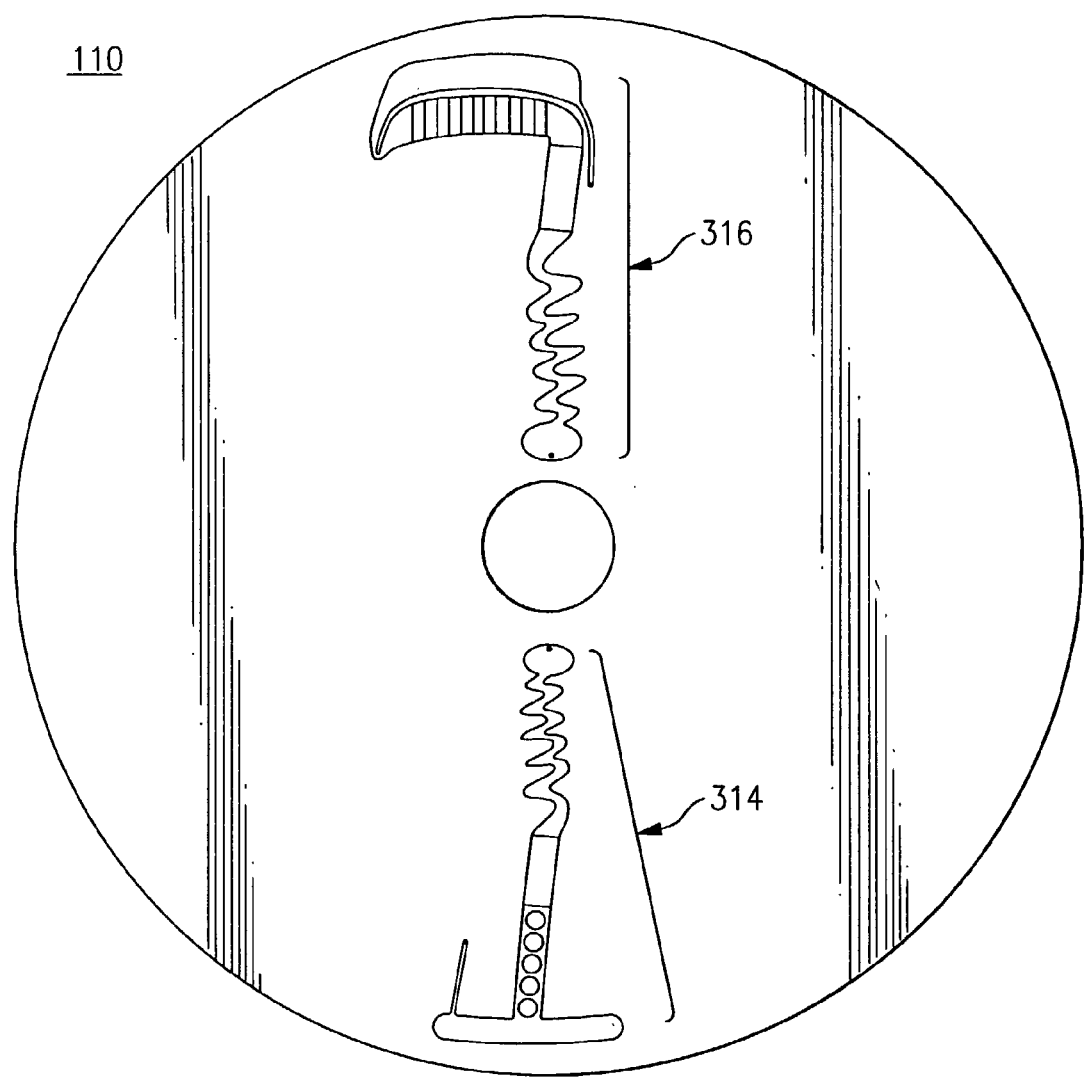
FIG. 61A is an illustration of an optical bio-disc having yet another embodiment of the fluidic circuit implemented to purify T cells from a whole blood sample.

Referring to FIG. 61A, there is depicted an optical bio-disc 110 having yet another embodiment of the fluidic circuit implemented to purify T cells from a whole blood sample. Two examples of this embodiment is shown in FIG. 61A including the "hammerhead" type fluidic circuit 314 and the "hockey stick" type fluidic circuit 316. Details relating to these fluidic circuits are discussed in below in conjunction with FIGS. 61B and 61C.

Figure 61B:
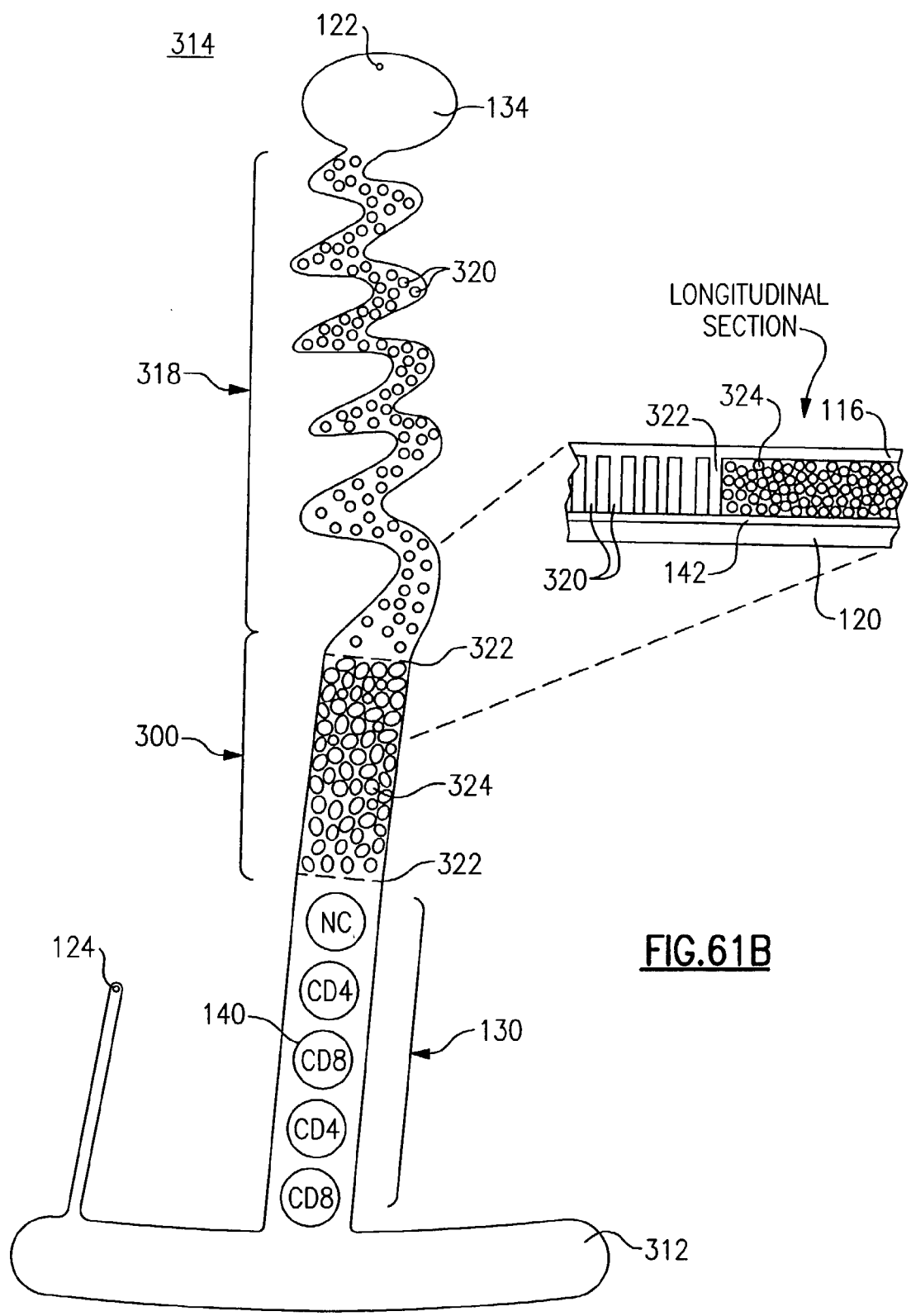
FIGS. 61B and 61C are illustrations of two embodiments of the fluidic circuit shown in FIG. 61A.
Figure 61C:
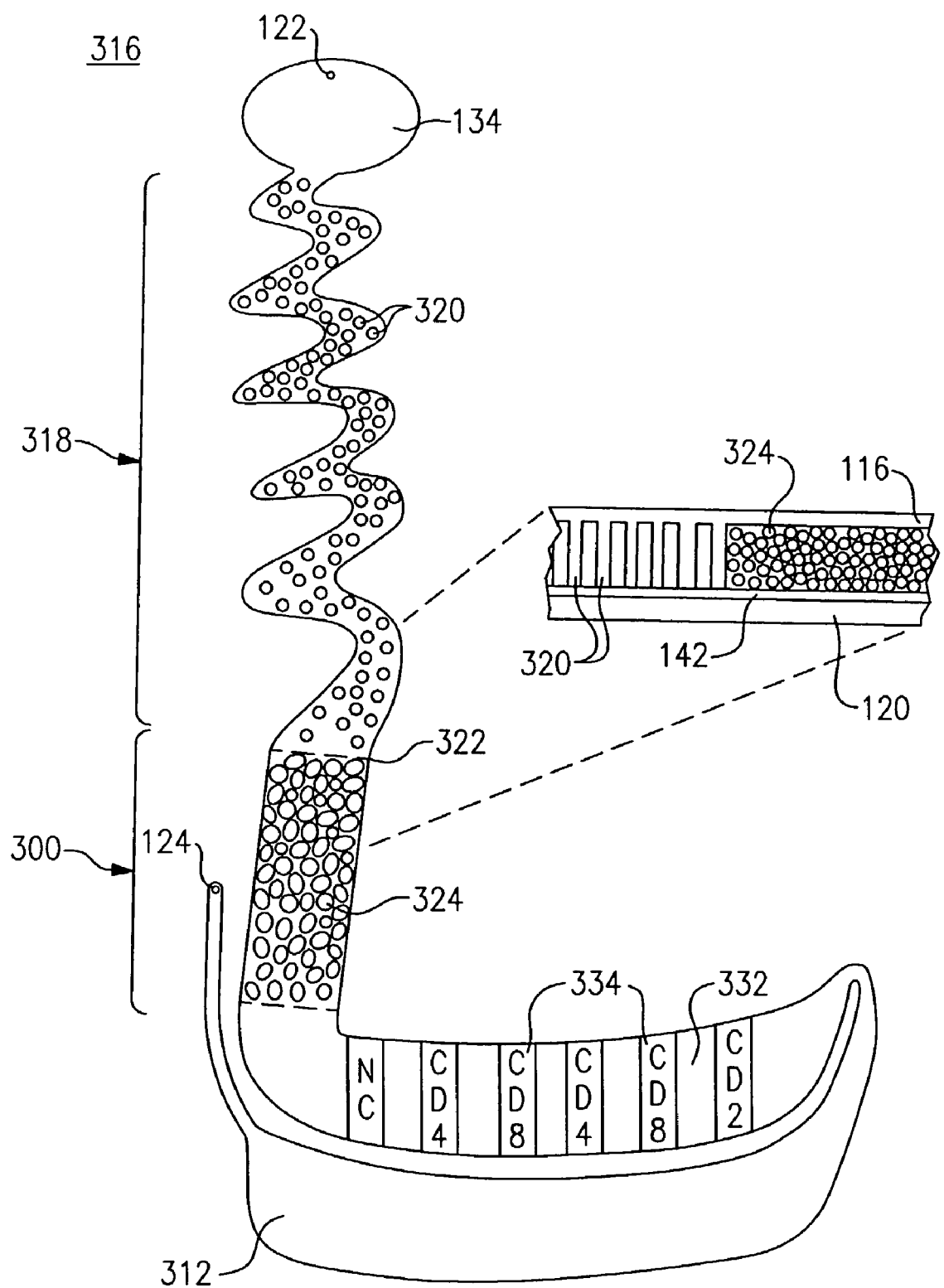

Referring now to FIG. 61B, there is shown the "hammerhead" fluidic circuit 314 for T cell analysis. The hammerhead fluidic circuit includes a mixing chamber 134 having an inlet port 122. The mixing chamber 134 is connected to a RBC capture zone 318. The RBC capture zone 318 shown is serpentine, wavy, or sinusoidal to increase the overall length of the RBC capture zone 308 thereby increasing its surface area. The RBC capture zone 318 may include "pier posts" 320 positioned vertically and is dispersed throughout the RBC capture zone 318 to further increase the surface area of capture zone 318 thereby maximizing its RBC capture efficiency. The surface of the RBC capture zone channel 318, including the surface of the "pier posts" 320, is lined with a RBC capture agent such as lectin such that when RBCs come in contact with the surface of the RBC capture zone 318 and the "pier posts" 320, RBCs bind and remain bound therein. The concentration or density of the capture agents bound to the surface of the RBC capture zone channel 318 can be determined by one of ordinary skill in the art by no more than routine experimentation. The "hammerhead" fluidic circuit 314 further includes of a T cell purification chamber or zone 300 similar to that shown and described above in conjunction with FIGS. 59 and 60. The T cell purification chamber or zone 300 contains beads 324 held in place by a barrier 322. The beads have purification agents attached thereto that are directed against surface markers of unwanted cells. For example, the capture beads 324 may have purification agents including for example, DNA, ligands, receptors, and antibodies such as anti-CD56 for NK cells, CD14 for monocytes, CD19 for B cells, CD9, CD31, or CD41 for platelets, and CD13, CD31, or CD43 for granulocytes attached thereto.

In use, whole blood is added to the mixing chamber 134 through inlet port 122 of the "hammerhead" fluidic circuit 314. The disc is then spun at a pre-determined speed and time sufficient to allow movement of the sample into the RBC capture zone 318 and allow RBCs to bind with the RBC capture agents lining the zone 318 and the "pier posts" 320. As the sample passes through the RBC capture zone 318 a majority, if not all, of the RBCs get captured and white blood cells pass through and enter the T cell purification zone 300. As the white blood cells pass through the T cell purification zone 300, unwanted cells are trapped or captured by the beads 324 in the T cell purification zone 300. The cells that move past the T cell purification zone 300 are purified T cells and are analyzed in the analysis chamber 130 wherein specific types of T cells including, for example, CD4+ and CD8+ cells, are captured and quantified. Excess buffer and sample moves to the waste chamber 312.

Referring next to FIG. 61B, there is shown another fluidic circuit for T cell analysis called the "hockey stick". The "hockey stick" is similar to the "hammerhead" except for a semicircular analysis chamber 332 instead of the radial analysis chamber 130 of the "hammerhead". Another difference in the "hockey stick" is the use of straight-radially-aligned capture zones 334.

Figure 62A:
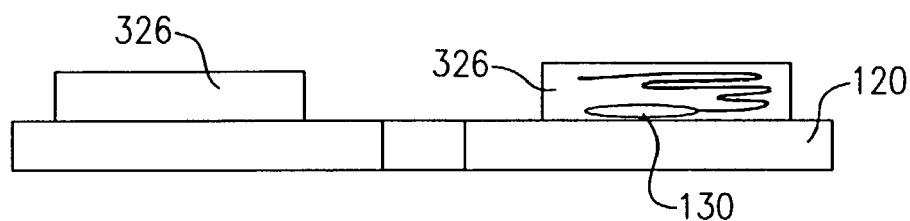
FIG. 62A is a cross sectional view of an optical bio-disc cut through the center showing a microfluidic cassette.
Figure 62B:
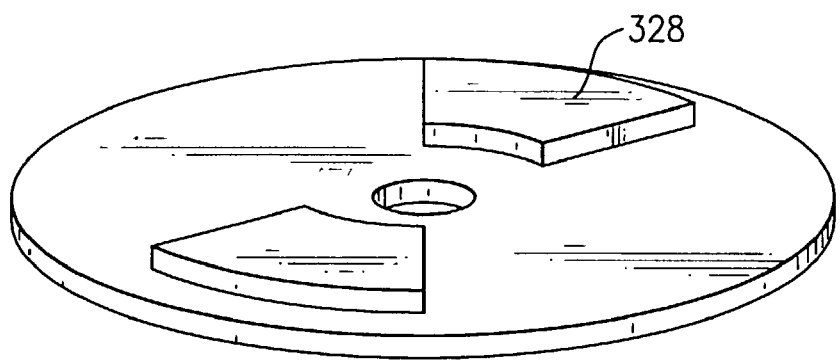
FIGS. 62B and 62C are top, side views of optical bio-discs having microfluidic cassettes attached thereto.
Figure 62C:
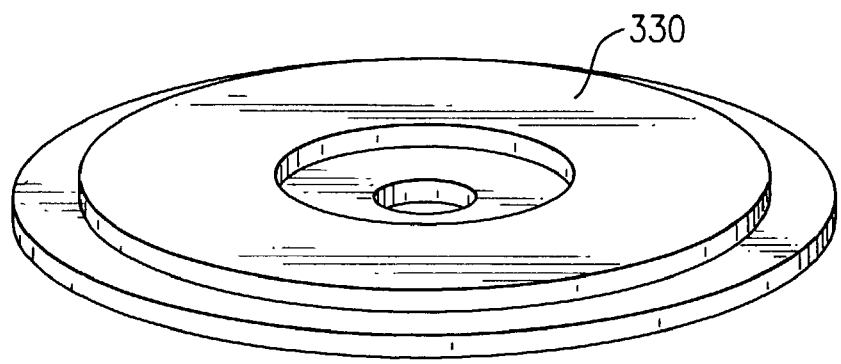

With reference now to FIG. 62A, there is illustrated another embodiment of the optical bio-disc 110 having a microfluidic cassette 326. In this embodiment, the fluidic circuits, channels, and fluidic reservoirs mentioned above is formed inside a microfluidic cassette 326 that is attached to the surface of the disc substrate. The sample processing may be carried out inside the cassette 326 and the analysis on the substrate 120 in an analysis chamber 130 of the bio-disc 110. The cassettes 326 may be semicircular 328 (FIG. 62B) of annular 330 (FIG. 62C).

Figure 63:
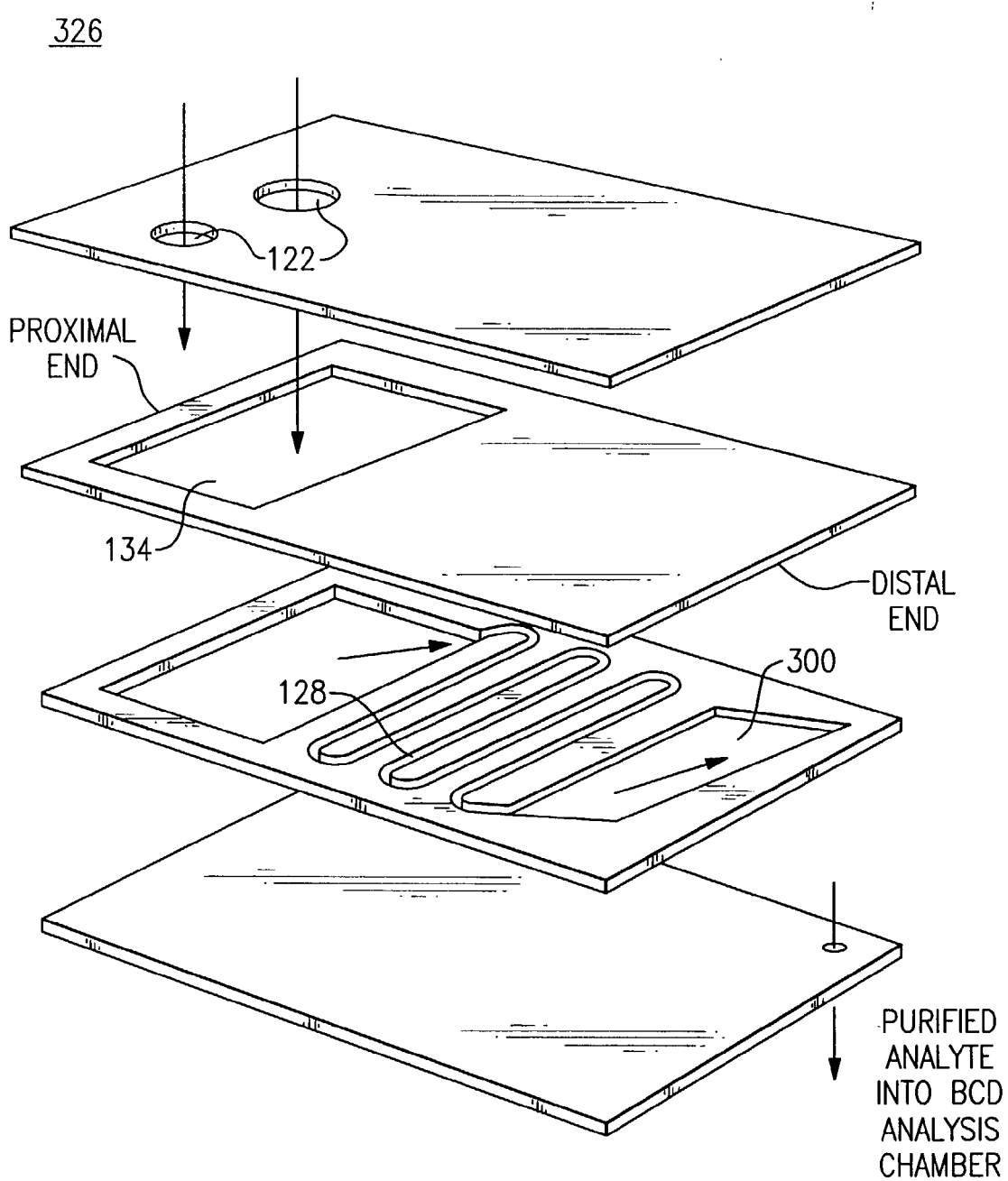
FIG. 63 is a perspective exploded view of the microfluidic cassette.

Turning next to FIG. 63, there is shown a perspective exploded view of one embodiment of the microfluidic cassette 326. The microfluidic cassette 326 may have four layers having portions cut out to form ports and fluidic circuits as shown. Each layer may be formed from plastic such as polycarbonate and polymethylmethacrylic (PMMA), or any bio-compatible material. The layers may be held together by adhesives including UV glues, or by plastic welding such as laser and ultrasonic welding. The microfluidic cassette 326 is situated on the optical bio disc such that the proximal end is closest to the center of the disc and the distal end is furthest from the center of the disc. As illustrated in FIG. 63, the microfluidic cassette 326 may include inlet ports 122 where buffer and samples are loaded. As indicated by the arrows, the sample flows into the mixing chamber 134, where sample and buffers are mixed, then into the fluidic circuit 128 for further mixing. The sample then enters the sample purification zone 300 where unwanted contaminants such as unwanted cells are removed as described above in conjunction with FIGS. 59, 60, 61B, and 61C. The purified analyte or sample is then directed into the analysis chamber 130. The movement of the sample through the various flow channels and chambers within the microfluidic cassette 326 may be controlled by centrifugal force by spinning the disc at pre-determined speeds and duration.

Turning next to FIG. 64, there is shown a bar graph representation of data collect from a CD Marker Assay using the optical bio-disc 110 of the present invention. In this experiment, CD4+ and CD8+ cells were purified using magnetic beads and tested using the optical bio-disc 110. The capture agents used in this particular experiment were anti-CD19, anti-CD2, anti-CD4, and anti-CD8 antibodies. The bar graph of FIG. 64 shows the number of cells captured in each capture zone. Details relating to this experiment are discussed below in conjunction with Example 10.

Experimental Details

While this invention has been described in detail with reference to the drawing figures, certain examples and further illustrations of the invention are presented below.

EXAMPLE 1

FIG. 17A illustrates a pictorial flow chart showing the preparation of a sample, use of a bio-disc, and the provision of results which are shown in greater detail in FIGS. 52 and 53. The details of the following example such as the individual time duration of process steps, rotation rates, and other details are more particular than those described above with reference to FIGS. 17A, 52, and 53. The basic steps of the present example are, nonetheless, similar to those described above.

A. Disc Manufacturing Including Substrate Preparation and Chemistry Deposition

In this example, a reflective disc or transmissive disc substrate 120 (FIGS. 2 and 5, respectively) is cleaned using an air gun to remove any dust particles. The disc is rinsed twice with iso-propanol, using a spin coater. A 2% polystyrene is spin coated on the disc to give a very thick coating throughout.

The chemistry is then deposited. One embodiment includes a three step deposition protocol that incubates: streptavidin, incubated for 30 minutes; biotinylated first antibody incubated for 60 minutes; and a second capture antibody incubated for 30 minutes. The first antibody can be raised in a first species (e.g., sheep) against a type of immunoglobulin (e.g., IgG, IgE, IgM) of a second species (e.g., mouse). The second capture antibody is raised in the second species against a specific cell surface antigen (e.g., CD4, CD8). The steps are done at room temperature in a humidity chamber using washing and drying steps between depositions.

A 1 µl ratio of 1 mg/ml streptavidin in phosphate buffered saline is layered over each window and incubated for 30 minutes. Excess streptavidin is rinsed off using distilled water and the disc is dried. Equal volumes of biotinylated anti-mouse IgG (125 µg/ml in PBS) and activated dextran aldehyde (200 µg/ml) are combined. Dextran aldehyde (DCHO)-biotinylated anti-mouse IgG is layered over streptavidin in each capture window and incubated for 60 minutes or overnight in refrigerator. Excess reagent is rinsed and the disc is spun dry.

As shown in FIG. 47, there can be a number of radially oriented viewing windows with different tests, such as CD4 (window 2), CD8 (window 3), CD3 (window 4), and CD45 (window 5), and negative control (window 6), using mouse IgG antibodies against these human cell surface antigens. This prepared substrate is incubated for 30 minutes or overnight in the refrigerator.

The pattern of chemistry deposition is provided below in Table 3.

TABLE 3

| Window | 1–2 | 3–4 | 5–6 | 7–8 |
|---|---|---|---|---|
| 1st Layer | Streptavidin | Streptavidin | Streptavidin | Streptavidin |
| Secondary Antibodies | B-anti Mouse IgG + DCHO | B-anti Mouse IgG + DCHO | B-anti Mouse IgG + DCHO | B-anti Mouse IgG + DCHO |
| Primary Antibodies | Mouse Anti-human CD4 | Mouse Anti-human CD8 | Mouse Anti-human CD3 | Mouse Anti-human CD45 |

B. Disc Assembly

The disc is assembled using an adhesive layer that may, for example, be 25, 50, or 100 microns thick (channel layer 118 in FIGS. 2 and 5), with a stamped out portion, such as a U-shape or "e-rad" channel, to create a fluidic channel, and a clear cap 116 (FIG. 5, for use with a transmissive disc with a top detector) or a cap 116 with a reflective layer 142 located over the capture zones (FIG. 2, for use with a reflective disc with a bottom detector).

In one embodiment, the disc is a forward Wobble Set FDL21:13707 or FDL21:1270 CD-R disc coated with 300 nm of gold as the encoded information layer. On a reflective disc, viewing windows of size 2×1 mm oval are etched out of the reflective layer by known lithography techniques. In some designs of transmissive disc, no separate viewing windows are etched, and the entire disc is available for use. In this particular example, the channel layer is formed from Fraylock adhesive DBL 201 Rev C 3M94661. The cover is a clear disc with 48 sample inlets each with a diameter of 0.040 inches located equidistantly at radius 26 mm. The data disc is scanned and read with the software at speed 4× and sample rate 2.67 MHz using CD4/CD8 counting software.

C. Disc Leak Check

Because blood is being analyzed, the disc can be leak checked first to make sure none of the chambers leak during spinning of the disc with the sample in situ. Each channel is filled with a blocking agent, such as StabilGuard and PBS-Tween. The block is for at least 1 hour. The disc is spun at 5000 rpm for 5 minutes to leak proof and check disc stability. After checking for leaks, the disc is placed in a vacuum chamber for 24 hours. After vacuuming for 24 hours, discs are placed in a vacuum pouch and stored in refrigerator until use.

D. Sample Collection, Preparation, and Application to Disc

The following section is directed to sample processing steps which are generally shown in FIG. 17A. Mononuclear cells (MNC) are purified by a density gradient centrifugation method, e.g., using a Becton Dickinson CPT Vacutainer. Blood (4–8 ml) is collected directly into a 4 or 8 ml EDTA containing CPT Vacutainer. The tubes are centrifuged at 1500 to 1800×g in a biohazard centrifuge with horizontal rotor and swing out buckets for 25 minutes at room temperature. The blood is preferably used within two hours of collection. After centrifugation, plasma overlying the mononuclear cell fraction is removed, leaving about 2 mm of plasma above an MNC layer. MNC are collected and washed with PBS. Cells are pelleted by centrifuge at 300×g for 10 minutes at room temperature. The supernatant is removed and the pellet containing the MNC is resuspended in PBS by tapping the tube gently. One more washes are done at 300×g for 10 minutes each at room temperature to remove platelets. The final pellet is resuspended to a cell count of 10,000 cells/µl. An 18 µl volume of the MNC is introduced to one or more the analysis chamber or channel, incubated for 15 minutes at room temperature with the disc stationary. The channels are sealed. The disc is then spun at 3000 rpm for 3 to 4 minutes using a disc drive. The disc is preferably scanned and read with the software at speed 4× and sample rate 2.67 MHz.

If a blood sample cannot be processed immediately, mononuclear cells after the first centrifugation can be resuspended in plasma by gently inverting the CPT tube several times and stored for up to 24 hours at room temperature. Within 24 hours, the cells in the plasma can be collected and washed as described above.

E. CD4/CD8 Assay Format

The assay in this example is a generic homogeneous solid phase cell capture assay for the rapid determination of absolute number of CD4+ and CD8+ T-lymphocyte populations and ratio of CD4+/CD8+ lymphocytes in blood samples. The test, which is run within a small chamber incorporated into a CD-ROM, determines the number of CD4+, CD8+, CD2+, CD3+ and CD45+ cells captured by the specific antibodies on the capture zones in 7 µl of mononuclear cells (MNC) isolated from whole blood. The test is based upon the principle of localized cell capture on specific locations on the disc. Several specific cell capture zones are created on the disc by localized application of capture chemistries based upon monoclonal or polyclonal antibodies to particular blood cell surface antigens. Upon flooding the chamber with the MNC blood (30,000 cells/µl), cells expressing antigens CD4, CD8, CD2, CD3 and CD45 are captured in the capture zones on the disc. Also incorporated within the bar code are defined negative control areas.

F. On-Disc Analysis

MNC cells, prepared in step D above (18 µl in PBS), are injected into the disc chamber, and inlet and outlet ports of the chamber are sealed. The disc is incubated for 15 minutes at room temperature, and then scanned using a 780 nm laser in an optical drive with a top detector to image the capture field as described above.

Software is encoded on the disc to instruct the drive to automatically perform the following acts: (a) centrifuge the disc to spin off excess unbound cells in one or more stages, (b) image specific capture windows, and (c) process data including counting the specifically-captured cells in each capture zone and deriving the ratio of CD4/CD8 (or which ever ratio is programmed to be determined).

During the processing step, the software reads across each capture zone image and marks cells as it encounters them. For example, following estimation of number of CD4+ and CD8+ cells, the software calculates the ratio of CD4+/CD8+ cells and displays both the absolute numbers of cells in CD4+, CD8+, CD3+ and CD45+ capture zones per microliter of whole blood and also the CD4+/CD8+ ratio. The entire process takes about 12 minutes from inserting the disc into the optical drive to obtaining the numbers and ratios.

G. Reagents Used

Streptavidin (Sigma, cat. # S-4762): Add de-ionized water to make a 5 mg/ml solution, aliquot and store at −30° C. To use, add Tris buffer for a final concentration of 1 mg/ml.

Positive control: CD45 (Sigma, Lot # 038H4892, cat # C7556). Store at 2–8° C.

Secondary capture antibody: Biotinylated anti-mouse IgG (raised in sheep, Vector laboratories, lot # L0602, Catalog # BA-9200) Stock solution 1.5 mg/ml made in distilled water. Working b-IgG solution 125 µg/ml in 0.1M PBS. Store at 2–8° C. May be kept at −30° C. for long term storage.

Aldehyde activated Dextran (Pierce, lot # 97111761, cat # 1856167). Stock solution stock solution 5 mg/ml in PBS, store at 2–8° C.

Primary capture antibody: CD4 (DAKO, cat # M0716), CD8 (DAKO, cat # M0707), CD2 (DAKO, cat # M720), CD45 (DAKO, cat # M0701), CD14 (DAKO, cat # M825), and CD3 (DAKO, cat # M7193). Store at 2–8° C.

Negative control: Mouse IgG1 (DAKO, cat # X0931). Store at 2–8° C.

Phosphate Buffered Saline (PBS), pH 7.4 (Life Technologies/GIBCO BRL, cat. # 10010–023) or equivalent. Store at room temperature Isopropyl alcohol, 90–100%

H. RBC Lysing Protocol

Ammonium Chloride Lysing Buffer

A 1× stock of ammonium chloride lysing buffer should be stored at 2 to 8° C. Comprised of 0.155M $NH_4Cl$, 10 mM $KHCO_3$, and 0.1 mM disodium EDTA; pH 7.3 to 7.4. Store at 2–8° C. Bring to room temperature prior to use.

Procedure

1. For every 100 µl of blood add 2 ml of lysing buffer. (It is preferable to do this procedure in a biohazard hood.)
2. Vortex and incubate for 15 minutes at room temperature.
3. Centrifuge the blood at 500×g for 5 minutes at room temperature, using the centrifuge in the biohazard hood.
4. Remove supernatant and wash cells with 2% FCS or FBS in PBS. Centrifuge cells.
5. Calculate the total amount of WBCs and make the final concentration of WBCs 10,000 cells/µl for sample injection.

EXAMPLE 2

Mononuclear Cells Separation Procedure

Use Becton and Dickinson Vacutainer CPT (BD catalog # 362760 for 4 ml, #362761 for 8 ml) cell preparation tubes with sodium citrate. Do procedure in biohazard hood following all biohazard precautions. Steps:

1. Collect blood directly into a 4 or 8 ml EDTA containing CPT Vacutainer. If the blood sample is already in an anticoagulant, pour off the EDTA in the Vacutainer first and then pour 6–8 ml of blood sample into the CPT tube.
2. Centrifuge the tube at 1500 to 1800×g in a biohazard centrifuge with horizontal rotor and swing out buckets for 25 minutes at room temperature. For best results, the blood should be centrifuged within two hours of collection. However, blood older then 2 hours may be centrifuged with a decrease in MNC number and increase in RBC contamination.
3. After centrifugation, remove the plasma leaving about 2 mm of plasma above the MNC layer. Collect and transfer the whitish mononuclear layer into a 15 ml conical centrifuge tube.
4. Add 10–15 mls with PBS to MNC layer, gently mix the cells by inverting the centrifuge tube several times.
5. Wash cells by centrifuge at 200×g for 10 minutes at room temperature in biohazard centrifuge.
6. Remove supernatant. Resuspend cells by tapping the tube gently.
7. Wash one more time in 10 ml of PBS. Centrifuge at 200–300×g for 10 minutes at room temperature to remove platelets.
8. Remove supernatant and resuspend pellet in 50 ul PBS.
9. Estimate cell counts in the sample. Run CBC or dilute 2 ul of cells to 18 ul of trypan blue, gently mix and count cells with a hemocytometer. Make up the sample to a final cell count of 10,000 cells/ul for analysis.
10. If the cells cannot be processed immediately, resuspend mononuclear cells after the first centrifugation (step 2 above) in the separated plasma by gently inverting the CPT tube several times and store for up to 24 hours at room temperature. Within 24 hours, collect the cells in the plasma and continue with the washes as described above.

Total cell counts per ul=number of cells in 25 small squares×(times) 100.

EXAMPLE 3

Isolation of MNCs from Whole Blood Using Histopaque-1077

1 ml of Histopaque-1077 was placed in a 15 ml centrifuge tube and 1 ml of whole blood is gently layered over that. Then centrifuged at 400×g for 30 min at room temperature. The mixture was aspirated carefully with a pasture pipette and the opaque interface transferred to centrifuged tube. Then 10 ml of PBS was added to the centrifuge tube. The solution was then centrifuged at 250×g for 10 min. The supernatant was decanted and the cell pellet was resuspended in 10.0 ml PBS and spun at 250×g for 10 min. The cells were then washed one more time by resuspending the pellet in 10 ml PBS and spinning at 250×g. The final cell pellet was resuspended in 0.5 ml PBS.

EXAMPLE 4

CD4+ Cell Isolation with Dynal Beads

A. Materials
1. Cold PBS/2% FBS, pH 7.4
2. PBS /0.5% BSA, pH 7.4
3. CD4 Positive Dynal Isolation Kit
4. Dynal MPC, Dynal mixer, Centrifuge, Polypropylene tubes B. Procedure Run a CBC and determine the number of beads per cell needed (4–10 beads/cell). Add 1 ml of cold PBS/2% FBS to desired amount of beads ($1 \times 10^7$ beads/72 ul) and resuspend. Place tube in Dynal MPC for 30 seconds and pipette off the supernatant. Resuspend the washed beads to the original volume. Add the desired amount of beads to the cells. Incubate at 2–8° C. for 20 minutes in the Dynal mixer set to 11. Isolate the rosetted cells in the Dynal MPC for 2 minutes. Pipette off the supernatant. Wash the rosetted cells 4× in PBS/2% FBS. Resuspend the rosettes in 200–400 ul of PBS/2% FBS. Add 10 ul Detach-a-Bead per 100 ul cell suspension. Incubate at RT for 60 minutes in the Dynal mixer set to 11. Isolate the beads in the Dynal MPC for 2 minutes. Transfer and save the supernatant. Wash the beads 2–3 times in 500 ul PBS/2% FBS to obtain residual cells. Wash the collected cells in 400 ul PBS/0.5% BSA.

Run CBC to determine isolated cell concentration.

EXAMPLE 5

Disc Preparation and Chemistry Deposition (with Streptavidin)

A. Disc Manufacturing Including Substrate Preparation and Chemistry Deposition

In this example, a transmissive disc substrate was cleaned with an air gun to remove dust. The disc was then mounted in the spin coater and rinsed twice with a steady stream of iso-propanol. Next, a polystyrene solution with 2% polystyrene dissolved in 310 ml of toluene and 65 ml of iso-propanol was evenly coated onto the disc.

For the streptavidin deposition, streptavidin stock solution was diluted to 1 mg/ml in PBS. Using manual pin deposition, approximately 1 ul of the streptavidin was deposited in each capture zone on the disc. The disc was incubated in a humidity chamber for 30 minutes. Then excess unbound streptavidin was rinsed off the capture zones with D. I. water and the disc was spun dried.

For the secondary antibody deposition, a fresh solution of activated dextran aldehyde (200 ug/ml in PBS) was combined with an equal volume of the Vector IgG (125 ug/ml in PBS). Using manual pin deposition, approximately 1 ul of the IgG+DCHO complex was deposited (layered on top of the streptavidin layer) in each capture zone on the disc. The disc was incubated in a humidity chamber for 60 minutes. Excess antibody was rinsed off with D. I. water and the disc was spun dry.

For the primary antibody, DAKO CD4 was diluted to 50 ug/ml in PBS, DAKO CD8 was diluted to 25 ug/ml in PBS, and DAKO CD45 was diluted to 145 ug/ml in PBS. Using the manual pin applicator, deposited approximately 1 ul of each primary antibody on top of the bound secondary antibodies. The disc was then incubated in a humidity chamber for 30 minutes. The excess unbound antibody was removed by washing the capture zones with PBS and the disc was spun dried.

B. Disc Assembly

The cover disc used was a clear disc with a Fraylock adhesive channel layer attached thereto. Stamped into the adhesive were 4 U-shaped channels that created the fluidic circuits. The cover was placed onto the transmissive disc substrate so that the fluid channels were over the capture zones. Next, to secure the discs together, they were passed through a disc press 8 times.

C. Disc Leak Check, Blocking

Each fluid channel was filled with StableGuard and incubated for 1 hour. During the incubation, the disc was spun in the spin coater for 5 minutes at 5000 rpm. After the spin, the disc channels were checked for leaks. Next, the StableGuard was aspirated out of the channels, and the disc was placed under vacuum in a vacuum chamber overnight. The next morning, the disc was placed in a vacuum pouch and stored at 4° C.

EXAMPLE 6

Comparing Optical Bio-disc CD4/CD8 Ratios to FACs CD4/CD8 Ratios

A. Preparing of Clinical Blood Samples Using CPT Tubes 3 mls of clinical EDTA blood samples (Nos. 29, 30, 31, 32, 33, 34 and 35) were poured into individual CPT tubes that had the sodium citrate removed. The tubes were centrifuged for 25 minutes at 1500×g, at room temperature. After centrifugation, the upper plasmas, within 0.5 cm of the opaque MNC layers, were aspirated off. The remaining opaque MNC layers were transferred to clean 15 ml tubes and 12 ml of PBS were added to each.

Washing

The cell suspensions were then centrifuged at 250×g for 10 minutes. The supernatants were then aspirated off, and the cells resuspended in 14 ml of PBS. The suspensions were centrifuged at 250×g for 10 minutes again. Aspirated off the supernatants and resuspended each cell pellet with 200–175 ul of PBS. The cell concentrations for each sample were determined by counting the cells with a hemocytometer. Adjusted the final cell concentrations to 30,000 cells/ul for each sample.

B. Comparing Optical Bio-disc CD4/CD8 Ratios to FACs CD4/CD8 Ratios

Discs (Nos. 27a, 27b, 27c, 27d, 27e, 27f & 28) were prepared similar to example 5, using 25 um adhesive channels.

Each sample was injected into each corresponding disc as shown below in Table 4. After 30 minutes, the disc was centrifuged at 3000 rpm for 5 minutes. Light micrographs were then taken of the cells captured on the chemistry zones and the cells were counted. Each clinical sample also had a FACs analysis performed. The results from this experiment are shown below in Table 4.

TABLE 4

Comparing Optical Bio-disc CD4/CD8 Ratios to FACs CD4/CD8 Ratios

| Disk # | Sample # | Disc CD4/CD8 | FACs CD4/CD8 |
|---|---|---|---|
| 27a | 29 | 2.39 | 2.43 |
| 27b | 30 | 1.47 | 1.67 |
| 27c | 31 | 0.8 | 0.98 |
| 27d | 32 | 1.84 | 2.16 |
| 27e | 33 | 0.96 | 1.14 |
| 27f | 34 | 1.59 | 1.49 |
| 28 | 35 | 1.03 | 1.04 |

EXAMPLE 7

Disc Preparation and Chemistry Deposition

A. Disc Manufacturing Including Substrate Preparation and Chemistry Deposition

In this example, a transmissive disc substrate was cleaned with an air gun to remove dust. The disc was then mounted in the spin coater and rinsed twice with a steady stream of iso-propanol. Next, a polystyrene solution with 2% polystyrene dissolved in 310 ml of toluene and 65 mls of iso-propanol was evenly coated onto the disc.

For the secondary antibody deposition, a fresh solution of activated dextran aldehyde (200 ug/ml in PBS) was combined with an equal volume of the Vector IgG (125 ug/ml in PBS). Using manual pin deposition, approximately 1 ul of the IgG+DCHO complex was deposited in each capture zone on the disc. The disc was incubated in a humidity chamber for 60 minutes. Excess antibody was rinsed off with D. I. water and the disc was spun dry.

For the primary antibody, DAKO CD4 was diluted to 50 ug/ml in PBS, DAKO CD8 was diluted to 25 ug/ml in PBS, and DAKO CD45 was diluted to 145 ug/ml in PBS. Using the manual pin applicator, approximately 1 ul of each primary antibody was deposited on top of the absorbed secondary antibodies. Incubated in the humidity chamber for 30 minutes. Rinsed off the excess antibody with PBS and spun dry the disc.

B. Disc Assembly

The cover disc used was clear with a Fraylock adhesive channel layer attached thereto. Stamped into the adhesive were 4 U-shaped channels that created the fluidic circuits. The cover was placed onto the transmissive disc substrate so that the fluid channels were over the antibody zones. Next, to secure the discs together, they were passed through a disc press 8 times.

C. Disc Leak Check, Blocking

Each fluid channel was filled with StableGuard and incubated for 1 hour. During the incubation, the disc was spun in the spin coater for 5 minutes at 5000 rpm. After the spin, the disc channels were checked for leaks. Next, the StableGuard was aspirated out of the channels, and the disc was placed under vacuum in a vacuum chamber overnight. The next morning, the disc was placed in a vacuum pouch and stored at 4° C.

EXAMPLE 8

CD Marker Test of a Blood Sample

A. Preparing a Clinical Blood Sample Using Histopaque 1077

12 mls of blood (sample # 176) was drawn at 10:00 am into an EDTA tube. At 12:00 pm, 3 mls of blood was layered over 3 mls of Histopaque 1077 in 4×15 ml tubes. The tubes were centrifuged for 30 minutes at 400×g, at room temperature. After centrifugation, the upper plasma, within 0.5 cm of the opaque MNC layer, was aspirated off. The remaining opaque MNC layer was transferred to a clean 15 ml tube and 12 ml of PBS was added. Repeated this for the remaining 3 tubes.

Washing

The cell suspensions were then centrifuged at 250×g for 10 minutes. The supernatants were then aspirated off, and the cells resuspended in 14 ml of PBS. The suspensions were centrifuged at 250×g for 10 minutes again. Aspirated off the supernatants and resuspended each cell pellet with 175 ul of PBS. Then all 4 MNC suspensions were combined and the cell concentration determined by running a CBC with a Cell Dyne 1600 cell counter. The final volume was 650 ul with a concentration of 23.5K cells/ul. We then performed 6 serial dilutions to end up with concentrations ranging from 1000 cells/ul to 100,000 cells/ul, shown below in Table 5

B. Comparing CD4 Antibodies from DAKO and Serotec

Two discs (#338 & 339) with 6 channels each were made according to Example 7 using a 100 um adhesive layer. Another primary CD4 antibody from Serotec (50 ug/ml, cat# LN1298) was also used in this experiment.

We injected each channel of disc 338 with one serial dilution of sample 176. After 15 minutes, the disc was centrifuged at 3000 rpm for 5 minutes. Light micrographs were taken of the cells captured on the chemistry zones and the cells were counted using a cell counting software (Metamorph). Alternatively, the number of cells captured may be evaluated using an optical disc reader and accompanying software. This procedure was for disc 339. The counts of cells captured on the DAKO CD4 chemistry zones were compared to the cells captured on the Serotec CD4 chemistry zones. The data collected from this experiment is shown in Table 5.

EXAMPLE 9

Testing Discs with Lysed Blood Drawn in ACD Tubes

A. Preparing Clinical Samples Using Ammonium Lysing Buffer 4 ml of 1× ammonium chloride lysing buffer was added to 200 uls of each ACD blood sample (Nos. 251, 252, 253, 254, 255 & 256). The samples were vortexed and incubated for 15 minutes at room temperature. Next, the samples were centrifuged at 500×g for 5 minutes at room temperature. Removed the supernatant, and washed the cells with 3 mls of 2% FBS in PBS. Centrifuged again. Removed the supernatant, and resuspended the cells in 100 uls of 2% FBS in PBS. The final concentrations were between 10,000–5,500 cells/ul.

B. Testing Discs with Lysed Blood Drawn in ACD Tubes

Six discs (#499, 500, 501, 502, 503, & 504) with 6 B-Rad channels each were made according to example 7 using a 100 um adhesive layer.

We injected 3 channel of disc 499 with sample 251. After 15 minutes, the disc was centrifuged at 3000 rpm for 5 minutes. Light micrographs were taken of the cells captured on the chemistry zones and the cells were counted using a cell counting software (Metamorph); results are shown below in Table 6. Alternatively, the number of cells captured may be evaluated using an optical disc reader and accompanying software. This procedure was repeated for each of the remaining 5 discs and 5 samples.

TABLE 6

Average # of CD4 and CD8 Cells Captured From Lysed ACD Blood Samples

| Disc # | Sample # | CD4 cells | CD8 cells |
| --- | --- | --- | --- |
| 499 | 251 | 249 | 316 |
| 500 | 252 | 85 | 101 |
| 501 | 253 | 149 | 143 |
| 502 | 254 | 136 | 129 |
| 503 | 255 | 130 | 188 |
| 504 | 256 | 103 | 96 |

EXAMPLE 10

Test Discs with CD4 and CD8 Isolated Cell Populations

A. Preparing CD4 and CD8 Isolated Cell Populations

Prepared 12 ml of blood (sample # 269), by layering 3 ml of blood over 3 ml of Histopaque 1077 in 4×15 ml tubes, as

TABLE 5

Cells Captured using DAKO and Seroteck CD4 Capture Antibodies

| Sample 176 Cell Concentration | CD4 Dako Disc 338 | CD4 Dako Disc 339 | CD4 Dako Averages | CD4 Seroteck Disc 338 | CD4 Seroteck Disc 339 | CD4 Seroteck Averages |
| --- | --- | --- | --- | --- | --- | --- |
| 1,000 cells/ul | 76 | 59 | 68 | 71 | 49 | 60 |
| 5,000 cells/ul | 282 | 211 | 247 | 287 | 273 | 280 |
| 10,000 cells/ul | 559 | 526 | 543 | 530 | 525 | 528 |
| 25,000 cells/ul | 1168 | 1205 | 1187 | 1015 | 1040 | 1028 |
| 50,000 cells/ul | 2459 | 2595 | 2527 | 1726 | 1981 | 1854 |
| 100,000 cells/ul | 3686 | 3835 | 3761 | 3513 | 3372 | 3443 | in example 8. Ran a CBC and determine the isolated MNCs concentration was 25,000 cells/ul. Set aside 100 ul of the MNCs for the disc. Divided the remaining 500 ul of MNCs into equal volumes. Added 1 ml of cold PBS/2% FBS to 200 ul of CD4 and 200 ul of CD8 beads and resuspend the beads. Placed tubes in Dynal MPC for 30 seconds and pipetted off the supernatant. Resuspend the washed beads to the original volumes. Added the 200 ul of CD4 and CD8 beads to each corresponding tube of cells. Incubated at 2–8° C. for 20 minutes in the Dynal mixer set to 11. Isolated the rosetted cells in the Dynal MPC for 2 minutes. Pipetted off the supernatant. Wash the rosetted CD4 and CD8 cells 4× in PBS/2% FBS. Resuspend each set of cell rosettes in 200–400 ul of PBS/2% FBS. Added 15 ul of Detach-a-Bead per cell suspension. Incubated at RT for 60 minutes in the Dynal mixer set to 11. Isolated the CD4 and CD8 beads in the Dynal MPC for 2 minutes. Transfered and saved the supernatants. Washed the CD4 and CD8 beads 2–3 times in 500 uls PBS/2% FBS to obtain residual cells. Washed the collected cells in 400 ul PBS/0.5% BSA. Ran CBCs and determined the isolated cell concentrations. Recovered 360 uls of CD4 cells at 5000 cells/ul and 215 ul of CD8 cells at 5000 cells/ul.

B. Testing a Disc with CD4 and CD8 Isolated Cell Populations

One disc (#538) with 6 B-Rad channels was made according to example 7 using a 100 um adhesive layer.

We injected 1 channel each of disc 538, with the isolated MNCs, CD4 cells and CD8 cells from sample 269. After 15 minutes, the disc was centrifuged at 3000 rpm for 5 minutes. Light micrographs were taken of the cells captured on the chemistry zones and the cells were counted using a cell counting software (Metamorph). Results from this experiment is shown in Table 7 and illustrated in FIG. 64. Alternatively, the number of cells captured may be evaluated using an optical disc reader and accompanying software.

TABLE 7

MNCs and Isolated CD4 and CD8 Cell Captures

| Primary Antibodies | Isolated MNCs Captured | Isolated CD4 Cells Captured | Isolated CD8 Cells Captured |
|---|---|---|---|
| Negative Control | 36 | 15 | 12 |
| CD 19 | 249 | 30 | 28 |
| CD 2 | 337 | 516 | 445 |
| CD 4 | 247 | 501 | 35 |
| CD 8 | 260 | 24 | 458 |

Concluding Statements

Aspects of the present invention relating to the apparatus, methods, and processes disclosed herein are also presented in U.S. Provisional Application Ser. No. 60/323,682 entitled "Methods for Reducing Non-Specific Binding of Cells on Optical Bio-Discs Utilizing Blocking Agents" filed Sep. 20, 2001; U.S. Provisional Application Ser. No. 60/324,336 entitled "Methods for Reducing Bubbles in Fluidic Chambers Using Polyvinyl Alcohol and Related Techniques for Achieving Same in Optical Bio-Discs" filed Sep. 24, 2001; U.S. Provisional Application Ser. No. 60/326,800 entitled "Sealing Methods for Containment of Hazardous Biological Materials within Optical Analysis Disc Assemblies" filed Oct. 3, 2001; U.S. Provisional Application Ser. No. 60/328, 246 entitled "Methods for Calculating Qualitative and Quantitative Ratios of Helper/Inducer-Suppressor/Cytotoxic T-Lymphocytes Using Optical Bio-Disc Platform" filed Oct. 10, 2001; U.S. Provisional Application Ser. No. 60/386,072 entitled "Quantitative and Qualitative Methods for Characterizing Cancerous Blood Cells Including Leukemic Blood Samples Using Optical Bio-Disc Platform" filed Oct. 19, 2001; U.S. Provisional Application Ser. No. 60/386,073 entitled "Methods for Quantitative and Qualitative Characterization of Cancerous Blood Cells Including Lymphoma Blood Samples Using Optical Bio-Disc Platform" filed Oct. 19, 2001; U.S. Provisional Application Ser. No. 60/386,071 entitled "Methods for Specific Cell Capture by Off-Site Incubation of Primary Antibodies with Sample and Subsequent Capture by Surface-Bound Secondary Antibodies and Optical Bio-Disc Including Same" filed Oct. 26, 2001; U.S. Provisional Application Ser. No. 60/344,977 entitled "Quantitative and Qualitative Methods for Cell Isolation and Typing Including Immunophenotyping" filed Nov. 7, 2001; and U.S. Provisional Application Ser. No. 60/349,975 entitled "Methods for Reducing Non-Specific Binding of Cells on Optical Bio-Discs Utilizing Charged Matter Including Heparin, Plasma, or Poly-Lysine" filed Nov. 9, 2001, all of which are herein incorporated by reference.

All patents, provisional applications, patent applications, and other publications mentioned in this specification are incorporated herein in their entireties by reference.

While this invention has been described in detail with reference to certain preferred embodiments, it should be appreciated that the present invention is not limited to those precise embodiments. Rather, in view of the present optical bio-disclosure that describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

Furthermore, those skilled in the art will recognize, or be able to ascertain, using no more than routine experimentation, many equivalents to the specific embodiments of the invention described herein. Such equivalents are also intended to be encompassed by the following claims.

What is claimed is:

1. An optical bio-disc for conducting a cellular assay, said disc comprising:

a rotatable substrate;

a cap portion associated with said substrate; and a fluidic circuit formed between said substrate and said cap portion, said fluidic circuit comprising:

a mixing chamber, said mixing chamber including an inlet port configured to receive a fluid including RBC's;

a RBC capture zone in fluid communication with the mixing chamber so as to receive a fluid therefrom;

a plurality of posts with RBC capture agents coated thereon and located within the RBC capture zone, the posts being configured to capture RBC's while allowing passage through said RBC capture zone of non-RBC materials included in the fluid;

a purification chamber in fluid communication with said capture zone, the purification chamber configured to receive mixed fluid communicated from the mixing chamber;

a filter associated with said purification chamber;

an analysis chamber in fluid communication with said purification chamber, said analysis chamber including a capture zone; and a vent port associated with said analysis chamber.

2. The optical bio-disc according to claim 1 wherein said filter is selected from the group consistingof microspheres and a cellular sieve.

3. The optical bio-disc according to claim 2 wherein said microspheres are coated with a purification agent.

4. The optical bio-disc according to claim 3 wherein said purification agent is selected from the group consisting of monoclonal antibodies, polyclonal antibodies, oligonucleotides, ligands, receptors, and binding agents.

5. The optical bio-disc according to claim 4 wherein said monoclonal antibodies are selected from the group consisting of anti-CD56, anti-CD14, anti-CD19, anti-CD9, anti-CD31, anti-CD41, anti-CD13, and anti-CD43.

6. The optical bio-disc according to claim 1 wherein said capture zone is coated with a capture agent.

7. The optical bio-disc according to claim 6 wherein said capture agent is selected from the group consisting of monoclonal antibodies, polyclonal antibodies, oligonucleotides, ligands, receptors, and binding agents.

8. The optical bio-disc according to claim 7 wherein said monoclonal antibodies are selected from the group consisting of anti-CD4, anti-CD8, and anti-CD2.

9. The optical bio-disc according to claim 1 further comprising a lysis buffer reservoir, a lysis channel connecting said lysis buffer reservoir with said mixing chamber, and a lysis buffer valve located in said lysis channel; said lysis buffer reservoir being pre-filled with a lysis buffer.

10. The optical bio-disc according to claim 9 further comprising an analysis buffer reservoir, a buffer channel connecting said analysis buffer reservoir with said purification chamber, and an analysis buffer valve located in said buffer channel; said analysis buffer reservoir being pre-filled with an analysis buffer.

11. The optical bio-disc according to claim 10 further comprising a waste chamber in fluid communication with said analysis chamber and said vent port.

12. The optical bio-disc of claim 11 further comprising a sample mix valve located in the fluidic circuit connecting said mixing chamber and said purification chamber.

13. The optical bio-disc according to claim 1 wherein said posts are distributed throughout said RBC capture zone.

14. The optical bio-disc according to claim 1 wherein said RBC capture agent is lectin.

15. A method of using the optical bio-disc according to claim 1 for a cellular assay, said method of using comprising the steps of:
loading a whole blood sample into said mixing chamber through said inlet port;
loading the bio-disc into an optical reader;
rotating the bio-disc at a sufficient speed and time to move said sample through said RBC capture zone where red blood cells in the sample are captured, through said purification zone where unwanted cells in the sample are captured, and through said analysis chamber where specific cells are captured on the capture zone;
directing an incident beam of electromagnetic radiation to the capture zone;
detecting a beam of electromagnetic radiation formed after the incident beam interacts with the disc at the capture zone;
converting the detected beam into an output signal; and
analyzing the output signal to extract therefrom infonnation relating to the number of cells captured at the capture zone.

16. A method of making an optical bio-disc for use in cellular assays, said method of making comprising the steps of:
forming a rotatable optical disc substrate;
forming a cover disc with similar dimensions to said substrate;
forming a channel layer with cut out portions to form fluidic circuits; said fluidic circuits including an inlet port, a mixing chamber, a purification chamber, an analysis chamber, a vent port; a RBC capture zone in fluid communication with the mixing chamber so as to receive a fluid therefrom; and a plurality of posts with RBC capture agents coated thereon and located within the RBC capture zone; said posts configured to capture RBC's while allowing passage through said RBC capture zone of non-RBC materials; and said analysis chamber including capture zones;
binding capture probes onto said capture zones;
attaching said channel layer to said substrate;
loading a filter means into said purification chamber;
attaching said cover disc to said channel layer to thereby form the optical bio-disc.

17. The method of claim 16 wherein said attaching steps are achieved by techniques selected from the group comprising adhesives and plastic welding.

18. The method of claim 16 wherein said filter means is selected from the group consisting of microspheres and cellular sieves.

19. The method of claim 18 wherein said filter means is coated with a purification agent.

20. The optical bio-disc of claim 1, wherein mixing chamber is configured to receive a lysis buffer.

21. The optical bio-disc of claim 20, wherein the bio-disc is configured to transmit the lysis buffer to the mixing chamber after the disc is rotated at a first predetermined speed, and wherein the bio-disc is configured to release the contents of the mixing chamber after the disc is rotated at a second predetermined speed.

* * * * *